US010137109B2

(12) United States Patent
Tucker et al.

(10) Patent No.: US 10,137,109 B2
(45) Date of Patent: Nov. 27, 2018

(54) CARBAZOLE COMPOUNDS AND THERAPEUTIC USES OF THE COMPOUNDS

(71) Applicant: Incuron, LLC, Buffalo, NY (US)

(72) Inventors: John Tucker, San Diego, CA (US); Sergey Sviridov, Moscow (RU); Leonid Brodsky, Rehovet (IL); Catherine Burkhart, Collins, NY (US); Andrei Purmal, Orchard Park, NY (US); Katerina Gurova, Orchard Park, NY (US); Andrei Gudkov, East Aurora, NY (US)

(73) Assignee: INCURON, INC., Buffalo, NY (US)

( * ) Notice: Subject to any disclaimer, the term of this patent is extended or adjusted under 35 U.S.C. 154(b) by 16 days.

(21) Appl. No.: 15/386,020

(22) Filed: Dec. 21, 2016

(65) Prior Publication Data

US 2017/0165229 A1    Jun. 15, 2017

Related U.S. Application Data

(63) Continuation of application No. 14/731,202, filed on Jun. 4, 2015, now Pat. No. 9,566,265, which is a continuation of application No. 14/231,841, filed on Apr. 1, 2014, now Pat. No. 9,108,916, which is a continuation of application No. 13/121,051, filed as application No. PCT/US2009/059558 on Oct. 5, 2009, now Pat. No. 8,765,738.

(60) Provisional application No. 61/102,913, filed on Oct. 6, 2008.

(51) Int. Cl.
*C07D 209/86* (2006.01)
*A61K 31/403* (2006.01)
*C07D 209/88* (2006.01)
*C07D 401/04* (2006.01)
*C07D 487/04* (2006.01)
*A61K 9/00* (2006.01)
*A61K 31/439* (2006.01)
*A61K 31/454* (2006.01)
*A61K 31/506* (2006.01)
*A61K 31/5377* (2006.01)
*A61K 31/55* (2006.01)

(52) U.S. Cl.
CPC .......... *A61K 31/403* (2013.01); *A61K 9/0019* (2013.01); *A61K 31/439* (2013.01); *A61K 31/454* (2013.01); *A61K 31/506* (2013.01); *A61K 31/5377* (2013.01); *A61K 31/55* (2013.01); *C07D 209/86* (2013.01); *C07D 209/88* (2013.01); *C07D 401/04* (2013.01); *C07D 487/04* (2013.01)

(58) Field of Classification Search
USPC .......................... 548/418, 420, 421, 440, 441
See application file for complete search history.

(56) References Cited

U.S. PATENT DOCUMENTS

| | | | |
|---|---|---|---|
| 7,169,802 B2 | 1/2007 | Hudkins et al. | |
| 9,169,207 B2 * | 10/2015 | Gudkov | A61K 31/403 |
| 2005/0143442 A1 | 6/2005 | Hudkins et al. | |
| 2011/0305661 A1 * | 12/2011 | Tucker | C07D 209/86 |
| | | | 424/85.1 |
| 2015/0045406 A1 | 2/2015 | Gudkov et al. | |

FOREIGN PATENT DOCUMENTS

| | | |
|---|---|---|
| DE | 2715680 | 10/1978 |
| WO | 2004035580 A1 | 4/2004 |
| WO | 2008008155 A2 | 1/2008 |

OTHER PUBLICATIONS

Chen et al. Cancer Treat Rep. 64(1):31-40, abstract (1980) (Year: 1980).*
International Search Report in PCT Application No. PCT/US2009/059558 dated Jan. 21, 2010.
International Preliminary Report on Patentability in PCT Application No. PCT/US2009/059558 dated Apr. 12, 2011.
Pieters, Roland J. et al., "Reciprocal Template Effects in Bisubstrate Systems: A Replication Cycle," Tetrahedron, 1994, vol. 51, No. 2, pp. 485-498.
Li, Yuhuang et al., "Three-Point Hydrogen Bonding Assembly between a Conjugated PPV and a Functionalized Fullerence", Polymeric Materials: Science & Engineering, 2003, vol. 89, pp. 326-328.
Hannig et al., Carbazole Derivatives. III. Aminomethylation of Acylated Carbazoles, Archiv der Pharmazie, vol. 296, No. 8, pp. 536-543, 1963.

* cited by examiner

*Primary Examiner* — Nyeemah A Grazier
(74) *Attorney, Agent, or Firm* — Morgan, Lewis & Bockius LLP

(57) ABSTRACT

Compounds of the general structural formula (I) and (II) and use of the compounds and salts and hydrates thereof, as therapeutic agents are disclosed. Treatable diseases and conditions include cancers, inflammatory diseases and conditions, and immunodeficiency diseases. (I), (II).

19 Claims, 27 Drawing Sheets

CARBAZOLE COMPOUNDS AND THERAPEUTIC USES OF THE COMPOUNDS

CROSS-REFERENCE TO RELATED APPLICATION

This application is a continuation of U.S. application Ser. No. 14/231,841, filed Apr. 1, 2014, which is a continuation of U.S. application Ser. No. 13/121,051, which is a U.S. National Phase Application of PCT/US2009/059558, filed Oct. 5, 2009, which claims the benefit of and priority to U.S. Provisional Application No. 61/102,913, filed Oct. 6, 2008, each of which is incorporated herein by reference in its entirety.

FIELD OF THE INVENTION

This invention relates to carbazole compounds, to methods of preparing the compounds, to pharmaceutical compositions containing the compounds, and to their use as therapeutic agents. In particular, the invention relates to carbazole compounds and their use in a variety of therapeutic areas, including the treatment of cancers.

BACKGROUND OF THE INVENTION

The frequency of cancer in humans has increased in the developed world as the population has aged. For some types of cancers and the stage of disease at diagnosis, morbidity and mortality rates have not improved significantly in recent years despite extensive research. Induction of cell death is one of the most attractive cancer treatment strategies. There is a significant need to identify agents that are capable of inducing cell death in tumor cells and/or that potentiate chemotherapeutic and radiation therapies.

SUMMARY OF THE INVENTION

The present invention is directed to compounds and compositions that induce cell death, and to therapeutic uses of the compounds in the treatment of a cancer and other conditions in individuals in need of such treatment. The present invention also is directed to methods of preparing the therapeutic compounds.

More particularly, the present invention is directed to compounds and methods of treating diseases and conditions such as cancers, inflammatory diseases, microbial infections, viral infections, and protozoan infections. The compounds are useful in a method comprising administering a therapeutically effective amount of a compound of structural formula (I) to an individual in need thereof.

In particular, the present invention is directed to carbazole compounds having a structural formula (I):

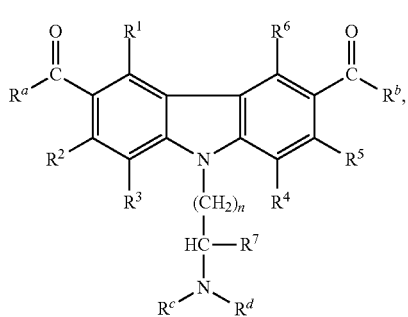

(I)

wherein $R^a$ is selected from the group consisting of hydrogen, $C_{1-6}$ alkyl, $C_{1-6}$ haloalkyl, cycloalkyl, heterocycloalkyl, aryl, heteroaryl, $OR^e$, $N(R^e)_2$, and $SR^e$; alternatively, either $R^a$ and $R^1$ or $NR^e$ and $R^1$ together with the carbon atoms to which they are attached form a five or six-membered aliphatic carbocyclic or heterocyclic ring;

$R^b$ is selected from the group consisting of hydrogen, $C_{1-6}$ alkyl, $C_{1-6}$ haloalkyl, cycloalkyl, heterocycloalkyl, aryl, heteroaryl, $OR^e$, $N(R^e)_2$, and $SR^e$, alternatively, either $R^b$ and $R^6$ or $NR^e$ and $R^6$ together with the carbon atoms to which they are attached form a five or six-membered aliphatic carbocyclic ring or a five or six-membered aliphatic carbocyclic or heterocyclic ring;

$R^c$ is selected from the group consisting of hydrogen, $C_{1-6}$ alkyl, $C_{1-6}$ hydroxyalkyl, cycloalkyl, heterocycloalkyl, aryl, heteroaryl, and $C(=O)R^e$, or $R^c$ and $R^d$ are taken together to form a five, six, or seven-membered aliphatic ring, optionally containing an oxygen atom;

$R^d$ is selected from the group consisting of hydrogen, $C_{1-6}$ alkyl, cycloalkyl, heterocycloalkyl, aryl, heteroaryl, and $C(=O)R^e$, or $R^d$ and $R^7$ together with the atoms to which they are attached form a five or six-membered aliphatic ring;

$R^e$, independently, is selected from the group consisting of hydrogen, $C_{1-6}$ alkyl, cycloalkyl, heterocycloalkyl, aryl, and heteroaryl, or two $R^e$ groups taken together with a nitrogen to which they are attached to form a five or six-membered aliphatic ring;

$R^1$, $R^2$, $R^3$, $R^4$, $R^5$, and $R^6$, independently, are selected from the group consisting of hydrogen, $C_{1-6}$ alkyl, cycloalkyl, heterocycloalkyl, aryl, heteroaryl, halo, $OR^e$, $C(=O)R^e$, $C(=O)OR^e$, $OC(=O)R^e$, $C(=O)N(R^e)_2$, $C(=O)NR^eSO_2R^e$, $N(R^e)_2$, $NR^eC(=O)R^e$, $NR^eC(=O)N(R^e)_2$, $CN$, $NO_2$, $CF_3$, $OCF_3$, $SR^e$, $SOR^e$, $SO_2R^e$, $SO_2N(R^e)_2$, and $OSO_2CF_3$;

$R^7$ is selected from the group consisting of hydrogen, $C_{1-6}$ alkyl, cycloalkyl, heterocycloalkyl, aryl, and heteroaryl; and n is 0, 1, 2, 3, 4, or 5, or a pharmaceutically acceptable salt or hydrate thereof.

The present invention also is directed to carbazole compounds having a structural formula (II):

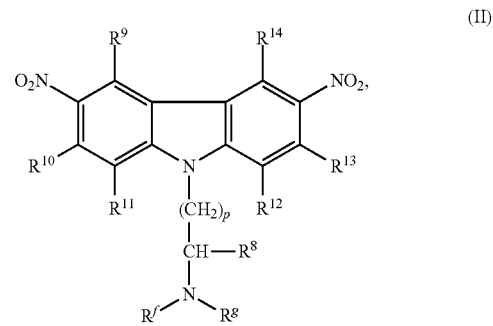

(II)

wherein $R^f$ is selected from the group consisting of hydrogen, $C_{1-6}$ alkyl, cycloalkyl, heterocycloalkyl, aryl, heteroaryl, and $C(=O)R^h$, or $R^f$ and $R^g$ are taken together to form a five, six, or seven-membered aliphatic ring optionally containing an oxygen atom;

$R^g$ is selected from the group consisting of hydrogen, $C_{1-6}$ alkyl, cycloalkyl, heterocycloalkyl, aryl, heteroaryl, and $C(=O)R^h$, or $R^g$ and $R^8$ together with the atoms to which they are attached form a five or six-membered aliphatic ring;

$R^h$, independently, is selected from the group consisting of hydrogen, $C_{1-6}$ alkyl, cycloalkyl, heterocycloalkyl, aryl, and heteroaryl, or two $R^h$ groups taken together with a nitrogen to which they are attached to form a five or six-membered aliphatic ring;

$R^8$ is selected from the group consisting of hydrogen, $C_{1-6}$ alkyl, cycloalkyl, heterocycloalkyl, aryl, and heteroaryl;

$R^9$, $R^{10}$, $R^{11}$, $R^{12}$, $R^{13}$, and $R^{14}$, independently, are selected from the group consisting of hydrogen, $C_{1-6}$ alkyl, cycloalkyl, heterocycloalkyl, aryl, heteroaryl, halo, $OR^h$, $C(=O)R^h$, $C(=O)OR^h$, $OC(=O)R^h$, $C(=O)N(R^h)_2$, $C(=O)NR^hSO_2R^h$, $N(R^h)_2$, $NR^eC(=O)R^h$, $NR^hC(=O)N(R^h)_2$, CN, $NO_2$, $CF_3$, $OCF_3$, $SR^h$, $SOR^h$, $SO_2R^h$, $SO_2N(R^h)_2$, and $OSO_2CF_3$;

p is 0, 1, 2, 3, 4, or 5, with the proviso that when p is 2, one of $R^f$ and $R^g$ is different from ethyl, or a pharmaceutically acceptable salt or hydrate thereof.

A disease or condition that can be treated in accordance with present invention includes, for example, a cancer, inflammation, autoimmune disease, microbial infection, protozoan infection, viral infection, graft versus host disease, a condition associated with HIV infection, or pre-cancerous cells. Forms of cancer that can be treated include, but are not limited to, renal cell carcinoma, sarcoma, prostate cancer, breast cancer, pancreatic cancer, myeloma, myeloid and lymphoblastic leukemia, neuroblastoma, glioblastoma, or a cancer caused by HTLV infection.

In some embodiments, the compound has a general structural formula (Ia):

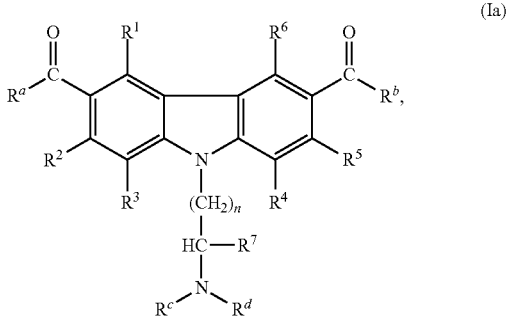

(Ia)

wherein $R^a$ is $C_{1-3}$ alkyl, $C_{1-4}$ haloalkyl, $C_{3-5}$ cycloalkyl, $N(R^e)_2$, or $OR^e$, or $R^a$ and $R^1$ together with the carbon atoms to which they are attached form a five or six-membered aliphatic carbocyclic ring;

$R^b$ is $C_{1-4}$ alkyl, $C_{1-4}$ haloalkyl, $C_{3-5}$ cycloalkyl, $N(R^e)_2$, or $OR^e$, or $R^b$ and $R^6$ together with the carbon atoms to which they are attached form a five or six-membered aliphatic carbocyclic ring or a five or six-membered aliphatic ring containing one nitrogen atom;

$R^c$ is $C_{1-6}$ alkyl, $C_{3-5}$ cycloalky, or $C_{1-3}$ hydroxyalkyl;

$R^d$ is hydrogen, $C_{1-4}$ alkyl, or $C_{3-5}$ cycloalkyl, or $R^d$ and $R^7$ together with the atoms to which they are attached form a five or six-membered aliphatic ring containing one nitrogen atom, or $R^c$ and $R^d$ are taken together to form a six- or seven-membered aliphatic ring, optionally containing an oxygen atom;

$R^e$, independently, is hydrogen or $C_{1-3}$ alkyl;

$R^1$ is hydrogen or $C_{1-3}$ alkyl;

$R^2$ is hydrogen, hydroxy, or $C_{1-3}$ alkoxy;

$R^3$ and $R^4$, independently, are hydrogen or $C_{1-3}$ alkyl;

$R^5$ is hydrogen, hydroxy, $C_{1-3}$alkoxy, or halo;

$R^6$ is hydrogen, $C_{1-3}$alkyl, $C_{1-3}$alkoxy, or halo;

$R^7$ is hydrogen or $C_{1-3}$ alkyl; and n is 0, 1, 2, 3, 4, or 5, or a pharmaceutically acceptable salt or hydrate thereof.

In other embodiments, the compound has a general structural formula (Ib):

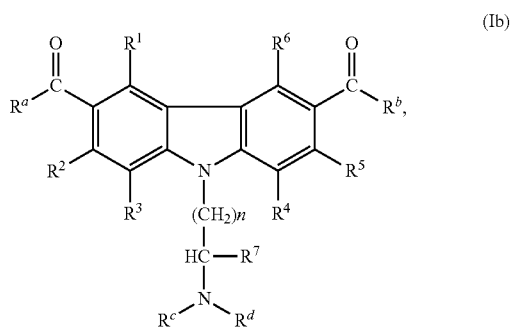

(Ib)

wherein $R^a$ is methyl, ethyl, n-propyl, cyclopropyl, $NH(CH_3)$, or $OCH_3$, or $R^a$ and $R^1$ together with the carbon atoms to which they are attached form a five-membered aliphatic carbocyclic ring;

$R^b$ is methyl, ethyl, n-propyl, cyclopropyl, $NH(CH_3)$, or $OCH_3$, or $R^b$ and $R^6$ together with the carbon atoms to which they are attached form a five-membered aliphatic carbocyclic ring or a five-membered aliphatic ring containing one nitrogen atom;

$R^c$ is methyl, ethyl, n-propyl, isopropyl, cyclobutyl, or 2-hydroxyethyl;

$R^d$ is hydrogen, methyl, ethyl, or cyclobutyl, or $R^d$ and $R^7$ together with the atoms to which they are attached form a five-membered aliphatic ring containing one nitrogen atom; or $R^c$ and $R^d$ are taken together to form a morpholino moiety; a tetrahydrofuryl moiety; a piperidinyl moiety; a

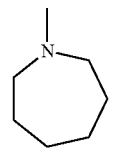

moiety, or a

moiety;

$R^1$ is hydrogen;

$R^2$ is hydrogen, hydroxy, or methoxy;

$R^3$ and $R^4$ are hydrogen;

$R^5$ is hydrogen, hydroxy, methoxy, or fluoro;

$R^6$ is hydrogen, methyl, methoxy or fluoro;

$R^7$ is hydrogen; and n is 1 or 2, or a pharmaceutically acceptable salt or hydrate thereof.

In other embodiments, the compound has a general structural formula (IIa):

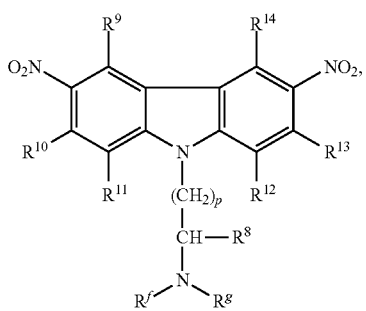

(IIa)

wherein $R^f$ is $C_{1-6}$ alkyl;

$R^g$ is hydrogen or $C_{1-4}$ alkyl, or $R^g$ and $R^8$ together with the atoms to which they are attached form a five or six-membered aliphatic ring containing one nitrogen atom;

$R^9$ is hydrogen or $C_{1-3}$ alkyl;

$R^{10}$ is hydrogen, hydroxy, or $C_{1-3}$ alkoxy;

$R^{11}$ and $R^{12}$, independently, are hydrogen or $C_{1-3}$ alkyl;

$R^{13}$ is hydrogen, hydroxy, $C_{1-3}$alkoxy, or halo;

$R^{14}$ is hydrogen, $C_{1-3}$alkyl, or $C_{1-3}$alkoxy;

$R^8$ is hydrogen or $C_{1-3}$ alkyl; and p is 0, 1, 2, 3, 4, or 5, with the proviso that when p is 2, one of $R^f$ and $R^g$ is different from ethyl, or a pharmaceutically acceptable salt or hydrate thereof.

In still other embodiments, the compound has a structural formula (IIb):

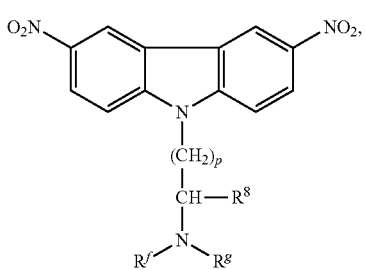

(IIb)

wherein $R^f$ is methyl or ethyl;

$R^g$ is hydrogen or methyl or $R^g$ and $R^8$ together with the atoms to which they are attached form a five-membered aliphatic ring containing one nitrogen atom;

$R^8$ is hydrogen; and p is 1 or 2, or a pharmaceutically acceptable salt or hydrate thereof.

One aspect of the present invention is to provide a method of treating a condition or disease by administering a therapeutically effective amount of one or more compound of structural formula (I), (Ia), (Ib), (II), (IIa), or (IIb), or a composition comprising one or more of a compound of structural formula (I), (Ia), (Ib), (II), (IIa), or (IIb), to an individual in need thereof. The composition can further comprise a death receptor activator of a TNF family polypeptide. The activator can be a TNF polypeptide, such as one or more of NGF, CD40L, CD137L/4-1BBL, TNF-α, CD134L/OX40L, CD27L/CD70, FasL/CD95, CD30L, TNF-β/LT-α, LT-β, and TRAIL.

Another aspect of the present invention is to provide pharmaceutical compositions comprising one or more compound of structural formula (I) or (II), and use of the compositions in a therapeutic treatment of a disease or condition.

Yet another aspect of the present invention is to provide a method of treating an individual undergoing a chemotherapeutic or radiotherapeutic treatment for a medical condition comprising administration of a compound of structural formula (I) and/or (II) in combination with a chemotherapeutic agent, a radiotherapeutic agent, or both, to the individual. A nonlimiting indication treated by this method is a cancer.

The above and additional aspects of the present invention will become apparent from the following nonlimiting detailed description of preferred embodiments of the present invention.

DETAILED DESCRIPTION OF THE PREFERRED EMBODIMENTS

Figure 1A:
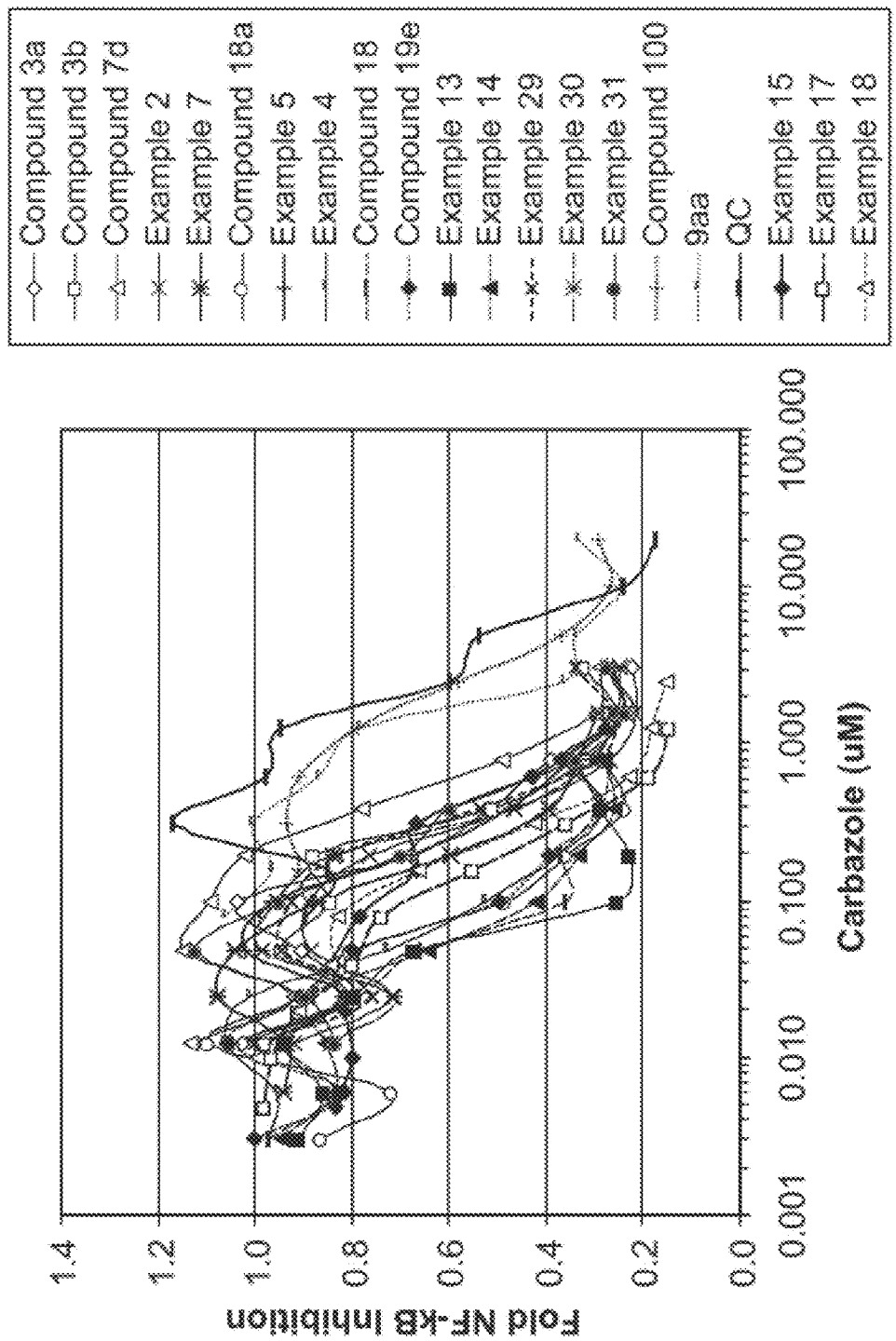
FIG. 1A is a plot of fold to NF-κB activity relative to DMSO control vs. concentration for carbazoles of the present invention.

With respect to the compounds, compositions, and methods disclosed herein, the terminology used is for the purpose of describing particular embodiments and is not intended to be limiting. As used in the specification and the appended claims, the singular forms "a," "an" and "the" include plural referents unless the context clearly dictates otherwise.

The present invention is directed to compounds having a general structural formula (I) and (II). The carbazole compounds disclosed herein are useful in the treatment of diseases and conditions, such as cancers, inflammatory disease, microbial infections, viral infections, protozoan infections, or an autoimmune disease.

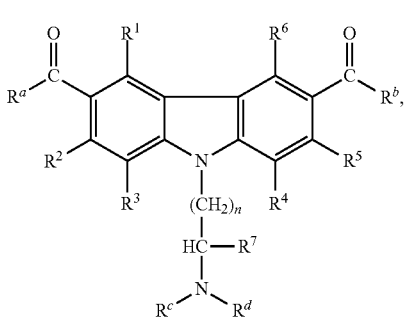

(I)

wherein $R^a$ is selected from the group consisting of hydrogen, $C_{1-6}$alkyl, $C_{1-6}$haloalkyl, cycloalkyl, heterocycloalkyl, aryl, heteroaryl, $OR^e$, $N(R^e)_2$, and $SR^e$, or either $R^a$ and $R^1$ or $NR^e$ and $R^1$ together with the carbon atoms to which they are attached form a five or six-membered aliphatic carbocyclic or heterocyclic ring;

$R^b$ is selected from the group consisting of hydrogen, $C_{1-6}$alkyl, $C_{1-6}$haloalkyl, cycloalkyl, heterocycloalkyl, aryl, heteroaryl, $OR^e$, $N(R^e)_2$, and $SR^e$, or either $R^b$ and $R^6$ or $NR^e$ and $R^6$ together with the carbon atoms to which they are attached form a five or six-membered aliphatic carbocyclic ring or a five or six-membered aliphatic carbocyclic or heterocyclic ring;

$R^c$ is selected from the group consisting of hydrogen, $C_{1-6}$alkyl, $C_{1-6}$hydroxyalkyl, cycloalkyl, heterocycloalkyl, aryl, heteroaryl, and $C(=O)R^e$, or $R^c$ and $R^d$ are taken together to form a five, six, or seven-membered aliphatic ring, optionally containing an oxygen atom;

$R^d$ is selected from the group consisting of hydrogen, $C_{1-6}$ alkyl, cycloalkyl, heterocycloalkyl, aryl, heteroaryl, and $C(=O)R^e$, or $R^d$ and $R^7$ together with the atoms to which they are attached form a five or six-membered aliphatic ring;

$R^e$, independently, is selected from the group consisting of hydrogen, $C_{1-6}$ alkyl, cycloalkyl, heterocycloalkyl, aryl, and heteroaryl, or two $R^e$ groups taken together with a nitrogen to which they are attached to form a five or six-membered aliphatic ring;

$R^1$, $R^2$, $R^3$, $R^4$, $R^5$, and $R^6$, independently, are selected from the group consisting of hydrogen, $C_{1-6}$ alkyl, cycloalkyl, heterocycloalkyl, aryl, heteroaryl, halo, $OR^e$, $C(=O)R^e$, $C(=O)OR^e$, $OC(=O)R^e$, $C(=O)N(R^e)_2$, $C(=O)NR^eSO_2R^e$, $N(R^e)_2$, $NR^eC(=O)R^e$, $NR^eC(=O)N(R^e)_2$, CN, $NO_2$, $CF_3$, $OCF_3$, $SR^e$, $SOR^e$, $SO_2R^e$, $SO_2N(R^e)_2$, and $OSO_2CF_3$;

$R^7$ is selected from the group consisting of hydrogen, $C_{1-6}$ alkyl, cycloalkyl, heterocycloalkyl, aryl, and heteroaryl; and n is 0, 1, 2, 3, 4, or 5, or a pharmaceutically acceptable salt or hydrate thereof.

In preferred embodiments, the compounds have general structural formula (Ia):

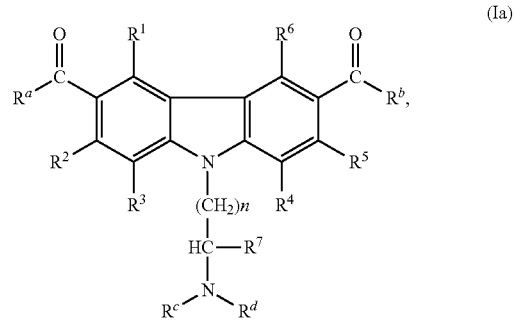

(Ia)

wherein $R^a$ is $C_{1-3}$ alkyl, $C_{1-4}$ haloalkyl, $C_{3-5}$ cycloalkyl, $N(R^e)_2$, or $OR^e$, or $R^a$ and $R^1$ together with the carbon atoms to which they are attached form a five or six-membered aliphatic carbocyclic ring;

$R^b$ is $C_{1-4}$ alkyl, $C_{1-4}$ haloalkyl, $C_{3-5}$ cycloalkyl, $N(R^e)_2$, or $OR^e$, or $R^b$ and $R^6$ together with the carbon atoms to which they are attached form a five or six-membered aliphatic carbocyclic ring or a five or six-membered aliphatic ring containing one nitrogen atom;

$R^c$ is $C_{1-6}$ alkyl, $C_{3-5}$ cycloalkyl, or $C_{1-3}$ hydroxyalkyl;

$R^d$ is hydrogen, $C_{1-4}$ alkyl, or $C_{3-5}$cycloalkyl, or $R^d$ and $R^7$ together with the atoms to which they are attached form a five or six-membered aliphatic ring containing one nitrogen atom or $R^c$ and $R^d$ are taken together to form a six or seven-membered aliphatic ring, optionally containing an oxygen atom;

$R^e$, independently, is hydrogen or $C_{1-5}$ alkyl;

$R^1$ is hydrogen or $C_{1-3}$ alkyl;

$R^2$ is hydrogen, hydroxy, or $C_{1-3}$ alkoxy;

$R^3$ and $R^4$, independently, are hydrogen or $C_{1-3}$ alkyl;

$R^5$ is hydrogen, hydroxy, $C_{1-3}$alkoxy, or halo;

$R^6$ is hydrogen, $C_{1-3}$alkyl, $C_{1-3}$alkoxy, or halo;

$R^7$ is hydrogen or $C_{1-3}$ alkyl; and n is 0, 1, 2, 3, 4, or 5, or a pharmaceutically acceptable salt or hydrate thereof.

In more preferred embodiments, the compounds have a general structural formula (Ib):

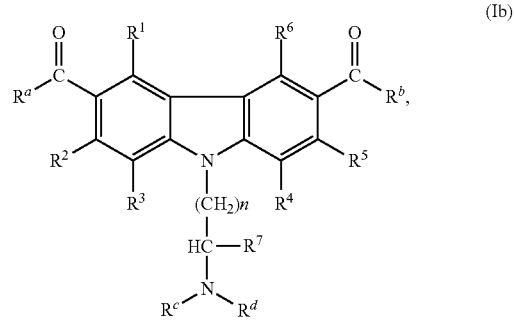

(Ib)

wherein $R^a$ is methyl, ethyl, n-propyl, cyclopropyl, $NH(CH_3)$, or $OCH_3$, or $R^a$ and $R^1$ together with the carbon atoms to which they are attached form a five-membered aliphatic carbocyclic ring;

$R^b$ is methyl, ethyl, n-propyl, cyclopropyl, $NH(CH_3)$, or $OCH_3$, or $R^b$ and $R^6$ together with the carbon atoms to which they are attached form a five-membered aliphatic carbocyclic ring or a five-membered aliphatic ring containing one nitrogen atom;

$R^e$ is methyl, ethyl, n-propyl, isopropyl, cyclobutyl, or 2-hydroxyethyl;

$R^d$ is hydrogen, methyl, ethyl, or cyclobutyl, or $R^d$ and $R^7$ together with the atoms to which they are attached form a five-membered aliphatic ring containing one nitrogen atom, or $R^c$ and $R^d$ are taken together to form a morpholino moiety, a tetrahydrofuryl moiety, a piperidinyl moiety, or a

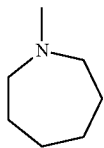

moiety, a

moiety;

$R^1$ is hydrogen;
$R^2$ is hydrogen, hydroxy, or methoxy;
$R^3$ and $R^4$ are hydrogen;
$R^5$ is hydrogen, hydroxy, methoxy, or fluoro;
$R^6$ is hydrogen, methyl, methoxy, or fluoro;
$R^7$ is hydrogen; and
n is 1 or 2, or a pharmaceutically acceptable salt or hydrate thereof.

In another embodiment, the present invention also is directed to carbazole compounds having a structural formula (II):

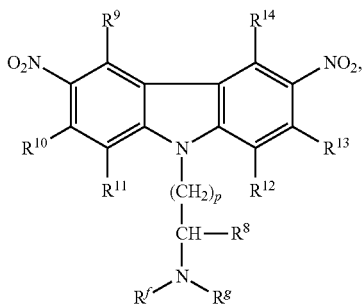

wherein $R^f$ is selected from the group consisting of hydrogen, $C_{1-6}$ alkyl, cycloalkyl, heterocycloalkyl, aryl, heteroaryl, and $C(=O)R^h$, or $R^f$ and $R^g$ are taken together to form a five, six, or seven-membered aliphatic ring optionally containing an oxygen atom;

$R^g$ is selected from the group consisting of hydrogen, $C_{1-6}$ alkyl, cycloalkyl, heterocycloalkyl, aryl, heteroaryl, and $C(=O)R^h$, or $R^g$ and $R^h$ together with the atoms to which they are attached form a five, six, or seven-membered aliphatic ring;

$R^h$, independently, is selected from the group consisting of hydrogen, $C_{1-6}$ alkyl, cycloalkyl, heterocycloalkyl, aryl, and heteroaryl, or two $R^h$ groups taken together with a nitrogen to which they are attached to form a five or six-membered aliphatic ring;

$R^9$, $R^{10}$, $R^{11}$, $R^{12}$, $R^{13}$, and $R^{14}$, independently, are selected from the group consisting of hydrogen, $C_{1-6}$ alkyl, cycloalkyl, heterocycloalkyl, aryl, heteroaryl, halo, $OR^h$, $C(=O)R^h$, $C(=O)OR^h$, $OC(=O)R^h$, $C(=O)N(R^h)_2$, $C(=O)NR^hSO_2R^h$, $N(R^h)_2$, $NR^hC(=O)R^h$, $NR^hC(=O)N(R^h)_2$, CN, $NO_2$, $CF_3$, $OCF_3$, $SR^h$, $SOR^h$, $SO_2R^h$, $SO_2N(R^h)_2$, and $OSO_2CF_3$;

$R^8$ is selected from the group consisting of hydrogen, $C_{1-6}$ alkyl, cycloalkyl, heterocycloalkyl, aryl, and heteroaryl; and p is 0, 1, 2, 3, 4, or 5, with the proviso that when p is 2, one of $R^f$ and $R^g$ is different from ethyl, or a pharmaceutically acceptable salt or hydrate thereof.

In other embodiments, the compound has a general structural formula (IIa):

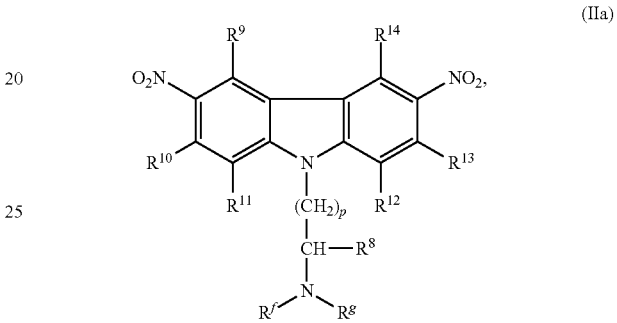

wherein $R^f$ is $C_{1-6}$ alkyl;

$R^9$ is hydrogen or $C_{1-4}$ alkyl, or $R^g$ and $R^8$ together with the atoms to which they are attached form a five or six-membered aliphatic ring containing one nitrogen atom;

$R^9$ is hydrogen or $C_{1-3}$ alkyl;
$R^{10}$ is hydrogen, hydroxy, or $C_{1-3}$ alkoxy;
$R^{11}$ and $R^{12}$, independently, are hydrogen or $C_{1-3}$ alkyl;
$R^{13}$ is hydrogen, hydroxy, $C_{1-3}$alkoxy, or halo;
$R^{14}$ is hydrogen, $C_{1-3}$alkyl, or $C_{1-3}$alkoxy;
$R^8$ is hydrogen or $C_{1-3}$ alkyl; and
p is 0, 1, 2, 3, 4, or 5, with the proviso that when p is 2, one of $R^f$ and $R^g$ is different from ethyl, or a pharmaceutically acceptable salt or hydrate thereof.

In still other embodiments, the compound has a structural formula (IIb):

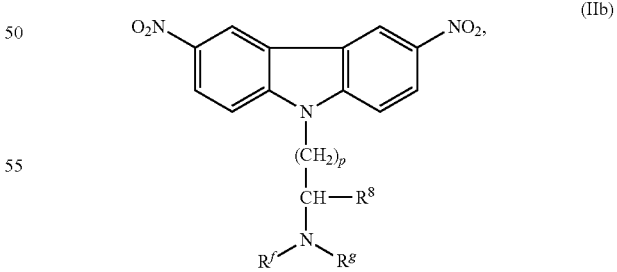

wherein $R^f$ is methyl or ethyl;

$R^g$ is hydrogen or methyl, or $R^g$ and $R^8$ together with the atoms to which they are attached form a five-membered aliphatic ring containing one nitrogen atom;

$R^8$ is hydrogen; and
p is 1 or 2, or a pharmaceutically acceptable salt or hydrate thereof.

As used herein, the term "alkyl" means straight chained and branched hydrocarbon groups containing the indicated number of carbon atoms, typically methyl, ethyl, and straight chain and branched propyl and butyl groups. The term "cycloalkyl" is defined as a cyclic hydrocarbon group containing the indicated number of carbon atoms, e.g., cyclopropyl, cyclobutyl, cyclohexyl, and cyclopentyl.

The term "heterocycloalkyl" means monocyclic, bicyclic, and, tricyclic cycloalkyl groups containing one or more heteroatoms selected from the group consisting of oxygen, nitrogen, and sulfur in the ring structure. A "heterocycloalkyl" group also can contain an oxo group (=O) attached to the ring. Nonlimiting examples of heterocycloalkyl groups include, but are not limited to, 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "halo" or "halogen" means fluorine, bromine, chlorine, and iodine.

The term "haloalkyl" means an alkyl group substituted with one or more, e.g., 1 to 3, halo substituents, either fluoro, chloro, bromo, iodo, or combinations thereof. Similarly, "halocycloalkyl" is defined as a cycloalkyl group having one or more halo substituents.

The term "aryl," alone or in combination, means a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" means a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazonyl, and thiadiazolyl.

The term "alkylene" means an alkyl group having a substituent. For example, the term "$C_{1-3}$alkylenearyl" refers to an alkyl group containing one to three carbon atoms and substituted with an aryl group.

The term "hydroxy" means —OH.

The term "alkoxy" means —OR, wherein R is alkyl.

The term "amino" means —NH$_2$, and the term "alkylamino" means —NR$_2$, wherein at least one R is alkyl and the second R is alkyl or hydrogen.

The term "acylamino" means R(=O)N—, wherein R is alkyl or aryl.

The term "alkylthio" means —SR, wherein R is alkyl.

The term "nitro" means —NO$_2$.

The term "trifluoromethyl" means —CF$_3$.

The term "trifluoromethoxy" means —OCF$_3$.

The term "cyano" means —CN.

The term "alkoxyalkyl" means an alkyl group wherein a hydrogen has been replaced by an alkoxy group.

The term "hydroxyalkyl" means an alkyl group wherein a hydrogen has replaced by a hydroxy group.

The term "alkylsulfinyl" means R—SO$_2$—, wherein R is alkyl.

The term "alkylsulfonyl" means R—SO$_3$—, wherein R is alkyl.

The term "morpholino moiety" means

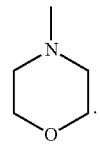

The term "tetrahydrofuryl moiety" means

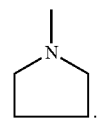

The term "piperidinyl moiety" means

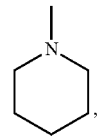

optionally substituted with an —OH or —CH$_2$OH group.

The terms "effective amount" and "therapeutically effective amount," when used in reference to a compound or composition, means a sufficient amount of the compound or composition to provide the desired result. The exact amount desired or required will vary depending on the particular compound or composition used, its mode of administration, and the like. Thus, it is not always possible to specify an exact "effective amount" or "therapeutically effective amount". However, an appropriate effective amount can be determined by one of ordinary skill in the art informed by the instant disclosure using only routine experimentation.

The term "suitable" means an entity, e.g., a moiety, substituent, or compound, that is compatible with the compounds or compositions as provided herein for the stated purpose. Suitability for the stated purpose may be determined by one of ordinary skill in the art using only routine experimentation.

The term "administer", when used to describe the dosage of a compound or composition, means a single dose or multiple doses of the compound or composition.

"In vivo" means within a living subject, as within an animal or human. In this context, agents can be used therapeutically in a subject to treat a condition or disease, or a symptom thereof. The agents also can be used as a prophylactic to prevent the occurrence or recurrence of a disease conditions or symptoms associated therewith.

"Ex vivo" means outside a living subject. Examples of ex vivo cell populations include in vitro cell cultures and biological samples such as fluid or tissue samples from humans or animals. Such samples can be obtained by methods well known in the art. Exemplary biological fluid samples include blood, cerebrospinal fluid, urine, saliva. Exemplary tissue samples include tumors and biopsies thereof. In this context, the present compounds can be in numerous applications, both therapeutic and experimental.

The term "radiosensitizer" means a compound administered to a human or other animal in a therapeutically effective amount to increase the sensitivity of cells to electromagnetic radiation and/or to promote the treatment of diseases treatable with electromagnetic radiation.

The terms "electromagnetic radiation" and "radiation" mean, but are not limited to, radiation having the wavelength of $10^{-20}$ to 100 meters.

The term "cell death" means a process wherein cell functioning, proliferation, and metabolism is stopped.

The term "cancer treatment" means any treatment for cancer known in the art including, but not limited to, chemotherapy and radiation therapy.

The term "combination with", when used to described administration of a present carbazole compound and any additional treatment, means that the carbazole compound can be administered prior to, simultaneously with, or after the additional treatment, or a combination thereof.

As used herein, the terms "treat," "treating," "treatment," and the like refer to eliminating, reducing, or ameliorating a disease or condition and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "mammal" includes humans, companion animals (e.g., dogs, cats, and horses), zoo animals (e.g., zebras, elephants, and large cats), food-source animals (e.g., cows, pigs, goats, and sheep), and research animals (e.g., rats, mice, goats, and guinea pigs).

The present invention is directed, in part, to the discovery that pharmaceutical compositions comprising a carbazole compound of general structural formulas (I) and (II) can be used to modulate NF-κB activity, such as NF-κB-mediated immune responses and conditions described in International Patent Application PCT/US05/25884, designating the United States, the contents of which are incorporated herein by reference.

In preferred embodiments of a carbazole compound of structural formula (I), $R^a$ is methyl, ethyl, NH(CH$_3$), OCH$_3$, or forms a five-membered aliphatic ring with $R^1$. In other preferred embodiments, $R^b$ is methyl, ethyl, NH(CH$_3$), OCH$_3$, forms a five-membered aliphatic ring with $R^6$, or forms a five-membered, nitrogen containing, aliphatic ring with $R^6$. In another preferred embodiment, $R^d$ is hydrogen, methyl, ethyl, or forms a five-membered aliphatic ring with $R^7$.

In preferred embodiments, $R^1$ is hydrogen or forms a five-membered aliphatic ring with $R^a$. In other preferred embodiments, $R^2$ is hydrogen or hydroxy. In still other preferred embodiments, $R^3$ is hydrogen. In further preferred embodiments, $R^4$ is hydrogen. In yet further preferred embodiments, $R^5$ is hydrogen or hydroxy. In some preferred embodiments, $R^6$ is hydrogen, forms a five-membered aliphatic ring with $R^b$, or forms a five-membered, nitrogen-containing aliphatic ring with $R^b$. In preferred embodiments, $R^7$ is hydrogen or forms a five-membered ring with $R^d$. In yet further preferred embodiments, n is 2 or 3.

In preferred embodiments of a carbazole compound of structural formula (II), $R^f$ is methyl or ethyl, $R^g$ is hydrogen, methyl, ethyl, or forms a five-membered, nitrogen containing aliphatic ring with $R^f$ and $R^8$, or $R^8$ is hydrogen, $R^9$, $R^{10}$, $R^{11}$, $R^{12}$, $R^{13}$, and $R^{14}$ are hydrogen. In yet further embodiments, p is 2 or 3.

Two additional carbazole compounds useful in the treatment of a variety of conditions and diseases are

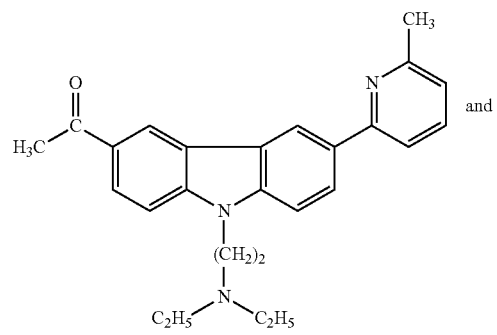

Example 26 and

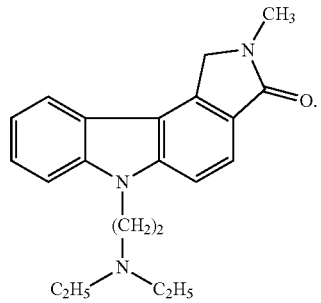

Compound 17b

The present invention includes all possible stereoisomers and geometric isomers of the compounds of structural formula (I) and (II). The present invention includes both racemic compounds and optically active isomers. When a compound of structural formula (I) or (II) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) or (II) are possible, the present invention is intended to include all tautomeric forms of the compounds.

Prodrugs of compounds of structural formula (I) and (II) also can be used as the compound in a method of the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)).

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the invention can exist as salts. Pharmaceutically acceptable salts of the compounds of the invention generally are preferred in the methods of the invention. As used herein, the term "pharmaceutically acceptable salts" refers to salts or zwitterionic forms of the compounds of structural formula (I) and (II). Salts of compounds of formula (I) and (II) can be prepared during the final isolation and purification of the compounds or separately by reacting the compound with an acid having a suitable cation. The pharmaceutically acceptable salts of compounds of structural formula (I) and (II) are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) and/or (II) as well as pharmaceutically acceptable salts, hydrates, or prodrugs thereof.

The compounds of structural formula (I) and (II) also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., Clin. Cancer Res. (2001) 7:3229).

Compounds of the present invention are potent inhibitors of NF-κB. Thus, compounds of formula (I) and (II) are of interest for use in therapy, specifically for the treatment of a variety of conditions where inhibition of NF-κB is considered beneficial. NF-κB inhibition is particularly attractive targets because such inhibition provides effects such as apoptosis, antimicrobial, antiprotozoan, antiviral, and anti-inflammatory, all of which are beneficial in the treatment of various disease states. The compounds of formula (I) and (II), therefore, have utility in the treatment of a number of disorders, diseases, and conditions.

The potency of a present carbazole compound is determined by measuring an ability of the compound to inhibit NF-κB activity or to activate p53. Activation of p53 typically is measured using a dose-response assay in which a sensitive assay system is contacted with a compound of interest over a range of concentrations, including concentrations at which no or minimal effect is observed, through higher concentrations at which partial effect is observed, to saturating concentrations at which a maximum effect is observed. Theoretically, such assays of the dose-response effect of activator compounds can be described as a sigmoidal curve expressing a degree of activation as a function of concentration. The curve also theoretically passes through a point at which the concentration is sufficient to increase activity to a level that is 50% that of the difference between a baseline and the maximal activity in the assay. This concentration is defined as the Effective Concentration (50%) or $EC_{50}$ value. Determination of an $EC_{50}$ value is made using conventional biochemical (acellular) assay techniques or cell-based assay techniques.

Comparisons of the efficacy of activators often are provided with reference to comparative $EC_{50}$ values, wherein a higher $EC_{50}$ indicates that the test compound is less potent, and a lower $EC_{50}$ indicates that the compound is more potent, than a reference compound. Compounds of the present invention exhibit unexpectedly good potency, i.e., p53 activation, in a luciferase reporter cell line assay. Compounds of the invention subjected to a cell-based assay described below exhibited $EC_{50}$ values for p53 activation of less than about 1.35 µM. In certain embodiments, compounds of the invention exhibited an $EC_{50}$ value of less than about 1.0 µM. In other embodiments, the inventive compounds exhibited $IC_{50}$ values of less than about 0.75 µM, about 0.50 µM, about 0.30 µM, less than about 0.20 µM, or less than 0.05 µM.

An especially important use of the present carbazole compounds is the treatment of a cancer, an inflammation, an autoimmune disease, a microbial, protozoan, or viral infection, a graft vs. host disease, a condition associated with HIV infection, or pre-cancerous cells which have acquired dependence on constitutively active NF-κB. Various cancers that can be treated in accordance with the present invention include, but are not limited to, renal cell carcinoma, sarcoma, prostate cancer, breast cancer, pancreatic cancer, myeloma, myeloid and lymphoblastic leukemia, neuroblastoma, glioblastoma, and a cancer caused by HTLV infection.

It is envisioned, therefore, that compounds of formula (I) and (II) are useful in the treatment of a variety of conditions and diseases. Thus, the present invention concerns the use of compounds of formula (I) and (II), or a pharmaceutically acceptable salt thereof, or a pharmaceutical composition containing either entity, for the manufacture of a medicament for the treatment of such conditions and diseases.

The compounds of the present invention can be therapeutically administered as the neat chemical, but it is preferred to administer compounds of structural formula (I) or (II) as a pharmaceutical composition or formulation. Thus, the present invention provides a pharmaceutical composition comprising a compound of the formula (I) or (II) together with a pharmaceutically acceptable diluent or carrier therefor. Also provided is a process of preparing a pharmaceutical composition comprising admixing a compound of formula (I) or (II) with a pharmaceutically acceptable diluent or carrier therefor.

Accordingly, the present invention further provides pharmaceutical formulations comprising a compound of structural formula (I) or (II), or a pharmaceutically acceptable salt, prodrug, or hydrate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Formulations of the present invention can be administered in a standard manner for the treatment of the indicated diseases, such as orally, parenterally, transmucosally (e.g., sublingually or via buccal administration), topically, transdermally, rectally, or via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™ (Powderject Pharmaceuticals, Plc, Oxford, England). The composition also can be administered in the form of an implant, which allows a slow release of the composition as well as a slow controlled i.v. infusion.

For oral administration, including buccal administration, the composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch, or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol or silica), disintegrants (for example, potato starch or sodium starch glycolate), or wetting agents (for example, sodium lauryl sulfate). The tablets can be coated according to methods well known in the art.

Alternatively, compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, for example suspending agents, such as sorbitol syrup, methyl cellulose, glucose/sugar syrup, gelatin, hydroxyethylcellulose, hydroxypropylmethylcellulose, carboxymethylcellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition of the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

The composition also can be formulated as a liposome preparation. The liposome preparation can comprise liposomes which penetrate the cells of interest or the stratum corneum, and fuse with the cell membrane, resulting in delivery of the contents of the liposome into the cell. Liposomes are described, for example, in U.S. Pat. No. 5,077,211, U.S. Pat. No. 4,621,023, and U.S. Pat. No. 4,508,703, each incorporated herein by reference.

For veterinary use, a compound of formula (I) or (II), or a pharmaceutically acceptable salt or prodrug, is administered as a suitably acceptable formulation in accordance with normal veterinary practice. The veterinarian can readily determine the dosing regimen and route of administration that is most appropriate for a particular animal. Animals treatable by the present compounds and methods include, but are not limited to, pets, livestock, show animals, and zoo specimens.

Synthetic Methods

Compounds of formula (I) and (II) can be prepared by any suitable method known in the art, or by the following processes which form part of the present invention. In particular, compounds of structural formula (I) and (II) can be prepared according to the following synthetic schemes.

In the synthetic methods, the examples, and throughout the specification, the abbreviations have the following meanings:

| | |
|---|---|
| DMF | dimethylformamide |
| NaH | sodium hydride |
| min | minutes |
| TLC | thin layer chromatography |
| $CH_2Cl_2$ | methylene chloride |
| $CHCl_3$ | chloroform |

-continued

| | |
|---|---|
| MeOH | methanol |
| Na$_2$SO$_4$ | sodium sulfate |
| AlCl$_3$ | aluminum chloride |
| AcCl | acetyl chloride |
| LC-MS | liquid chromatography-mass spectrometry |
| Et$_2$O | diethyl ether |
| Na$_2$CO$_3$ | sodium carbonate |
| HPLC | high performance liquid chromatography |
| h | hours |
| NaHCO$_3$ | sodium bicarbonate |
| NaCl | sodium chloride |
| HCl | hydrochloric acid |
| g | gram |
| eq | equivalent |
| mol | mole |
| mmol | millimole |
| mL | milliliter |
| H$_2$SO$_4$ | sulfuric acid |
| K$_2$CO$_3$ | potassium carbonate |
| Pd(OAc)$_2$ | palladium acetate |
| Pd(PPh$_3$)$_4$ | tetra(triphenylphosphino)palladium |
| P(OEt)$_3$ | triethoxyphosphine |
| NaH | sodium hydride |
| TfOH | triflic acid |
| EtOH | ethanol |
| NMR | nuclear magnetic resonance spectrometry |
| EtOAc | ethyl acetate |
| THF | tetrahydrofuran |
| NaOH | sodium hydroxide |
| NMP | N-methylpyn-olidinone |
| DBU | 1,8-diazabicyclo[5.4.0]undec-7-ene |
| MsCl | mesyl chloride |
| TEA | triethanolamine |
| Na$_2$SO$_4$ | sodium sulfate |
| (Boc)$_2$O | ditert-butyl carbonate |
| Py | pyridine |
| PdCl$_2$(PPh)$_3$ | dichloro-triphenylphosphino-palladium (II) |
| PhNO$_2$ | nitrobenzene |
| KOAc | potassium acetate |
| Pd(dppf)Cl$_2$ | dichloro-((bis-diphenylphosphino)ferrocenyl)-palladium(II) |
| AcOK | potassium acetate |
| PPh$_3$ | triphenylphosphine |
| PPh$_3$O | triphenylphosphine oxide |
| BBr$_3$ | tribromoboron |
| CH$_3$CN | acetonitrile |
| PhSH | thiophenol |
| Cs$_2$CO$_3$ | cesium carbonate |
| STAB | sodium triacetoxyborohydride |
| NEt$_3$ | triethylamine |
| DMF | dimethylformamide |

It should be understood that protecting groups can be utilized in accordance with general principles of synthetic organic chemistry to provide compounds of structural formula (I) and (II). Protecting group-forming reagents are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) and (II) not specifically exemplified herein can be prepared by persons skilled in the art.

In addition, compounds of formula (I) and (II) can be converted to other compounds of formula (I) and (II). Thus, for example, a particular R substituent can be interconverted to prepare another suitably substituted compound of formula (I) or (II). Examples of appropriate interconversions include, but are not limited to, OR$^a$ to hydroxy by suitable means (e.g., using an agent such as SnCl$_2$ or a palladium catalyst, like palladium-on-carbon), or amino to substituted amino, such as acylamino or sulphoylamino, using standard acylating or sulfonylating conditions.

Compounds of formula (I) and (II) can be prepared as individual stereoisomers as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

General Synthetic Procedures

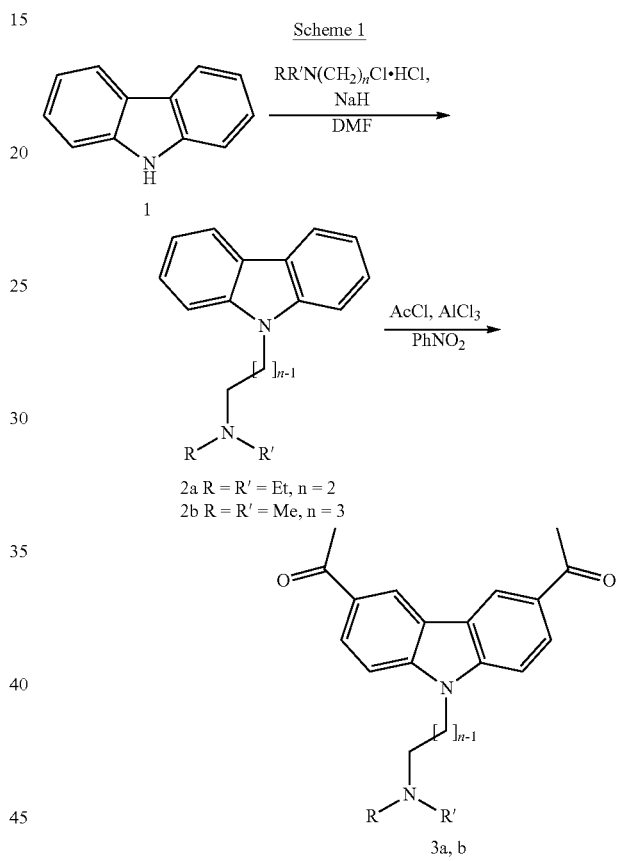

Scheme 1

2a R = R' = Et, n = 2
2b R = R' = Me, n = 3

3a, b

General Procedure for Alkylation of Carbazoles

Carbazole 1 was dissolved or suspended in DMF. Then, NaH (3 eq) was added. The mixture was stirred at room temperature over a period of 5-10 min until foaming ceased. A chloride hydrochloride (1.3 eq) was added, and the reaction mixture was kept at 50-60° C. over a period of 2-16 h (TLC monitoring; eluents: CH$_2$Cl$_2$/ethyl acetate, 1:1 for the presence of the starting carbazole; CHCl$_3$/MeOH, 9:1 for the product purity). The resulting mixture was diluted with water. If a precipitate formed, it was filtered off and air-dried. If no precipitate formed (Table 1), the mixture was extracted with ethyl acetate. The extract was dried over Na$_2$SO$_4$, evaporated, and the residue was purified by chromatography (silica gel, CHCl$_3$/MeOH). The yields of products 2a and 2b are shown in Table 1.

General Procedure for Acylation of Alkylated Carbazoles

A carbazole 2 was dissolved in nitrobenzene. The solution was cooled in an ice bath, then AlCl$_3$ (5 eq) and AcCl (5 eq) were added. The reaction mixture was held over a period of 2-16 h (LC-MS monitoring). A sample of the reaction mixture was diluted with Et$_2$O, and the latter was decanted from the precipitate, then dissolved in MeOH. The resulting mixture was diluted with water, neutralized with Na$_2$CO$_3$, and extracted with CHCl$_3$. The extract was evaporated. The residue was purified first by chromatography in a short silica gel column (CHCl$_3$/MeOH) to remove the nitrobenzene; then, if necessary, in a silica gel column or by HPLC. The yields of products 3a and 3b are shown in Table 1.

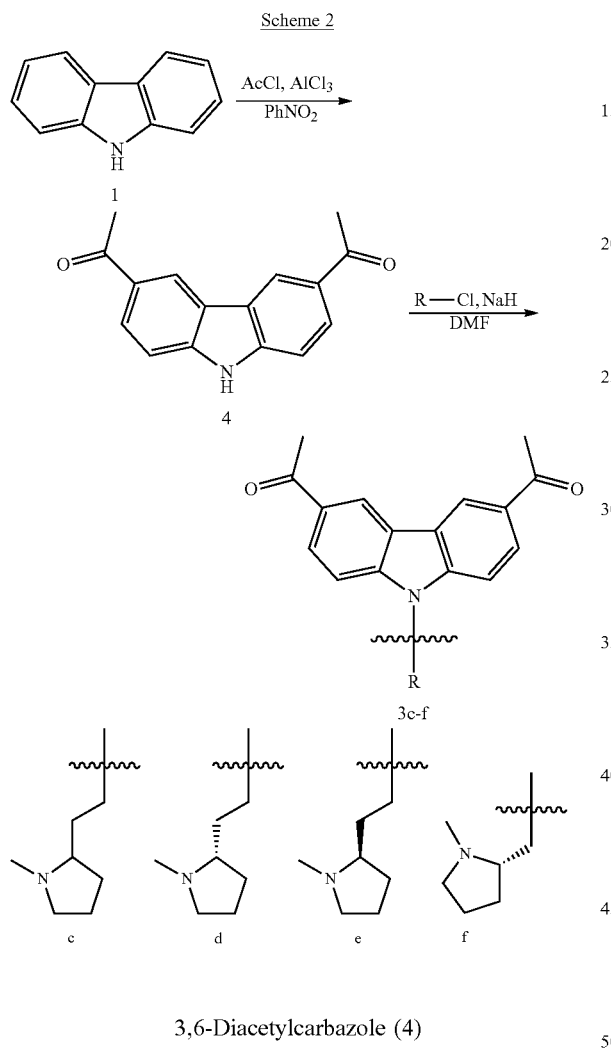

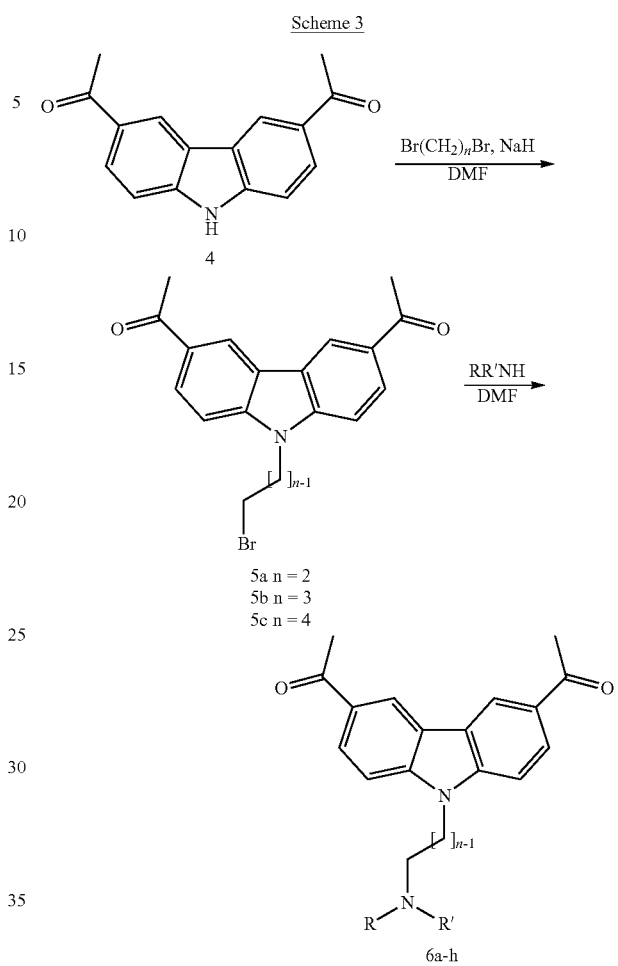

3,6-Diacetylcarbazole (4)

Carbazole 1 (16.9 g, 0.1 mol) was dissolved in nitrobenzene (300 mL). Anhydrous AlCl$_3$ (54.0 g, 0.4 mol) was added under stirring and cooling with an ice bath. Then, AcCl (55.5 g, 0.7 mol) was added slowly dropwise. The reaction mixture was allowed to warm to room temperature under stirring and kept over a period of 13 h. Water (500 mL) was added in small portions under cooling with an ice bath. The cooling bath was removed, and the mixture was refluxed over a period of 2 h and extracted with CHCl$_3$ (3×150 mL). The combined extracts were sequentially washed with saturated solutions of NaHCO$_3$ and NaCl, dried with anhydrous Na$_2$SO$_4$, and evaporated. The residue was purified by column chromatography (silica gel, CHCl$_3$/MeOH) to give 12.5 g (50%) of 3,6-diacetylcarbazole (4).

For the alkylation of compound 4, the general procedure for the alkylation of carbazoles was used. The yields of the products 3c-f are shown in Table 1.

Preparation of bromoalkyldiacetylcarbazoles 5a-c

Diacetylcarbazole 4 was dissolved in DMF, then NaH (3 eq) was added. The mixture was stirred over a period of 10 min at room temperature. A dibromoalkane (7 eq) was added. The reaction mixture was kept over a period of 1 h (5a at room temperature; 5b at 40° C.; 5c over a period of 20 min at 70° C.; TLC monitoring, CH$_2$Cl$_2$/ethyl acetate, ethyl acetate 4:1). The mixture then was diluted with water and extracted with ethyl acetate. The combined extracts were washed with water and brine, dried with Na$_2$SO$_4$, and evaporated. The residue was purified by column chromatography (silica gel, CHCl$_3$) to give 5a (21%), 5b (29%), and 5c (74%).

Alkylation of Amines with Bromoalkyldiacetylcarbazoles 5a-c.

A bromide 5 was dissolved in DMF, the an amine was added (excess, see Table 3). The mixture was kept at 60° C. overnight. (TLC monitoring, CH$_2$Cl$_2$/ethyl acetate, 1:1 for the presence of the starting carbazole; CHCl$_3$/MeOH, 9:1 for the product purity). The reaction mixture was diluted with water and extracted ethyl acetate. The combined extracts were dried with Na$_2$SO$_4$. The residue was purified by column chromatography (silica gel, CHCl$_3$/MeOH). The product was dissolved in a mixture of CH$_2$Cl$_2$ and MeOH. 4M HCl in dioxane was added, and the mixture was evaporated. The residue was triturated with Et$_2$O and, if necessary, with ethyl acetate or acetone. The yields of the products 6a-h are shown in Table 3.

Scheme 4

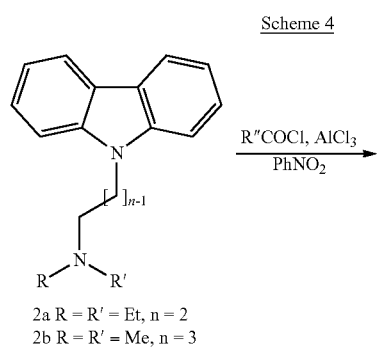

2a R = R' = Et, n = 2
2b R = R' = Me, n = 3

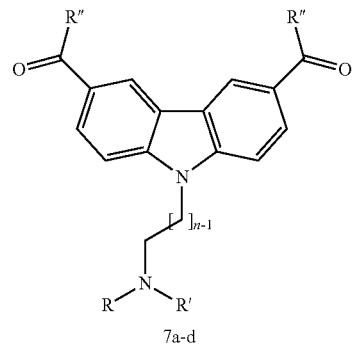

7a-d

For the acylation of 2, a procedure similar to that described in Scheme 1 was used. The yields of products 7a-d are shown in Table 4.

Scheme 5

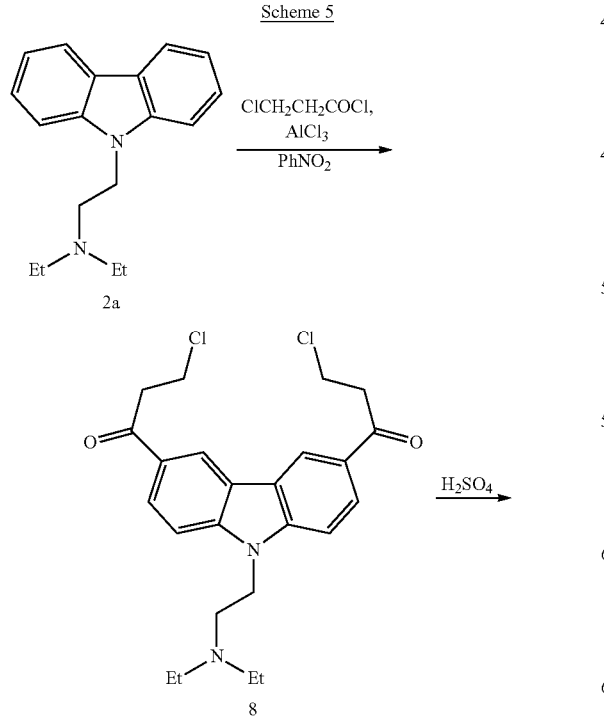

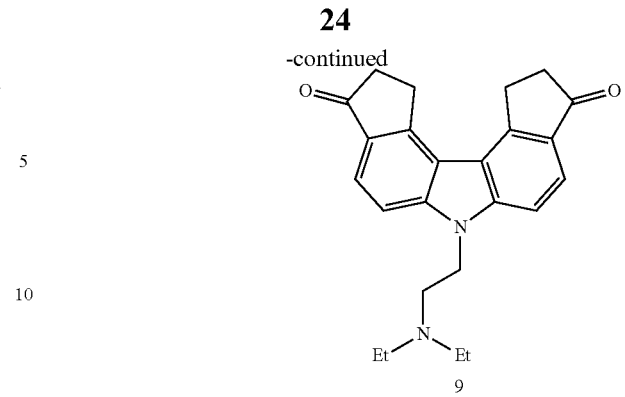

9

3,6-Bis(chloropropionyl)-9-N,N-diethylaminoethyl-carbazole (8)

A solution of 1-N,N-diethylaminoethylcarbazole (0.23 g, 0.86 mmol) in 2 mL of nitrobenzene was cooled in an ice bath. AlCl$_3$ (0.57 g, 4.3 mmol) and 3-chloropropionyl chloride (0.4 mL, 4.2 mmol) were added. The reaction mixture was stirred overnight (LC-MS monitoring) and diluted with aqueous HCl. The product was extracted with CHCl$_3$, and the filtrate was evaporated. The residue was quickly purified by chromatography in a short silica gel column (CHCl$_3$/MeOH) to give 0.38 g (91%) of the compound 8 as its hydrochloride.

1,2,10,11-Tetrahydro-6-N,N-dimethylaminoethyl-6H-dicyclopenta[c,g]carbazole-3,9-dione (9)

Compound 2 (0.38 g, 0.79 mmol) was dissolved in 98% H$_2$SO$_4$ (3 mL). The reaction mixture was heated to 95° C., kept at this temperature over a period of 2.5 h (TLC monitoring, CHCl$_3$/MeOH, 4:1), and poured into ice. The resulting mixture was neutralized with dry Na$_2$CO$_3$ and extracted with CHCl$_3$. The extract was evaporated, and the residue was purified by column chromatography (CHCl$_3$/MeOH). The obtained crude product (0.08 g) was dissolved in MeOH. 4M HCl in dioxane was added, and the mixture was evaporated. The residue was suspended in MeOH, and the suspension was refluxed. (The solid did not dissolve in the process.) The suspension was cooled, and the solid was filtered off to give 0.007 g (2%) of compound 9 as its hydrochloride.

Scheme 6

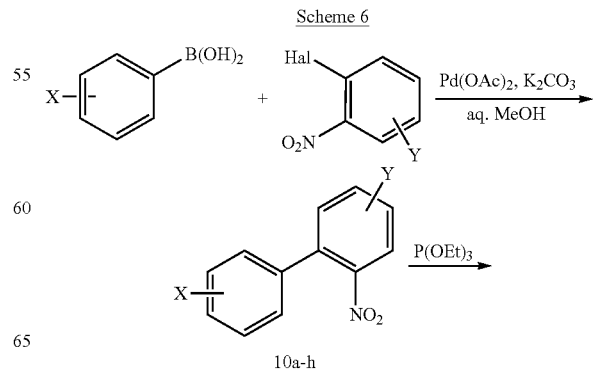

10a-h

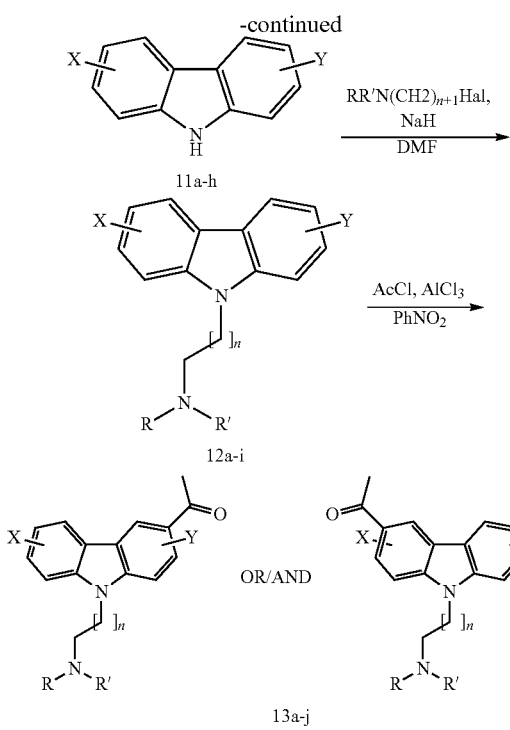

2-Methyl-2'-nitro-1,1'-biphenyl (10a)

2-Methylphenylboronic acid (0.64 g, 4.7 mmol) and 2-nitroiodobenzene (1.0 g, 4.0 mmol) were dissolved in a mixture of MeOH (20 mL) and water (4 mL). $K_2CO_3$ (1.1 g, 8.0 mmol) and $Pd(OAc)_2$ (0.018 g, 0.08 mmol) were added. The reaction mixture was flushed with argon, heated to 50° C., kept overnight at this temperature, and filtered through Celite. The latter was washed with MeOH. The filtrate was evaporated, and the residue was used further without purification.

4,4'-Dimethoxy-2-nitro-1,1'-biphenyl (10h)

4-Methoxyphenylboronic acid (3.00 g, 19.7 mmol) and 4-chloro-3-nitroanisole (3.69 g, 11.6 mmol) were dissolved in a mixture of dioxane (40 mL) and water (10 mL). $K_2CO_3$ (5.44 g, 23.2 mmol) and $Pd(PPh_3)_4$ (1.14 g, 0.6 mmol) were added. The reaction mixture was heated in argon to 80° C., kept at this temperature overnight (TLC monitoring: hexane/ethyl acetate, 4:1), cooled, and filtered through Celite. The latter was washed with $CH_2Cl_2$, and the filtrate was evaporated. The residue was dissolved in $CH_2Cl_2$, and the solution was evaporated to give 6.0 g of crude biphenyl 10h that was cyclized without purification.

An analogous procedure was used to obtain biphenyls 10b-g.

General Procedure for the Synthesis of Carbazoles

A crude biphenyl 10 was dissolved in $(EtO)_3P$. The reaction mixture was kept at 125-140° C. in a flow of argon over a period of about 48 h (TLC monitoring: hexane/ethyl acetate, 1:1) and diluted with water. The precipitate was filtered off and washed with $Et_2O$. If no precipitate formed, the product was extracted with ethyl acetate, the extract was evaporated, and the residue was purified in a short silica gel column (hexane/ethyl acetate). The yields of the products 11a-g are shown in Table 5.

2,7-Dimethoxy-9H-carbazole (11h)

The reaction was carried out in a vial. The crude biphenyl 10h (6.0 g) was dissolved in $P(OEt)_3$ (36 mL). The vial was flushed with argon. The reaction mixture was heated to 90° C., kept at this temperature overnight, and cooled. As a result the carbazole precipitated. $Et_2O/CH_2Cl_2$ mixture was added. The precipitate was filtered off and washed with $CH_2Cl_2$. The filtrate was evaporated. $P(OEt)_3$ was added again, and the mixture was left for cyclization for 24 h. These operations were repeated until the precipitate formation ceased, and TLC indicated that the starting biphenyl disappeared. In total 2.9 g of the carbazole was obtained (65% calculated for two steps.)

For the alkylation of compound 11, the general procedure for the alkylation of carbazoles was used. The yields of the compounds 12a-i are shown in Table 1.

For the acylation of 12, a procedure similar to that described for Scheme 1 was used. However, for the monoacetylation the amount of AcCl and $AlCl_3$ was decreased to 1.5 eq. The yields of compounds 13a-j are shown in Table 2.

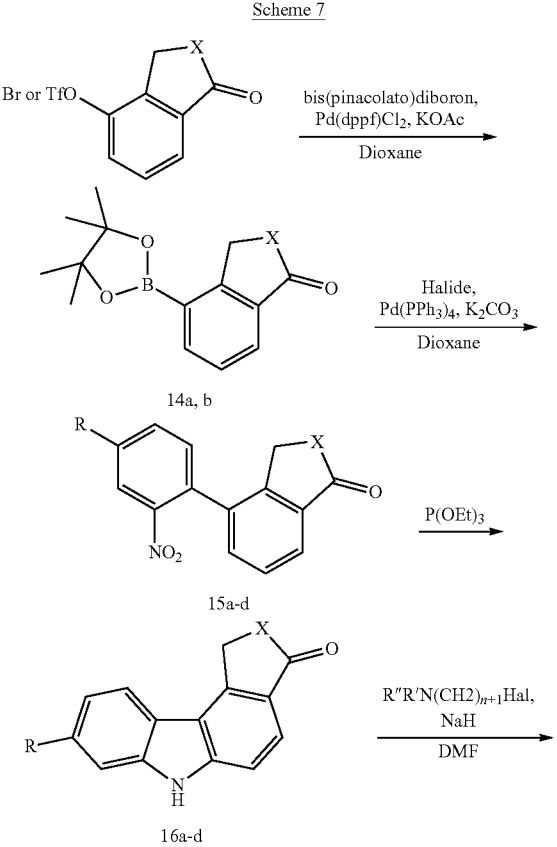

Scheme 7

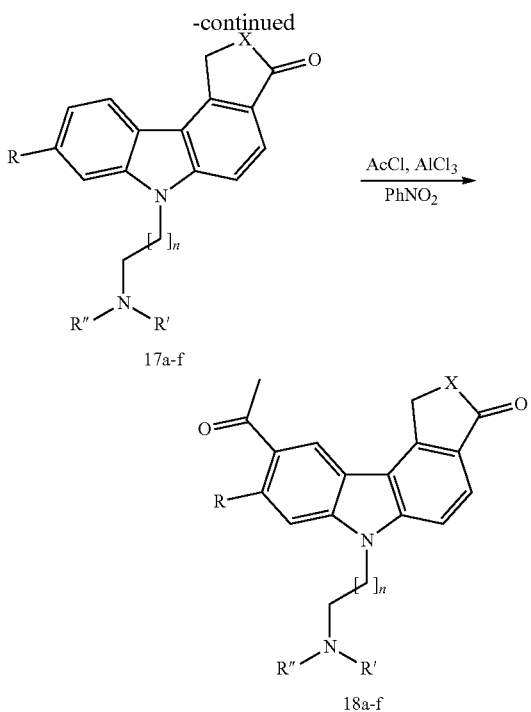

4,4,5,5-Tetramethyl-2-(4-indanone-1-yl)-[1,3,2]-dioxoborolane (14a X=CH₂)

4-Trifluoromethylsulfonyloxy-1-indanone (9.7 g, 34.6 mmol) and bis(pinacolato)diboron (11.4 g, 45.0 mmol) were dissolved in dioxane (100 mL). AcOK (6.8 g, 69.2 mmol) and Pd(dppf)₂Cl₂ (1.3 g, 1.8 mmol) were added. The reaction mixture was heated in a flow of argon to 80° C., kept at this temperature overnight, cooled, and filtered through Celite. The filtrate was evaporated. The residue was dissolved in CH₂Cl₂ and purified in a short silica gel column (hexane/ethyl acetate) to give 9.5 g of a product containing 20% (mass) of bis(pinacolato)diboron. The product was used for the next step without additional purification.

The boronic ester from the bromide was prepared in the same way. If 1 eq of bis(pinacolato)diboron was used, a more pure product was obtained.

4,4,5,5-Tetramethyl-2-[4-(2-methylisoindolin-1-one)-yl]-[1,3,2]-dioxoborolane (14b X=NMe)

4-Bromo-2-methylisoindolin-1-one (3.23 g, 14.3 mmol) and bis(pinacolato)diboron (4.72 g, 18.6 mmol) were dissolved in dioxane (60 mL). AcOK (2.80 g, 28.6 mmol) and Pd(dppf)₂Cl₂ (0.5 g, 0.7 mmol) were added. The reaction mixture was heated in a flow of argon to 80° C., kept at this temperature overnight, cooled, and filtered through Celite. The filtrate was evaporated. The residue was dissolved in CH₂Cl₂ and purified in a short silica gel column (hexane/ethyl acetate) to give 4.2 g of a product containing 20% (mass) of bis(pinacolato)diboron. The product was used for the next step without additional purification.

Biphenyl 15a (X=CH₂, R=H)

4,4,5,5-Tetramethyl-2-(4-indanone-1-yl)-[1,3,2]-dioxoborolane (2.17 g, 8.4 mmol) and o-nitroiodobenzene (2.70 g, 10.9 mmol) were dissolved in a mixture of dioxane (30 mL) and water (5 mL). K₂CO₃ (2.30 g, 16.7 mmol) and Pd(PPh₃)₄ (0.48 g, 0.4 mmol) were added. The reaction mixture was heated in a flow of argon to 80° C., kept at this temperature over a period of 24 h (TLC monitoring: hexane/ethyl acetate, 4:1), cooled, and filtered through Celite. The filtrate was evaporated. The residue was dissolved in CH₂Cl₂. An undissolved precipitate was filtered off. The filtrate was partially evaporated, and the product was purified in a short silica gel column (hexane/ethyl acetate) to give 2.5 g of a product containing PPh₃O. The product was cyclized without additional purification.

Biphenyl 15b (X=CH₂, R=OMe)

4,4,5,5-Tetramethyl-2-(4-indanone-1-yl)-[1,3,2]-dioxoborolane (1.20 g, 4.6 mmol) and o-nitroiodobenzene (0.87 g, 4.6 mmol) were dissolved in a mixture of dioxane (10 mL) and water (2 mL). K₂CO₃ (1.28 g, 9.2 mmol) and Pd(PPh₃)₄ (0.27 g, 0.2 mmol) were added. The reaction mixture was heated in a flow of argon to 80° C., kept at this temperature over a period of 24 h (TLC monitoring: hexane/ethyl acetate, 4:1), cooled, and filtered through Celite. The filtrate was evaporated. The residue was dissolved in CH₂Cl₂. An undissolved precipitate was filtered off. The filtrate was partially evaporated, and the product was purified in a short silica gel column (hexane/ethyl acetate) to give 1.25 g of a product containing PPh₃O. The product was cyclized without additional purification.

Biphenyl 15c (X=NMe, R=H)

4,4,5,5-Tetramethyl-2-[4-(2-methylisoindolin-1-one)-yl]-[1,3,2]-dioxoborolane (2.43 g, 8.9 mmol) and o-nitroiodobenzene (2.44 g, 9.80 mmol) were dissolved in a mixture of dioxane (30 mL) and water (6 mL). K₂CO₃ (2.50 g, 18.1 mmol) and Pd(PPh₃)₄ (0.51 g, 0.4 mmol) were added. The reaction mixture was heated in a flow of argon to 80° C., kept at this temperature over a period of 24 h (TLC monitoring: hexane/ethyl acetate, 4:1), cooled, and filtered through Celite. The filtrate was evaporated. The residue was dissolved in CH₂Cl₂. An undissolved precipitate was filtered off. The filtrate was partially evaporated, and the product was purified in a short silica gel column (hexane/ethyl acetate) to give 2.3 g of a product containing PPh₃O. The product was cyclized without additional purification.

Biphenyl 15d (X=NMe, R=OMe)

4,4,5,5-Tetramethyl-2-[4-(2-methylisoindolin-1-one)-yl]-[1,3,2]-dioxoborolane (0.97 g, 3.6 mmol) and 4-chloro-3-nitroanisole (0.67 g, 3.6 mmol) were dissolved in a mixture of dioxane (10 mL) and water (2 mL). K₂CO₃ (0.98 g, 7.2 mmol) and Pd(PPh₃)₄ (0.21 g, 0.2 mmol) were added. The reaction mixture was heated in a flow of argon to 80° C., kept at this temperature over a period of 24 h (TLC monitoring: hexane/ethyl acetate, 4:1), cooled, and filtered through Celite. The filtrate was evaporated. The residue was dissolved in CH₂Cl₂. An undissolved precipitate was filtered off. The filtrate was partially evaporated, and the product was purified in a short silica gel column (hexane/ethyl acetate) to give 0.76 g of a product containing PPh₃O. The product was cyclized without additional purification.

Carbazole 16a (X=CH₂, R=H)

The reaction was carried out in a vial. 4-(2-Nirophenyl)indanone-1 (2.54 g, 10.0 mmol) was dissolved in P(OEt)₃ (8 mL). The vial was flushed with argon. The reaction mixture was heated to 90° C., kept at this temperature overnight, and cooled. As a result the carbazole precipitated. CH$_2$Cl$_2$ was added. The precipitate was filtered off and washed with CH$_2$Cl$_2$. The filtrate was evaporated. P(OEt)$_3$ (2 mL) was added again, and the mixture was left for cyclization for 24 h. These operations were repeated until the precipitate formation ceased, and TLC indicated that the starting biphenyl disappeared. In total 0.58 g of the carbazole was obtained.

Carbazole 16b (X=CH$_2$, R=OMe)

The reaction was carried out in a vial. 4-(4-Methoxy-2-nitrophenyl)-indanone-1 (1.25 g, 4.4 mmol) was dissolved in P(OEt)$_3$ (8 mL). The vial was flushed with argon. The reaction mixture was heated to 90° C., kept at this temperature overnight, and cooled. As a result the carbazole precipitated. CH$_2$Cl$_2$ was added. The precipitate was filtered off and washed with CH$_2$Cl$_2$. The filtrate was evaporated. P(OEt)$_3$ (1 mL) was added again, and the mixture was left for cyclization for 24 h. These operations were repeated until the precipitate formation ceased, and TLC indicated that the starting biphenyl disappeared. In total 0.39 g of the carbazole was obtained.

Carbazole 16c (X=NMe, R=H)

The reaction was carried out in a vial. 4-(2-Nitrophenyl)-2-methylisoinolin-1-one (2.29 g, 8.5 mmol) was dissolved in P(OEt)$_3$ (10 mL). The vial was flushed with argon. The reaction mixture was heated to 90° C., kept at this temperature overnight, and cooled. As a result the carbazole precipitated. CH$_2$Cl$_2$ was added. The precipitate was filtered off and washed with CH$_2$Cl$_2$. The filtrate was evaporated. P(OEt)$_3$ (0.5 mL) was added again, and the mixture was left for cyclization for 24 h. These operations were repeated until precipitate formation ceased, and TLC indicated that the starting biphenyl disappeared. In total 0.4 g of the carbazole was obtained.

Carbazole 16d (X=NMe, R=OMe)

The reaction was carried out in a vial. 4-(4-Methoxy-2-nitrophenyl)-2-methylisoinolin-1-one (0.76 g, 2.6 mmol) was dissolved in P(OEt)$_3$ (6 mL). The vial was flushed with argon. The reaction mixture was heated to 90° C., kept at this temperature overnight, and cooled. As a result the carbazole precipitated. CH$_2$Cl$_2$ was added. The precipitate was filtered off and washed with CH$_2$Cl$_2$. The filtrate was evaporated. P(OEt)$_3$ (0.5 mL) was added again, and the mixture was left for cyclization for 24 h. These operations were repeated until precipitate formation ceased, and TLC indicated that the starting biphenyl disappeared. In total, 0.34 g of the carbazole was obtained.

For the alkylation of 16, the general procedure for the alkylation of carbazoles was used. The yields of the products 17a-f are shown in Table 1.

For the acylation of 17, a procedure similar to that described for Scheme 1 was used. The yields of the products 18a-d are shown in Table 2.

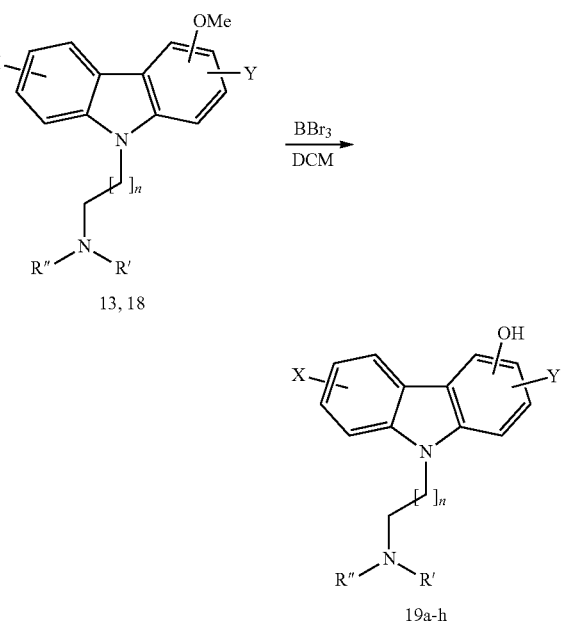

Scheme 8

13, 18

19a-h

General Procedure for Dimethylation.

A methoxy compound was dissolved in CH$_2$Cl$_2$. The solution was cooled to −40° C. A 0.5M solution of BBr$_3$ in DCM (4 eq, for one methoxy group) was added in a flow of argon. After 10 min the cooling bath was removed. The reaction mixture was heated to room temperature, kept over a period of 1 h (TLC monitoring, CHCl$_3$/MeOH, 4:1), and poured into a mixture of aqueous NaHCO$_3$ and CH$_2$Cl$_2$. The organic layer was separated, and the aqueous one was extracted once more with CH$_2$Cl$_2$. The combined extracts were dried with Na$_2$SO$_4$ and evaporated. The product was purified by column chromatography (CHCl$_3$/MeOH). The yields of the products 19a-h are shown in Table 6.

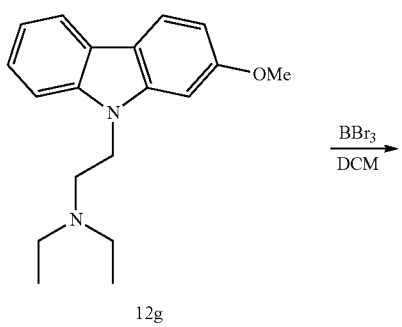

Scheme 9

12g

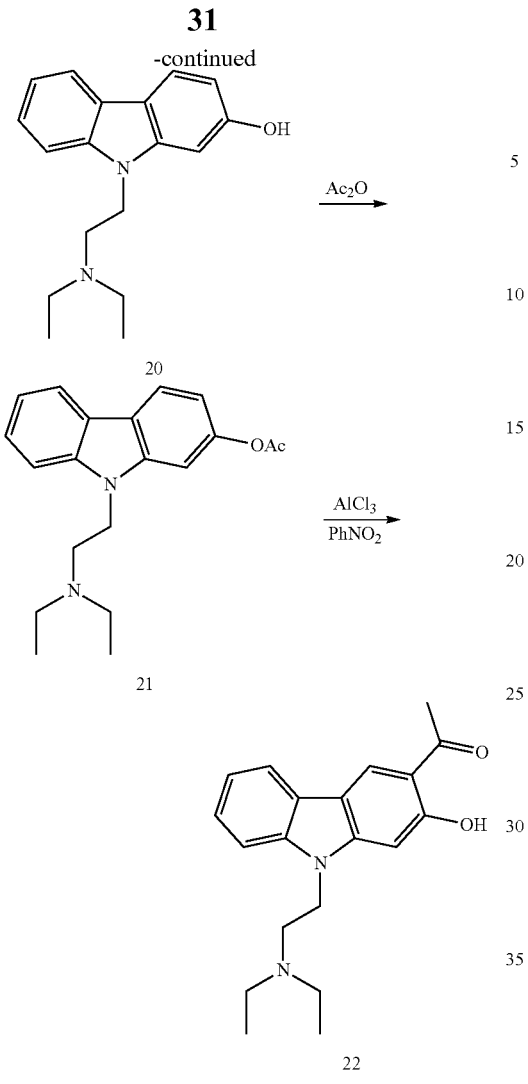

2-Hydroxy-9-N,N-diethylaminoethylcarbazole (20)

2-Methoxy-9-N,N-diethylaminoethylcarbazole 12 g was dissolved in CH$_2$Cl$_2$ (10 mL). The solution was cooled to −40° C. A 0.5M solution of BBr$_3$ DCM (6 mL, 3.00 mmol) was added in a flow of argon. As a result an orange suspension formed. The reaction mixture was heated to room temperature, kept over a period of 1.5 h, and poured into a mixture of aqueous NaHCO$_3$ and CH$_2$Cl$_2$. The organic layer was separated, and the aqueous layer was extracted once more with CH$_2$Cl$_2$. The combined extracts were dried with Na$_2$SO$_4$ and evaporated. The product was purified by column chromatography (CHCl$_3$/MeOH) to give 0.176 g (92%) of the product.

2-Acetoxy-9-N,N-diethylaminoethylcarbazole (21)

A solution of compound 20 (0.176 g, 0.62 mmol) in Ac$_2$O (2 mL) was refluxed over a period of 30 min and poured into water. The resulting mixture was neutralized with NaHCO$_3$ and extracted ethyl acetate. The extract was evaporated to give 0.16 g (79%) of the product.

3-Acetyl-2-hydroxy-9-N,N-diethylaminoethylcarbazole (22)

Compound 21 (0.16 g, 0.49 mmol) was dissolved in PhNO$_2$ (2 mL), and AlCl$_3$ (0.1 g, 0.75 mmol) was added. The reaction mixture was heated in an oil bath to 100° C., kept at this temperature over a period of 2 h, diluted with water, neutralized with Na$_2$CO$_3$, and extracted with HCl$_3$. The extract was evaporated. The residue was purified by chromatography in a short silica gel column (CHCl$_3$/MeOH) to give 0.044 g (28%) of compound 22.

TABLE 1

Alkylation of carbazoles

TABLE 1-continued
Alkylation of carbazoles
| | | Yield |
|---|---|---|
| 12c | 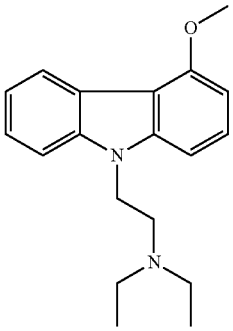 [SMILES: CCN(CC)CCn1c2ccccc2c2c(OC)cccc21] | 59%[a] |
| 12d | 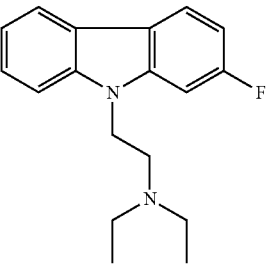 [SMILES: CCN(CC)CCn1c2ccccc2c2ccc(F)cc21] | ~25%[b] |
| 12e | 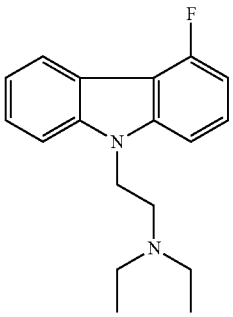 [SMILES: CCN(CC)CCn1c2ccccc2c2c(F)cccc21] | 39%[c] |
| 12f | 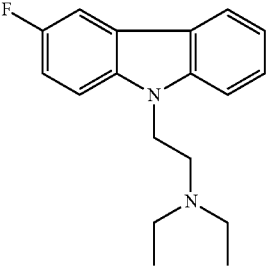 [SMILES: CCN(CC)CCn1c2ccccc2c2cc(F)ccc21] | 91% |
| 12g | 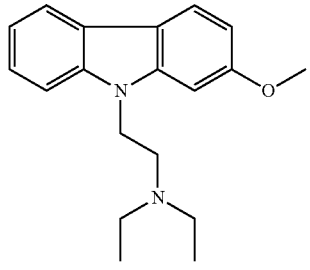 [SMILES: CCN(CC)CCn1c2ccccc2c2ccc(OC)cc21] | 91%[a] |
| 17a | 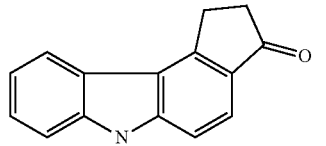 | 31% |
| 17b | 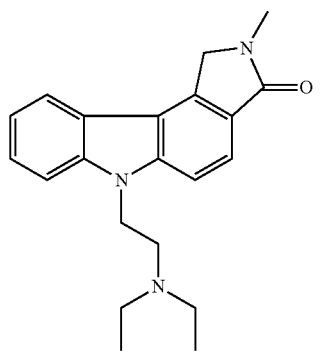 [SMILES: CCN(CC)CCn1c2ccccc2c2c3c(ccc21)C(=O)N(C)C3] | 28% |
| 12h[d] | 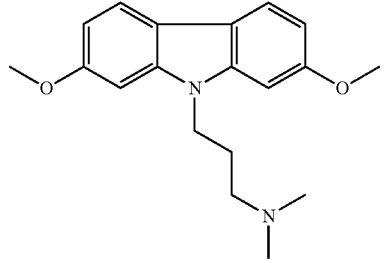 | 100% |
| 17c | 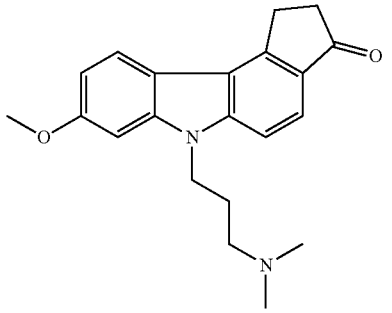 [SMILES: COc1ccc2c3c4c(ccc3n(CCCN(C)C)c2c1)C(=O)CC4] | 67% |
| 12i[d] | 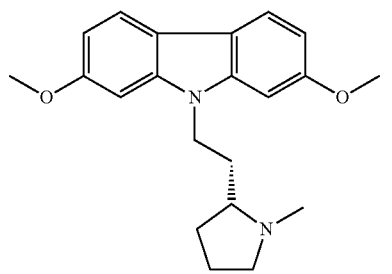 | 100% |

TABLE 1-continued

Alkylation of carbazoles

| | | Yield |
|---|---|---|
| 17d | [structure] | 42% |
| 17e | [structure] | 32% |
| 3c | [structure] | 64% |
| 3d | [structure] | 78% |
| 3e | [structure] | 80% |
| 3f | [structure] | 73% |

[a]Contains DMF.
[b]The yield is not precise. Crude carbazole was used for the preparation. Purification via hydrochloride.
[c]Purification via hydrochloride.
[d]Isolated as crystalline substances immediately after diluting the reaction mixture with water.

TABLE 2

Acetylation of alkylated carbazoles

| | | Yield |
|---|---|---|
| 3a | [structure] | 57% |
| 3b | [structure] | 64% |

TABLE 2-continued
Acetylation of alkylated carbazoles
| | | Yield |
|---|---|---|
| 13a | 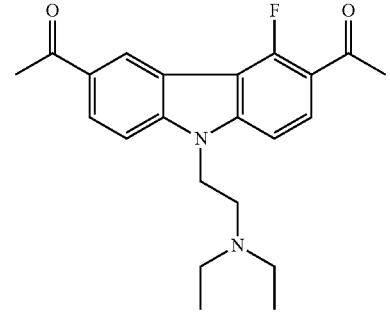 | 55% |
| 13b | | 31% |
| 13c | | 63% |
| 13d | | 92% |
| 13e | 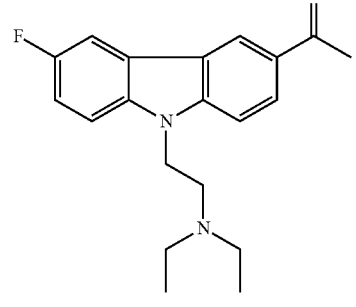 | 88% |
| 13f | | 95% |
| 13g | | 69% |
| 13h | | 57%[a] |

TABLE 2-continued
Acetylation of alkylated carbazoles
| | | Yield |
|---|---|---|
| 18a | 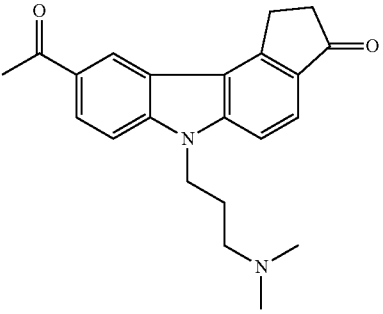 | 33% |
| 13i | 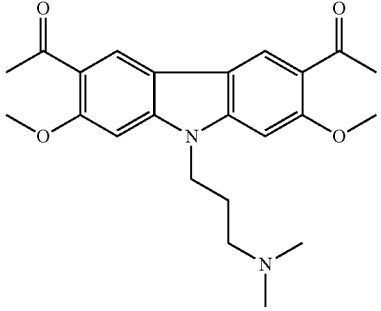 | 74% |
| 18b | 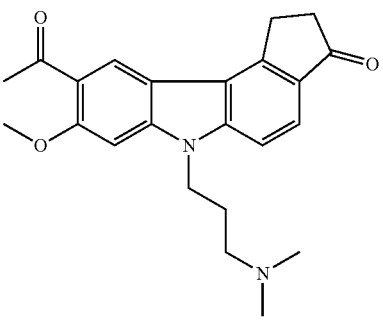 | b |
| 13j | 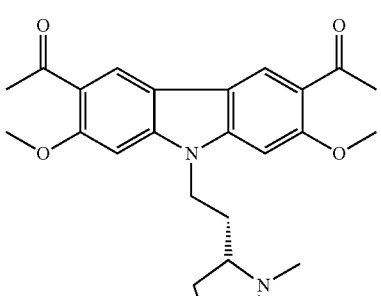 | 48% |
| 18c | 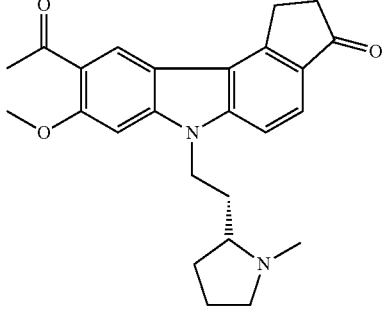 | 46%[a] |
| 18d | 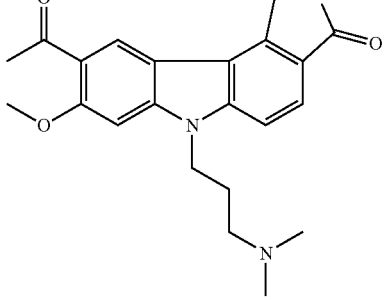 | 81% |
[a] After HPLC Purification.
[b] A mixture with the starting compound was isolated and was used further without separation.
TABLE 3
Alkylation of carbazoles with bromoalkyldiacetylcarbazoles
| | | Yield |
|---|---|---|
| 6a | 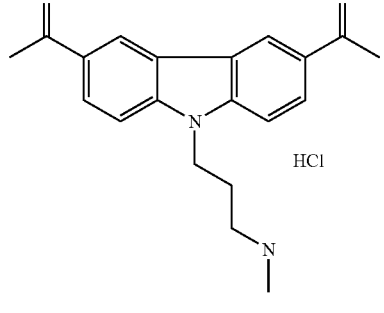 | 78% |
| 6b | 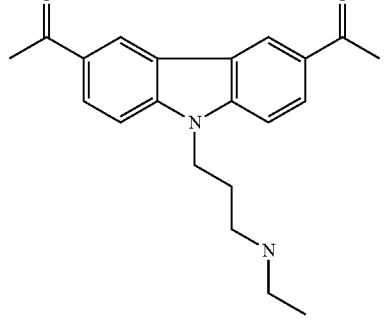 | 96% |

TABLE 3-continued

Alkylation of carbazoles with bromoalkyldiacetylcarbazoles

| | Yield |
|---|---|
| 6c | 73% |
| 6d | 77% |
| 6e | 41% |
| 6f | 54% |
| 6g | 54% |
| 6h | 46% |

TABLE 4

| | Yield |
|---|---|
| 7a | 32% |
| 7b | 54% |

TABLE 4-continued
| | | Yield |
|---|---|---|
| 7c | 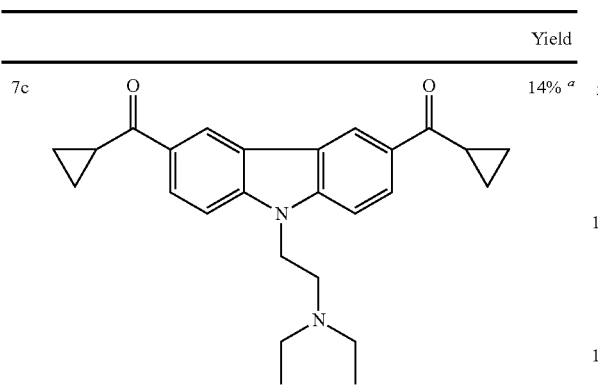 | 14%[a] |
| 7d | 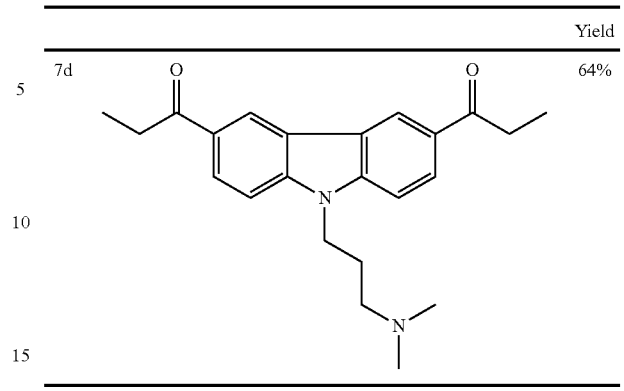 | 64% |
[a] After HPLC purification
TABLE 5
| | Boronic acid | Halide | Biphenyl | Carbazole | Yield (calculated for the halide) |
|---|---|---|---|---|---|
| 11a | | | | | 35% |
| 11b[a] | | | | | 39% |
| 11c | | | | | 82% |
| 11d | | | | | [b] |
| 11e | | | | | 37% |

TABLE 5-continued

| | Boronic acid | Halide | Biphenyl | Carbazole | Yield (calculated for the halide) |
|---|---|---|---|---|---|
| 11f | 3-fluorophenylboronic acid pinacol ester | 1-iodo-2-nitrobenzene | 3'-fluoro-2-nitrobiphenyl | 3-fluorocarbazole | 16%[c] |
| 11g[a] | 4-methoxyphenylboronic acid pinacol ester | 1-iodo-2-nitrobenzene | 4'-methoxy-2-nitrobiphenyl | 3-methoxycarbazole | 48% |

[a] Precipitated as crystals.
[b] The product contained (EtO)$_3$PO and was used without purification.
[c] Only the yield of the target regioisomer is given.

TABLE 6

| | Structure | Yield |
|---|---|---|
| 19a | | 43% |
| 19b | | 23%[a] |
| 19c | | 29%[b] |
| 19d | | 34%[b] |
| 19e | | 10%[a] |

TABLE 6-continued

| | | Yield |
|---|---|---|
| 19f | 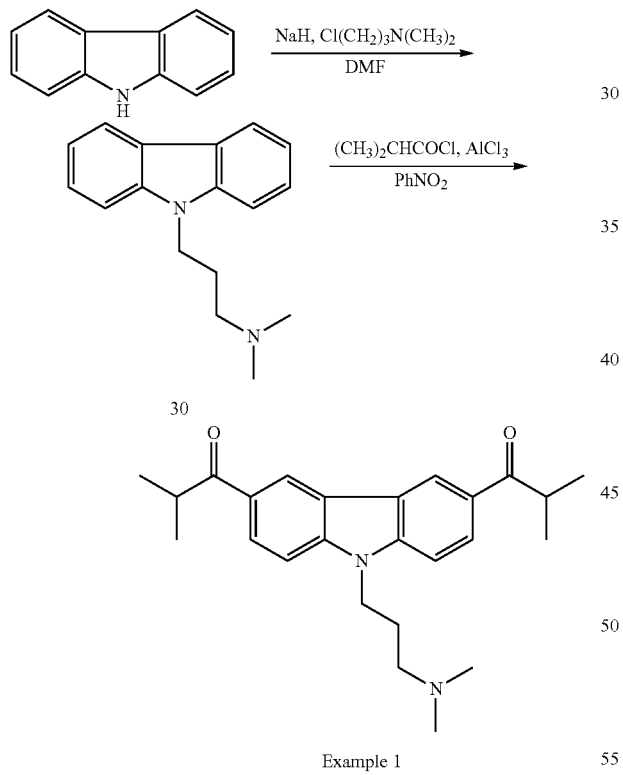 (structure) | 23%[c] |

[a]After HPLC purification.
[b]Obtained after working with a mixture separated by HPLC.
[c]Purification via hydrochloride.

EXAMPLES

Example 1

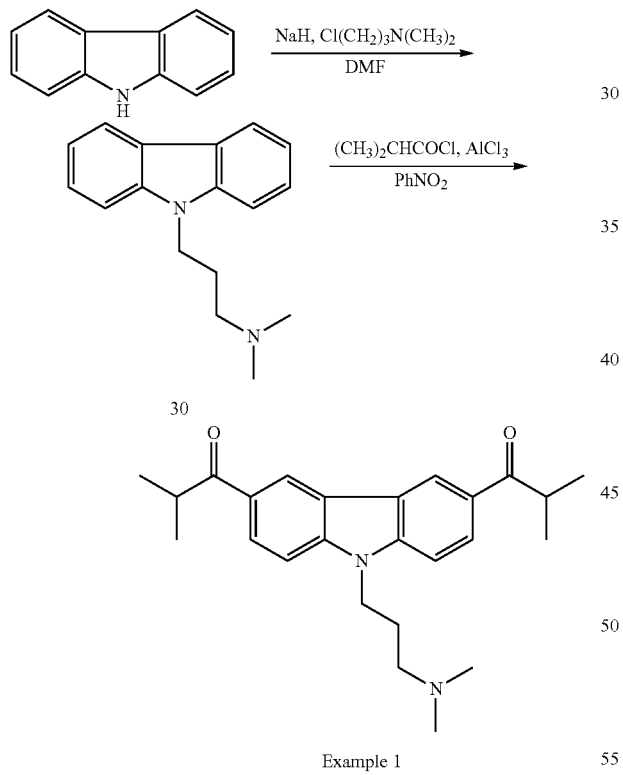

Example 1

[3-(9H-carbazol-9-yl)propyl]dimethylamine (30)

Carbazole 3.0 g (18.0 mmol) was dissolved in DMF (20 mL). Then, 60% NaH in paraffin (2.5 g, 62.5 mmol) was added, and the mixture was stirred for 10 min. 2-N,N-dimethylaminopropyl chloride 3.0 g (19.0 mmol) was added in portions, whereupon the temperature rose to 45-50° C. The reaction mixture was kept at this temperature for 2.5 h (TLC monitoring, CHCl$_3$/MeOH, 9:1). The obtained mass was carefully poured into ice/water mixture and extracted with ethyl acetate. The extract was dried with Na$_2$SO$_4$ and evaporated to give compound 30 (4.8 g, 100%) as a brown fluid oil.

1,1'-{9-[3-(dimethylamino)propyl]-9H-carbazole-3,6-diyl}bis(2-methylpropan-1-one) (Example 1)

Compound 30 (0.25 g, 1.0 mmol) was dissolved in nitrobenzene (5 mL). AlCl$_3$ (0.6 g, 4.5 mmol) and then isobutyroyl chloride (0.6 mL, 5.7 mmol) were added in portions. The reaction mixture was stirred for 40 min (LC/MS monitoring). The obtained mixture was poured into ice/water mixture and extracted with CHCl$_3$. The combined extracts were evaporated, and the residue was purified by chromatography in a short thick silica gel column (eluent: CHCl$_3$/MeOH 99:1→90:10) to afford 0.189 g (47%) of the product. $^1$H NMR (DMSO-d$_6$): δ 1.20 (12H, d, J=6.7 Hz); 1.90-1.97 (2H, m); 2.11 (6H, s); 2.18 (2H, t, J=6.7 Hz); 3.91 (2H, septet, J=6.7 Hz), 4.50 (2H, t, J=6.6 Hz); 7.76 (2H, d, J=8.7 Hz); 8.14 (2H, dd, J=8.7 Hz, J=1.5 Hz); 9.11 (2H, d, J=1.5 Hz). ELI-MS: 100%, ESI-MS: m/z 392 [M+H]$^+$.

Example 2

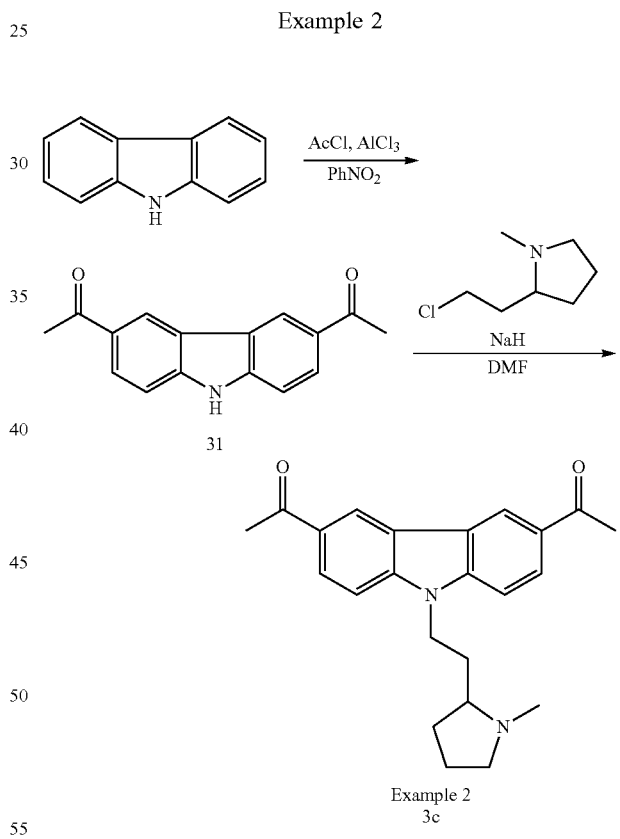

Example 2
3c

1,1'-(9H-Carbazole-3,6-diyl)diethanone (31)

Carbazole (16.9 g, 0.1 mol) was dissolved in nitrobenzene (300 mL). Anhydrous AlCl$_3$ (54.0 g, 0.4 mol) was added under stirring in an ice bath. Then AcCl (55.5 g, 0.7 mol) was added slowly dropwise. The reaction mixture was allowed to warm to room temperature under stirring and kept for 13 h. Water (500 mL) was added in small portions under cooling in an ice bath in order to avoid violent foaming. The cooling bath was removed, and the mixture was refluxed with a condenser for 2 h. The product was extracted with chloroform (3×150 mL). The combined extracts were sequentially washed with saturated solutions of NaHCO$_3$ and NaCl, dried with anhydrous Na$_2$SO$_4$, and evaporated. The residue was purified by column chromatography (silica gel, CHCl$_3$-MeOH) to afford 1 12.5 g (50%).

1,1'-{9-[2-(1-Methylpyrrolidin-2-yl)ethyl]-9H-carbazole-3,6-diyl}diethanone (Example 2, 3c)

The diacetyl derivative 31 (0.97 g, 3.86 mmol) was dissolved in DMF (7 mL). NaH (0.54 g, 13.5 mmol) was added, and the mixture was stirred for 3-5 min at room temperature. 2-(2-Chloroethyl)-1-methylpyrrolidine hydrochloride (1.07 g, 5.8 mmol) was added. The reaction mixture was stirred for 24 h at 60° C. (TLC monitoring, CHCl$_3$/MeOH, 9:1), diluted with water, and extracted with ethyl acetate. The extract was dried with Na$_2$SO$_4$ and evaporated. The residue was purified by column chromatography (silica gel, CHCl$_3$/MeOH 99:1→:10) to give 0.90 g (64%) of the product. $^1$H NMR (DMSO-d$_6$): δ 1.41-1.49 (1H, m); 1.54-1.73 (3H, m); 1.76-1.85 (1H, m); 1.97-2.13 (3H, m); 2.14 (3H, s); 2.70 (6H, s); 2.86-2.93 (1H, m); 4.46-4.50 (2H, m); 7.72 (2H, d, J=8.8 Hz); 8.12 (2H, dd, J=8.8 Hz, J=1.6 Hz); 9.04 (2H, d, J=1.6 Hz). ELSD: 100%, ESI-MS: m/z 363 [M+H]$^+$.

Example 3

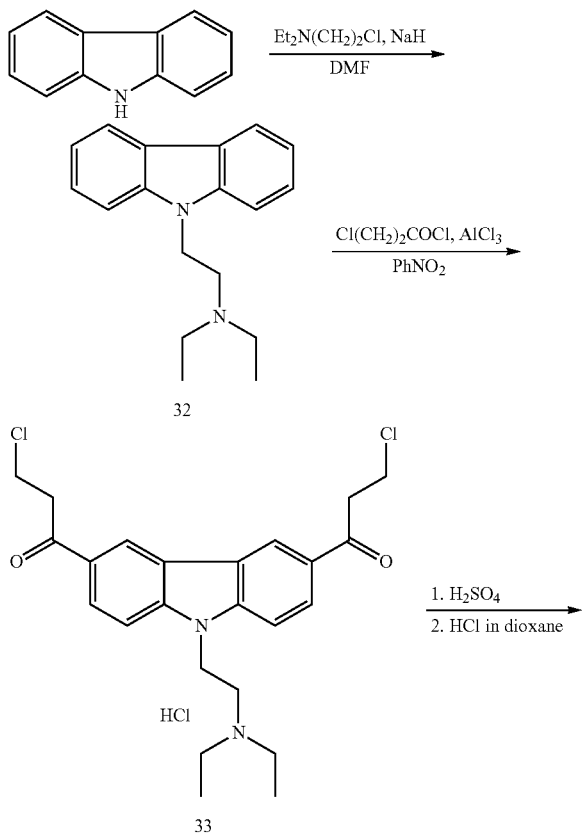

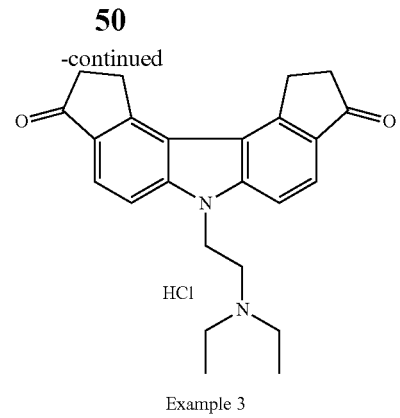

Example 3

[2-(9H-Carbazol-9-yl)ethyl]diethylamine (32)

Carbazole (10.0 g, 59.8 mmol) was dissolved in DMF (60 mL). Then, 60% NaH in paraffin (7.2 g, 180.0 mmol) was added in portions. The mixture was stirred for 10 min. 2-N,N-Diethylaminoethyl chloride hydrochloride (10.5 g, 61.0 mmol) was added in portions, whereupon the temperature rose to 50° C. The reaction mixture was kept at this temperature for 2.5 h (TLC monitoring, hexane/ethyl acetate 4:1). The resulting mass was carefully poured into ice/water mixture and extracted with ethyl acetate. The extract was dried with Na$_2$SO$_4$ and evaporated to give compound 1 (16.0 g, 100%) as a fluid brown oil.

1,1'-{9-[2-(Diethylamino)ethyl]-9H-carbazole-3,6-diyl}bis(3-chloropropan-1-one) hydrochloride (33)

A solution of compound 32 (17.9 g, 67.3 mmol) in nitrobenzene (150 mL) was cooled in an ice bath. AlCl$_3$ (45.0 g, 337.1 mmol) was added in portions. Then 3-chloropropionyl chloride (32.4 mL, 336.7 mmol) was added dropwise for 10 min. The reaction mixture was stirred for 40 min (LC/MS monitoring), poured into a mixture of ice with diluted HCl, and extracted with CHCl$_3$. The extract was evaporated. The residue was purified by chromatography in a thick short column (silica gel, CHCl$_3$/MeOH 99:1→90:10) to afford 22.9 g (76.3%) of the hydrochloride 33.

6-[2-(Diethylamino)ethyl]-10,11-dihydro-1H-dicyclopenta[c,g]carbazole-3,9(2H,6H)-dione hydrochloride (Example 3)

The hydrochloride 2 (22.9 g, 51.3 mmol) was dissolved in 98% H$_2$SO$_4$ (150 mL). The solution was kept at 80° C. for 4 h (TLC monitoring, CHCl$_3$/MeOH 4:1) and poured into ice. The resulting mixture was neutralized with Na$_2$CO$_3$ and extracted with CHCl$_3$. The extract was evaporated. The residue was purified by chromatography in a short thick column (silica gel, CHCl$_3$/MeOH 99:1→90:10) and recrystallized from MeOH to give 0.562 g (3%) of the product. The latter was dissolved in CH$_2$Cl$_2$, HCl in dioxane was added, and the mixture was evaporated to dryness. The residue was washed with ether and dried to give 0.6358 g the hydrochloride. $^1$H NMR (DMSO-d$_6$): δ 1.26 (6H, t, J=7.4 Hz); 2.77-2.80 (4H, m); 3.42-3.47 (2H, m); 3.23-3.34 (4H, m); 3.83-3.85 (4H, m); 5.88 (2H, t, J=7.8 Hz); 7.84 (2H, d, J=8.6 Hz); 7.97 (2H, d, J=8.6 Hz); 10.75 (1H, br.s). ELSD: 100%, ESI-MS: m/z 375 [M+H]$^+$.

Example 4

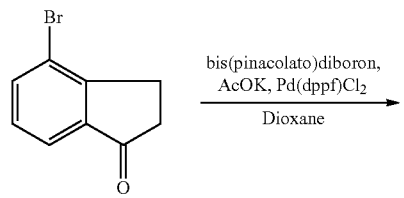

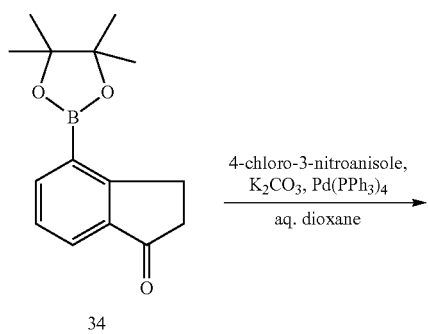

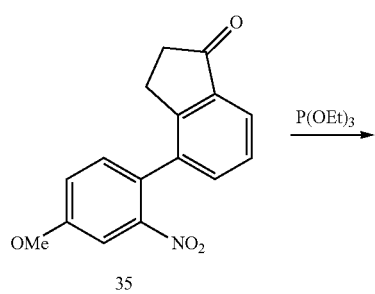

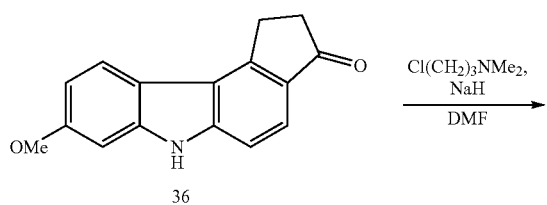

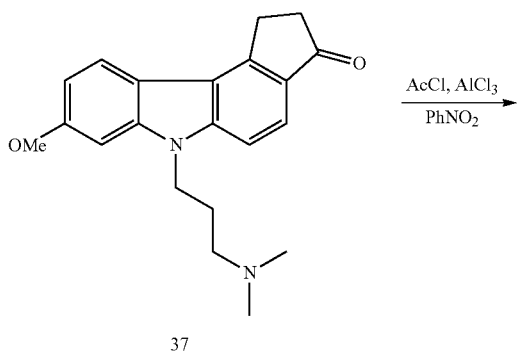

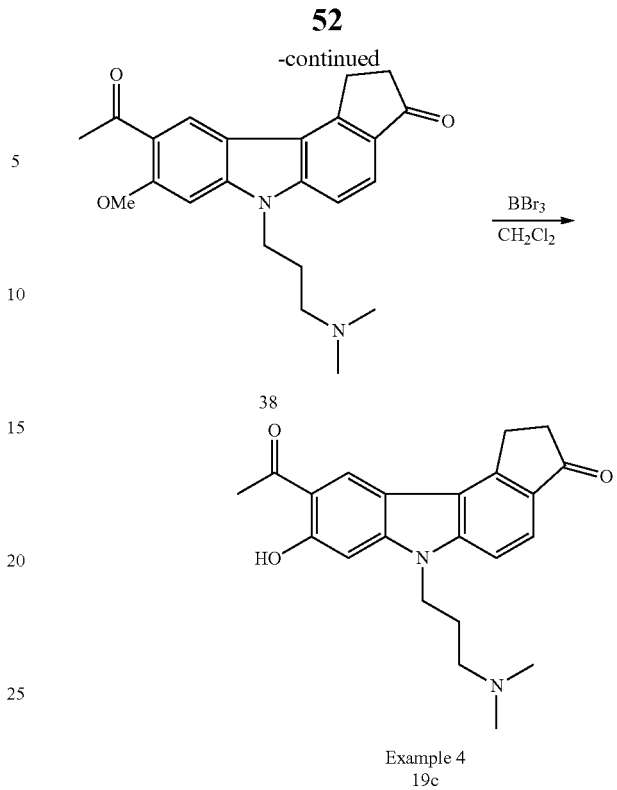

Example 4
19c

4-(4,4,4,5,5-Tetramethyl-1,3,2-dioxaborolan-2-yl)indan-1-one (34)

Potassium acetate (17.8 g, 181.6 mmol) and Pd(dppf)Cl$_2$ (3.3 g, 4.5 mmol) were added to a solution of 4-bromo-1-indanone (19.3 g, 91.5 mmol) and bis(pinacolato)diboron (23.2 g, 91.3 mmol) in dioxane (300 mL). The mixture was heated to 80° C. under argon, kept at this temperature for 16 h, cooled, filtered through Celite, and evaporated. The residue was dissolved in CH$_2$Cl$_2$. The product was purified on a short thick column with silica gel (eluent: hexane-ethyl acetate 100:0→50:50). Yield of 34: 23.4 g. The product containing bis(pinacolato)diboron (about 7 molar %) was used in the next step without additional purification.

4-(4-Methoxy-2-nitrophenyl)indan-1-one (35)

Potash (7.5 g, 54.3 mmol) and Pd(PPh$_3$)$_4$ (1.6 g, 1.4 mmol) were added to a solution of 4-(4,4,5,5-tetramethyl-1,3,2-dioxaborolan-2-yl)indan-1-one 34 (7.0 g, 27.1 mmol) and 4-chloro-3-nitroanisole (5.1 g, 27.1 mmol) in a mixture of dioxane (80 mL) and water (20 mL). The mixture obtained was heated to 80° C. under argon, kept at this temperature for 16 h (TLC monitoring, eluent: hexane-ethyl acetate, 1:1), cooled, filtered through Celite, evaporated, and dissolved in CH$_2$Cl$_2$. Then the mixture was filtered off from the insoluble portion, evaporated with silica gel, and purified on a short thick column with silica gel (eluent: hexane-CH$_2$Cl$_2$ 100:0→0:100, CH$_2$Cl$_2$-ethyl acetate 100:0→50:50). Yield of 35: 5.59 g. The product was used in the next step without additional purification.

8-Methoxy-1,6-dihydrocyclopenta[c]carbazol-3(2H)-one (36)

Biphenyl 35 obtained (5.59 g) was divided into five portions (1.11 g each); then P(OEt)$_3$ (per 7 mL) was added to each portion. The resulting mixture was subjected to argon blow in a flask, heated up to 90° C., kept at this temperature for 3 days, and cooled down. Carbazole was precipitated. Then the reaction mixture was diluted with ether, the precipitate was filtered off and washed with CH$_2$Cl$_2$. If the initial biphenyl remained in the filtrate (TLC monitoring, eluent: hexane-ethyl acetate, 1:1), this filtrate was evaporated and P(OEt)$_3$ (per 1 mL into each flask) was added. The mixture was subjected to repeated cyclization for a day. The procedure repeated until the precipitation ceased and TLC data showed the absence of the initial biphenyl. Total yield of carbazole 36: 2.16 g.

6-[3-(Dimethylamino)propyl]-8-methoxy-1,6-dihydrocyclopenta[c]carbazol-3(2H)-one (37)

Compound 36 (1.0 g, 3.98 mmol) was suspended in CH$_2$Cl$_2$ (10 mL); NaH (0.75 g, 12.0 mmol, 3 eq.) was added. The mixture was stirred at room temperature for 5-10 min; then 3-dimethylamino-1-propyl chloride hydrochloride (0.75 g, 4.74 mmol, 1.2 eq.) was added. The reaction mixture was heated to 70° C., kept at this temperature for 2 h (TLC monitoring, eluent: CH$_2$Cl$_2$-ethyl acetate, 1:1—the presence of initial carbazole, CHCl$_3$-MeOH, 9:1—purity of the product). The resulting mixture was diluted with water, extracted with ethyl acetate, evaporated, and purified on a short thick column with silica gel, eluent: CHCl$_3$-MeOH 99:1→90:10. Yield of 37: 0.84 g (63%).

9-Acetyl-6-[3-(dimethylamino)propyl]-8-methoxy-1,6-dihydrocyclopenta[c]carbazol-3(2H)-one (38)

A solution of compound 37 (0.84 g, 2.51 mmol) in PhNO$_2$ (20 mL) was cooled in an ice bath. Then AlCl$_3$ (1.7 g, 12.7 mmol, 5 eq.) and after that, AcCl (0.9 mL, 12.7 mmol, 5 eq.) were added. The mixture was kept for 40 min (LC/MS monitoring), diluted with water, neutralized with Na$_2$CO$_3$, extracted with CHCl$_3$, and evaporated. The product was purified on a short thick column, eluent: CHCl$_3$-MeOH 99:1→90:10. Yield of 38: 0.658 g (69%).

9-Acetyl-6-[3-(dimethylamino)propyl]-8-hydroxy-1,6-dihydrocyclopenta[c]carbazol-3(2H)-one (Example 4; 19c)

A 0.5 M solution of BBr$_3$ (16.5 mL, 5 eq.) was added dropwise under argon to a solution of compound 38 (0.658 g, 1.74 mmol) in CH$_2$Cl$_2$ (100 mL) cooled to −40° C. The mixture was kept for 10 min; then a cooling bath was removed and the mixture was heated to room temperature and kept for 1-2 h (TLC monitoring, eluent: CHCl$_3$/NH$_3$-MeOH, 9:1). The resulting mixture was poured in a mixture of aqueous NaHCO$_3$ solution and CH$_2$Cl$_2$. The organic layer was separated; the aqueous one was extracted with CH$_2$Cl$_2$, dried over Na$_2$SO$_4$, evaporated, and dissolved in a mixture: CHCl$_3$-MeOH-water, 40:9:1. The product was purified in a silica gel column with the use of the latter mixture as an eluent. Yield of Example 4: 0.258 g (41%). For the preparation of hydrochloride, the product isolated was dissolved in a mixture: CH$_2$Cl$_2$-MeOH; a solution of HCl in dioxane was added. The resulting mixture was evaporated to dryness; the residue was washed with ether.

$^1$H NMR spectrum (DMSO-d$_6$): δ 2.14-2.20 (2H, m); 2.70 (6H, d, J=4.9 Hz); 2.78-2.81 (2H, m); 3.12-3.17 (2H, m); 3.60-3.62 (2H, m); 4.51 (2H, t, J=7.1 Hz); 7.28 (1H, s); 7.73 (2H, s—degenerated AB system); 8.55 (1H, s); 10.40 (1H, br. s); 12.76 (1H, s). ELSD: 100%, ESI-MS: m/z 364 [M+H].$^+$ Example 5

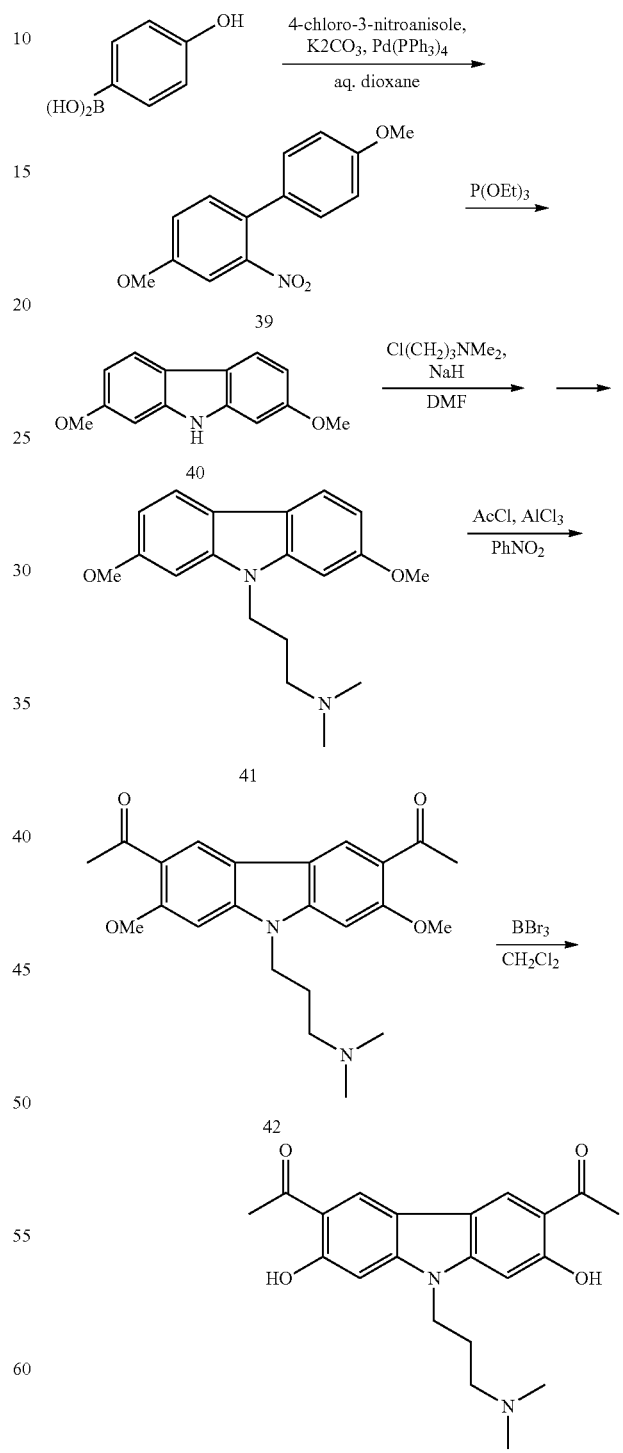

Example 5
19b

4,4'-dimethoxy-2-nitrobiphenyl (39)

Potash (9.10 g, 65.9 mmol) and Pd(PPh₃)₄ (1.90 g, 1.6 mmol) were added to a solution of 4-methoxyphenylboronic acid (5.0 g, 32.9 mmol) and 4-chloro-3-nitroanizole (6.17 g, 32.9 mmol) in a mixture of dioxane (80 mL) and water (20 mL). The resulting mixture was heated to 80° C. under argon, kept at this temperature for 16 h (TLC monitoring, eluent: hexane-ethyl acetate, 4:1), cooled, and filtered through Celite. The product was washed off with CH₂Cl₂. The residue was dissolved in CH₂Cl₂ and purified on a short thick column (eluent: hexane-CH₂Cl₂ 100:0→0:100, CH₂Cl₂-ethyl acetate 100:0→50:50). Yield of 1: 8.47 g.

2,7-dimethoxy-9H-carbazole (40)

Compound 39 (8.47 g) was divided into eight portions (1.06 g each). Then, P(OEt)₃ (per 7 mL) was added to each portion. The resulting mixtures were subjected to argon blow, heated to 90° C., kept at this temperature for 3 days, cooled, and diluted with ether. The precipitate obtained was filtered and washed with CH₂Cl₂. Yield of carbazole 40: 3.33 g.

[3-(2,7-dimethoxy-9H-carbazol-9-yl)propyl]dimethylamine (40)

Compound 40 (0.7 g, 3.1 mmol) was suspended in DMF (6 mL). Sodium hydride (0.4 g, 10.0 mmol) was added and the mixture was stirred at room temperature for 5-10 min. Then 3-dimethylamino-1-propyl chloride hydrochloride (0.73 g, 4.6 mmol) was added. The mixture obtained was heated to 50-60° C., kept at this temperature for 16 h (TLC monitoring, eluent: CH₂Cl₂-ethyl acetate, 1:1—the presence of the initial carbazole; CH₂Cl₂-MeOH, 9:1—the purity of the product), and diluted with water. The white precipitate obtained was left to settle for 1 h, filtered off, and dried in air. Yield of 41: 0.96 g (100%).

1,1'-{9-[3-(dimethylamino)propyl]-2,7-dimethoxy-9H-carbazole-3,6-diyl}diethanone (42)

Compound 41 (0.96 g, 3.2 mmol) was dissolved in PhNO₂ (20 mL); the solution was cooled on an ice bath. Then, AcCl (1.1 mL, 15.4 mmol) was added, followed by AlCl₃ (2.1 g, 15.7 mmol) in portions. The resulting mixture was kept for 40 min (LC/MS monitoring), diluted with water, neutralized with Na₂CO₃, extracted with CHCl₃, and evaporated. The product was purified on a short thick column with silica gel. Yield of 42: 0.787 g (62%).

1,1'-{9-[3-(dimethylamino)propyl]-2,7-dihydroxy-9H-carbazole-3,6-diyl}diethanone (Example 5; 19b)

A 0.5 M solution of BBr₃ (22.5 mL) was added dropwise under argon to a solution of compound 42 (0.787 g, 1.99 mmol) in CH₂Cl₂ (90 mL), cooled to −40° C. After 10 min, a cooling bath was removed; the mixture was heated up to room temperature and kept for 1-2 h (TLC monitoring, eluent: chloroform-methanol, 4:1). The resulting mixture was poured in a mixture of aqueous soda solution and CH₂Cl₂. The organic layer was separated. The aqueous layer was extracted with CH₂Cl₂, dried over Na₂SO₄, evaporated, and dissolved in a mixture CHCl₃-MeOH-water, 40:9:1. The product was purified on a column. Yield of Example 5: 0.379 g (52%).

Then the product was dissolved in a mixture CH₂Cl₂-MeOH. A solution of HCl in dioxane was added. The resulting solution was evaporated to dryness; the residue was washed with CH₃CN and ether. From a base form of the product (0.379 g) 0.339 g of the hydrochloride was isolated.

¹H NMR (DMSO-d₆) δ: 2.09-2.13 (2H, m); 2.72 (6H, s); 2.77 (6H, s); 3.13-3.16 (2H, m); 4.34 (2H, t, J=7.1 Hz); 7.13 (2H, s); 8.84 (2H, s); 10.17 (1H, br. s); 12.82 (2H, s). ELSD: 100%, ESI-MS: m/z 369 [M+H]⁺.

Example 6

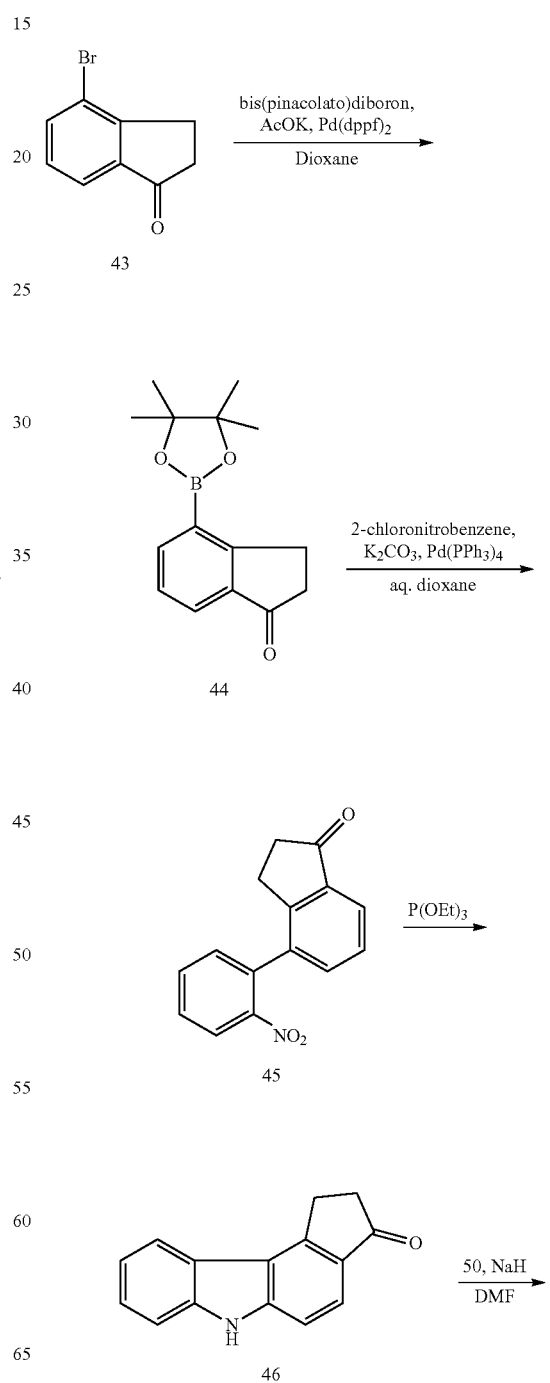

-continued

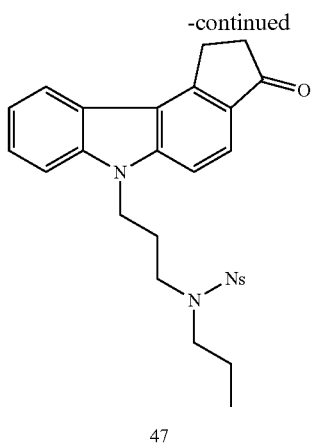

47

AcCl, AlCl₃
―――――→
PhNO₂

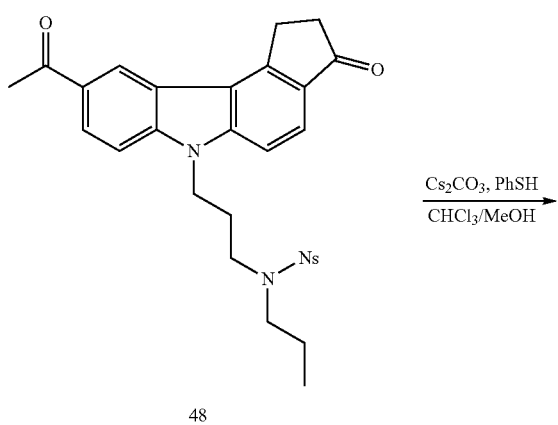

48

Cs₂CO₃, PhSH
―――――――→
CHCl₃/MeOH

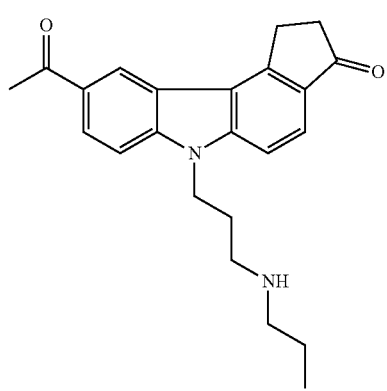

Example 6

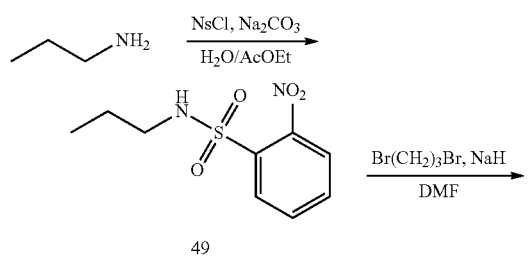

49

Br(CH₂)₃Br, NaH
―――――――→
DMF

-continued

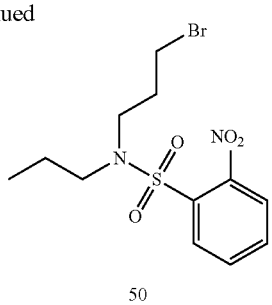

50

Potash (8.1 g, 58.7 mmol) and Pd(PPh₃)₄ (1.7 g, 1.5 mmol) were added to a solution of compound 44 (7.51 g, 29.1 mmol) and 4-chloro-3-nitrobenzene (4.6 g, 29.1 mmol) in a mixture of dioxane (80 mL) and water (20 mL). The mixture obtained was heated under argon to 80° C., kept at this temperature for 16 h (TLC monitoring, eluent: hexane-ethyl acetate, 1:1), cooled, filtered through Celite, and evaporated. The resulting product was dissolved in CH₂Cl₂ and an insoluble residue was filtered off. The resulting product was evaporated with silica gel and purified on a short thick column (eluent: hexane-CH₂Cl₂100:0→0:100, CH₂Cl₂-ethyl acetate 100:0→50:50). Compound 45 (5.0 g) was isolated and used in the next step without purification.

1,6-Dihydrocyclopenta[c]carbazol-3(2H)-one (46)

Compound 45 (5.0 g) was divided into five portions (1.0 g each). P(OEt)₃ (per 7 mL) was added to each portion. The resulting product was subjected to argon blow in a flask, heated to 90° C., kept at this temperature for 3 days, then cooled. The carbazole precipitate was diluted with ether. The precipitate was filtered and washed with ether. If the initial biphenyl was present in the filtrate (TLC monitoring, eluent: hexane-ethyl acetate, 1:1), this filtrate was evaporated, then P(OEt)₃ was added (1 mL to each flask), and subjected to cyclization for 1 day. The procedure was repeated until the precipitation ceased and TLC showed the absence of the initial biphenyl. Carbazol 46 (2.7 g) was obtained.

2-Nitro-N-propylbenzenesulfonamide (49)

A solution of 2-nitrophenylsulfochloride (8 g, 36 mmol) in ethyl acetate (25 mL) was added dropwise at room temperature to a mixture of propylamine (3 mL, 36.0 mmol), ethyl acetate (15 mL), Na₂CO₃ (4 g, 37.7 mmol), and water (25 mL). The resulting solution was stirred for 2 h (TLC monitoring, eluent: CH₂Cl₂). The organic layer was separated, washed with water, a citric acid solution, dried over Na₂SO₄, and evaporated. The precipitate crystallized as a white mass, which was washed off with hexane. Yield of 49: (7.47 g, 85%).

N-(3-Bromopropyl)-2-nitro-N-propylbenzenesulfonamide (50)

1,3-Dibromopropane (8.5 mL, 82.0 mmol, 10 eq.) was added to a solution of compound 49 (2.0 g, 8.2 mmol) in DMF (20 mL). Then NaH (0.6 g, 15.0 mmol) was added in portions. The temperature rose to 50-60° C. The mixture was stirred at this temperature for 20 min (TLC monitoring, eluent: CH₂Cl₂). Then the mixture was carefully poured into ice. The product was extracted with ethyl acetate, and the extract was evaporated. The residue was washed from 1,3-dibromopropane with hexane. The resulting product was dissolved in CH$_2$Cl$_2$ and purified on a short thick column with silica gel, eluent: hexane-CH$_2$Cl$_2$ 100:0→0:100. Compound 50 (1.87 g, 62%) was isolated as rapidly crystallizable oil.

2-Nitro-N-[3-(3-oxo-2,3-dihydrocyclopenta[c]carbazol-6(1H)-yl)propyl]-N-propylbenzenesulfonamide (47)

Compound 46 (0.538 g, 2.43 mmol) and bromide 50 (0.9 g, 2.46 mmol) were dissolved in CH$_2$Cl$_2$ (30 mL). Then NaH (0.15 g, 3.75 mmol, 1.5 eq.) was added. The reaction mixture was stirred for 20 min (TLC monitoring, eluent: hexane-ethyl acetate, 1:1). Then, the mixture was poured onto ice. The product was extracted with ethyl acetate, and the extract was evaporated in a rotary evaporator. The residue of CH$_2$Cl$_2$ was removed in high vacuum. Methanol was added to the hardened precipitate. The product was triturated; the precipitate was filtered off. Yield of 47: 0.638 g (52%).

N-[3-(9-Acetyl-3-oxo-2,3-dihydrocyclopenta[c]carbazol-6(1H)-yl)propyl]-2-nitro-N-propylbenzenesulfonamide (48)

Compound 47 (0.638 g, 1.26 mmol) was dissolved in PhNO$_2$ (7 mL). The solution was cooled on an ice bath, AlCl$_3$ (0.67 g, 5.02 mmol) and then AcCl (0.45 mL, 6.31 mmol) were added. The mixture was kept for 40 min (LC/MS monitoring), diluted with water. The product was extracted with CH$_2$Cl$_2$. The extract was evaporated. The residue was evaporated, and the product was passed through Celite, eluent: CH$_2$Cl$_2$-ethyl acetate 100:0→50:50. Yield of 48: 0.453 g (66%).

9-Acetyl-6-[3-(propylamino)propyl]-1,6-dihydrocyclopenta[c]carbazol-3(2H)-one (Example 6)

Compound 48 (0.496 g, 0.91 mmol) was suspended in a mixture of MeOH (10 mL) and CHCl$_3$ (15 mL). The mixture was heated to boiling. Then Cs$_2$CO$_3$ (0.6 g, 1.82 mmol) was added and at once PhSH (0.2 mL, 1.96 mmol) was poured (the solution turned blue). The resulting solution was refluxed for 2 h (TLC monitoring, eluent: CHCl$_3$-MeOH, 9:1). During this period the reaction mixture turned green. Then, the mixture was evaporated to dryness. A dilute solution of citric acid was added. A yellow precipitate was filtered off, washed with ether, suspended in CH$_3$CN, and refluxed. After cooling, the beige precipitate was filtered off from the yellow filtrate, and then washed with ether. The resulting product (0.251 g, 76%) was isolated. For the transformation of basic form into hydrochloride, the product was dissolved in CH$_2$Cl$_2$-methanol mixture. (The mixture was added until the product was completely dissolved.) Then, a solution of hydrochloric acid in dioxane was added. The solution was evaporated to dryness. A dark-lilac precipitate obtained was washed with methanol and acetonitrile. Yield of Example 6 as hydrochloride: 0.118 g.

H$^1$-NMR (400 MHz, DMSO-d$_6$) spectrum: δ 0.88 (3H, t, J=7.32 Hz); 1.53-1.62 (2H, m); 2.13-2.20 (2H, m); 2.73 (2H, s); 2.80-2.83 (4H, m); 2.95-2.96 (2H, m); 3.65-3.68 (2H, m); 4.68 (2H, t, J=7.3 Hz); 7.81 (1H, d, J=8.6 Hz); 7.85 (1H, d, J=8.6 Hz); 8.15 (1H, dd, J=8.6 Hz, 1.3 Hz); 8.70 (1H, br. s); 8.71 (1H, d, J=1.3 Hz). ELSD: 100%, ESI-MS: m/z 362 [M+H]$^+$.

Example 7

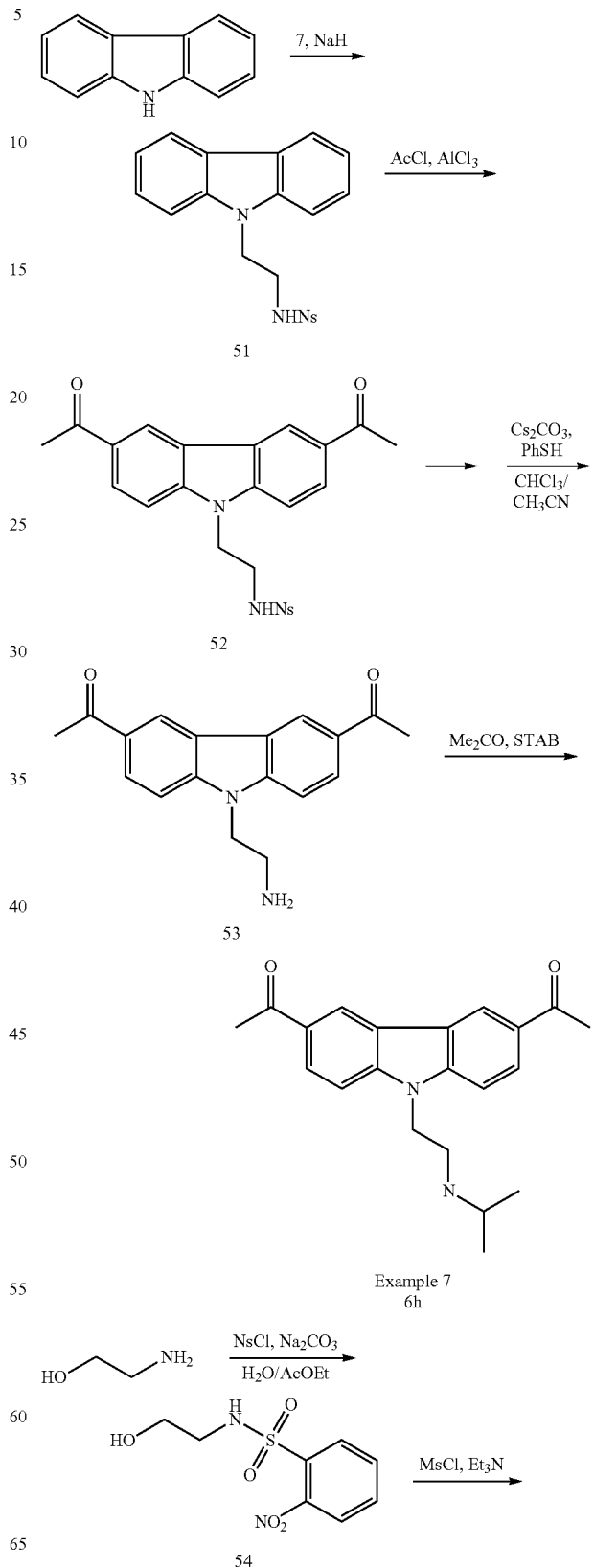

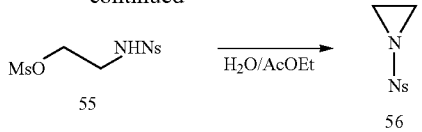

N-(2-Hydroxyethyl)-2-nitrobenzenesulfonamide (54)

Ethanolamine (10 mL, 165 mmol) was dissolved in ethyl acetate (60 mL). Then a solution of $Na_2CO_3$ (22.7 g, 214.2 mmol) in water (100 mL) was added. Then, a solution of 2-nitrobenzenesulfonyl chloride (35.0 g, 157.9 mmol) in ethyl acetate (100 mL) was added dropwise under stirring. The resulting solution was stirred at room temperature for 2 h (TLC monitoring, eluent: $CH_2Cl_2$). The organic layer was separated, washed with water and a solution of citric acid, dried over $Na_2SO_4$, and evaporated. Yield of 54: 29.5 g (73%) as white crystals.

2-{[(2-Nitrophenyl)sulfonyl]amino}ethyl methanesulfonate (55)

Triethylamine (20 mL, 144.6 mmol) was added to a solution of compound 54 (29.5 g, 119.9 mmol) in ethyl acetate (300 mL). The mixture was cooled to 10° C. in an ice bath. Then, a solution of mesyl chloride (10.2 mL, 131.8 mmol) in ethyl acetate (50 mL) was added dropwise at a temperature ≤20° C. The resulting solution was stirred at room temperature for 3 h (TLC monitoring, eluent: hexane-ethyl acetate, 4:1). The reaction mixture was filtered to remove the precipitate—triethylamine hydrochloride. The filtrate was washed with aqueous $NaHCO_3$, water, and evaporated. Yield of 55: 32.2 g (83%) as crystals.

1-[(2-Nitrophenyl)sulfonyl]aziridine (56)

A solution of KOH (1.73 g, 31 mmol) in water (50 mL) was added to a solution of compound 55 (10 g, 31 mmol) in ethyl acetate (100 mL). The aqueous layer stained in yellow. The mixture was stirred at room temperature for 1 h (TLC monitoring, eluent: $CH_2Cl_2$-ethyl acetate, 1:1). If necessary, additional portions of KOH solution (0.5 eq.) were added. The organic layer was separated, washed thoroughly with water, a solution of citric acid (to pH 7), again with water, dried over $Na_2SO_4$, and evaporated. Yield of 56: 6.6 g (93%) as a yellowish fluid oil.

N-[2-(9H-Carbazol-9-yl)ethyl]-2-nitrobenzenesulfonamide (51)

Carbazole (1.10 g, 6.59 mmol) was dissolved in $CH_3CN$ (40 mL). Then sodium hydrate (0.33 g, 8.25 mmol) was added, and the mixture was stirred at room temperature for 15-20 min. Then, a solution of aziridine 56 (1.5 g, 7.89 mmol) in $CH_3CN$ (30 mL) was added in one portion. The resulting mixture was stirred for 1 h (TLC monitoring, eluent: hexane-ethyl acetate, 1:1), poured into water, acidified with HCl to pH 1, and stirred again at room temperature. Gradually, an orange product precipitated from the turbid solution. The precipitate was filtered, and washed with MeOH and ether. Yield of 51: 2.15 g (83%) as orange crystals.

N-[2-(3,6-Diacetyl-9H-carbazol-9-yl)ethyl]-2-nitrobenzenesulfonamide (52)

Compound 51 (5.0 g, 12.7 mmol) was dissolved in $PhNO_2$ (30 mL). The solution was cooled in an ice bath. Then $AlCl_3$ (8.5 g, 63.7 mmol) and after that AcCl (4.5 mL, 63.1 mmol) were added. The mixture was kept for 40 min (LC/MS monitoring), diluted with water, extracted with chloroform, and evaporated. The product was purified on a short thick column with silica gel, eluent: $CH_2Cl_2$-ethyl acetate 100:0→50:50. A mixture of ethanol and 25% aqueous ammonia (4:1) was added to the residue. The resulting product was refluxed for 1.5-2 h. A hot suspension was filtered off. Product 52 was isolated (4.11 g, 68%) as beige crystals.

1,1'-[9-(2-Aminoethyl)-9H-carbazole-3,6-diyl]diethanone (53)

Compound 52 (4.11 g, 8.58 mmol) was dissolved under reflux in a mixture of $CH_3CN$ (150 mL) and methanol (50 mL). Then, $Cs_2CO_3$ (8.4 g, 25.78 mmol) was added and at once PhSH (2.6 mL, 25.48 mmol) was poured in. The resulting mixture was refluxed for 2.5 h (TLC monitoring, eluent: chloroform-methanol, 9:1) and evaporated to dryness. Then, water and a solution of HCl were added. As a result, all the solid products were dissolved. The acidic aqueous solution was extracted with ethyl acetate until the latter ceased to become yellow. The aqueous layer was neutralized with a saturated solution of $NaHCO_3$, extracted with a $CH_2Cl_2$-MeOH mixture (4:1), and the extract was evaporated. The residue was washed off with MeCN and washed with ether. Yield of 53: 1.25 g (50%) as beige crystals.

1,1'-{9-[2-(Isopropylamino)ethyl]-9H-carbazole-3,6-diyl}diethanone (Example 7; 6h)

Acetone (5 mL, 68.10 mmol) was added to a solution of compound 53 (1.25 g, 4.25 mmol) in $CH_2Cl_2$ (50 mL). Then STAB (3.0 g, 14.15 mmol) was added. The mixture obtained was stirred at room temperature for 4.5 h (TLC monitoring, eluent: $CHCl_3$-MeOH, 9:1) and then poured into an aqueous solution of $NaHCO_3$. The organic layer was separated. The aqueous layer was extracted with $CH_2Cl_2$. The product was dried over $Na_2SO_4$ and evaporated. The residue was purified on a column, eluent: $CHCl_3$-MeOH 99:1→90:10. Example 7 (1.04 g, 73%) was isolated as a rapidly crystallizing oil. For the preparation of its hydrochloride, the base was dissolved in $CH_2Cl_2$. Then, a solution of HCl in dioxane was added. The mixture was evaporated to dryness. The product was washed with ether.

$^1$H NMR (DMSO-$d_6$) spectrum: δ 1.25 (6H, d, J=6.6 Hz); 2.72 (6H, s); 3.33-3.39 (3H, m); 4.87 (2H, t, J=7.3 Hz); 7.92 (2H, d, J=8.7 Hz); 8.17 (2H, dd, J=8.7 Hz, J=1.6 Hz); 9.01 (2H, d, J=1.6 Hz); 9.24 (1H, br. s); 9.33 (1H, br. s). ELSD: 100%, ESI-MS: m/z 336 [M+H].$^+$ Example 8

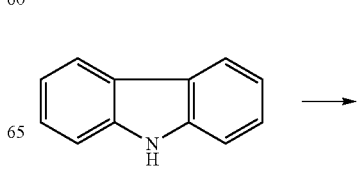

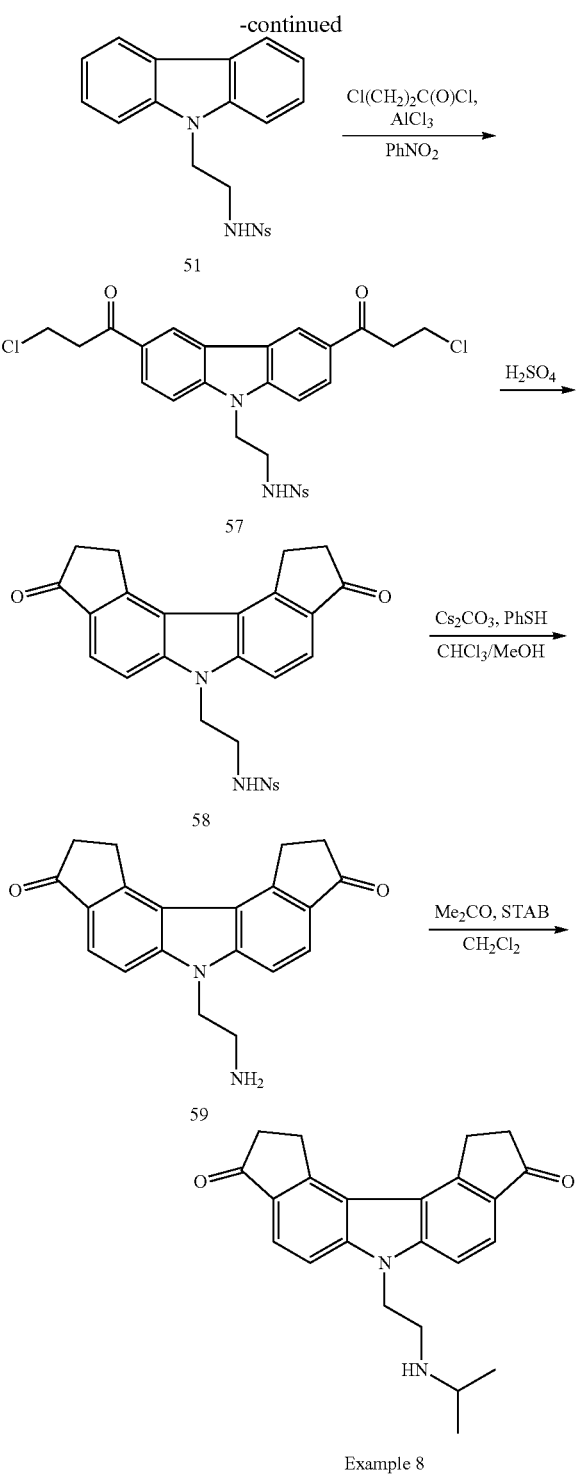

The synthesis of compound 51 was described in Example 7.

N-{2-[3,6-bis(3-chloropropanoyl)-9H-carbazol-9-yl]ethyl}-2-nitrobenzenesulfonamide (57)

Compound 51 (20.0 g, 50.6 mmol) was dissolved in PhNO$_2$ (130 mL) and the solution was cooled in an ice bath. Then AlCl$_3$ (34.0 g, 254.7 mmol) and after that, 3-chloropropionyl chloride (25.0 mL, 259.8 mmol) were added. The mixture was kept for 40 min (LC/MS monitoring), poured in a mixture of diluted HCl and ice, extracted with CHCl$_3$, and left for 16 h. The straw-colored precipitated obtained was filtered and washed with ether. Yield of 57: 18.47 g (63%).

N-[2-(3,9-dioxo-1,2,3,9,10,11-hexahydro-6H-dicyclopenta[c,g]carbazol-6-yl)ethyl]-2-nitrobenzenesulfonamide (58)

Sulfuric acid (200 mL) was heated to 40° C. Then, compound 57 (18.47 g, 32.12 mmol) was added in portions. The mixture was heated to 90° C. and kept at this temperature for 1.5-2 h (TLC monitoring, eluent: CH$_2$Cl$_2$-ethyl acetate, 4:1). The resulting mixture was poured onto ice. The grey precipitate was filtered off, washed on a filter with a mixture of CHCl$_3$-MeOH (4:1). The remaining precipitate (on a filter) was recrystallized with DMF, washed with CH$_3$CN and ether. Yield of pure 58: 2.2 g (14%).

6-(2-aminoethyl)-10,11-dihydro-1H-dicyclopenta[c,g]carbazole-3,9(2H,6H)-dione (59)

Compound 58 (2.2 g, 4.38 mmol) was suspended in a mixture of chloroform (200 mL) and methanol (200 mL). Then Cs$_2$CO$_3$ (4.3 g, 13.20 mmol) and at once PhSH (1.3 mL, 12.74 mmol) were added. The solution was refluxed for 18 h (LC/MS monitoring) and evaporated to dryness. Then, an aqueous solution of citric acid was added. The solution obtained was neutralized with an aqueous NaHCO$_3$ solution. The precipitate was filtered off, washed with CH$_3$CN and ether. The product isolated was used in the next step without purification.

6-[2-(isopropylamino)ethyl]-10,11-dihydro-1H-dicyclopenta[c,g]carbazole-3,9(2H,6H)-dione (Example 8)

Crude compound 59 (1.69 g) was suspended in CH$_2$Cl$_2$ (200 mL). Then acetone (4 mL) and STAB (3.4 g) were added. The mixture was stirred for 24 h (TLC monitoring, eluent: CHCl$_3$-MeOH, 9:1), then poured into an aqueous NaHCO$_3$ solution. Then, another portion of CH$_2$Cl$_2$ and MeOH was added. The organic layer was separated, evaporated, washed with MeCN and ether. Yield of Example 8: 0.759 g. For the preparation of hydrochloride, the isolated product was suspended in a mixture of CH$_2$Cl$_2$ and MeOH, then a solution of HCl in dioxane was added. The resulting mixture was evaporated to dryness, and ethanol was added to the residue. The ethanolic solution was refluxed and cooled, and the precipitate was filtered. Yield of compound Example 8 hydrochloride: 0.684 g. $^1$H-NMR (DMSO-D$_6$) spectrum: δ 1.24 (6H, d, J=6.6 Hz); 2.77-2.79 (4H, m); 3.34-3.43 (3H, m); 3.81-3.84 (4H, m); 4.91 (2H, t, J=7.3 Hz); 7.83 (2H, d, J=8.6 Hz); 7.91 (2H, d, J=8.6 Hz); 9.11 (2H, br. s). ELSD: 100%, ESI-MS: m/z 360 [M+H].$^+$ Example 9

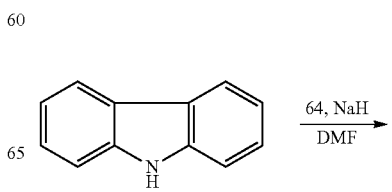

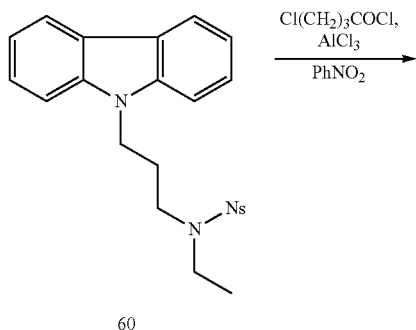
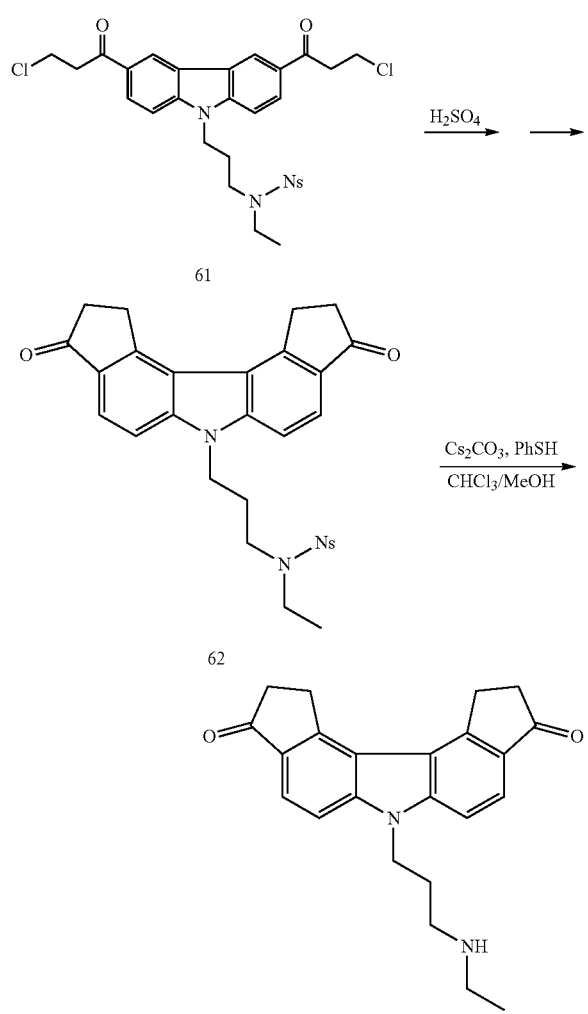
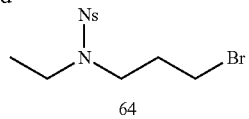

N-Ethyl-2-nitrobenzenesulfonamide (63)

A solution of 2-nitrobenzenesulfonyl chloride (140 g, 361 mmol) in ethyl acetate (250 mL) was added dropwise at room temperature to a mixture of 70% aqueous ethylamine (50 mL, 630 mmol), ethyl acetate (100 mL), $Na_2CO_3$ (67 g, 632 mmol), and water (250 mL). The reaction mixture was stirred for 4 h (TLC monitoring, $CH_2Cl_2$). The organic layer was separated, washed with water, with a solution of citric acid, dried with $Na_2SO_4$, and evaporated. The residue solidified into a white crystalline mass. The latter was triturated with hexane, filtered off, and dried to give 134 g (92%) of the product.

N-(3-Bromopropyl)-N-ethyl-2-nitrobenzenesulfonamide (64)

Compound 63 (7.8 g, 33.9 mmol) was dissolved in DMF (100 mL). 1,3-Dibromopropane (35 mL, 343.0 mmol) and then in portions NaH (2.7 g, 67.5 mmol) were added, whereupon the temperature rose to 50-60° C. The reaction mixture was stirred at this temperature for 1 h (TLC monitoring, $CH_2Cl_2$), carefully poured into ice/water mixture, and extracted with ethyl acetate. The extract was evaporated. The residue washed with hexane to remove the 1,3-dibromopropane. Compound 64 (9.7 g, 82%) was obtained as a viscous yellow oil.

N-[3-(9H-Carbazol-9-yl)propyl]-N-ethyl-2-nitrobenzenesulfonamide (60)

Carbazole (4.15 g, 24.8 mmol) and bromide 64 (9.7 g, 27.6 mmol) were dissolved in DMF (30 mL). NaH (2.0 g, 50.0 mmol, 2 eq) was added in portions, whereupon the temperature rose to 60° C. The reaction mixture was stirred for 1 h (TLC monitoring, hexane/ethyl acetate 3:2), poured into ice/water mixture, and extracted with ethyl acetate. The residue was triturated with ether. The yellow precipitate was filtered off and dried to afford 6.65 g (61%) of the product.

N-{3-[3,6-Bis(3-chloropropanoyl)-9H-carbazol-9-yl]propyl}-N-ethyl-2-nitrobenzenesulfonamide (61)

Compound 63 (6.65 g, 15.2 mmol) was dissolved in $PhNO_2$ (70 mL). The solution was cooled in an ice bath. $AlCl_3$ (12.2 g, 91.4 mmol) and then 2-chloropropionyl chloride (8.8 mL, 91.4 mmol) were added. The reaction mixture was kept for 40 min (LC/MS monitoring), diluted with water, and extracted with $CH_2Cl_2$. The extract was evaporated. The residue was purified by chromatography in a short thick column (eluent: $CH_2Cl_2$/ethyl acetate 0:100→50:50). The residue was triturated with ether, filtered off, and dried to give 7.60 g (81%) of a greenish crystalline product.

N-[3-(3,9-Dioxo-1,2,3,9,10,11-hexahydro-6H-dicyclopenta[c,g]carbazol-6-yl)propyl]-N-ethyl-2-nitrobenzenesulfonamide (62)

$H_2SO_4$ (110 mL) was heated to 40° C. Compound 61 (7.6 g, 12.3 mmol) was added in portions. The reaction mixture was heated to 100° C., kept at this temperature for 2 h (TLC monitoring, CH$_2$Cl$_2$/ethyl acetate 4:1), and poured into ice. The formed gray precipitate was filtered off. Then CHCl$_3$/MeOH 4:1 (500 mL) was poured into the filter. The solid on the filter dissolved, and the formed solution was transferred into a separation funnel. An aqueous solution of Na$_2$CO$_3$ was added. The organic layer was separated, dried with Na$_2$SO$_4$, and evaporated. Acetonitrile was added to the residue. A beige precipitate was filtered off, washed with acetonitrile, with ether, and dried to give 1.56 g (23%) of a beige crystalline product.

6-[3-(Ethylamino)propyl]-10,11-dihydro-1H-dicyclopenta[c,g]carbazole-3,9(2H,6H)-dione (Example 9)

Compound 62 (1.56 g, 2.86 mmol) was suspended in a mixture of CHCl$_3$ (80 mL) and MeOH (80 mL). Cs$_2$CO$_3$ (2.8 g, 8.59 mmol) and then immediately PhSH (0.87 mL, 8.53 mmol) were added. The reaction mixture was refluxed for 6 h (TLC monitoring, CHCl$_3$/MeOH 9:1) and evaporated to dryness. Aqueous citric acid was added. The solution was neutralized with a solution of NaHCO$_3$. The formed precipitate was filtered off, washed with ethyl acetate, acetonitrile, water, again with acetonitrile, and with ether to give 0.75 g (73%) of the product. The latter was transformed to its hydrochloride. After evaporation with 4M HCl in dioxane the residue was washed with MeOH to afford 0.59 g of the hydrochloride. $^1$H NMR (DMSO-d$_6$): δ 1.66 (3H, t, J=7.3 Hz); 2.09-2.17 (2H, m); 2.73-2.77 (4H, m); 2.86-2.91 (2H, m); 2.95-3.10 (2H, m); 3.77-3.80 (4H, m); 4.70 (2H, t, J=7.3 Hz); 7.80 (2H, d, J=8.6 Hz); 7.89 (2H, d, J=8.6 Hz); 8.83 (2H, br.s). ELSD: 100%, ESI-MS: m/z 360 [M+H]$^+$.

Examples 10 and 11

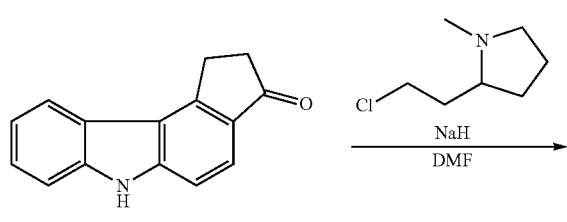

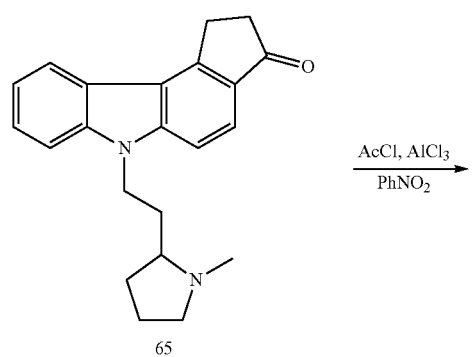

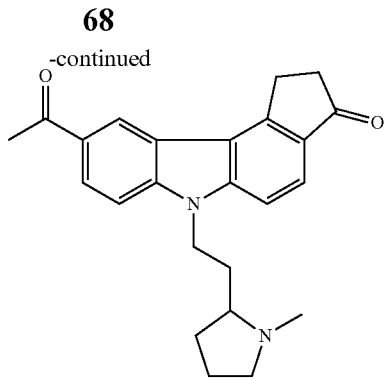

Example 10/11

The synthesis of compound 46 is described in Example 6

6-[2-(1-methylpyrrolidin-2-yl)ethyl]-1,6-dihydrocyclopenta[c]carbazol-3(2H)-one (65)

Carbazole 46 (0.4 g, 1.81 mmol) was dissolved in CH$_2$Cl$_2$ (7 mL), then NaH (0.22 g, 5.50 mmol) was added. The mixture was stirred at room temperature for 5-10 min, and 2-(2-chloroethyl)-1-methylpyrrolidine hydrochloride (0.4 g, 2.17 mmol) was added. The mixture was heated to 60° C. and kept at this temperature for 4 h (TLC monitoring, eluent: CHCl$_3$-MeOH, 9:1). The resulting mixture was poured into water. The product was extracted with ethyl acetate, dried over Na$_2$SO$_4$, and evaporated. The residue was triturated with ether. The precipitate was filtered off. Yield of 65: 0.365 g (61%)—S-isomer and 0.336 g (55%)—R-isomer.

9-acetyl-6-[2-(1-methylpyrrolidin-2-yl)ethyl]-1,6-dihydrocyclopenta[c]carbazol-3(2H)-one (Examples 10 and 11)

Compound 65 (0.336 g, 1.00 mmol) was dissolved in PhNO$_2$ (7 mL). The solution was cooled down in an ice bath. Then, AlCl$_3$ (0.67 g, 5.02 mmol) and after that, AcCl (0.36 mL, 5.04 mmol) were added. The resulting mixture was kept for 40 min (LC/MS monitoring), diluted with water, neutralized with aqueous NaHCO$_3$ solution, extracted with CHCl$_3$, and evaporated. The product was purified on a short thick column, eluent: 100:0→90:10. Yield of product: 0.307 g (82%) (R); S-isomer was obtained similarly (77%).

Example 10

$^1$H-NMR (DMSO-D$_6$) spectrum: δ 1.69-1.79 (1H, m); 1.86-2.01 (2H, m); 2.07-2.24 (2H, m); 2.42-2.56 (1H, m); 2.73 (3H, s); 2.75 (3H, d, J=5.12 Hz); 2.79-2.82 (2H, m); 2.96-3.05 (1H, m); 3.36-3.43 (1H, m); 3.49-3.57 (1H, m); 3.64-3.67 (2H, m); 4.62-4.75 (2H, m); 7.80 (1H, d, J=8.6 Hz); 7.87 (1H, d, J=8.6 Hz); 7.96 (1H, d, J=8.6 Hz); 8.19 (1H, dd, J=8.6 Hz, J=1.5 Hz); 8.70 (1H, d, J=1.5 Hz); 10.63 (1H, br. s). ELSD: 100%, ESI-MS: m/z 374 [M+H]$^+$.

Example 11

$^1$H-NMR (DMSO-D$_6$): δ 1.69-1.79 (1H, m); 1.86-2.01 (2H, m); 2.05-2.24 (2H, m); 2.40-2.46 (1H, m); 2.73 (3H, s); 2.75 (3H, d, J=5.12 Hz); 2.79-2.82 (2H, m); 2.98-3.02 (1H, m); 3.36-3.43 (1H, m); 3.47-3.57 (1H, m); 3.63-3.66 (2H, m); 4.62-4.75 (2H, m); 7.80 (1H, d, J=8.6 Hz); 7.87 (1H, d, J=8.6 Hz); 7.96 (1H, d, J=8.8 Hz); 8.18 (1H, dd, J=8.8 Hz, J=1.4 Hz); 8.69 (1H, d, J=1.4 Hz); 10.72 (1H, br. s). ELSD: 100%, ESI-MS: m/z 374 [M+H]⁺.

Synthesis of Example 50

Step 2. 1-oxo-2,3-dihydro-1H-inden-4-yl trifluoromethanesulfonate (87)

Triflic anhydride (152 g, 0.54 mol) was added dropwise to solution 80 g of compound 86 and 60 g of NEt₃ in 1 L CH₂Cl₂ at 0° C. The resulting mixture was refluxed for 2 h, cooled to room temperature, filtered, washed with water (0.5

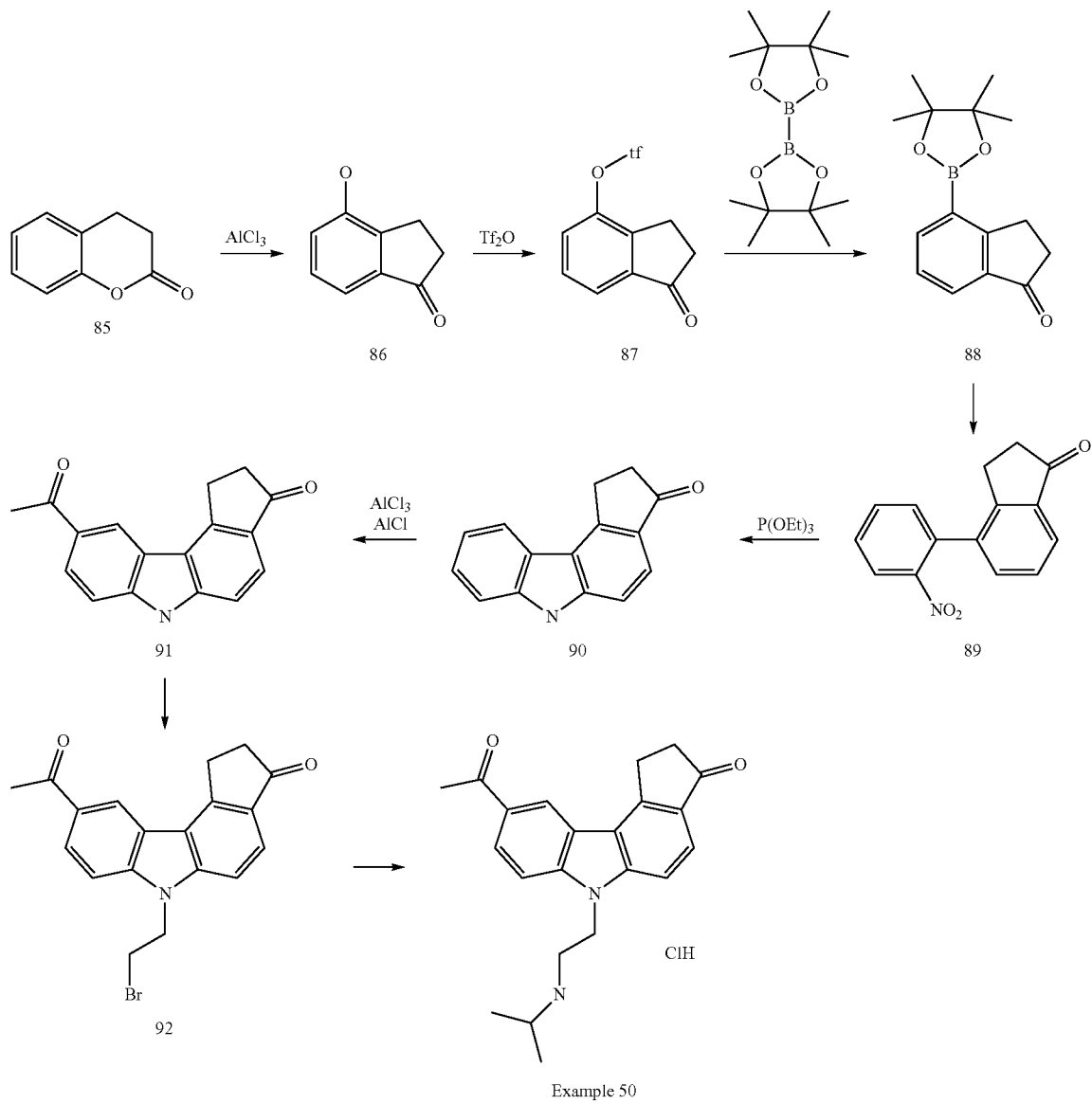

Step 1. 4-hydroxyindan-1-one (86)

Chromanone 85 (100 g, 0.68 mol) was added dropwise to mixture 150 g NaCl and 500 g AlCl₃ at 150° C. The resulting mixture was heated to 180° C., then stirred for 8 h. The mixture then was cooled to room temperature and 1 kg of crushed ice was added with intensive stirring. After homogenization, the mixture was filtered, washed with 1L cold water, and dried to give about 80 g (80%) 4-hydroxyindan-1-one (86) as gray solid.

L), aqueous citric acid (50 g/0.5 L), brine (0.5 L), dried on Na₂SO₄, and evaporated to give about 100 g (67%) of compound 87 as dark liquid.

Step 3. 4-(4,4,5,5-tetramethyl-1,3,2-dioxaborolan-2-yl)indan-1-one (88)

A mixture consisting of potassium acetate (48 g, 0.5 mol, 1.5 eq), triflate 87 (100 g, 0.36 mol, 1.1 eq), bis(pinacolo) diborane (100 g, 0.38 mol, 1.2 eq), PPh₃ (5 g, 0.02 mol, 0.06 eq), and PdCl₂(PPh₃)₂ (6.9 g, 0.01 mol, 0.03 eq) in degassed toluene (2 L) was refluxed under argon atmosphere overnight. The resulting mixture was evaporated to dryness and chromatographed with eluted by EtOAc/hexanes 1/5. Fractions containing desired product was collected and evaporated to give about 50 g (57%) of compound 88 as light-yellow solid.

Step 4. 4-(2-nitrophenyl)-indan-1-one (89)

Degassed toluene (0.5 L), borolan 88 (10 g, 39 mmol), 2-chloro-1-nitrobenzene (6.3 g, 40 mmol), Pd(PPh$_3$)$_4$ (3 g, 2.6 mmol) and 2M Na$_2$CO$_3$ (200 mL) were mixed under a rapid flow of argon, and the resulting mixture was refluxed overnight. Water (200 mL) and EtOAc (500 mL) were added. The aqueous layer was separated and extracted with EtOAc (2×500 mL), and the combined extracts dried over Na$_2$SO$_4$. The solvent was evaporated at reduced pressure and the crude product purified by column chromatography (20% EtOAc in hexanes) to give 9 g (91%) of the biphenyl intermediate 89 as a yellow solid.

Step 5. 1,2-dihydro-6H-cyclopenta[c]carbazole-3-one (90)

Biphenyl 89 (9 g, 35 mmol) and triethylphosphite were added to a sealed bomb and heated at 120° C. overnight. After cooling to room temperature, the mixture was filtered to give 4 g of 1,2-dihydro-6H-cyclopenta[c]carbazole-3-one. Precipitation with diethyl ether yielded an additional 2 g of desired product. Common yield 90 as yellow powder was 77.5%.

Step 6. 9-acetyl-1,2-dihydro-6H-cyclopenta[c]carbazole-3-one (91)

1,2-dihydro-6H-cyclopenta[c]carbazole-3-one 90 (6 g, 27.1 mmol) was suspended in dry CH$_2$Cl$_2$ (100 mL). Anhydrous AlCl$_3$ (6 g, 45 mmol) was added with stirring on ice bath, followed by the dropwise addition of AcCl (2.4 mL, 33.2 mmol). The reaction mixture was stirred at about 5° C. for 24 h, and poured into ice water. The precipitated grey solid was filtered off, washed with water (2×100 mL), acetone (3×50 mL), diethyl ether (3×50 mL) to give 4 g (56.3%) of 9-acetyl-1,2-dihydro-6H-cyclopenta[c]carbazole-3-one 91.

Step 7. 9-acetyl-1,2-dihydro-6-(2-bromoethyl)-cyclopenta[c]carbazole-3-one (92)

NaH (2 g of 60%, 50 mmol) was added to a suspension of compound 91 (4 g, 15.2 mmol) in dry DMF (100 mL), and the mixture was stirred at room temperature about 1 h until the evolution of hydrogen ceased. 1,2-dibromoethane (20 g, 106 mmol) was added in dropwise under nitrogen. The reaction mixture was stirred for 30 min at room temperature, then at 60° C. for 24 h, and poured into ice water (300 mL). The precipitated grey solid was filtered off and the crude product purified by column chromatography (CHCl$_3$) to give 2 g of starting material and about 1 g (2.7 mmol, 35.5% from converted material) of the alkylated carbazole 92 as a cream solid.

Step 8. 9-acetyl-1,2-dihydro-6-(2-(2-propyl)aminoethyla)-cyclopenta[c] carbazole-3-one hydrochloride (Example 50)

Bromide 92 (1 g, 2.7 mmol) and 2-propylamine were added to sealed bomb and heated at 180° C. overnight. After cooling to room temperature, the mixture was evaporated to dryness, the residue was worked up with 100 ml saturated water solution of sodium bicarbonate and filtered. Filter cake was purified by column chromatography (CHCl$_3$/MeOH 10/1). Fractions containing desired product were collected, evaporated to dryness, diluted with 40% water HCl (10 mL), evaporated to dryness and reevaporated with toluene (2×100 mL) to give 200 mg (0.52 mmol, 19%) of 9-acetyl-1,2-dihydro-6-(2-(2-propyl)aminoethyl)-cyclopenta[c] carbazole-3-one hydrochloride (Example 50) as a gray solid.

1H-NMR (DMSO-d$_6$): 1.23 d (6H), 2.74 s (3H), 2.83 m (2H), 3.67 m (2H), 4.87 m (2H), 7.85 dd (2H), 7.97 d (1H), 8.22 d (1H), 8.71 s (1H), 8.9-9.2 wide s (2H).

Synthesis of Example 51

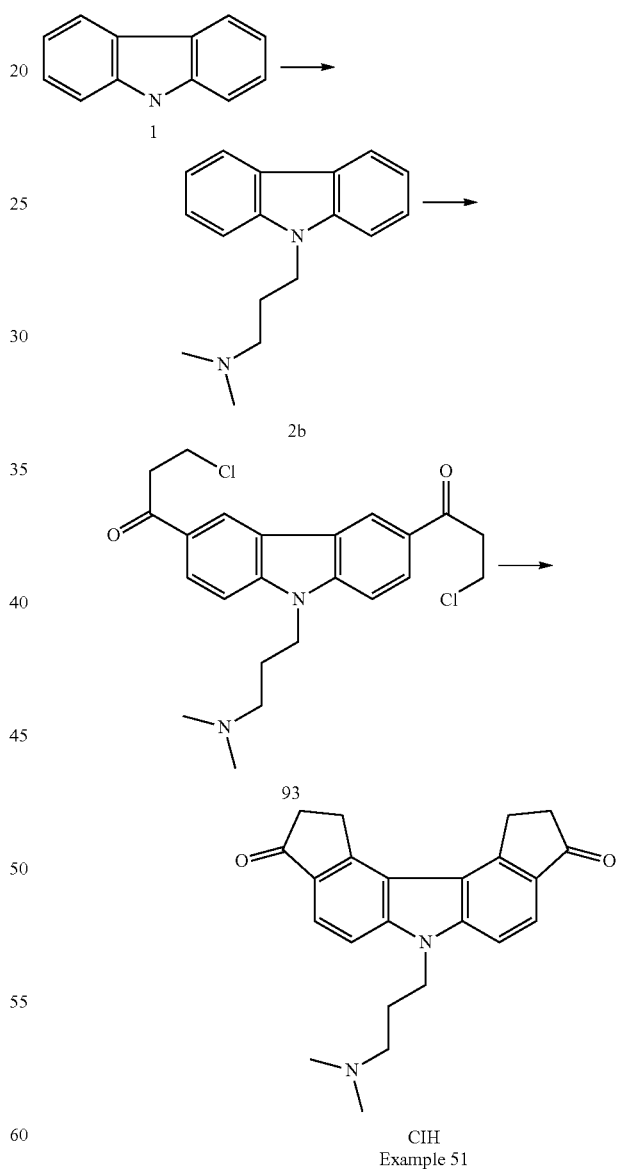

Step 1. 9-(3-dimethylaminopropyl)-carbazole (2b)

NaH (14.4 g of 60%, 360 mmol) was added portion-wise under argon to a suspension of carbazole 1 (20 g, 119.8 mmol) in dry DMF (200 mL). The mixture was stirred at room temperature for about 1 h until the evolution of the hydrogen ceased. 3-Dimethylaminopropylchloride hydrochloride (28 g, 180 mmol) was added portion-wise at room temperature. The reaction mixture was stirred for 20 min at room temperature, then at 60° C. for 3 hrs, and poured into cold water (500 mL). The product was extracted with EtOAc (2×500 mL). The organic layer was back extracted with 10% HCl (200 mL) and the acidic layer was extracted with EtOAc to remove the unreacted carbazole. Saturated ammonia (200 mL) was added and the product extracted again with EtOAc. Evaporation of the solvent afforded 25 g (99 mmol, 83%) of 9-(2-dimethylaminopropyl)carbazole 2b as a brown oil.

Step 2. 3,6-di(4-chloropropan-2-one-yl)-9-(2-dimethylaminopropyl)carbazole (93)

9-(2-Dimethylaminopropyl)carbazole 2b (25 g, 99 mmol) was dissolved in dry $CH_2Cl_2$ (150 mL). Anhydrous $AlCl_3$ (40 g, 300 mmol) was added portion-wise with stirring and cooling in an ice bath. 3-Chloro-propionyl chloride (30 mL, 312 mmol) was added dropwise, while maintaining the internal temperature below 5° C. The reaction mixture was stirred at this temperature overnight, poured into crushed ice and extracted with $CHCl_3$/MeOH 1/1 (3×500 mL). The extracts were evaporated to dryness, and the resulting green oil was triturated with diethyl ether (2×250 mL) to give 20 g (46 mmol, 47%) of 3,6-di(3-chloropropionyl)-9-(2-dimethylaminopropyl)-carbazole 93 as gray powder.

Step 3. 6-(3-Dimethylaminopropyl)-1,2,10,11-tetrahydro-6H-bis-(cyclopenta[c]carbazol-3,9-dione (Example 51)

3,6-Di-(3-chloropionyl)-9-(2-dimethylaminopropyl) carbazole 93 (20 g, 46 mmol) was added portion-wise to trifluoromethanesulfonic acid (100 g) with stirring at room temperature and the reaction mixture was heated to 95° C. overnight. After cooling to room temperature, the reaction mixture was poured into ice water. The precipitate was filtered off, worked up with saturated sodium bicarbonate, and filtered off again. The resulting filter cake contained about 80% desired product and 20% isomer. After a single crystallization from methanol, the precipitate was worked up with 4N HCl/dioxane (100 ml), evaporated to dryness and recrystallized from EtOH to give about 2.8 g (7.1 mmol, 15.4%) of 95% Example 51 as white solid.

LCMS: 100%; 1H-NMR (DMSO-$d_6$) 95%: 2.18 m (2H), 2.71 s (6H), 2.78 m (4H), 3.15 m (2H), 3.83 m (4H), 4.68 m (2H), 7.85 dd (4H), 10.0 br s (1H).

Alternative Synthesis of Examples 15 and 17 and Synthesis of Example 20

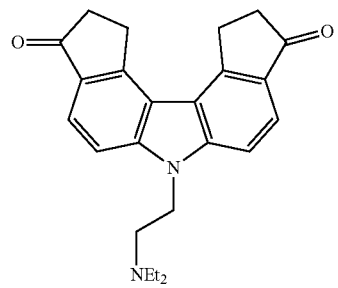

Example 15

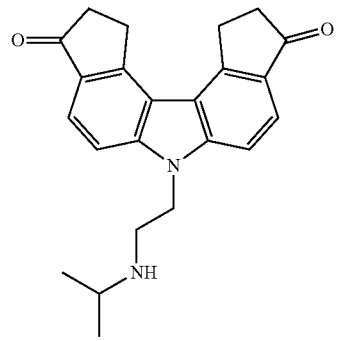

Example 17

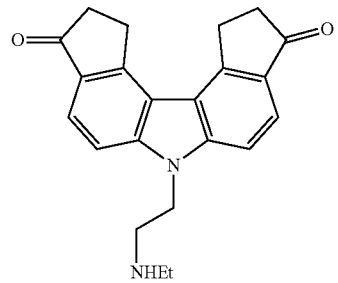

Example 20

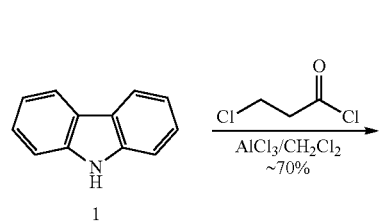  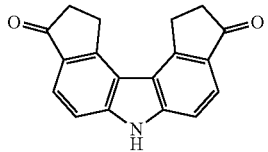

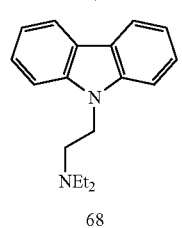 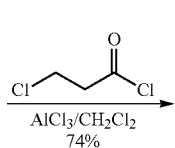 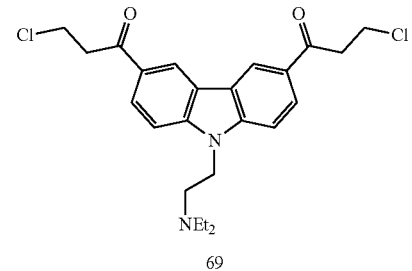  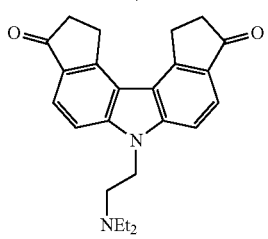

Example 15

Unless otherwise noted, reagents and solvents were used as received from commercial suppliers. Proton nuclear magnetic resonance spectra were obtained on a Bruker ARX 400 spectrometer at 400 MHz. The solvent peak was used as the reference peak for proton spectra. The progress of reactions was controlled by TLC or/and LC-MS analysis.

9-(2-Diethylaminoethyl)-carbazole (68)

NaH (14.4 g of 60%, 360 mmol, 3 eq) was added portion-wise under argon to a suspension of carbazole (1) (20 g, 119.8 mmol, 1 eq) in dry DMF (200 mL). The mixture was stirred at room temperature for 30 min until the evolution of the hydrogen ceased. 2-Diethylaminoethylchloride hydrochloride (31 g, 180 mmol, 1.5 eq) was added in portion-wise at room temperature. The reaction mixture was stirred for 20 min at room temperature, then at 60° C. for 3 hrs (TLC monitoring), and poured into cold water (1 L). The product was extracted with EtOAc (5×200 mL); the organic layer was back extracted with 10% HCl (400 mL) and acidic layer was extracted with EtOAc to remove the un-reacted carbazole. The pH of aqueous layer was adjusted to about 9 with $K_2CO_3$ and the product extracted again with EtOAc. Evaporation of the solvent afforded 29.5 g (93%) of 9-(2-diethylaminoethyl)carbazole (68) as a brown oil.

3,6-Di(4-chloropropan-2-one-yl)-9-(2-diethylaminoethyl)carbazole hydrochloride (69)

9-(2-Diethylaminoethyl)carbazole (68) (17.9 g, 67.3 mmol, 1 eq) was dissolved in dry dichloromethane (150 mL). Anhydrous $AlCl_3$ (45 g, 337 mmol, 5 eq) was added portion-wise with stirring and cooling in an ice bath. 3-chloro-propionyl chloride (32.4 mL, 337 mmol, 5 eq) was added dropwise, while maintaining the internal temperature below 5° C. The reaction mixture was stirred at this temperature for 15 h, poured into cold 3% HCl (violent foaming should be avoided) and extracted with $CHCl_3$ (5×500 mL). The extracts were evaporated and the resulted green oil triturated with diethyl ether (5×50 mL) to give 24 g (74%) of 3,6-di(3-chloropropionyl)-9-(2-diethylaminoethyl)-carbazole hydrochloride (69) as dark grey solid.

$^1$H-NMR (DMSO-$d_6$): 1.27 (t, 6H), 2.72 (q, 4H), 3.75 (m, 6H), 4.02 (m, 4H), 5.00 (t, 2H), 8.00 (d, 2H), 8.17 (d, 2H), 9.16 (s, 2H), 11.42 (s, 1H).

6-(3-Diethylaminoethyl)-1,2,10,11-tetrahydro-6H-bis-(cyclopenta[c]carbazol-3,9-dione (70)

3,6-Di-(3-chloropropionyl)-9-(2-diethylaminoethyl)carbazole hydrochloride (69) (5 g, 10.33 mmol, 1 eq) was added portion-wise to trifluoromethanesulfonic acid (50 g, 333 mmol, 32 eq) with stirring at room temperature and the reaction mixture was heated to 95° C. overnight. After cooling to room temperature, the reaction mixture was poured into ice water. The pH of the aqueous solution was adjusted to 9 with 10% NaOH and the product extracted with EtOAc/THF=3/1 mixture. The solvents were evaporated out and the crude product purified by column chromatography (10% EtOH in EtOAc) to give 1.12 g (29%) of pure intermediate 70 as white solid.

MS(ESI): m/z=375.3 [M+H]$^+$; $^1$H-NMR (DMSO-$d_6$): 0.70 (t, 6H), 2.41 (q, 4H), 2.68 (m, 6H), 3.73 (m, 4H), 4.55 (t, 2H), 7.77 (s, 4H).

Example 15

Intermediate 70 (1.12 g, 2.99 mmol, 1 eq) was dissolved in $CH_2Cl_2$ (20 mL) and 10% HCl solution in ethanol (3.4 g, 93.15 mmol, 30 eq) was added causing formation of a voluminous precipitate. The solvents were evaporated at reduced pressure and the residue triturated with hot MeOH to give 1.17 g (98%) of Example 15 as an off-white solid.

Purity: 97.3% by HPLC; MS(ESI): m/z=375.3 [M−HCl+H]⁺; m.p.=312.1-314.7° C.

Examples 17 and 20 are prepared by an identical process using the proper chloroamine, i.e., (CH₃)₂CH—NH—H₂CH₂—Cl or (C₂H₅)NHCH₂CH₂—Cl.

Alternative Synthesis of Example 7 (Compound 6h)

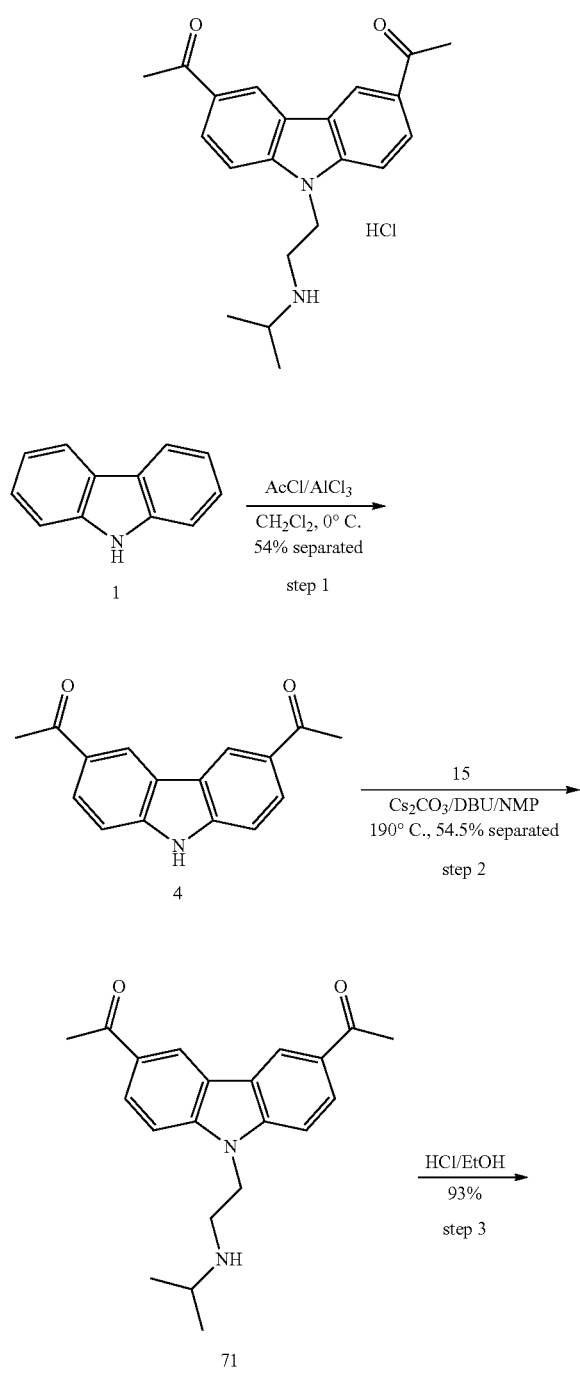

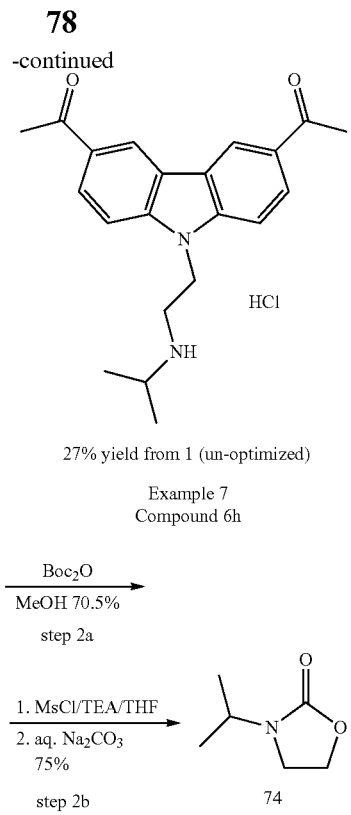

27% yield from 1 (un-optimized)

Example 7
Compound 6h

Experimental

Unless otherwise noted, reagents and solvents were used as received from commercial suppliers. Proton nuclear magnetic resonance spectra were obtained on a Bruker ARX 400 spectrometer at 400 MHz. The solvent peak was used as a reference peak for proton spectra. TLCs were run on silica, unless otherwise noted.

3,6-Diacetylcarbazole (4)

Carbazole (20 g, 0.12 mol, 1 eq) was suspended in anhydrous CH₂Cl₂ (300 mL) under argon and the resulting mixture cooled to 0° C. AlCl₃ (95.5 g, 0.72 mol, 6 eq) was added to the mixture followed by the drop-wise addition of acetyl chloride (25.5 mL, 0.36 mol, 3 eq), while maintaining the internal temperature at about 0° C. After 3 hours stirring at 0° C., another portion of acetyl chloride (5 mL, 0.07 mol, 0.6 eq) was added and the stirring continued for another 2 hours.

The reaction mixture was poured into ice while stirring. The solid was collected by filtration, washed with CH₂Cl₂ then water and dried in a vacuum oven at 50° C. Yield 16.3 g (54%) of carbazole 4. The filtrate and washings were combined and extracted with CH₂Cl₂ (3×300 mL). The CH₂Cl₂ extracts were washed with saturated NaHCO₃ (1×300 mL) and brine (1×300 mL). After drying over Na₂SO₄, the filtrate was evaporated to dryness to give the crude product, which was used without further purification. MS(ESI): m/z=252.0 [M+H]⁺

2-N-Boc-2-N-isopropylaminoethanol (14)

(Boc)₂O (50.8 g, 0.23 mol, 2 eq) was added to a solution of 2-N-isopropylaminoethanol (72) (22.3 mL, 70%, 0.136 mol) in MeOH (200 mL). The reaction mixture was stirred at ambient temperature for 4 hours then diluted with water (1.2 L) and the product extracted with EtOAc (4×400 mL). The combined EtOAc extracts were washed with brine (1×400 mL) and dried over Na₂SO₄. The solvent was evaporated out and the crude product purified by column (eluent Hexanes: EtOAc from 4:1 to 1:1) to give 19.5 g (70.5% yield) of pure 73 as viscous oil.

3-Isopropyl-2-oxazolidinone (74)

MsCl (8.5 mL, 0.109 mol) was added dropwise to a solution of the alcohol (73) (18.5 g, 0.091 mol) and TEA (19 mL, 0.137 mol) in anhydrous THF (200 mL) cooled to −20° C. with vigorous stirring. The reaction was allowed to warm up slowly to ambient temperature (3 hours). The solids were removed by filtration and washed with THF (20 mL). Saturated Na₂CO₃ (100 mL) was added to the filtrate and the resulting mixture stirred at ambient temperature overnight, then diluted with water (200 mL) and extracted with EtOAc (3×200 mL). The combined EtOAc extracts were washed with 1% HCl (1×200 mL), brine (1×200 mL) an dried over Na₂SO₄. The solvent was evaporated out to give 8.8 g (75% yield) of cyclic carbamate (74), which was used further without purification.

MS(ESI): m/z=130.1 [M+H]⁺

3,6-Diacetyl-9-(2-N-isopropylaminoethyl)-carbazole (71)

A mixture of 3,6-diacetylcarbazole (4) (15.12 g, 0.06 mol), 3-isopropyl-2-oxazolidinone (74) (7.80 g, 0.06 mol), Cs₂CO₃ (39.2 g, 0.12 mol), and DBU (9 mL, 0.06 mol) in NMP (150 mL) was stirred at 190° C. for 24 hours, then poured into H₂O (500 mL) and extracted with EtOAc (3×300 mL). The combined EtOAc extracts were washed with brine (2×200 mL) and dried over Na₂SO₄. The solvent was evaporated and the crude product purified by column chromatography (eluent—(5 to 20%) MeOH (containing 0.1% of NH₃H₂O)/EtOAc). The first fractions contained the un-reacted starting material (~1.7 g). The pure fractions were combined and solvent evaporated to dryness to give 9.36 g (contained 20% EtOAc by NMR) of pure (71). The less pure fractions were combined, evaporated to dryness and the residue triturated with EtOAc to give another 3.47 g of the pure product. Total yield—54.5% (after subtracting the amount of EtOAc); (61.6% yield based on reacted starting material).

MS(ESI): m/z=337.1 [M+H]⁺

Compound 6h

Intermediate (71) (3.47 g, 0.0103 mol) was dissolved in CH₂Cl₂ (30 mL) and the resulting solution cooled to about 5° C. 10% HCl/EtOH solution (5.6 g, 0.0153 mol) was added dropwise with stirring. After 40 minutes the solvent was removed under vacuum, the residue was dried under high vacuum at 40° C. to give 3.5 g (93% yield) of 6h. Similarly, the other crop of 71 (9.36 g, 20% EtOAc) was converted into 6h.

Analysis Data: Purity: 99.5% by HPLC; MS(ESI): m/z=337.3 [M−HCl+H]⁺; m.p.=292.7-294.1° C.

Alternative Synthesis of Example 4

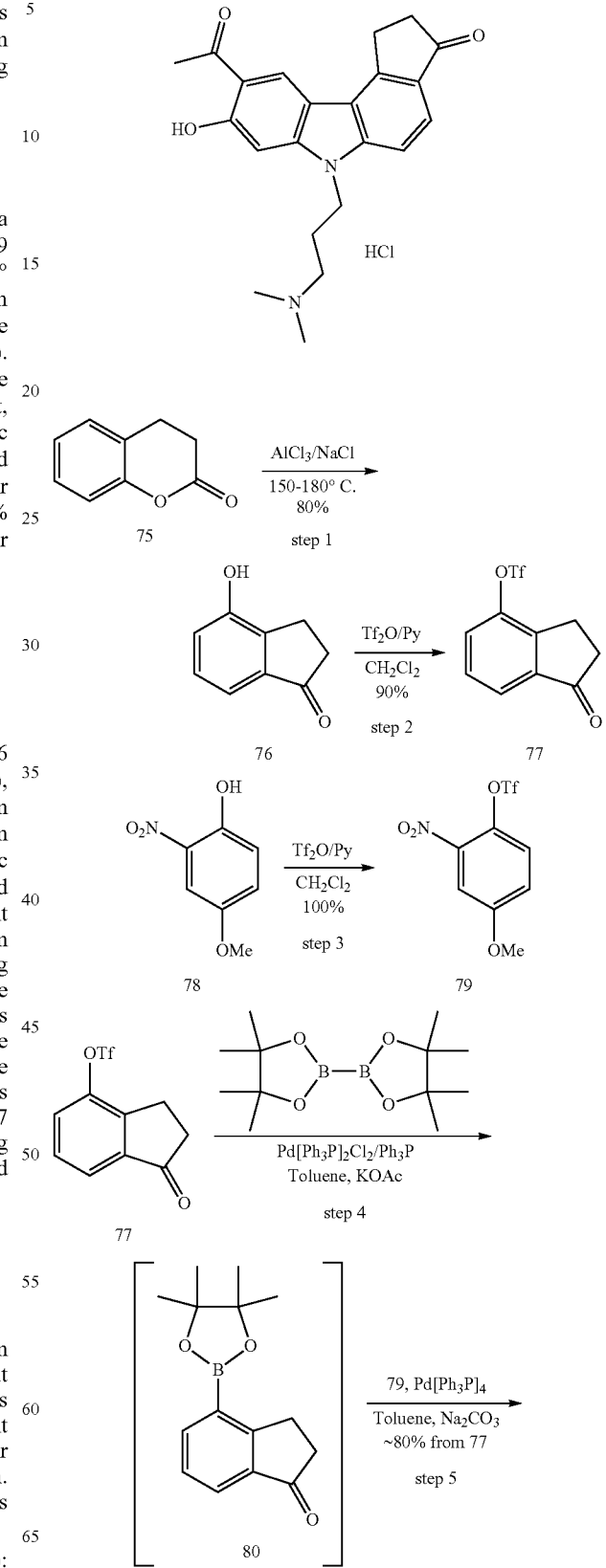

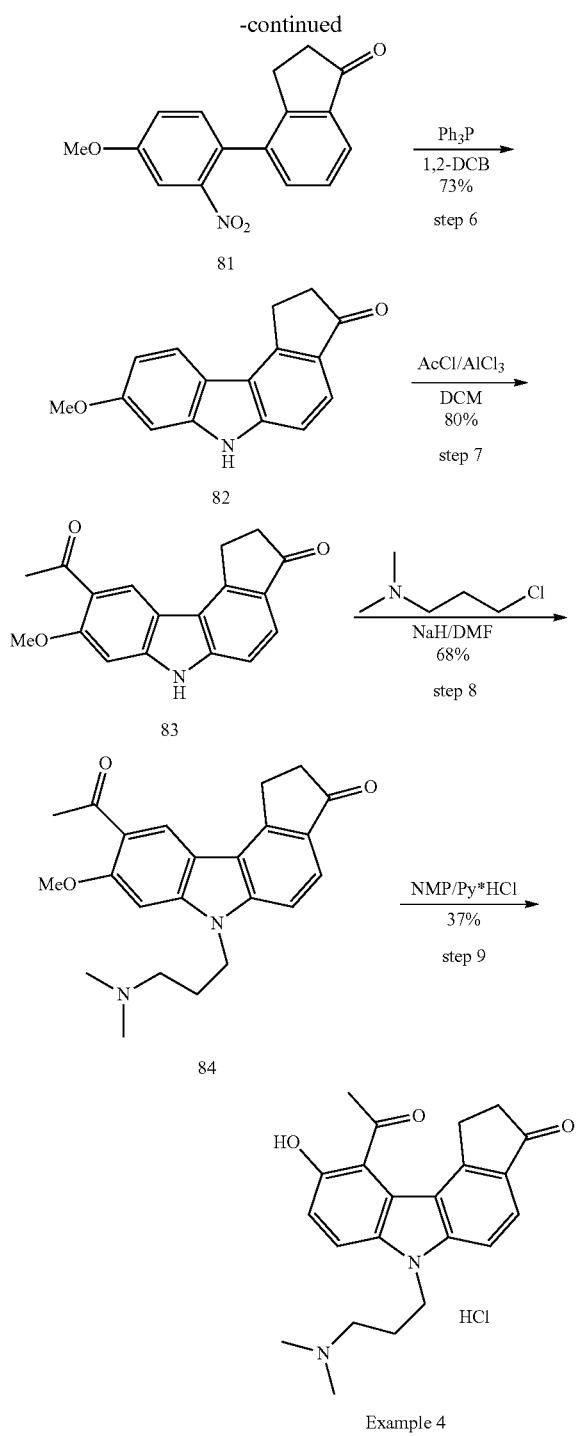

Step 3.

Triflate (79) was synthesized in the same manner with quantitative yield, starting from 50 g of 4-methoxy-2-nitrophenol (78).

Steps 4 and 5.

Following the protocol for a one-pot synthesis of biphenyl compounds from *Synthetic Communications,* 2006, 36 p. 3809-3820, intermediate (81) was obtained in 80% yield starting from 60 g of triflate (77).

Step 6.

The cyclization of the biphenyl intermediate (81) by heating with excess of triphenylphosphine in 1,2-dichlorobenzene was carried out on a small scale first to afford the expected carbazole (82) with ~50% yield (un-optimized) after precipitation from the reaction mixture with ether. The same reaction was scaled up to 42 g of (81), yielding 27 g (73% yield) of pure (82).

Step 7.

The acetylation of the intermediate (82) (27.8 g scale) was carried out in CH$_2$Cl$_2$ according to the standard protocol to give 26 g (80% yield) of the intermediate (83).

Step 8.

After an exhaustive extraction with a 1:1 mixture of EtOAc/THF, about 68% yield of the crude product (84), containing a baseline impurity by TLC, was obtained. It was used for the de-methylation step without further purification.

Step 9.

The removal of the methyl group from (84) was accomplished by heating the substrate in a 1:1 mixture of Py*HCl/NMP at 190° C. for 10 h. After purification by column chromatography, 7.8 g (37% yield) of Example 4 (free base) was obtained. It was treated with 10% HCl solution in EtOH to give 8.4 g of pure Example 4.

Experimental

Unless otherwise noted, reagents and solvents were used as received from commercial suppliers. Proton nuclear magnetic resonance spectra were obtained on a Bruker ARX 400 spectrometer at 400 MHz. The solvent peak was used as the reference peak for proton spectra. The progress of reactions was controlled by TLC or/and LCMS analysis.

4-Hydroxy-1-indanone (76)

Anhydrous aluminum chloride (550 g, 4.135 mol, 4 eq) and sodium chloride (105 g, 1.795 mol, 2.7 eq) were mixed and heated to 150° C. Dihydrocoumarin (75) (100 g, 675.7 mol, 1 eq) was added slowly maintaining the internal temperature between 150-160° C. After the addition, the temperature was increased to 200° C. and the reaction mixture stirred for 1.5 h, and while hot, poured into a porcelain dish to cool. The solidified mass was broken and added to a vigorously stirred mixture of ice and water (4 L) containing 400 mL conc. HCl. The resulting suspension was stirred for 1 h, filtered, washed with water and dried to give 85 g (85%) of crude 4-hydroxy-1-indanone (76) as a grey solid. It was sufficiently pure to be used in the next step.

Trifluoromethanesulfonic acid 1-oxoindan-4-yl ester (77)

Trifluoromethanesulfonic acid anhydride (72.3 mL, 429.7 mmol, 1.2 eq) was added to a suspension of 4-hydroxy-1-indanone (77) (53 g, 358.1 mmol, 1 eq) in dry CH$_2$Cl$_2$ (450 mL) and pyridine (87 mL, 1074 mmol, 3 eq), while maintaining the internal temperature below 5° C. The reaction mixture was allowed to warm up to room temperature and Step 1.

4-Hydroxy-1-indanone (76) was synthesized by aluminum chloride induced re-cyclization of dihydrocoumarin (75), according to *Org. Lett.,* 2007, 9(15), p. 2915-2918. The reaction was performed on 100 g of (75) to furnish (76) with 85% yield.

Step 2.

The indanone (76) was converted to triflate (77) with 90% yield by reaction with triflic anhydride in CH$_2$Cl$_2$ in the presence of Py, followed by flash chromatography.

the stirring continued for 1 h. CH$_2$Cl$_2$ (300 mL) and water (100 mL) were added to the reaction mixture, the organic layer was separated, washed subsequently with 2% HCl solution (3×100 mL), and saturated NaHCO$_3$ (2×100 mL), and dried over Na$_2$SO$_4$. CH$_2$Cl$_2$ was evaporated out and the crude product purified by flash chromatography (5% to 10% EtOAc in Hexanes) to give 90 g (90%) of pure 77 as a brown liquid.

$^1$H-NMR (DMSO-d$_6$): 2.76 (t, 2H), 3.19 (t, 2H), 7.65 (dd, 1H), 7.94 (2d, 2H).

Trifluoromethanesulfonic acid
4-methoxy-2-nitrophenyl ester (78)

Trifluoromethanesulfonic acid anhydride (60 mL, 350 mmol, 1.2 eq) was added to a solution of 4-methoxy-2-nitrophenol (78) (50.57 g, 298.9 mmol, 1 eq) in dry CH$_2$Cl$_2$ (550 mL) and pyridine (72.5 mL, 897 mmol, 3 eq), while maintaining the internal temperature below 5° C. The reaction mixture was allowed to warm to room temperature and stirred overnight. Water (100 mL) was added to the reaction mixture, the organic layer was separated, washed subsequently with solutions of 7% HCl solution, then saturated NaHCO$_3$, and dried over Na$_2$SO$_4$. The CH$_2$Cl$_2$ solution was filtered through a pad of SiO$_2$ and the solvent removed in vacuum to give 89 g (99%) of the pure triflate 79 as a pale yellow liquid.

$^1$H-NMR (DMSO-d$_6$): 3.92 (s, 3H), 7.49 (dd, 1H), 7.71 (d, 1H), 7.81 (d, 1H).

4-(4-Methoxy-2-nitrophenyl)-indan-1-one (81)

A mixture consisting of potassium acetate (29.44 g, 0.3 mol, 1.5 eq), triflate (77) (61.44 g, 0.22 mol, 1.1 eq), bis(pinacolo)diborane (60.94 g, 0.24 mol, 1.2 eq), PPh$_3$ (3.15 g, 0.012 mol, 0.06 eq), and PdCl$_2$(PPh$_3$)$_2$ (4.21 g, 0.006 mol, 0.03 eq) in degassed toluene (2 L) was refluxed under argon atmosphere overnight. The triflate (79) (60.24 g, 0.2 mol, 1 eq), Pd(PPh$_3$)$_4$ (11.55 g, 0.01 mol, 0.05 eq), and 2M Na$_2$CO$_3$ (800 mL) were added consecutively to the same flask under a rapid flow of argon, and the resulting solution was refluxed overnight. Water (200 mL) and EtOAc (500 mL) were added, the aqueous layer was separated and extracted with EtOAc (2×500 mL) and the combined extracts dried over Na$_2$SO$_4$. The solvent was evaporated at reduced pressure and the crude product purified by column chromatography (20% EtOAc in hexanes) to give 44 g (80%) of the biphenyl intermediate (81) as a yellow solid.

8-Methoxy-1,2-dihydro-6H-cyclopenta[c]carbazole-3-one (82)

A solution of 4-(4-methoxy-2-nitrophenyl)-indan-1-one (81) (42 g, 148.4 mmol, 1 eq) and triphenylphosphine (116 g, 445 mmol, 3 eq) in o-dichlorobenzene (400 mL) was refluxed with vigorous stirring for 4 h, then cooled to 0° C. Diethyl ether (4 L) was added and the precipitate filtered off, washed with diethyl ether (3×100 mL) and dried to give 17 g (46%) of (82). The filtrate was evaporated out and the residue washed with cold MeOH (5×100 ml) to give an additional 10 g (27%) of the carbazole (82). Total yield 27 g (73%).

$^1$H-NMR (DMSO-d$_6$): 2.74 (m, 2H), 3.50 (m, 2H), 3.88 (s, 3H), 6.90 (d, 1H), 7.08 (s, 1H), 7.47 (d, 1H), 7.58 (d, 1H), 7.97 (d, 1H), 11.79 (s, 1H).

9-Acetyl-8-methoxy-1,2-dihydro-6H-cyclopenta[c]carbazole-3-one (83)

8-Methoxy-1,2-dihydro-6H-cyclopenta[c]carbazole-3-one (82) (27.8 g, 110.8 mmol, 1 eq) was dissolved in dry dichloromethane (300 mL). Anhydrous AlCl$_3$ (29.5 g, 221.5 mmol, 2 eq) was added in portions with stirring and cooling, followed by the dropwise addition of AcCl (24 mL, 332.4 mmol, 3 eq). The reaction mixture was stirred at about 5° C. for 24 h and poured into ice water (violent foaming should be avoided). The precipitated orange solid was filtered off, washed with water (10×100 mL), CH$_2$Cl$_2$ (3×50 mL), acetone (3×50 mL) to give 26 g (80%) of 9-acetyl-8-methoxy-1,2-dihydro-6H-cyclopenta[c]carbazole-3-one (83).

9-Acetyl-8-methoxy-1,2-dihydro-6-(3-dimethylaminopropyl)-cyclopenta[c] carbazole-3-one (84)

NaH (6.88 g of 60%, 171.95 mmol, 2.5 eq) was added to a suspension of 9-acetyl-8-methoxy-1,2-dihydro-6H-cyclopenta[c]carbazole-3-one (83) (26 g, 68.78 mmol, 1 eq) in dry CH$_2$Cl$_2$ (300 mL), and the mixture was stirred at room temperature for 20-30 min until the evolution of hydrogen ceased. 3-Dimethylaminopropylchloride hydrochloride (16.3 g, 103.16 mmol, 1.5 eq) was added portionwise under nitrogen. The reaction mixture was stirred for 30 min at room temperature, then at 60° C. for 24 h and poured into ice water (4 L). The aqueous solution was acidified to pH about 2 with conc. HCl and the unreacted starting material extracted with EtOAc/THF=3/1 mixture. Upon adjusting the pH of the water layer to about 9, the product was extracted with 1:1 EtOAc:THF mixture (10×500 mL). The combined extracts were washed with brine, dried over Na$_2$SO$_4$ and solvent evaporated out to afford 22 g (68%) of crude carbazole (84), reasonable pure by LC/MS. It was used in the next step without further purification.

$^1$H-NMR (DMSO-d$_6$): 1.88 (t, 2H), 2.13 (s, 6H), 2.16 (t, 2H), 2.62 (s, 3H), 2.75 (m, 2H), 3.47 (m, 2H), 4.01 (s, 3H), 4.52 (t, 2H), 7.32 (s, 2H), 7.65 (dd, 4H), 8.32 (s, 2H).

9-Acetyl-8-hydroxy-1,2-dihydro-6-(3-dimethylaminopropyl)-cyclopenta [c]carbazole-3-one A solution of 9-acetyl-8-methoxy-1,2-dihydro-6-(3-dimethylaminopropyl)-cyclopenta[c]carbazole-3-one (84) (22 g, 58.2 mmol, 1 eq) and pyridine hydrochloride (134.4 g, 1164 mmol, 20 eq) in NMP (150 mL) was refluxed for 10 h. The reaction mixture was cooled to room temperature and poured into the 10% aqueous K$_2$CO$_3$ solution (3 L). The precipitated dark green solid was filtered off, washed with water (5×100 mL) and dried. The crude product was purified by column chromatography (eluent 10%-20% MeOH in EtOAc) to give 7.81 (37%) of pure 9-acetyl-8-hydroxy-1,2-dihydro-6-(3-dimethylaminopropyl)-cyclopenta[c]carbazole-3-one as a pale yellow solid.

MS(ESI): m/z=363.3 [M+H]$^+$

NMR $^1$H (DMSO): 1.86 (t, 2H), 2.17 (s, 6H), 2.20 (t, 2H), 2.79 (m, 2H), 2.81 (s, 3H), 3.52 (m, 2H), 4.43 (t, 2H), 7.15 (s, 2H), 7.66 (dd, 4H), 8.50 (s, 2H), 12.71 (s, 1H).

Example 4

9-Acetyl-8-hydroxy-1,2-dihydro-6-(3-dimethylaminopropyl)-cyclopenta[c]carbazole-3-one (7.81 g, 21.46 mmol, 1 eq) was dissolved in a mixture of water (20 mL) and 10% HCl solution (20 mL) in ethanol (200 mL), and the homogeneous solution evaporated to dryness. The residue was dried in vacuum overnight to give 8.47 g of Example 4 as a gray solid.

Purity: 99.2% by HPLC; MS(ESI): m/z=363.3 [M−HCl+H]$^+$; m.p.=241.3° C. (Decomposition); $^1$H-NMR (DMSO-$d_6$): 2.15 t (2H), 2.68 s (3H), 2.69 s (3H), 2.80 m (2H), 2.82 s (3H), 3.11 m (2H), 3.55 m (2H), 4.53 t (2H), 7.29 s (2H), 7.73 dd (4H), 8.52 s (2H), 11.00 s (1H), 12.76 s (1H).

Compounds of structural formula (II) are prepared similarly to compounds of structural formula (I), and include for example,

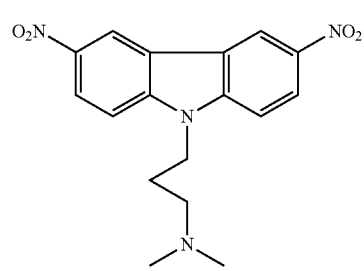

Example 21

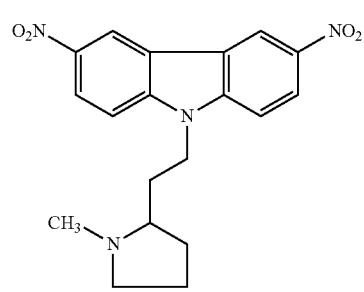

Example 22

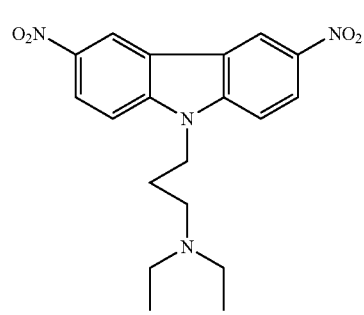

Example 23

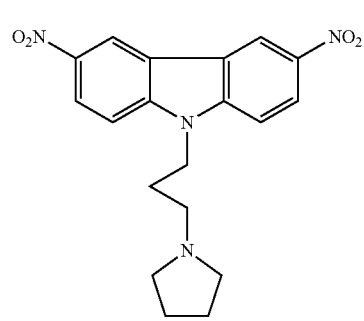

Example 24

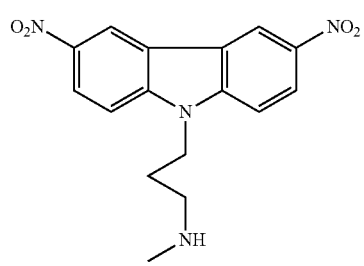

Example 25

Additional carbazole compounds of the present invention are:

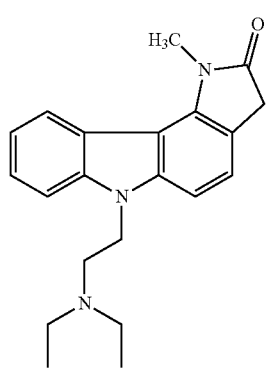

Example 17b

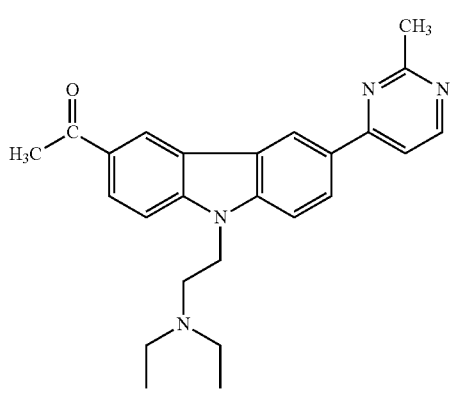

Example 26

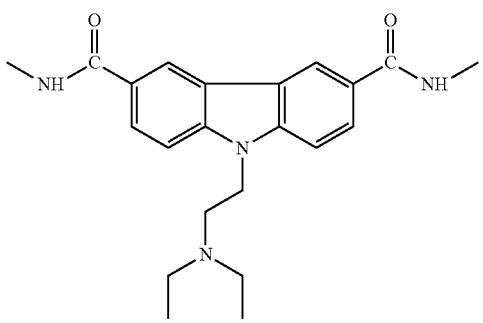

Example 27

Example 28
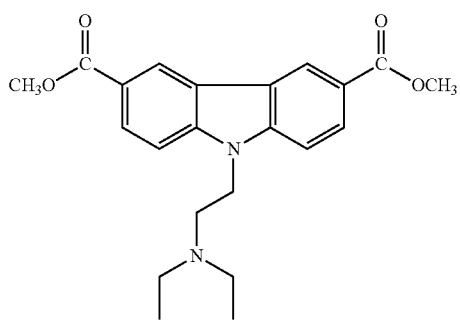
Example 37
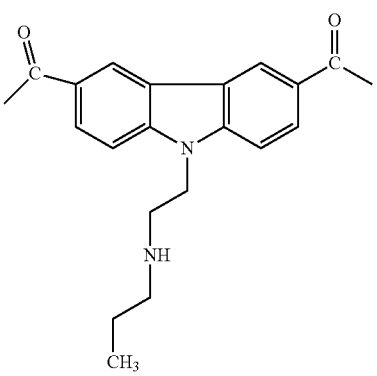
A compound useful in the methods of the present invention has a structure:
Compound 100
Additional examples having a structural formula (I) include, but are not limited to:
Example 29
Example 30
Example 31
Example 32
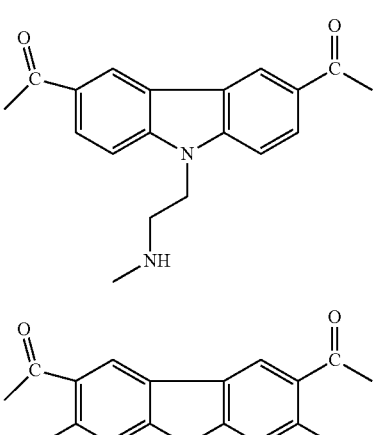
Example 33
Example 34
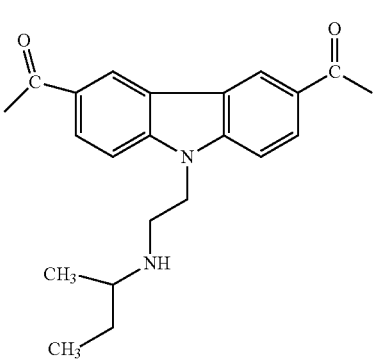
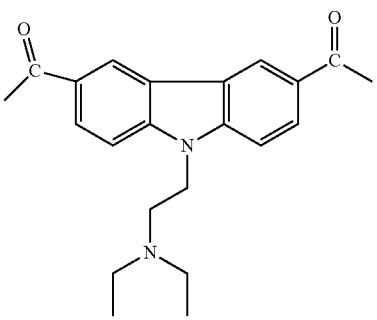

-continued
Example 35
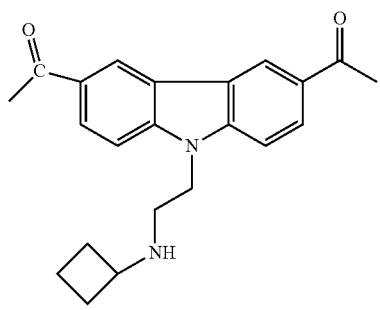
Example 40
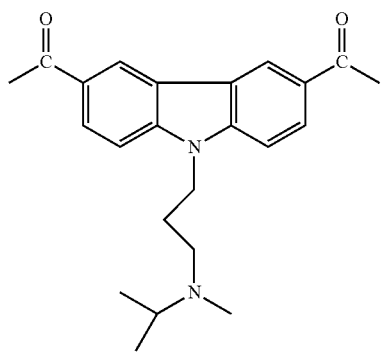
Example 36
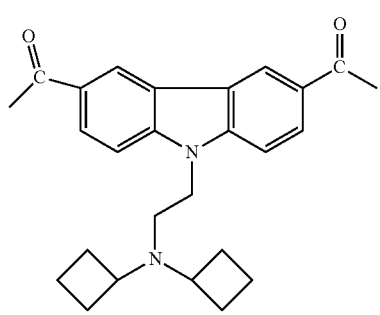
Example 41
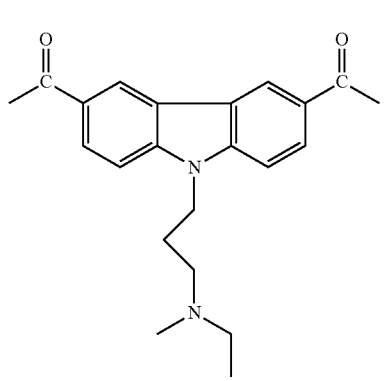
Example 38
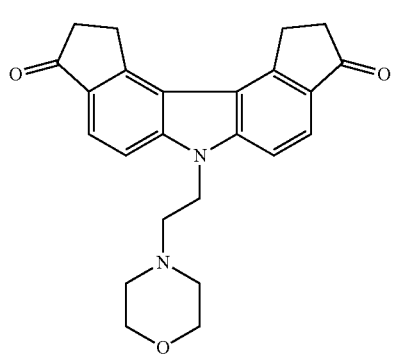
Example 42
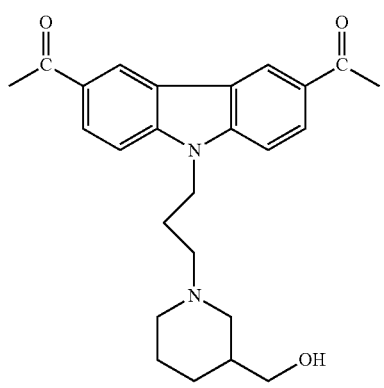
Example 39
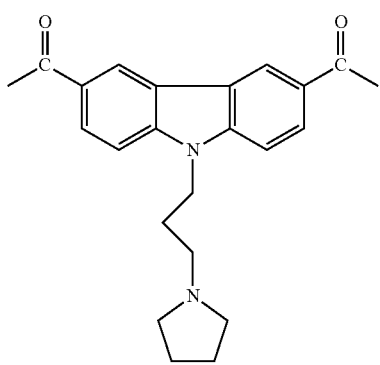
Example 43
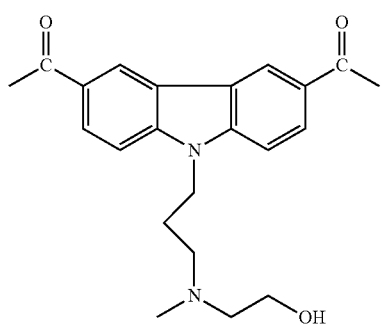

Example 44
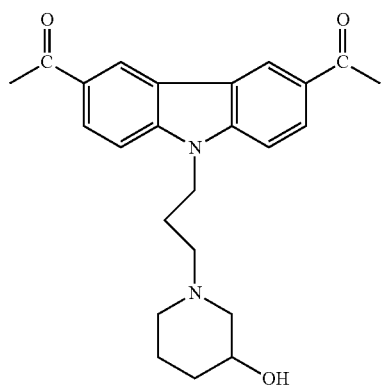
Example 45
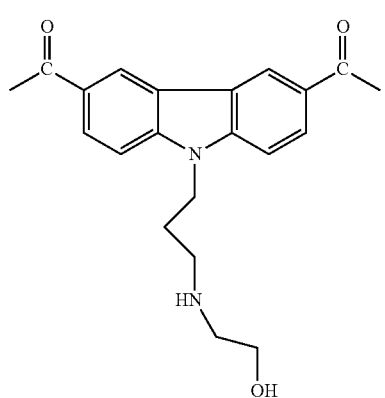
Example 46
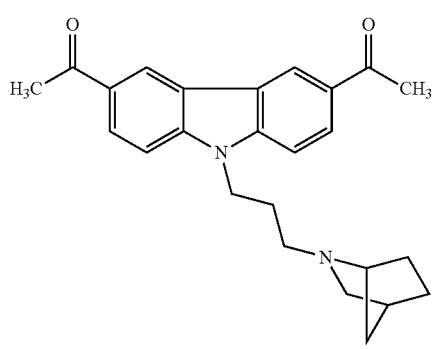
Example 47
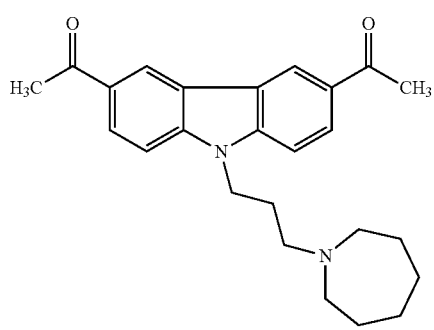
Example 48
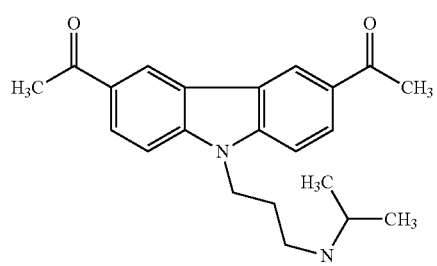
Example 49
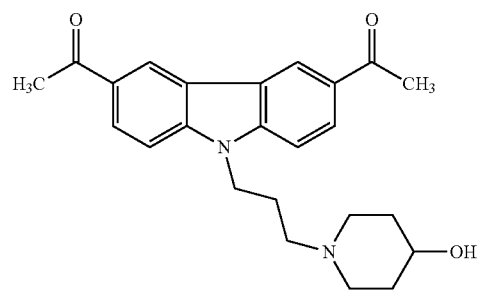
Compounds of the present invention therefore include, but are not limited to:
3a
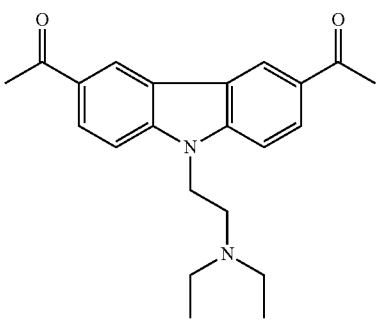 [SMILES: CCN(CC)CCn1c2ccc(C(C)=O)cc2c2cc(C(C)=O)ccc21]
,
3b
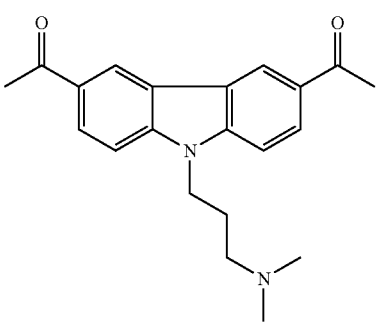 [SMILES: CC(=O)c1ccc2c(c1)c1cc(C(C)=O)ccc1n2CCCN(C)C]
,

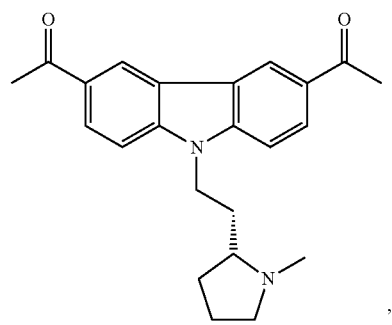
3d
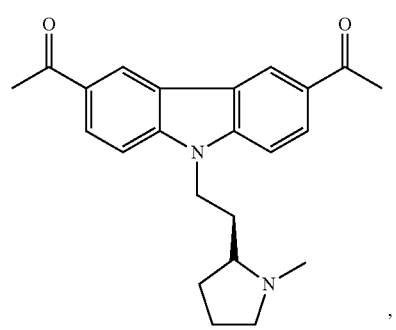
3e
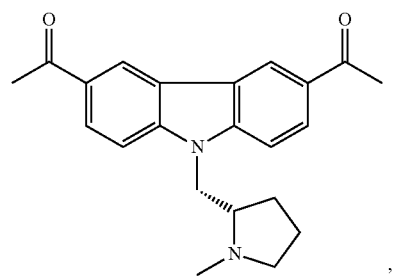
3f
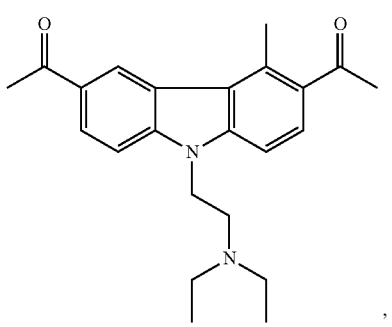
13a
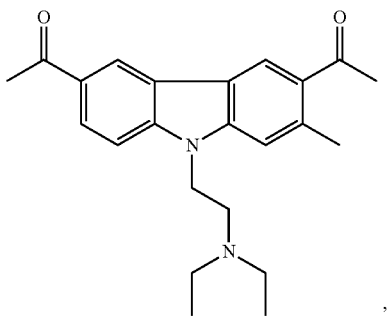
13b
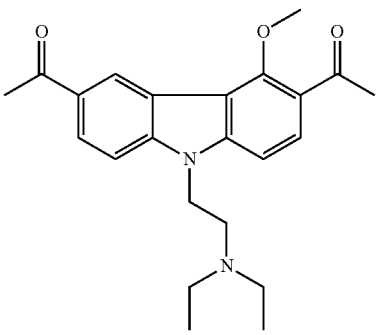 [SMILES: CCN(CC)CCn1c2ccc(C(C)=O)cc2c2c(OC)c(C(C)=O)ccc21]
13c
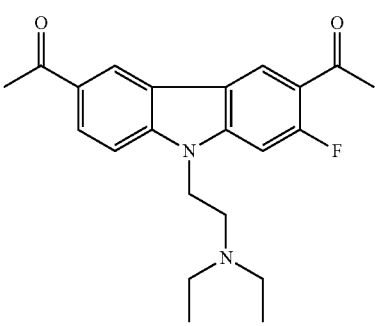
13d
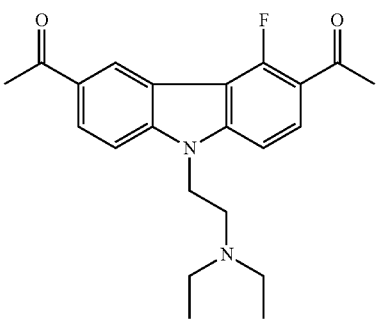 [SMILES: CCN(CC)CCn1c2ccc(C(C)=O)cc2c2c(F)c(C(C)=O)ccc21]
13e
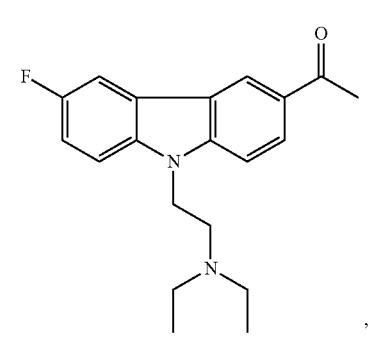
13f
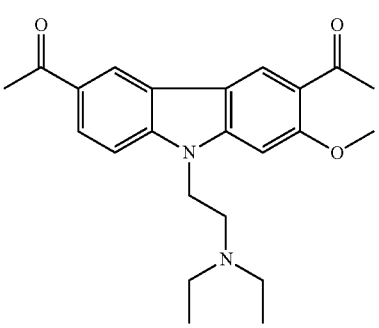 [SMILES: CCN(CC)CCn1c2ccc(C(C)=O)cc2c2cc(C(C)=O)c(OC)cc21]
13g

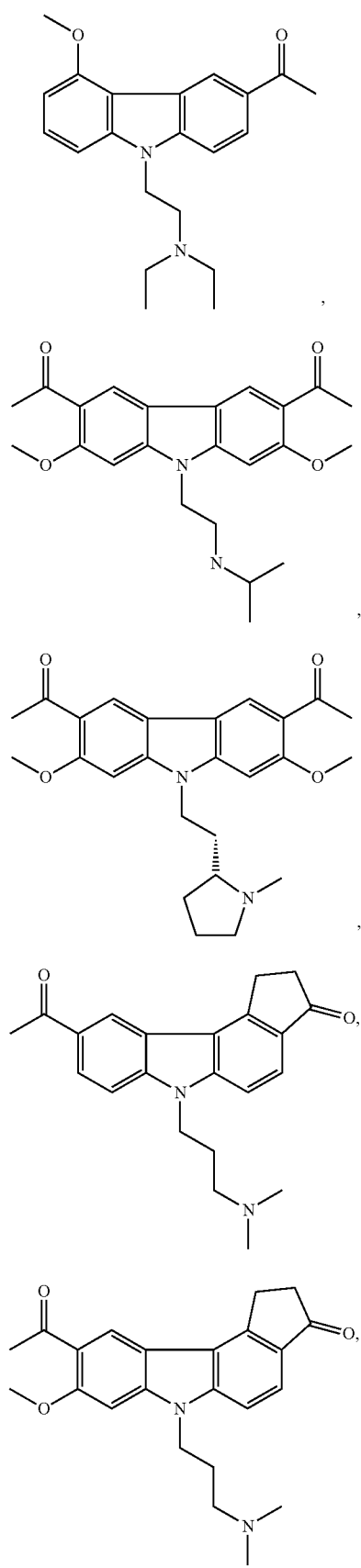
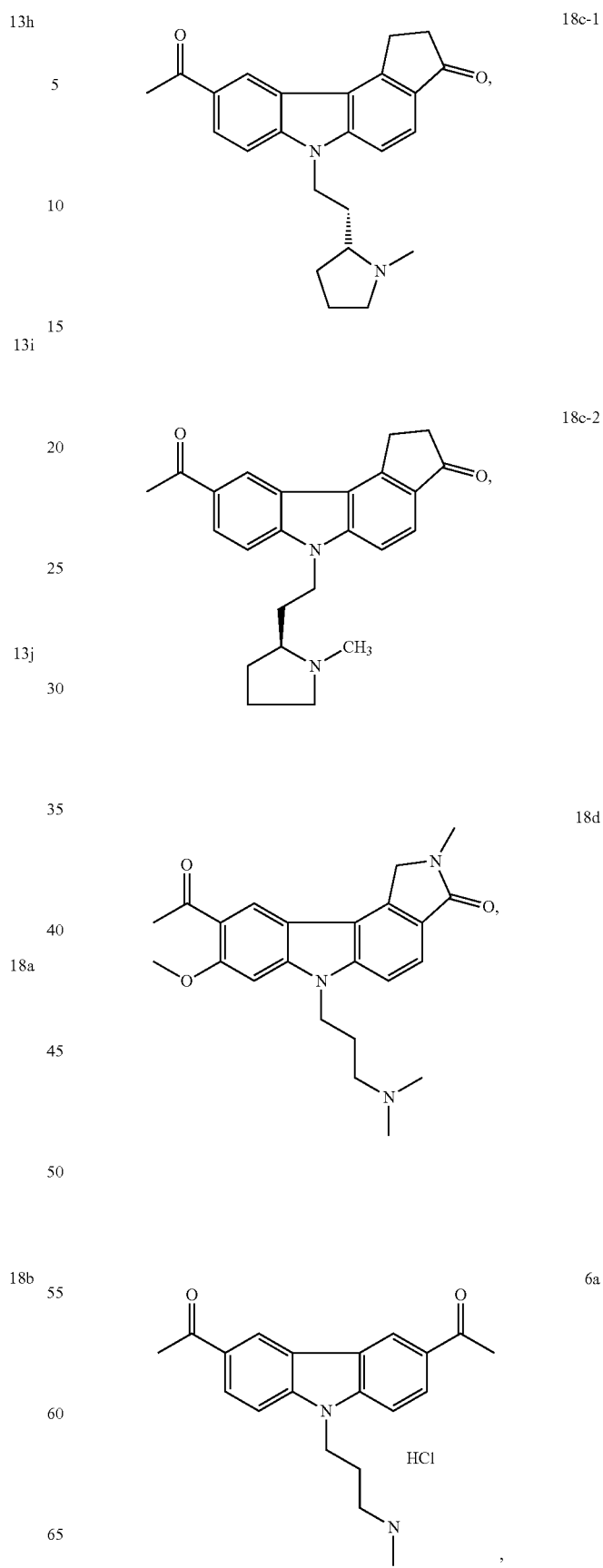

| 6b | 6f |
|---|---|
| 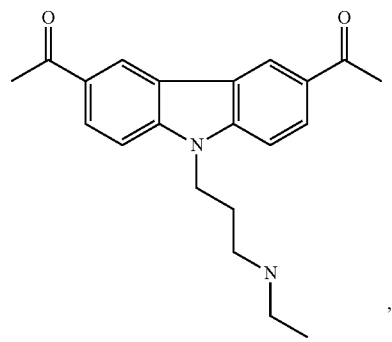 | 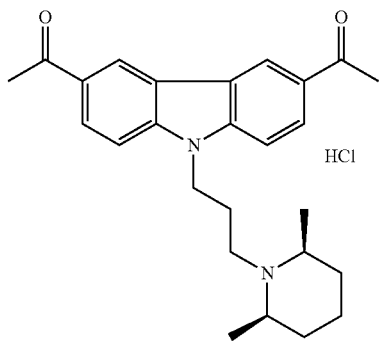 |
| 6c | 6g |
| 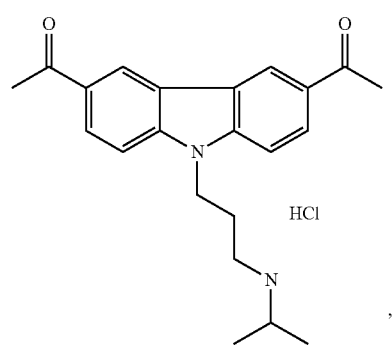 | 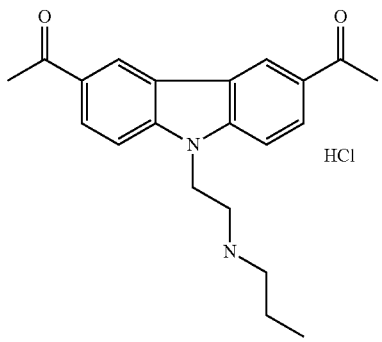 [SMILES: CCNCCCn1c2ccc(C(C)=O)cc2c2cc(C(C)=O)ccc21] |
| 6d | 6h |
| 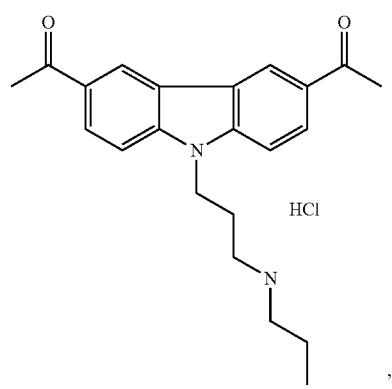 | 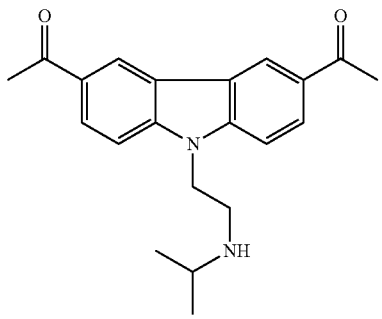 |
| 6e | 7a |
| 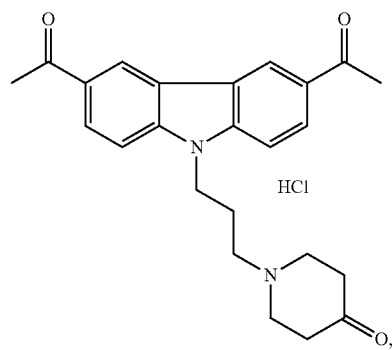 | 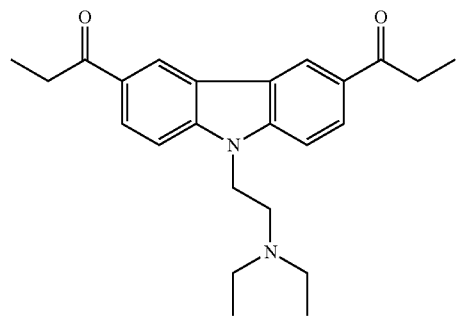 [SMILES: CCC(=O)c1ccc2c(c1)c1cc(C(=O)CC)ccc1n2CCN(CC)CC] |
| | 7b |
| | 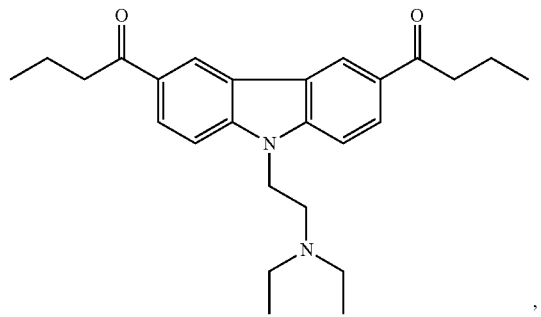 |

-continued
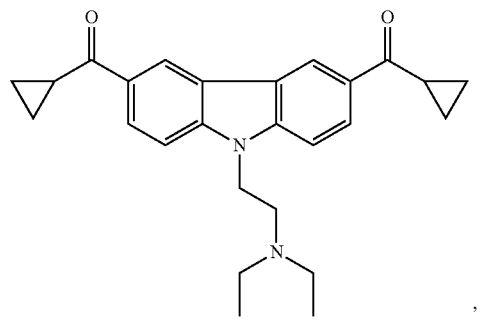
7c
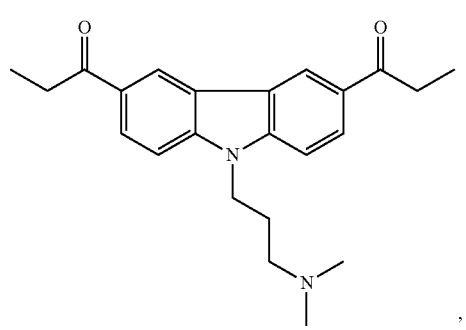
7d
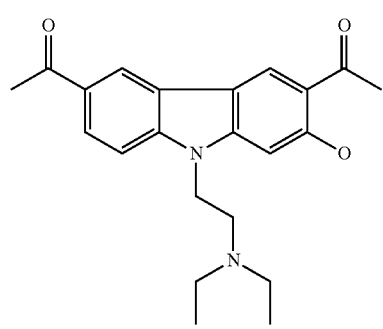
19a
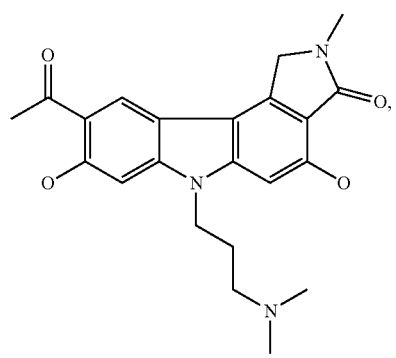
19e
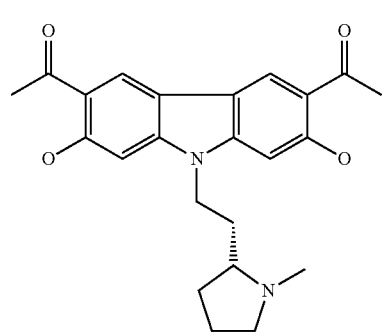
19f
-continued
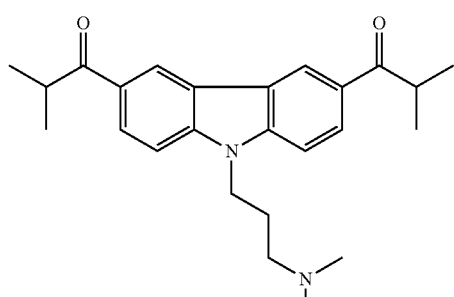
Example 1
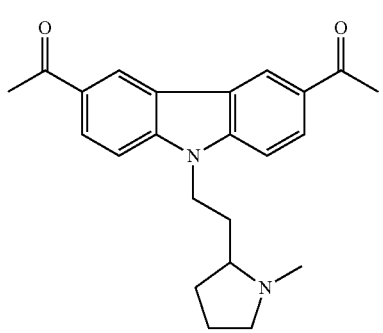
Example 2
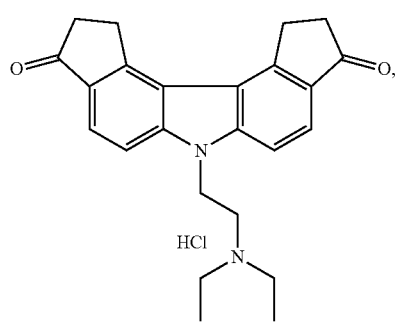
Example 3
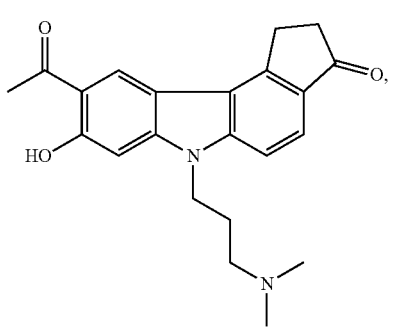
Example 4
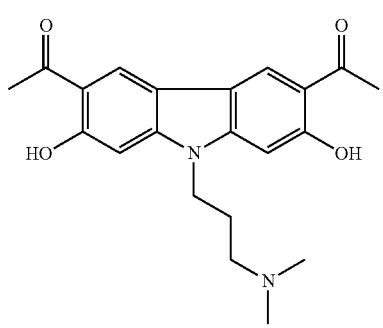 [SMILES: CC(=O)c1cc2c3cc(C(C)=O)c(O)cc3n(CCCN(C)C)c2cc1O]
Example 5

Example 6
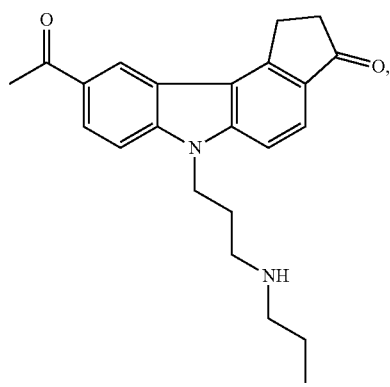
Example 7
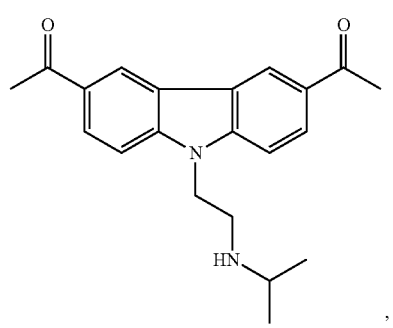
Example 8
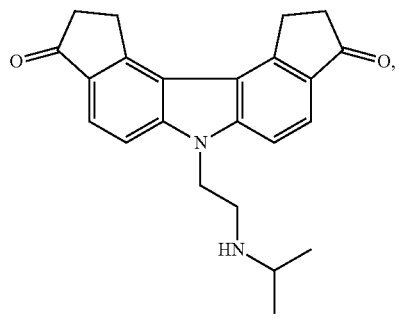
Example 9
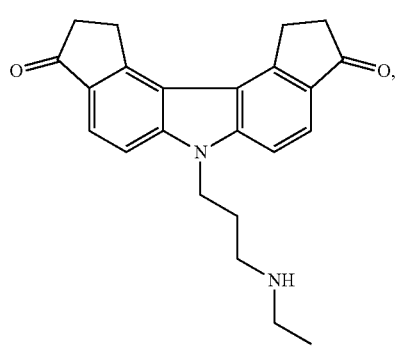
Examples 10/11
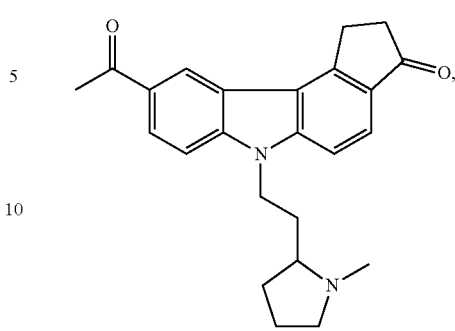
Example 12
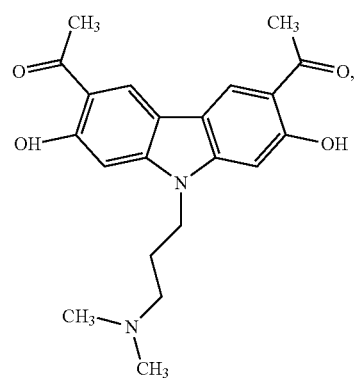
Example 13
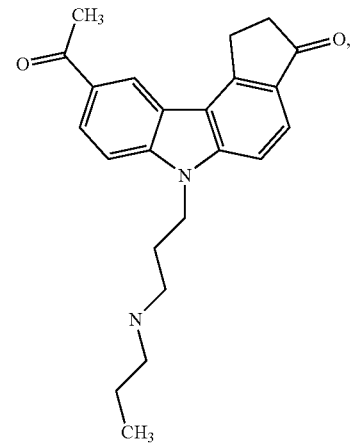
Example 14
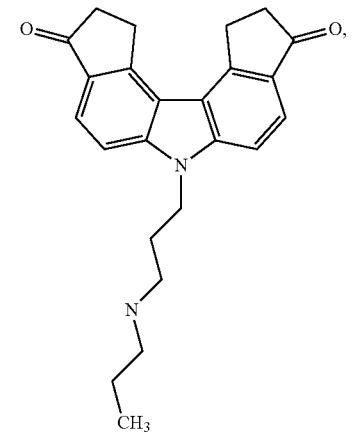

-continued
Example 15
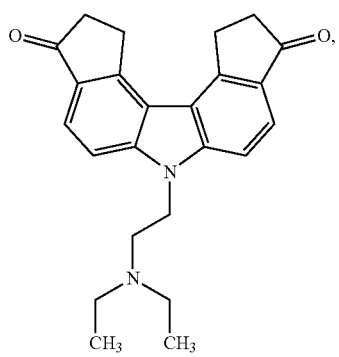
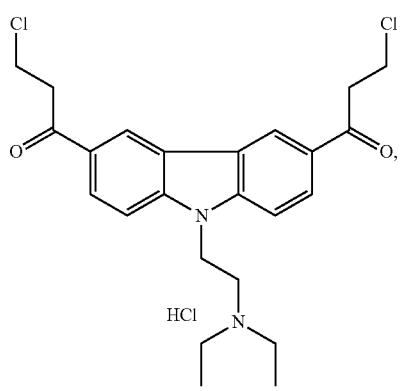
Example 16
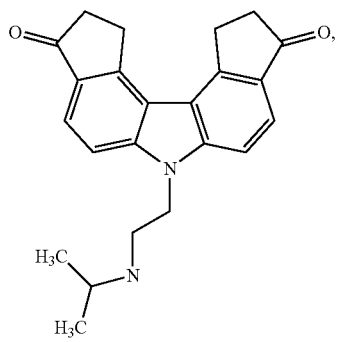
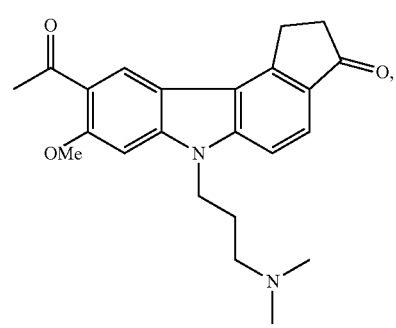
Example 17
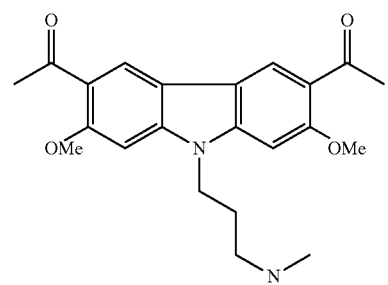
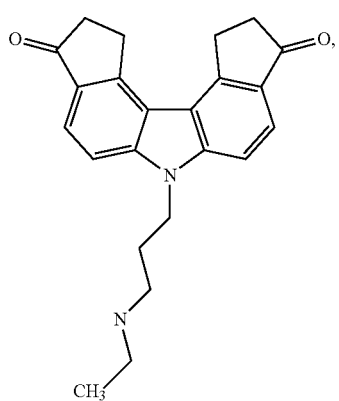
Example 18
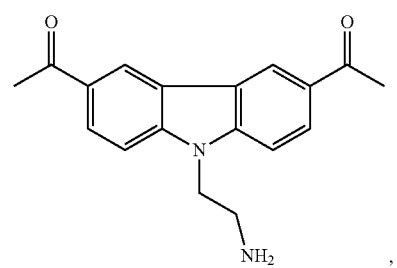
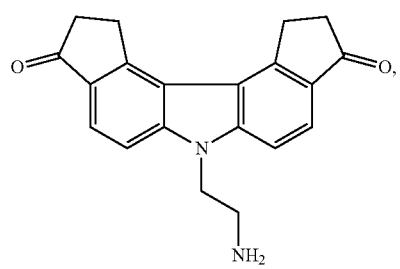

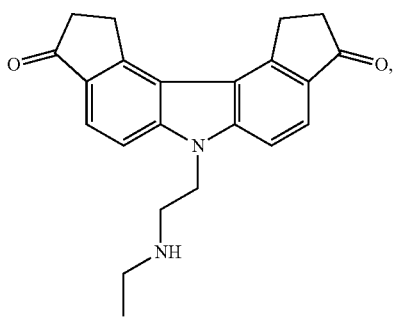

Example 28
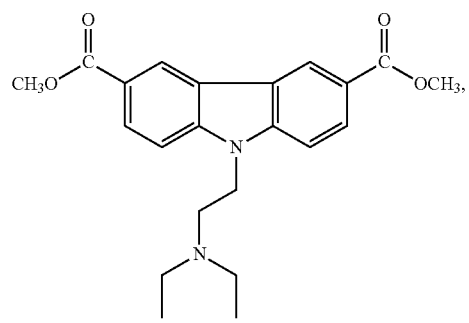
Example 29
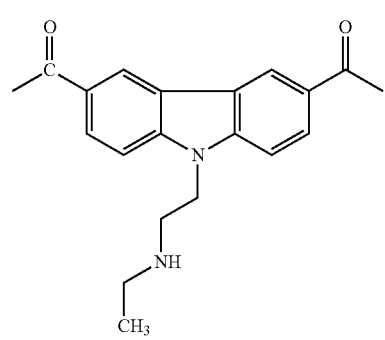
Example 30
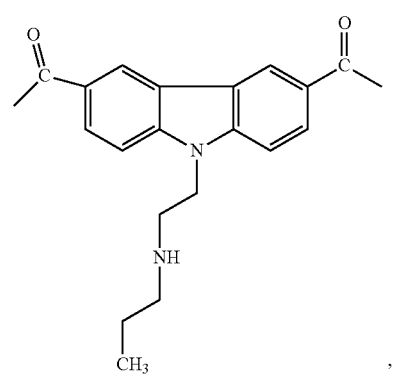
Example 31
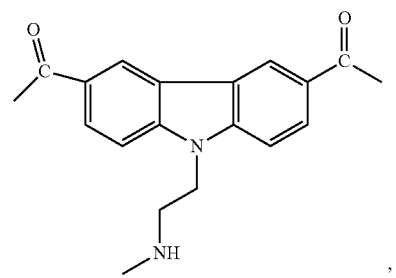
Example 32
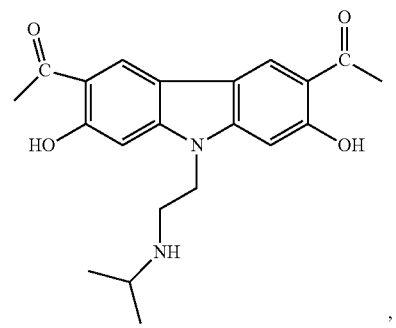
Example 33
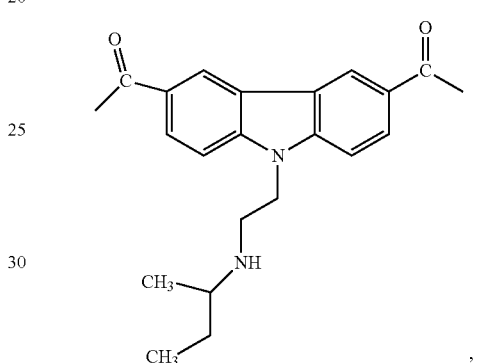
Example 34
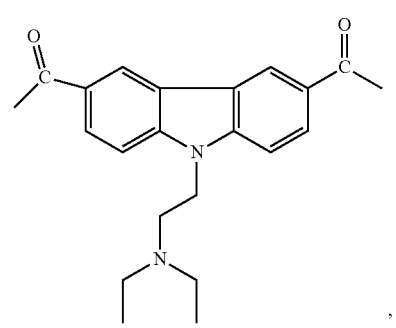
Example 35
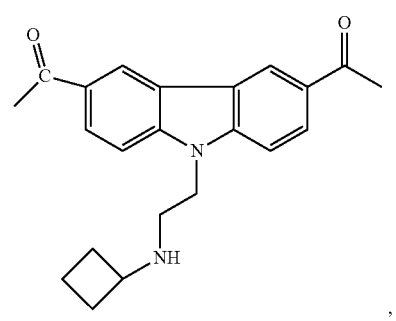

| | |
|---|---|
| 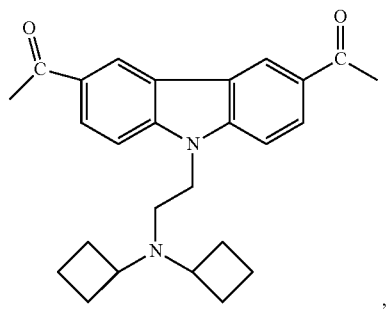 Example 36 | 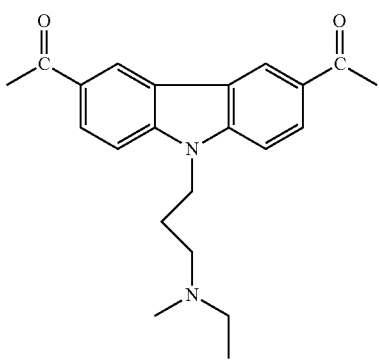 Example 41 |
| 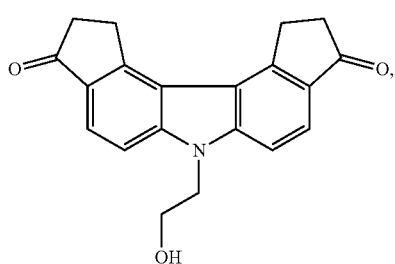 Example 37 | |
| 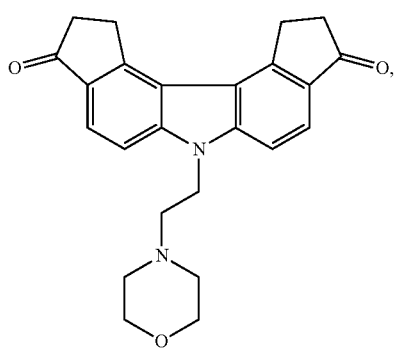 Example 38 | 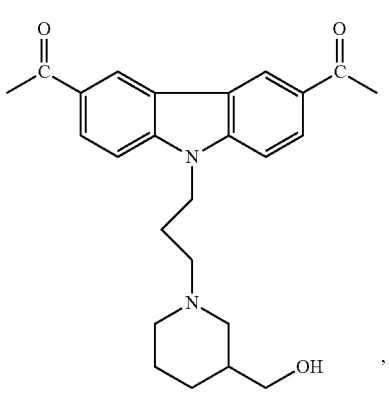 Example 42 |
| 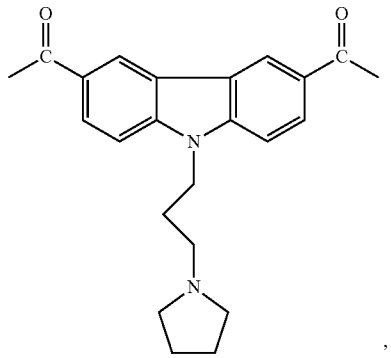 Example 39 | 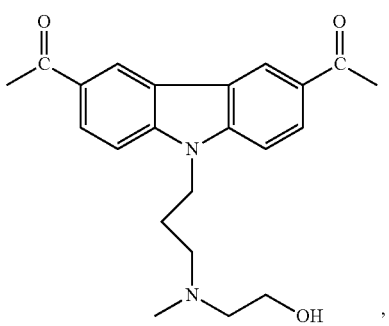 Example 43 |
| 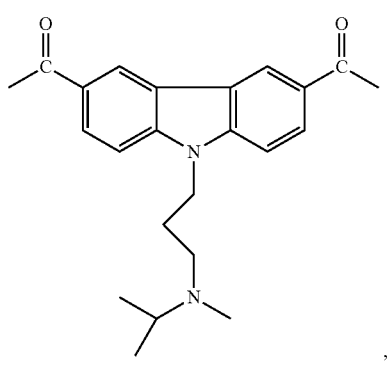 Example 40 | 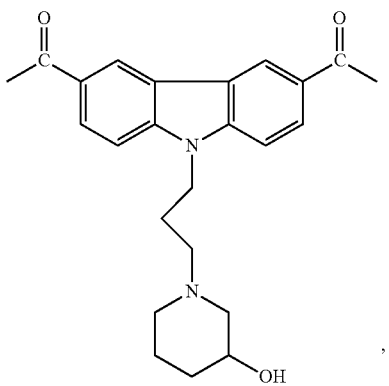 Example 44 |

Example 45

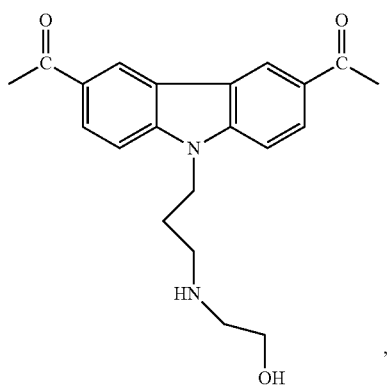

Example 46

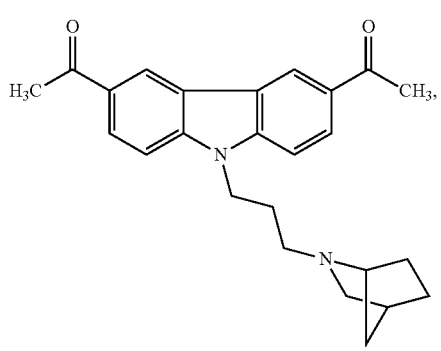

Example 47

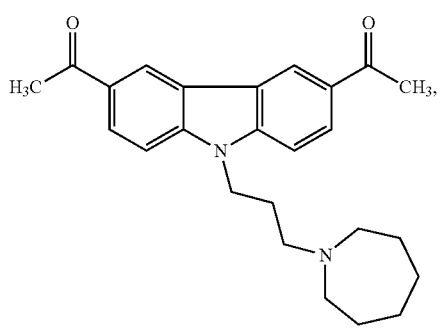

Example 48

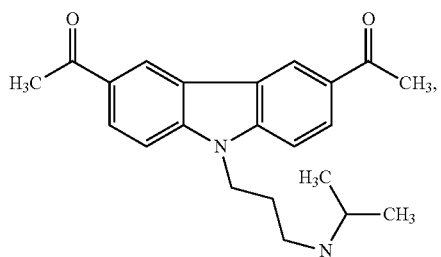

Example 49

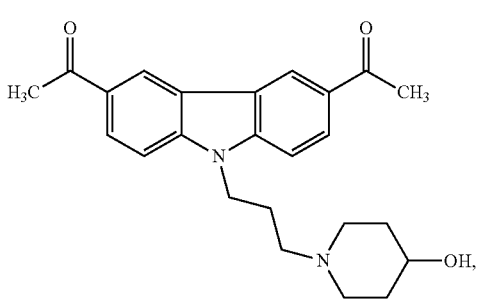

Example 50

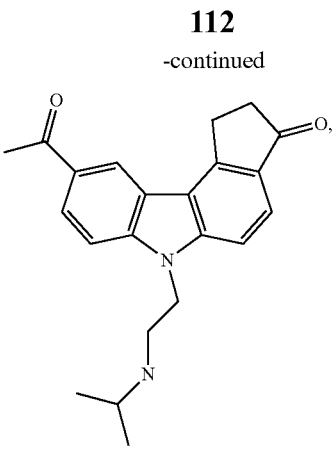

Example 51

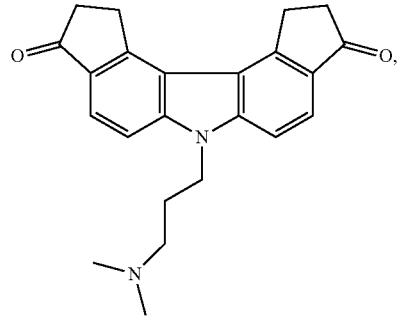

Example 52

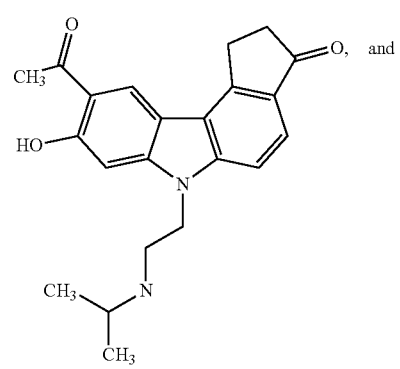

Example 53

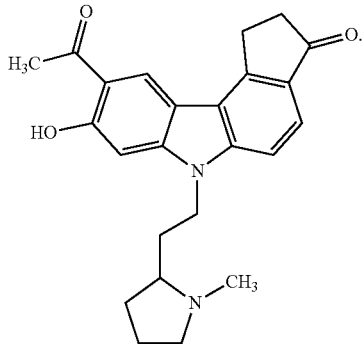

The potency of a carbazole compound is determined by measuring an ability of the compound to activate p53. In particular, a p53 responsive luciferase reporter cell line is used to identify compounds capable of activating p53. The activation of p53 is reported as the $EC_{50}$ value, which is the effective concentration of the compound needed to increase p53 activity by 50% over a baseline p53 activity.

The p53 activation assay for determination of the $EC_{50}$ value was performed as follows:

Definitions and Terminology

ConALuc: p53 responsive luciferase reporter construct
DMSO: Dimethyl sulfoxide
FBS: fetal bovine serum Equipment
  96 well luminometer-fluoroscan (e.g., Fluoroscan, Lab-Systems, Inc, settings-program, integration time is 0.1 sec, PMT voltage is 1000, and zero lag time
  Multichannel pipette 50-300 uL range
  96 well plates Materials
  Reporter cell lines:
    HT1080-L (human fibrosarcoma cells with ConALuc reporter)
    RCC45ConALuc (human renal cell carcinoma cell line with ConALuc reporter)

4. The next day, various carbazole compounds were prepared by dilution of stock solutions in standard DMEM medium such that the cells were treated with the final chemical concentrations in Table 1 below. Stock solutions were made up in DMSO. Typically, chemicals were made up as 20 mM stock solutions. However, this concentration is dependent on the solubility of a given compound and therefore actual stock concentrations were noted at time of experiment (e.g., less soluble compounds can have a stock concentration of 5 or 10 mM).

5. Each tested compound used two rows of a 96-well plate, thus four compounds (e.g., W, X, Y, Z) were tested in one plate simultaneously. In addition to test compounds, each plate included positive and negative controls. As positive control, 9aa was used at a dose of 3 µM. As a negative control, DMSO was used in final concentration 0.1%.

TABLE 1

Scheme of an experimental plate with final concentrations of chemicals

|  | Neg Control | Pos. Control | Library compound (Cpd W, X, Y, Z) (uM) | | | | | | | | |
| --- | --- | --- | --- | --- | --- | --- | --- | --- | --- | --- | --- |
| Cpd W | DMSO | 3 uM 9aa | 0.039 | 0.078 | 0.156 | 0.313 | 0.625 | 1.25 | 2.5 | 5 | 10 | 20 |
| Cpd W | DMSO | 3 uM 9aa | 0.039 | 0.078 | 0.156 | 0.313 | 0.625 | 1.25 | 2.5 | 5 | 10 | 20 |
| Cpd X | DMSO | 3 uM 9aa | 0.039 | 0.078 | 0.156 | 0.313 | 0.625 | 1.25 | 2.5 | 5 | 10 | 20 |
| Cpd X | DMSO | 3 uM 9aa | 0.039 | 0.078 | 0.156 | 0.313 | 0.625 | 1.25 | 2.5 | 5 | 10 | 20 |
| Cpd Y | DMSO | 3 uM 9aa | 0.039 | 0.078 | 0.156 | 0.313 | 0.625 | 1.25 | 2.5 | 5 | 10 | 20 |
| Cpd Y | DMSO | 3 uM 9aa | 0.039 | 0.078 | 0.156 | 0.313 | 0.625 | 1.25 | 2.5 | 5 | 10 | 20 |
| Cpd Z | DMSO | 3 uM 9aa | 0.039 | 0.078 | 0.156 | 0.313 | 0.625 | 1.25 | 2.5 | 5 | 10 | 20 |
| Cpd Z | DMSO | 3 uM 9aa | 0.039 | 0.078 | 0.156 | 0.313 | 0.625 | 1.25 | 2.5 | 5 | 10 | 20 |

Standard DMEM Medium
Standard RPMI Medium
Pen/strep 100×
Trypsin-EDTA 10×-dilute to 1× in sterile PBS
PBS
Bright-Glo luciferase assay system (Fisher PR-E2620)
9-aminoacridine (9aa) 20 mM in DMSO (Sigma A38401), p53 activator (positive control)
Compound 100 20 mM in DMSO (Chembridge), p53 activator (positive control)
DMSO (Fisher D128-500) (negative control)

Method
1. Two types of standard cells were used, either HT1080-L or RCC45ConALuc cells. Both cell lines stably express a p53 responsive luciferase reporter construct.

2. HT1080-L cells were grown in DMEM medium containing 10% FBS. RCC45ConALuc cells were grown in RPMI medium containing 10% FBS (Pen/Strep can be added to a final concentration of 1%, if desired). Both cell lines were grown in a humidified incubator at 37° C. with 5% $CO_2$. For normal culturing, both cell lines were split using 1× trypsin-EDTA at a ratio of 1:20 for HT1080-L and 1:5 for RCC45ConALuc cells every 3-4 days (when cells are 80-90% confluent).

3. A day before the experiment, the cells are trypsinized for about 5 minutes in 1× tripsin/EDTA solution in 37° C. incubator and plated in 96 well plates. HT1080-L cells were seeded at a density of $1 \times 10^4$/well in standard DMEM medium in a volume of 50 µl. RCC45ConALuc were seeded at a density of $2 \times 10^4$/well in the volume of 50 uL in standard RPMI medium.

1. Dilutions of chemicals added to the plate were made up as 2× concentrations in standard DMEM and added to corresponding well in a volume of 50 µl.

2. Chemicals were diluted in standard DMEM by two time serial dilutions starting from 40 µM (2× of highest concentration, e.g., 20 µM). For one cell line, the minimum volume was 125 µL of 2× working solution of chemical of each concentration in standard DMEM.

3. In addition to a positive control added in one concentration in each plate, a positive control of Compound 100, or the most active compound on each stage of screening, was added to each assay run in a full concentration range to ensure proper and robust assay performance (estimated by comparison of dose response curves of p53 activation among runs).

4. Sixteen hours following compound addition, all wells with the highest concentrations of compounds are checked microscopically for the presence of toxic effect, because death of cells caused by compounds may not allow detecting luciferase activity. If cytotoxicity is evident, other doses of the same compounds were checked for the presence of toxicity. The lowest dose causing toxic effect was recorded. In case cytotoxicity was observed at 3-4 lowest compound doses (in a current dose scheme at 0.3 and lower uM), the compound was retested separately in a lower concentration range, allowing at least 4 two-fold-different doses of compound to be tested without signs of cytotoxicity).

5. After microscopic examination, 15 µl of Bright Glo luciferase assay system were added to each well and after 5 min incubation at RT, the plates were read on a 96 well plate luminometer with a measurement time of 0.1 sec. A shaking step was included before measurement.

6. The folds of luciferase activation for each concentration of each chemical were calculated by dividing the detected luciferase activity at each chemical concentration by the average of the luciferase activity for the DMSO control on the same plate. The folds then were plotted versus the chemical concentration to determine whether compounds are active. From the data, both the maximum fold activation and the Emax (concentration causing maximal p53 activation) were determined.

7. For each compound, this assay is repeated two additional times. Once three runs were complete, the raw data was used to calculate the $EC_{50}$ value.

An assay was considered invalid when:

a difference between two duplicates increases 10% for more than 10% of readings;

death of DMSO treated cells is observed;

less than 3 times luciferase induction in cells treated with positive control (Compound 3a, 0.4 uM) versus luciferase activity of DMSO treated cells;

inability to get dose-dependent curve of luciferase induction with positive control (e.g. Compound 100, 0.03-20 uM).

The following are nonlimiting examples of $EC_{50}$ values for various carbazole compounds useful in the method of the present invention:

| Compound | $EC_{50}$ value (p53 activation, µM) |
|---|---|
| Compound 100 | 1.30 |
| Example 21 | 0.83 |
| Example 22 | 0.53 |
| Compound 3a | 0.29 |
| Compound 3b | 0.49 |
| Compound 7d | 0.64 |
| Example 23 | 0.88 |
| Example 24 | 0.78 |
| Example 25 | 0.88 |
| Example 2 | 0.64 |
| Example 27 | 0.54 |
| Example 15 | 0.03 |
| Compound 19a | 0.40 |
| Compound 3e | 0.78 |
| Example 7 | 0.37 |
| Example 4 | 0.07 |
| Compound 18c-1 | 0.08 |
| Compound 18c-2 | 0.10 |
| Compound 19e | 0.07 |
| Example 13 | 0.22 |
| Example 14 | 0.05 |
| Example 6 | 0.24 |
| Example 17 | 0.04 |
| Example 18 | 0.09 |
| Example 38 | 0.12 |

Compounds and pharmaceutical compositions of the present invention include those wherein the active ingredient is administered in a therapeutically effective amount to achieve its intended purpose. A "therapeutically effective amount" refers to that amount of a present carbazole compound that results in achieving the desired effect. Toxicity and therapeutic efficacy of the carbazole compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such data can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a carbazole compound of structural formula (I) or (II) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the carbazole compound that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present carbazole compound can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a carbazole compound of structural formula (I) or (II), or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention.

When administered in combination with other therapeutics, a present carbazole compound may be administered at relatively lower dosages. In addition, the use of targeting agents may allow the necessary dosage to be relatively low. Certain compounds may be administered at relatively high dosages due to factors including, but not limited to, low toxicity and high clearance.

For human use, a compound of structural formula (I) or (II) can be administered alone, but generally is administered in admixture with a pharmaceutical carrier selected with regard to the intended route of administration and standard pharmaceutical practice. Pharmaceutical compositions for use in accordance with the present invention can be formulated in a conventional manner using one or more physiologically acceptable carrier comprising excipients and auxiliaries that facilitate processing of compounds of formula (I) or (II) into pharmaceutical preparations.

The present carbazole compounds can be administered simultaneously or metronomically with other anti-cancer treatments, such as chemotherapy and/or radiation therapy. The term "simultaneous" or "simultaneously" means that the other anti-cancer treatment and the carbazole compound are administered within 6 hours, 3 hours or less, of each other. The term "metronomically" means the administration of the other anti-cancer treatments at times different from the anti-cancer treatments and at a certain frequency relative to repeat administration and/or the anti-cancer treatment regiment.

The carbazole compound, or compositions containing the carbazole compound, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. The carbazole compound also can be administered in the form of an implant, which allows a slow release of the compound, as well as a slow controlled i.v. infusion.

The carbazole compounds of the present invention can be used to treat a variety of diseases and conditions. For example, compounds of the present invention can be used in combination with radiation and/or a chemotherapeutic agent in the treatment of cancers. For example, the carbazole compounds can be used to enhance treatment of tumors that are customarily treated with an antimetabolite, e.g., methotrexate or 5-fluorouracil (5-FU).

Use of carbazole compounds of the present invention can result in partial or complete regression of cancer cells, i.e., the partial or complete disappearance of such cells from the cell population. For example, a method of the invention can be used to slow the rate of tumor growth, decrease the size or number of tumors, or to induce partial or complete tumor regression.

A present carbazole compound can be used for treating a disease or condition in vivo by administration to an individual in need thereof. The disease or condition can be a cancer. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Transformation induced by tax of HTLV, a causative agent of human adult T-lymphoblastic leukemia (ATL), may share the same molecular targets involved in RCC. For example, NF-κB is constitutively active in tax-transformed cells. Similar to RCC, p53 activity is inhibited through activation of NF-κB in tax-transformed cells and p53 inhibition does not involve sequestering of p300. Based on the shared mechanism of p53 activation, the compositions may also be used to treat HTLV-induced leukemia. Regardless of their p53 status, the majority of human cancers have constitutively hyperactivated NF-κB. The composition also is capable of inhibiting NF-κB by reprogramming transactivation NF-κB complexes into transrepression complexes, which can be used for treatment of any tumor regardless of their p53 status. The compositions further can be used for treating HIV infections because HIV LTRs are strongly dependent on NF-κB activity.

The composition also can be used as an adjuvant therapy to overcome anti-cancer drug resistance that can be caused by constitutive NF-κB activation. The anti-cancer drug can be a chemotherapeutic or radiation, as described herein.

One method of the present invention comprises administration of a therapeutically effective amount of a present carbazole compound in combination with a chemotherapeutic agent that can effect single- or double-strand DNA breaks or that can block DNA replication or cell proliferation. Alternatively, a method of the present invention comprises administration of a therapeutically effective amount of at least one present carbazole compound in combination with therapies that include use of an antibody, e.g., herceptin, that has activity in inhibiting the proliferation of cancer cells. Accordingly, cancers, for example, colorectal cancers, head and neck cancers, pancreatic cancers, breast cancers, gastric cancers, bladder cancers, vulvar cancers, leukemias, lymphomas, melanomas, renal cell carcinomas, ovarian cancers, brain tumors, osteosarcomas, and lung carcinomas, are susceptible to enhanced treatment by administration of a present carbazole in combination with a chemotherapeutic agent or an antibody.

Cancers treatable by the present invention also include solid tumors, i.e., carcinomas and sarcomas. Carcinomas include malignant neoplasms derived from epithelial cells which infiltrate (i.e., invade) surrounding tissues and give rise to metastases. Adenocarcinomas are carcinomas derived from glandular tissue, or from tissues that form recognizable glandular structures. Another broad category of cancers includes sarcomas, which are tumors whose cells are embedded in a fibrillar or homogeneous substance, like embryonic connective tissue. The present invention also enables treatment of cancers of the myeloid or lymphoid systems, including leukemias, lymphomas, and other cancers that typically are not present as a tumor mass, but are distributed in the vascular or lymphoreticular systems.

Additional forms of cancer treatable by the present carbazole compounds include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Accordingly, administration of a present carbazole compound is expected to enhance treatment regimens.

Compounds of the present invention also can potentiate the efficacy of drugs in the treatment of inflammatory diseases. The present carbazole compounds are potent inhibitors of NF-κB response, which involves the suppression of expression/secretion of pro-inflammatory NF-κB targets, such as TNF, IL-1, IL-6, IL-8, and many others. Therefore, the inhibition of NF-κB by a present carbazole would lead to the suppression of local and systemic inflammatory reactions. Quinacrine, which is hypothesized to act by a mechanism very similar to the present carbazole, was widely used as an anti-inflammatory agent for the treatment of autoimmune diseases and chronic inflammation.

Examples of diseases that can benefit from combination therapy with compounds suitable for the method of the present invention are rheumatoid arthritis, psoriasis, vitiligo, Wegener's granulomatosis, and systemic lupus erythematosus (SLE). Treatment of arthritis, Wegener's granulomatosis, and SLE often involves the use of immunosuppressive therapies, such as ionizing radiation, methotrexate, and cyclophosphamide. Such treatments typically induce, either directly or indirectly, DNA damage. Inhibition of NF-κB and/or activation of p53 within the offending immune cells render the cells more sensitive to control by these standard treatments. Psoriasis and vitiligo commonly are treated with ultraviolet radiation (UV) in combination with psoralen. The present carbazole compounds induce the killing effect of UV and psoralen, and increase the therapeutic index of this treatment regimen. In general, the carbazole compounds useful in methods of the present invention potentiate control of inflammatory disease cells when in combination with currently used immunosuppressive drugs.

In addition to the above conditions, the present invention also can be used in methods of treating conditions such as, but not limited to, atherosclerosis, restenosis, vasculitis, nephritis, retinopathy, renal disease, proliferative skin disorders, psoriasis, keloid scarring, actinic keratosis, Stevens-Johnson Syndrome, rheumatoid arthritis (RA), systemic-onset juvenile chronic arthritis (JCA), osteoporosis, systemic lupus erythmatosis, hyperproliferative diseases of the eye including epithelial down growth, proliferative vitreoretinopathy (PVR), diabetic retropathy, Hemangio-proliferative diseases, ichthyosis, and papillomas.

Carbazoles of the present invention also exhibit antimicrobial activity, e.g., agent Germ-positive and Germ-negative bacteria, including *Salmonella*; antiprotozoan activity; and antiviral activity.

As appreciated by persons skilled in the art, additional active or ancillary agents can be used in the methods described herein. Reference herein to treatment also extends to prophylaxis, as well as to treatment of established diseases or symptoms.

The present invention can be applied to cell populations ex vivo. For example, the present carbazole compounds can be used ex vivo to determine the optimal schedule and/or dosing of administration of the present carbazole compound for a given indication, cell type, patient, and other parameter. Information gleaned from such use can be used for experimental purposes or in the clinic to set protocol for in vivo treatment. Other ex vivo uses for which the invention is suited are apparent to those skilled in the art.

A present carbazole compound also can be administered in combination with radiation. Diseases that are treatable with electromagnetic radiation include neoplastic diseases, benign and malignant tumors, and cancerous cells.

Electromagnetic radiation treatment of other diseases not listed herein also is contemplated by the present invention. Preferred embodiments of the present invention employ the electromagnetic radiation of: gamma-radiation ($10^{-20}$ to $10^{-13}$ m), X-ray radiation ($10^{-12}$ to $10^{-19}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present carbazole compound, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a carbazole compound of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful for the method of the present invention are listed in the following table.

TABLE 1

| Alkylating agents | Natural products |
|---|---|
| Nitrogen mustards | Antimitotic drugs |
| | |
| mechlorethamine | Taxanes |
| cyclophosphamide | paclitaxel |
| ifosfamide | Vinca alkaloids |
| melphalan | vinblastine (VLB) |
| chlorambucil | vincristine |
| uracil mustard | vinorelbine |
| temozolomide | vindesine |
| Nitrosoureas | Taxotere ® (docetaxel) |
| | |
| carmustine (BCNU) | estramustine |
| lomustine (CCNU) | estramustine phosphate |
| semustine (methyl-CCNU) | Epipodophylotoxins |
| | |
| chlormethine | etoposide |
| streptozocin | teniposide |
| Ethylenimine/Methyl-melamine | Antibiotics |
| | |
| triethylenemelamine (TEM) | actimomycin D |
| triethylene thiophosphoramide (thiotepa) | daunomycin (rubidomycin) |
| hexamethylmelamine (HMM, altretamine) | doxorubicin (adriamycin) |
| | mitoxantroneidarubicin |
| Alkyl sulfonates | bleomycin |
| | splicamycin (mithramycin) |
| busulfan | mitromycin-C |
| pipobroman | dactinomycin |
| Triazines | aphidicolin |
| | |
| dacarbazine (DTIC) | epirubicin |
| Antimetabolites | idarubicin |
| Folic Acid analogs | daunorubicin |

TABLE 1-continued

| methotrexate | mithramycin |
|---|---|
| trimetrexate | deoxy co-formycin |
| pemetrexed | Enzymes |
| | |
| (Multi-targeted antifolate) | L-asparaginase |
| Pyrimidine analogs | L-arginase |
| | |
| 5-fluorouracil | Radiosensitizers |
| | |
| fluorodeoxyuridine | metronidazole |
| gemcitabine | misonidazole |
| cytosine arabinoside (AraC, cytarabine) | desmethylmisonidazole |
| | pimonidazole |
| 5-azacytidine | etanidazole |
| 2,2'-difluorodeoxy-cytidine | nimorazole |
| floxuridine | RSU 1069 |
| pentostatine | EO9 |
| Purine analogs | RB 6145 |
| | |
| 6-mercaptopurine | Nonsteroidal antiandrogens |
| | |
| 6-thioguanine | SR4233 |
| azathioprine | flutamide |
| 2'-deoxycoformycin (pentostatin) | nicotinamide |
| | 5-bromodeozyuridine |
| erythrohydroxynonyl-adenine (EHNA) | 5-iododeoxyuridine |
| fludarabine phosphate | bromodeoxycytidine |
| 2-chlorodeoxyadenosine | Miscellaneous agents |
| (cladribine, 2-CdA) | Platinium coordination complexes |
| | |
| Type I Topoisomerase Inhibitors | cisplatin |
| | |
| camptothecin | carboplatin |
| topotecan | oxaliplatin |
| irinotecan | anthracenedione |
| Biological response modifiers | mitoxantrone |
| | |
| G-CSF | Substituted urea |
| | |
| GM-CSF | hydroxyurea |
| Differentiation Agents | Methylhydrazine derivatives |
| | |
| retinoic acid derivatives | N-methylhydrazine (MIH) |
| Hormones and antagonists | procarbazine |
| Adrenocorticosteroids/antagonists | Adrenocortical suppressant |
| | |
| prednisone and equivalents | mitotane (o,p'-DDD) |
| dexamethasone | ainoglutethimide |
| ainoglutethimide | Cytokines |
| | |
| Progestins | interferon ($\alpha$, $\beta$, $\gamma$) |
| | |
| hydroxyprogesterone caproate | interleukin-2 |
| medroxyprogesterone acetate | Photosensitizers |
| | |
| megestrol acetate | hematoporphyrin derivatives |
| Estrogens | PHOTOFRIN ® |
| | |
| diethylstilbestrol | benzoporphyrin derivatives |
| ethynyl estradiol/equivalents | Npe6 |
| Antiestrogen | tin etioporphyrin (SnET2) |
| | |
| tamoxifen | pheoboride-a |
| Androgens | bacteriochlorophyll-a |
| | |
| testosterone propionate | naphthalocyanines |
| fluoxymesterone/equivalents | phthalocyanines |
| Antiandrogens | zinc phthalocyanines |
| | |
| flutamide | Radiation |
| | |
| gonadotropin-releasing hormone analogs | X-ray |
| | ultraviolet light |
| leuprolide | gamma radiation |
| | visible light |
| | infrared radiation |
| | microwave radiation |

Examples of chemotherapeutic agents that are particularly useful in conjunction with radiosensitizers include, for example, camptothecin, carboplatin, cis-platin, daunorubicin, doxorubicin, interferon (alpha, beta, gamma), irinotecan, hydroxyurea, chlorambucil, 5-fluorouracil (5-FU), methotrexate, 2-chloroadenosine, fludarabine, azacytidine, gemcitabine, pemetrexed, interleukin 2, irinotecan, docetaxel, paclitaxel, topotecan, CPT-11, anastrazole, letrazole, capecitabine, reloxafine, cyclophosphamide, ifosamide, droloxafine, and therapeutically effective analogs and derivatives of the same.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 397:268-272; Vasquez (1997) Mol. Biol. Cell. 8:973-985; and Panda (1996) J. Biol. Chem 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminogluthimide, estramustine, medroxyprogesteroneacetate, leuprolide, flutamide, toremifene, zoladex.

Other cytostatic agents are antiangiogenics such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

Due to their unique ability to induce apoptosis in tumor cells, TNF family members are considered to be potential anticancer pharmaceuticals. However, many tumor cells escape proapoptotic acid of death ligands, thereby reducing the use of these agents to death ligand-sensitive cancers and allowing the tumor to escape host immune response. The use of an inhibitor of NF-κB may be used to sensitize tumor cells to the killing of a death ligand, such as a TNF polypeptide.

The TNF polypeptide can be a member of the TNF superfamily of ligands. Representative examples of TNF polypeptides include, but are not limited to, NGF, CD40L, CD137L/4-1BBL, TNF-α, CD134L/OX40L, CD27L/CD70, FasL/CD95, CD30L, TNF-β/LT-α, LT-β, and TRAIL. Members of the TNF superfamily are natural proteins that are implicated in the maintenance and function of the immune system and that can trigger apoptosis. The TNF polypeptide may be TRAIL, which induces apoptosis mainly in tumor but not in normal cells. The activity of these so-called "death ligands" is believed to be mediated by binding with members of the TNF receptor family, which contain structurally similar death domains in their intracellular portions. Ligation of these receptors, specific for each death ligand, trigger activation of a cascade of events resulting in caspase activation. Representative examples of TNF-R receptors bound by the TNF polypeptides include, but are not limited to, LNGFR/p75, CD40, CD137/4-1BB/ILA, TNFRI/p55/CD120a, TNFRII/p75/CD120b, CD134/OX40/ACT35, CD27, Fas/CD95/APO-1, CD30/Ki-1, LT-β R, DR3, DR4, DR5, DcR1/TRID, TR2, GITR and osteoprotegerin.

It also contemplated that other agents can be used in the place of the TNF polypeptide. For example, an antibody that mimics the activity of a TNF polypeptide can be used. Representative examples of such antibodies include, but are not limited to, an agonist antibody to FAS, TRAIL receptor, or TNFR. In addition, aptamers and other synthetic ligands capable to activate the corresponding receptors may be used.

It also is possible to diagnose whether a tumor in a patient is capable of being treated by a present carbazole compound. A sample of the tumor is obtained from the patient. Cells of the tumor then are transduced with a p53 reporter system, such as a p53-responsive lacZ reporter. The transduced cells then are incubated with the compound. The production of a p53-mediated signal above controls indicates that the tumor can be treated by the carbazole compound.

Figure 1B:
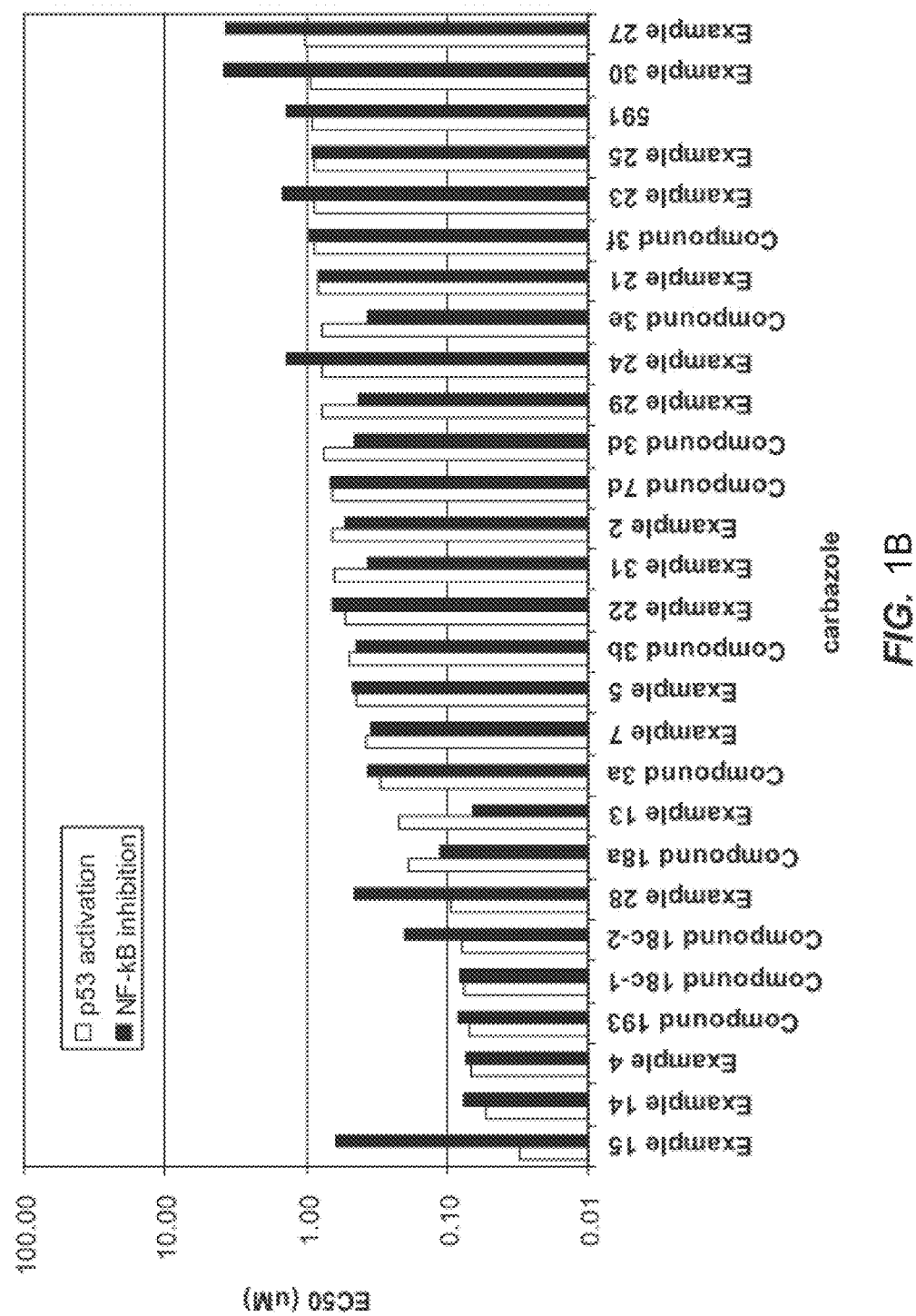
FIG. 1B is a plot of $EC_{50}$ (μM) for p53 activation and NF-κB inhibition for carbazoles of the present invention.

FIGS. 1A and 1B are plots showing that the present carbazoles inhibit NF-κB transcriptional activity in TNF-treated cells (FIG. 1A) and a comparison of active concentration ($EC_{50}$ values) on p53 activation and NF-κB inhibition (FIG. 1B).

Figure 2A:
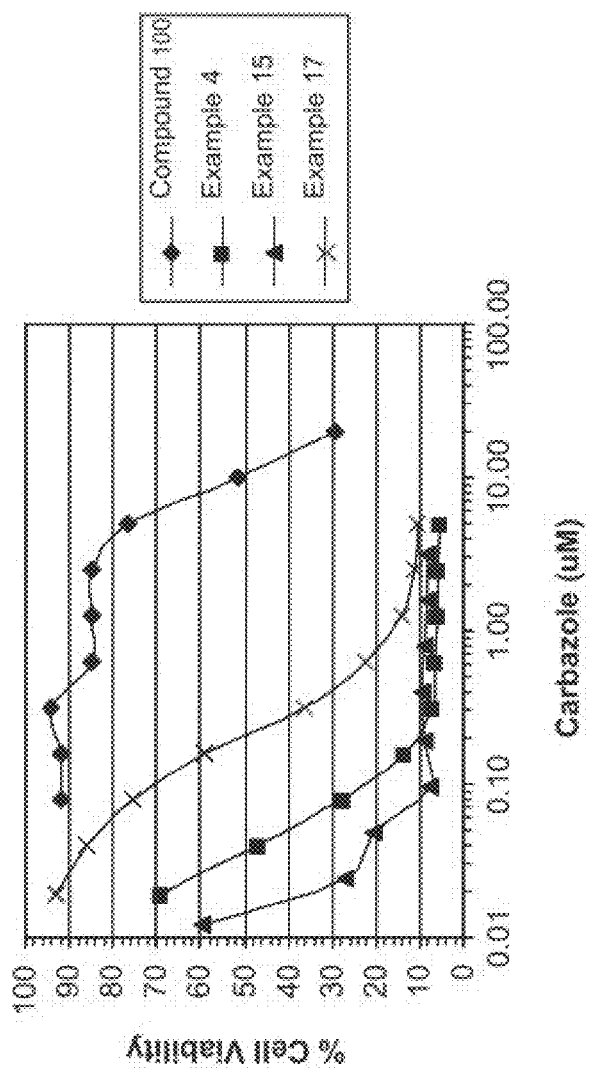
FIGS. 2A through 2K are plots of % cell viability vs. concentration (μM) for various tumor cells treated with carbazoles of the present invention.
Figure 2B:
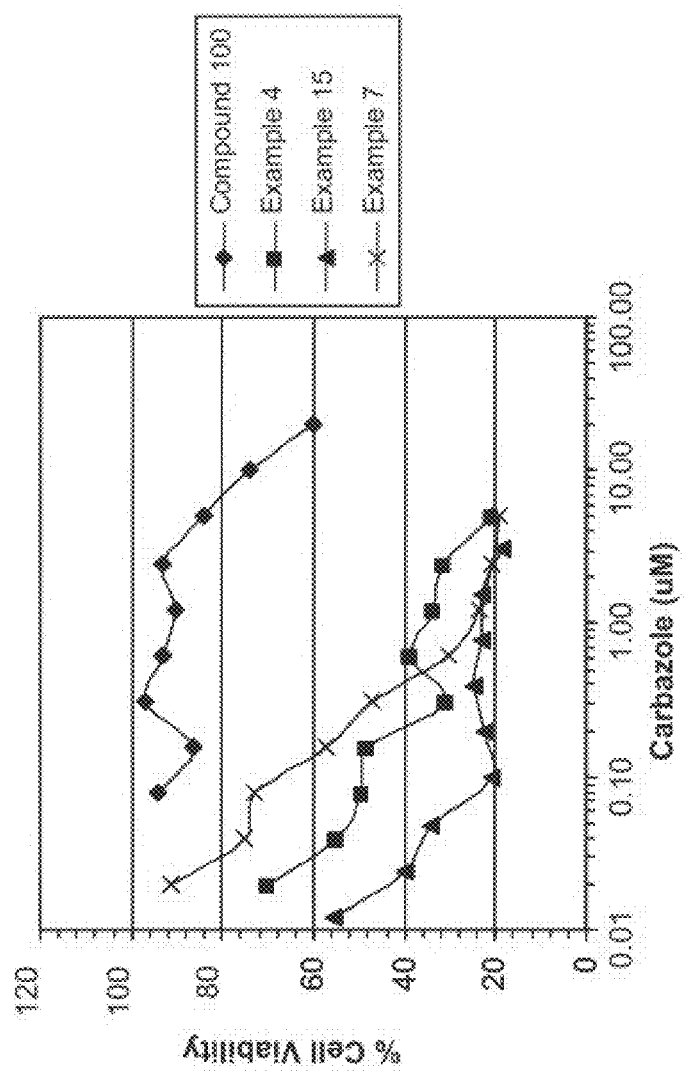
Figure 2C:
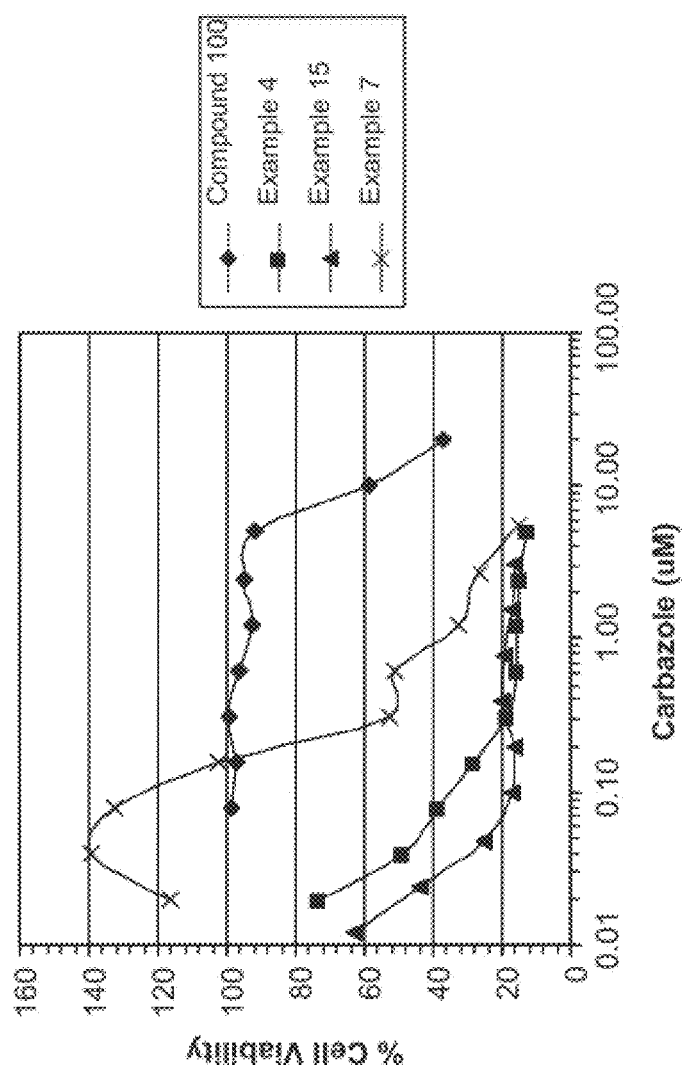
Figure 2D:
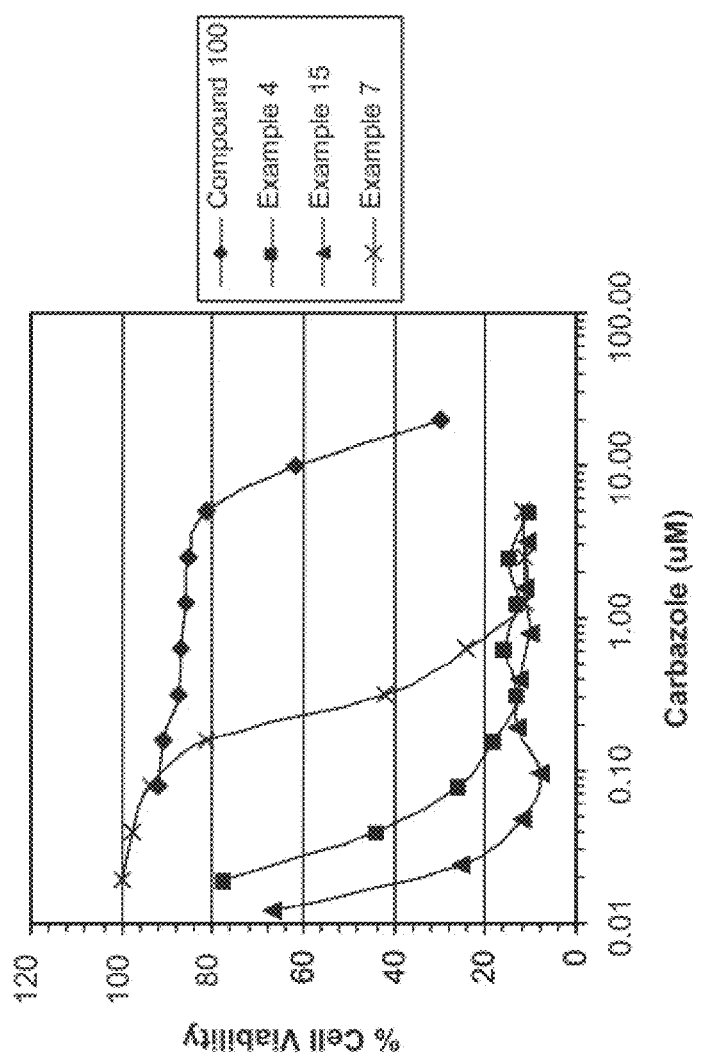
Figure 2E:
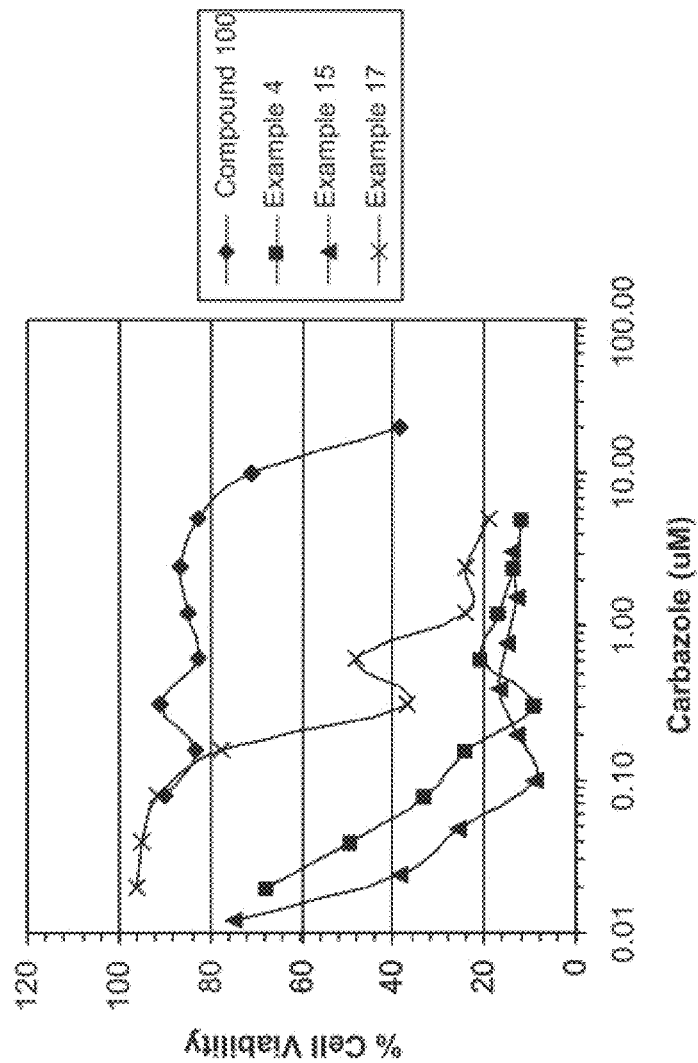
Figure 2F:
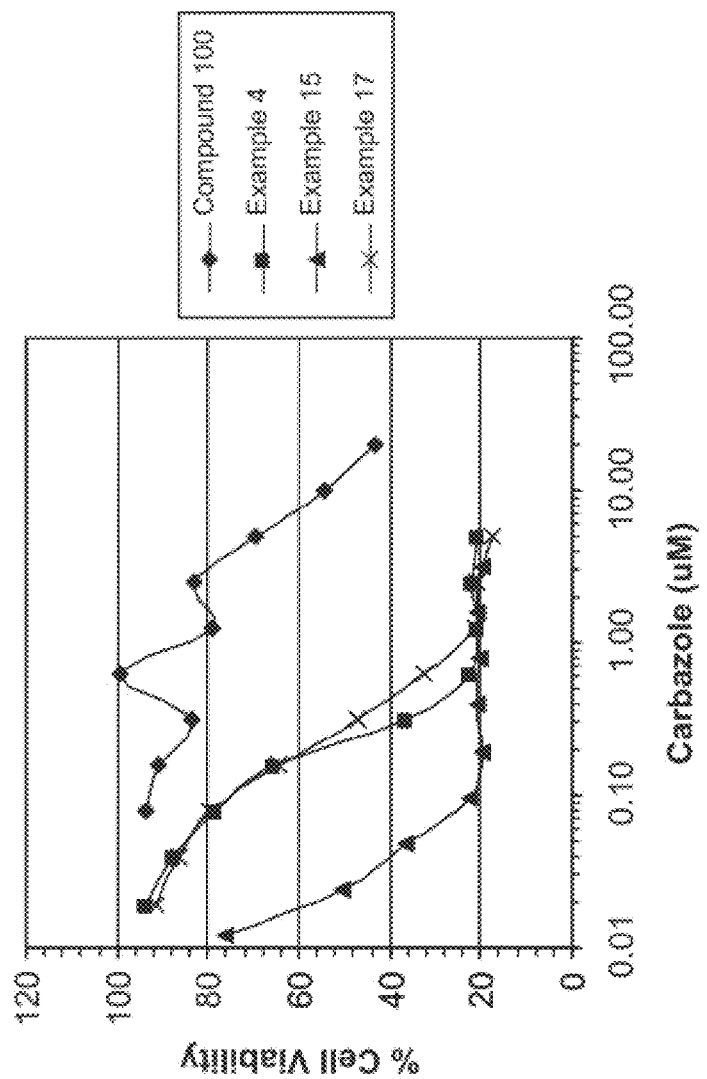
Figure 2G:
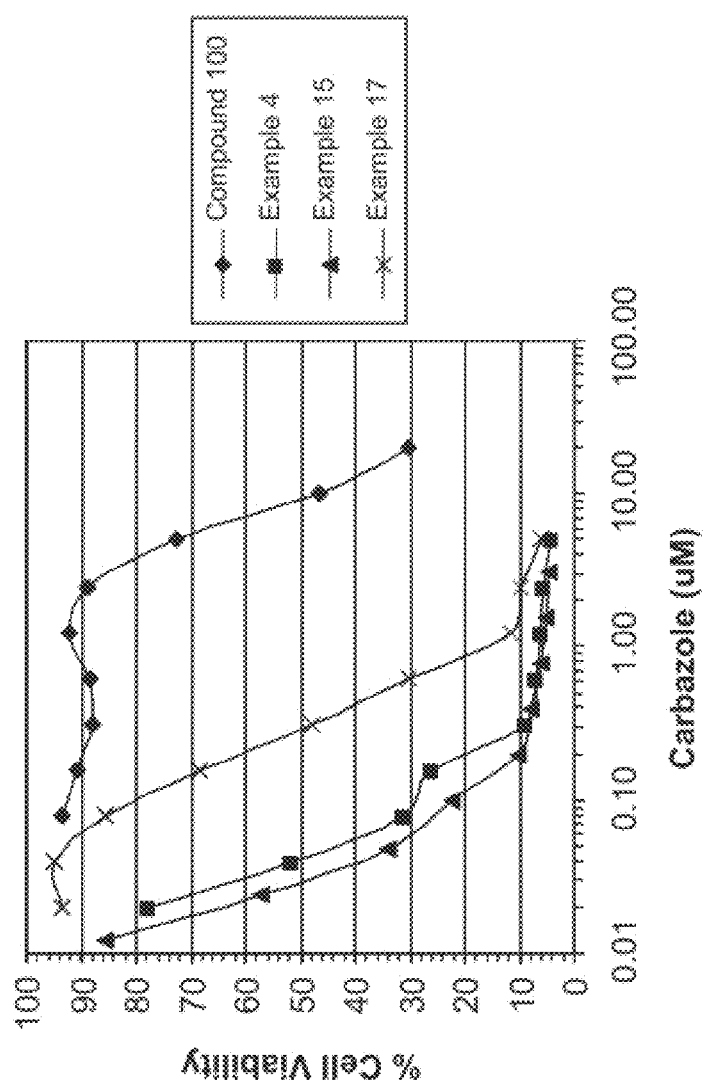
Figure 2H:
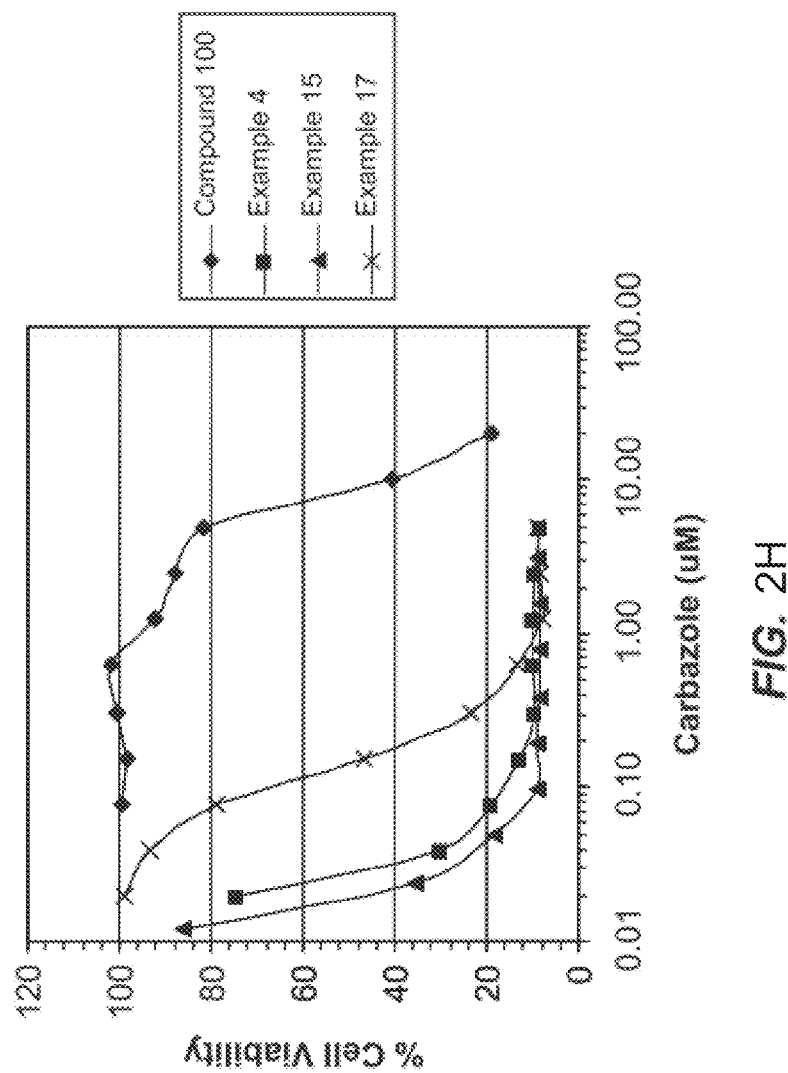
Figure 2I:
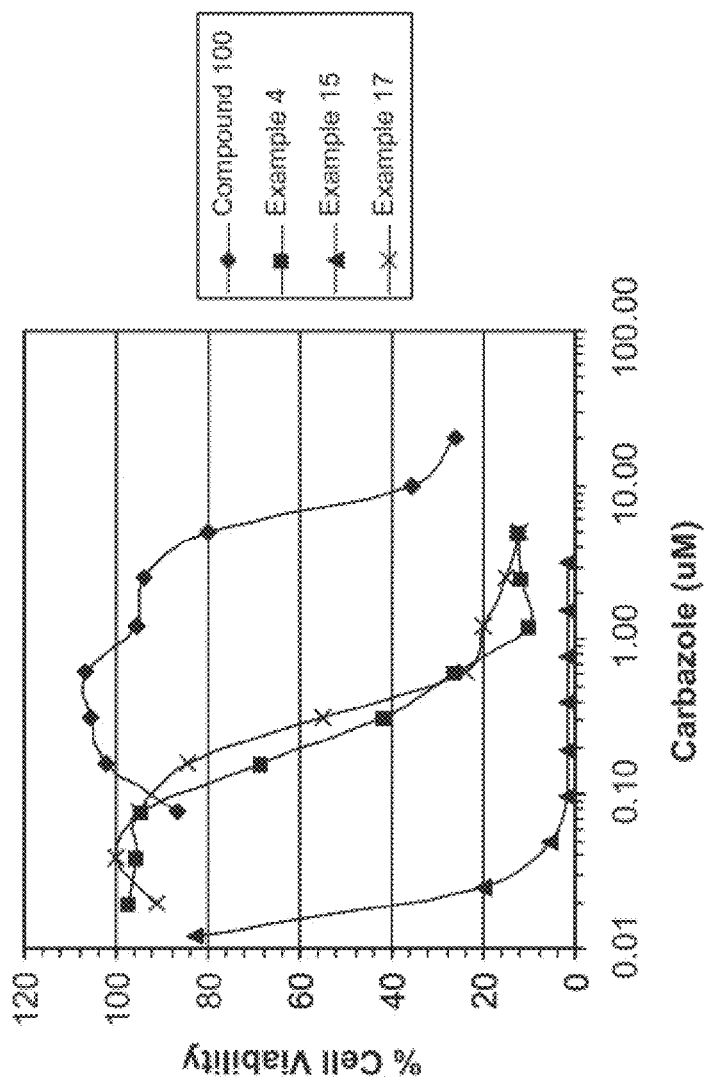
Figure 2J:
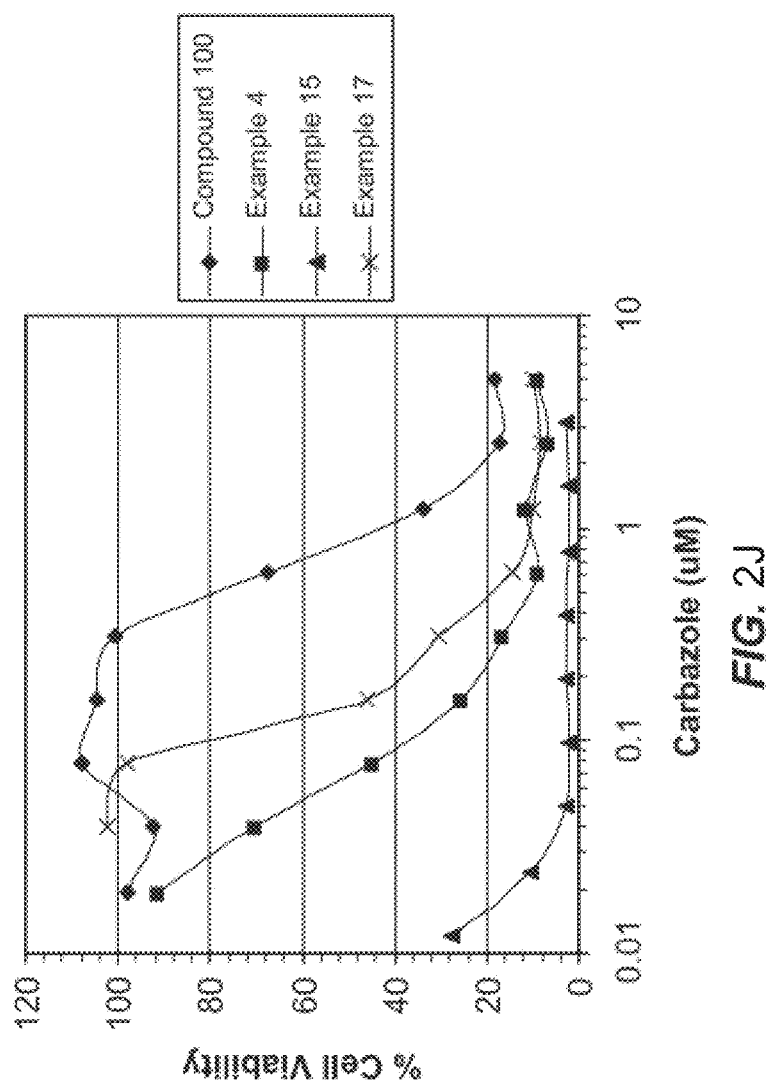
Figure 2K:
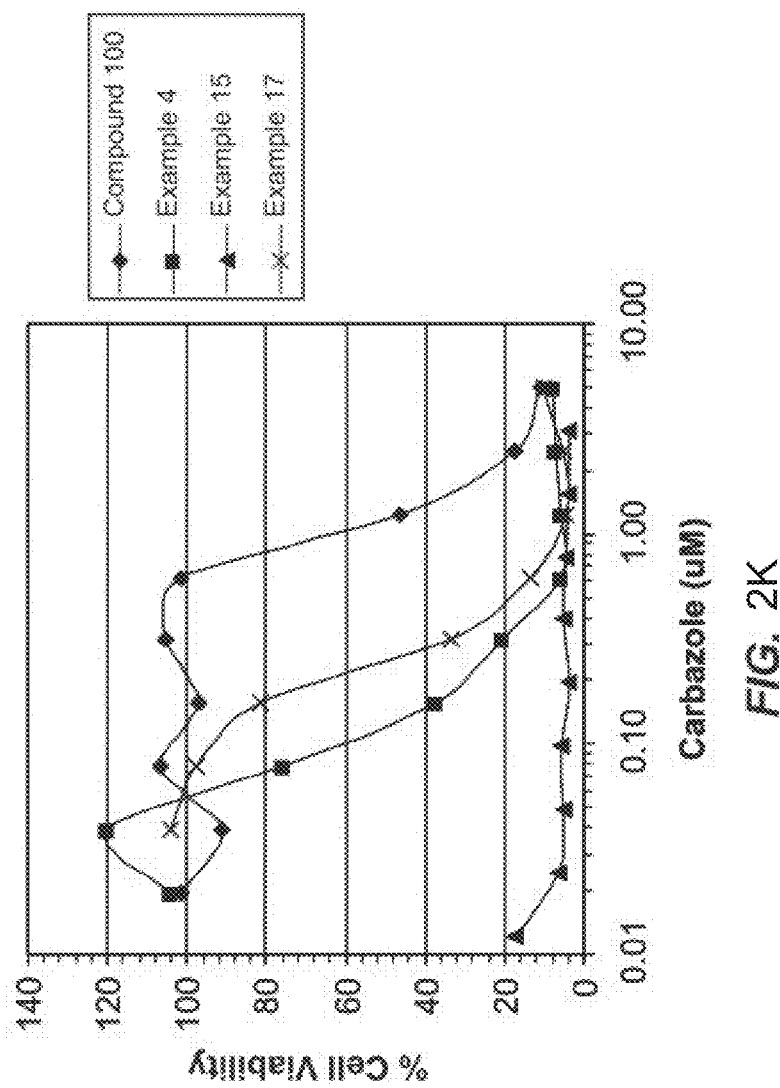
Figure 3:
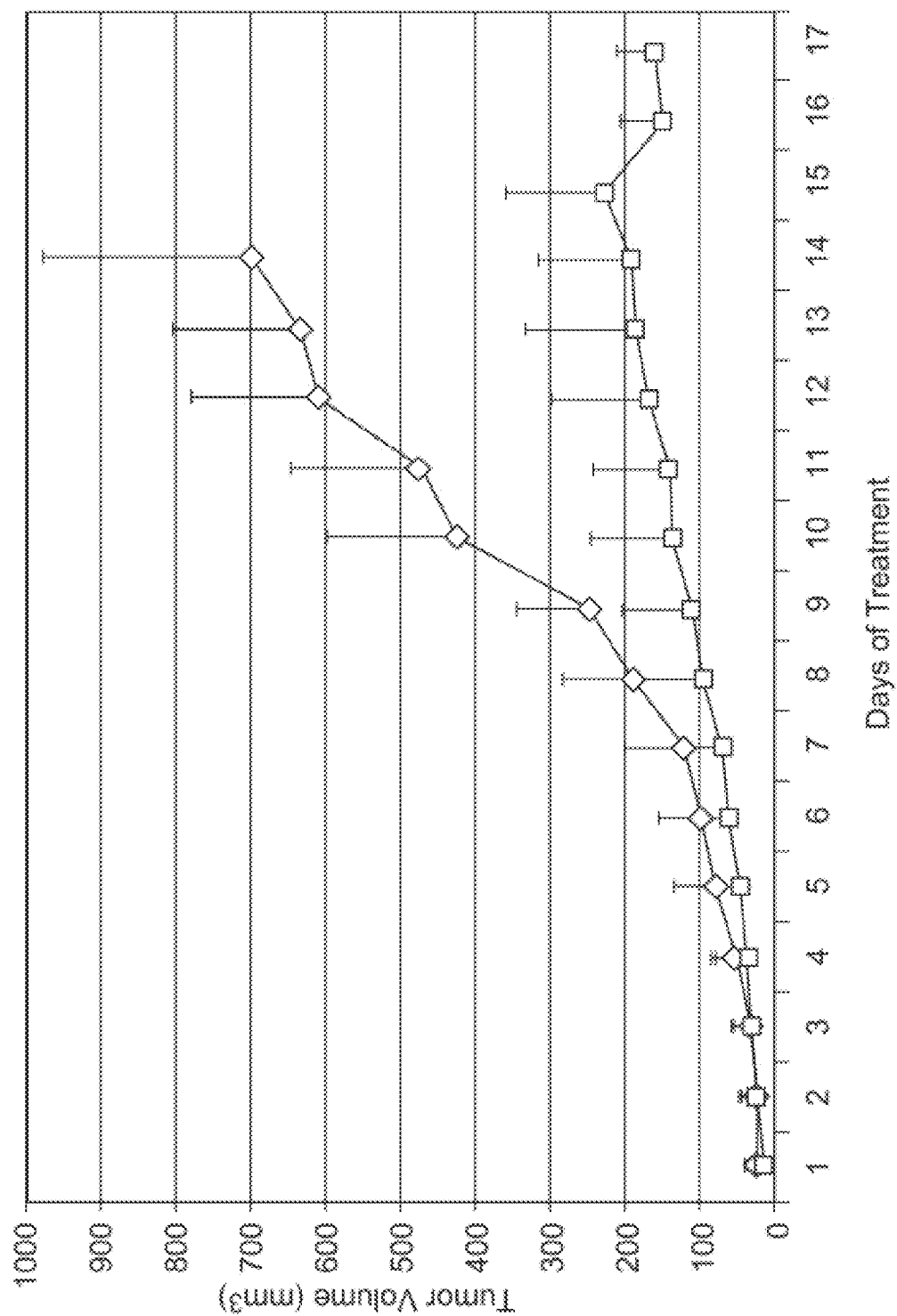
FIG. 3 contains a plot of tumor volume vs. days of treatment in an HCT 116 sc xenograft model using the compound of Example 7.

The present carbazole compounds have significant anticancer properties in vitro (FIGS. 2A-K) and in vivo (FIG. 3). FIGS. 2A-K show the effect of various carbazole compounds on tumor cells differing in their p53 states after treatment for 1 hour with different concentrations of four present carbazole compounds. Cell survival was assessed at 72 hours by methylene blue staining. Therefore, it is theorized, but not relied upon, that p53 activation by the present carbazole compounds may not be the primary death-inducing signal, but may rather reflect a type of cell stress caused by inactivation of constitutively active NF-κB.

The tumor cells tested were HCT116 colon adenocarcinoma p53 wt (FIG. 2A), MDA-MB-231 breast adenocarcinoma p53 mut (FIG. 2B), DLD1 colon carcinoma p53 wt (FIG. 2C), A549 lung adenocarcinoma p53 wt (FIG. 2D), Caki1 renal cell carcinoma p53 wt (FIG. 2E), HT29 colon adenocarcinoma p53 mut (FIG. 2F), H1299 lung adenocarcinoma p53 deletion (FIG. 2G), MCF7 breast adenocarcinoma p53 wt (FIG. 2H), RCC45 renal cell carcinoma p53 wt (FIG. 2I), ACHN renal cell carcinoma (FIG. 2J), and HT1080 lung fibrosarcoma (FIG. 2K). The tumor cell tested in FIG. 3 is the HCT116 sc xenograft model.

The present carbazole compounds analyzed did not induce DNA damage (Table I). It therefore is theorized, that the cytotoxicity of the present carbazole compounds results from a unique type of non-genotoxic cell stress involving NF-κB suppression to which cancer cells are more sensitive than normal cells. This illustrates that the present carbazoles are a highly effective, novel class of anti-cancer therapeutics.

TABLE I

Summary of the effects of present carbazole compounds and doxorubicin to compare DNA and DNA-damage responsive signaling.

| Compound | cellular localization | γH2AX staining | ATM/ATR activation | Chk1/2 phospho | p53 phosphor | Topo II inhibition in cells | Topo II inhibition in vitro | Ames test |
|---|---|---|---|---|---|---|---|---|
| Compound 100 | cytoplasmic | no | no | no | S392 | no | ligation | negative |
| Compound 6h | cytoplasmic | no | no | no | S392 | ND | ligation | negative |
| Example 3 | cytoplasmic | no | no | no | ND | ND | ligation | negative |
| doxorubicin | nuclear | yes | yes | yes | S15, 46, 392 | yes | relegation | negative |

ND—not determined

Figure 4:
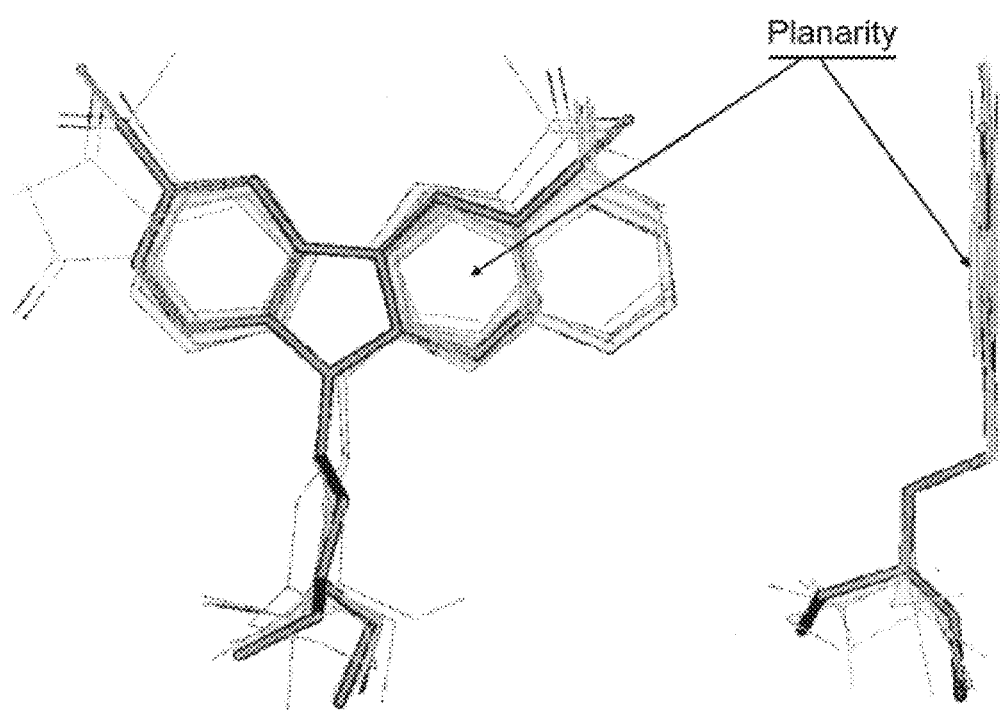
FIG. 4 is a schematic showing the three dimensional analysis of active carbazole compounds.
Figure 5:
FIG. 5 is a schematic showing the three dimensional analysis of inactive carbazole compounds.
Figure 6:
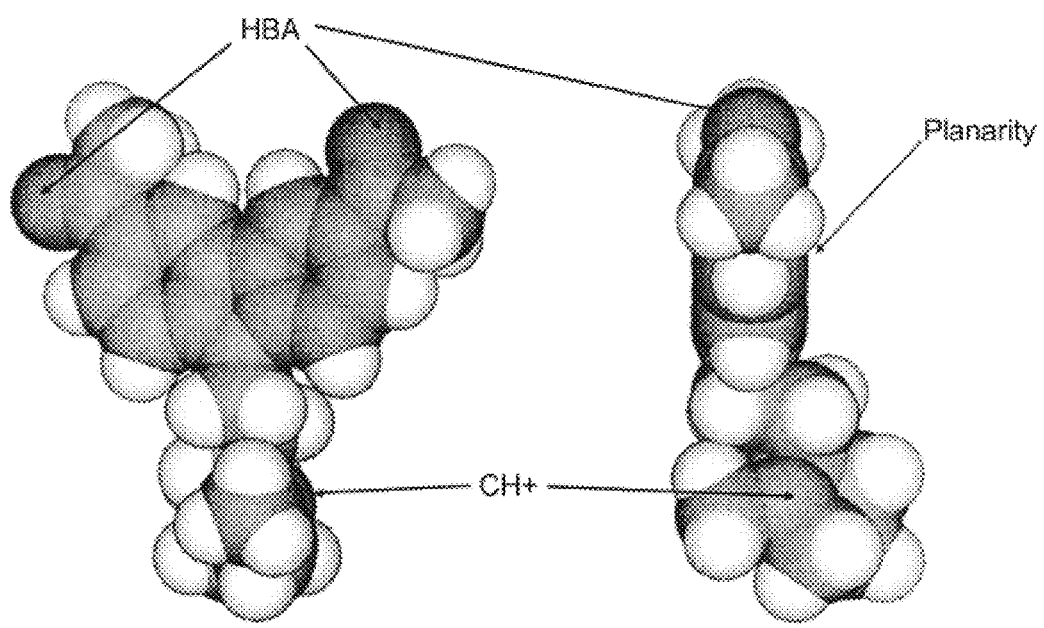
FIG. 6 is a schematic showing the three dimensional structure of an active carbazole compound, i.e., Example 2.
Figure 7:
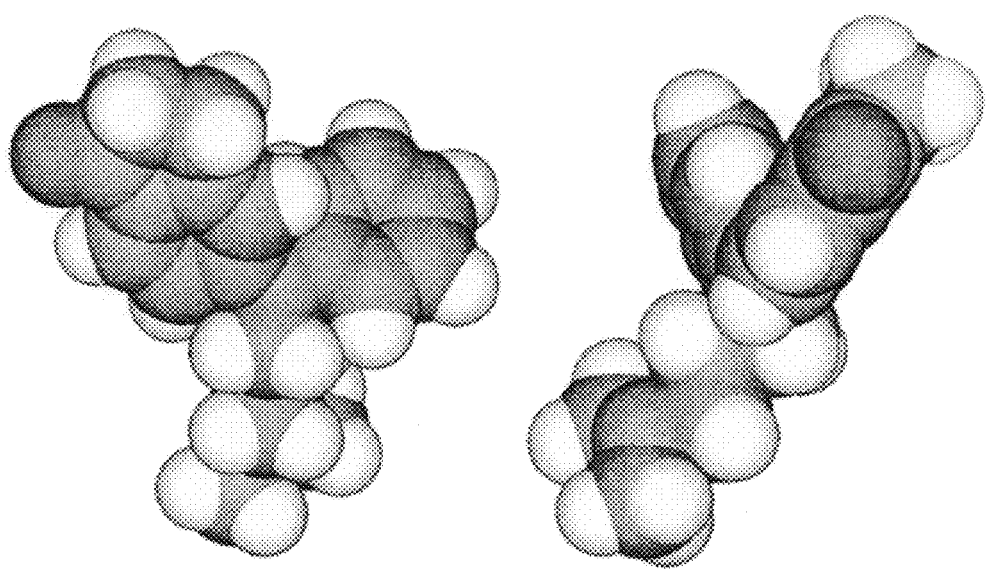
FIG. 7 is a schematic showing the three dimensional structure of an inactive carbazole compound, i.e., Compound 200.

In accordance with an important feature of the present invention, a three dimensional (3D) superimposition of conformers of active and inactive carbazole molecules revealed characteristics of the compounds that contributes to their activity. One important characteristic is the planarity of the carbazole core. Comparing multiple three dimensional alignments of the conformers, it was found that in all active carbazole compounds, the carbazole core region was planar (FIG. 4). Inactive compounds can be planar or non-planar (FIG. 5). Additional structural studies of compounds having similar atom distributions over the molecular architecture confirmed that planarity of the carbazole ring area is important in determining potency of p53 activation by the carbazole compound (FIGS. 6 and 7). An active carbazole, i.e., Example 2, is shown in FIG. 6. An inactive carbazole, i.e., Compound 200, is shown in FIG. 7. Compound 200 has a structural formula:

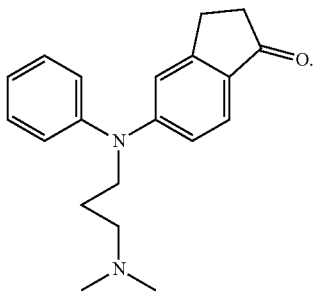 [SMILES: CN(C)CCCN(c1ccccc1)c1ccc2c(c1)CCC2=O]

The finding that carbazole compounds able to activate p53 have planar structure led to an unrelied upon hypothesis that the mechanism of action of these compounds is mediated via DNA intercalation. It is hypothesized that the correlation between p53 activation potency and the planar structure of carbazole core reflects an ability to intercalate DNA. To test this hypothesis, the carbazole compounds were virtually intercalated into the three dimensional DNA structure taken from the p53-DNA complex (1TUP PDB structure). The initial intercalation was performed as follows. An active carbazole molecule, i.e., Compound 300, was superimposed upon the DNA structure such that the planar ring area was positioned between and parallel to two stacking base pairs. The intercalated molecule then was placed against Arg280 of p53. The Arg280 residue was considered to be crucial for p53-DNA interaction. See M. Kitayner et al., *Molecular Cell*, 22, pages 741-753, June 2006. Such a brute force superimposition violates Van der Waals interactions between atoms of the two structures. Using the MOLOC molecular mechanics software package, the tertiary DNA-carbazole analog-p53 complex was optimized to reduce Van der Waals and torsion angle tensions in the combined DNA-molecule structure. After the optimization, the position of the active molecule was fitted to the cavity in DNA with the ring plane that is parallel to DNA stacking base pairs. As a result of this optimization procedure, hydrogen bond acceptors (HBA) located on the carbazole ring substituents were positioned in the major groove and the side chain attached to the carbazole nitrogen was positioned in the narrow minor groove. The structural formula for Compound 300 is:

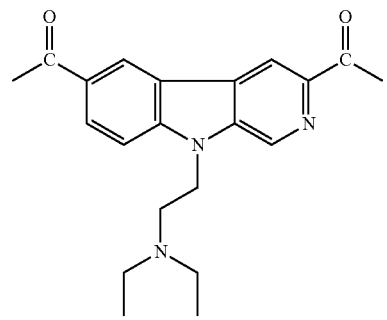 [SMILES: CCN(CC)CCn1c2ccc(C(C)=O)cc2c2cc(C(C)=O)ncc21]

As a result of this study, a dsDNA fragment with an inside cavity better shaped to accommodate p53 activating carbazole compounds was created. Using the GOLD software package, molecular docking was performed on a variety of carbazole compounds with known p53 activity. It was demonstrated that, on average, highly active molecules (p53 activation $EC_{50}$<130 μM) were much better fitted to this cavity than molecules with $EC_{50}$>130 μM. The conformers of highly active carbazole compounds are uniformly positioned inside the cavity, whereas the quality of fit diminished among carbazole compounds having weak p53 activation potency. The majority of inactive molecules were characterized by very poor quality of fit.

A proper positioning of the substituent attached to the carbazole nitrogen into the minor groove of DNA may be important for achieving good p53 activity. Simply, the fit of the side chain into the minor groove improves the overall fit of the carbazole compound. In addition, the atom voting analysis of the three dimensional superimposition of active carbazole compounds shows that a positively charged amino group in the side chain is important for achieving activity.

The positions of HBA (hydrogen bonding) atoms on the carbazole substituents, and their identity are important to achieve p53 activity. The low quality of HBA atoms (i.e., nitrogen) leads to a weak activity of the carbazole compound. The absence of HBA atoms on carbazole substituents renders a compound inactive. All highly active compounds have non-rotated carbazole substituents. The docking of highly active ($EC_{50}$<130 nM) and active molecules ($EC_{50}$ about 1 nM) into the DNA cavity demonstrates that rotated carbazole substituents with good HBA atoms can create hydrogen bonds with DNA atoms. In contrast, the non-rotated carbazole substituents do not hydrogen bond with DNA, which leads to their high activity.

The antitumor activity of Example 7 (Compound 6h) was demonstrated using the B16 melanoma singenic tumor model as follows. C57BL/6 mice were inoculated intradermally at 2 sites of the abdomen with $5 \times 10^4$ murine B16 melanoma cells. When at least one of the tumor inoculation sites developed a tumor (average size about 6 $mm^3$), treatment commenced. Mice were treated daily by oral gavage for up to 14 days with either 0.5% methylcellulose vehicle control or 30 mg/kg Example 7 (n=5 mice/treatment group). Tumor measurements were collected by digital calipers every 1-2 days. The effect of treatment on individual tumors is presented in FIGS. 8A and 8B. With the exception of one mouse from Example 7 treatment group, no effect was observed on overall mouse weight for either treatment group (<10% changes). By Day 9, there was an approximately 3-fold decrease in tumor growth in Example 7 treatment group compared to the vehicle control group (68% growth suppression).

To confirm the anti-tumor activity of Example 7, the carbazole compound (30 mg/kg) was delivered orally using the HCT116 xenograft model. In this test, athymic nude mice were inoculated with $5 \times 10^6$ of HCT116 tumor cells into two sites. 90% of tumors appeared between the seventh and eleventh days after inoculation. Oral daily treatments with 30 mg/kg of the compound of Example 7 in 0.5% methylcellulose or a 0.5% methylcellulose vehicle control began when at least one tumor per mouse reached 20-25 $mm^3$ in size. The mice were treated until control tumors reached 1000 $mm^3$. Following commencement of treatment, mice were monitored for overall condition, weight loss, and survival, as well as for the size of tumors measured every other day.

der of the mice in group 2 fluctuated in the range of 95-105% of original weight. No any other abnormal signs were noticed in mouse appearance, activity, or behavior of group 2.

In control group 1, HCT116 tumors grew exponentially, as expected with in a regular deviation between faster and slower growing tumors. In Example 7 treated group 2, growth of all tumors was delayed compared with vehicle control treated group 1. On day 14 after start of treatment, no treated tumors attained the size of the slowest growing control tumor (530 $mm^3$). In average growth of tumors, treatment with Example 7 suppressed tumor growth by a factor of about 3.5 (73% of inhibition) compared to vehicle control group 1. Importantly, one treated tumor was completely cured, and, on autopsy, only a minimal connective tissue type formation was found in place of the tumor. The size of several treated tumors not only increased more slowly than control tumors, but decreased, which is indicative of tumor cell death and tumor destruction as a result of treatment with the compound of Example 7. This result was observed for the first 3-5 days of treatment, then the treated tumors continued to slowly grow.

This experiment shows that the compound of Example 7 has a suppressive effect on the growth of HCT116 subcutaneous xenograft tumors in nude mice. The growth suppression value is 73%, which is considered by NCI standards as a significant anti-cancer activity (≥42%). The above results are illustrated in FIGS. 3 and 8A-B, 9A-C, and 10A-B.

Figure 8A:
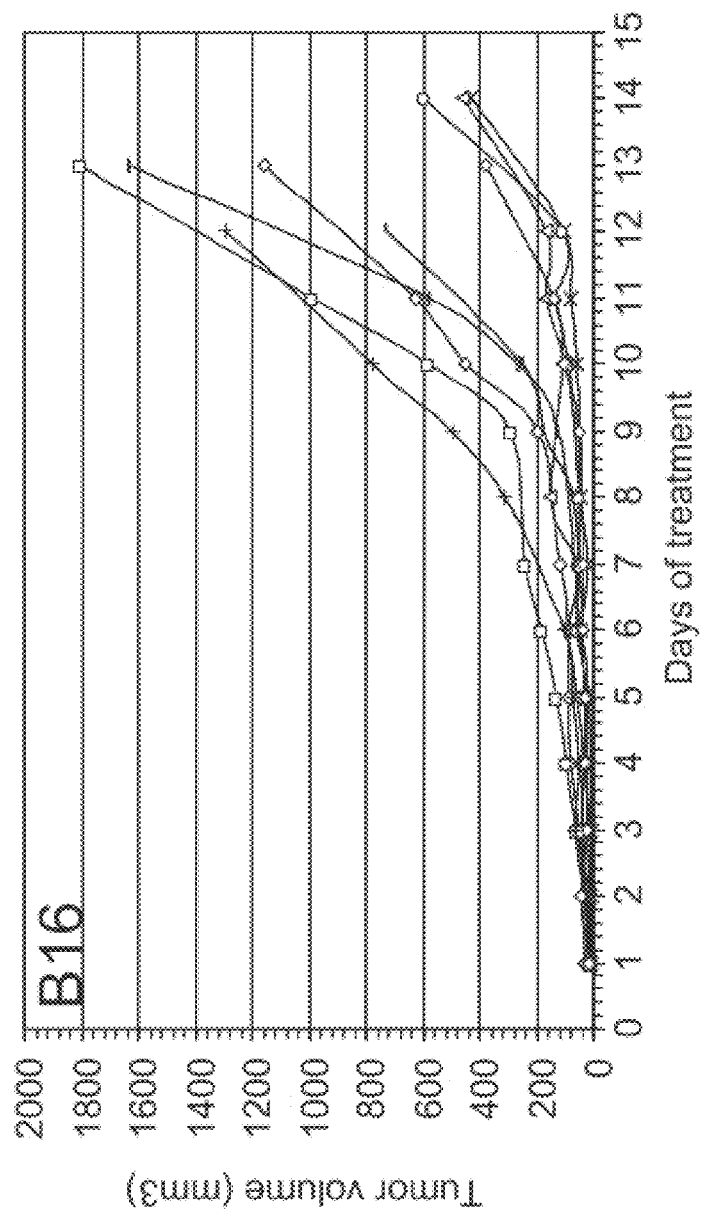
FIGS. 8A-B contain plots of tumor volume ($mm^3$) vs. days of treatment for individual tumor growth in mice treated with a control vehicle (FIG. 8A) and in mice treated with the compound of Example 7 (FIG. 8B)
Figure 8B:
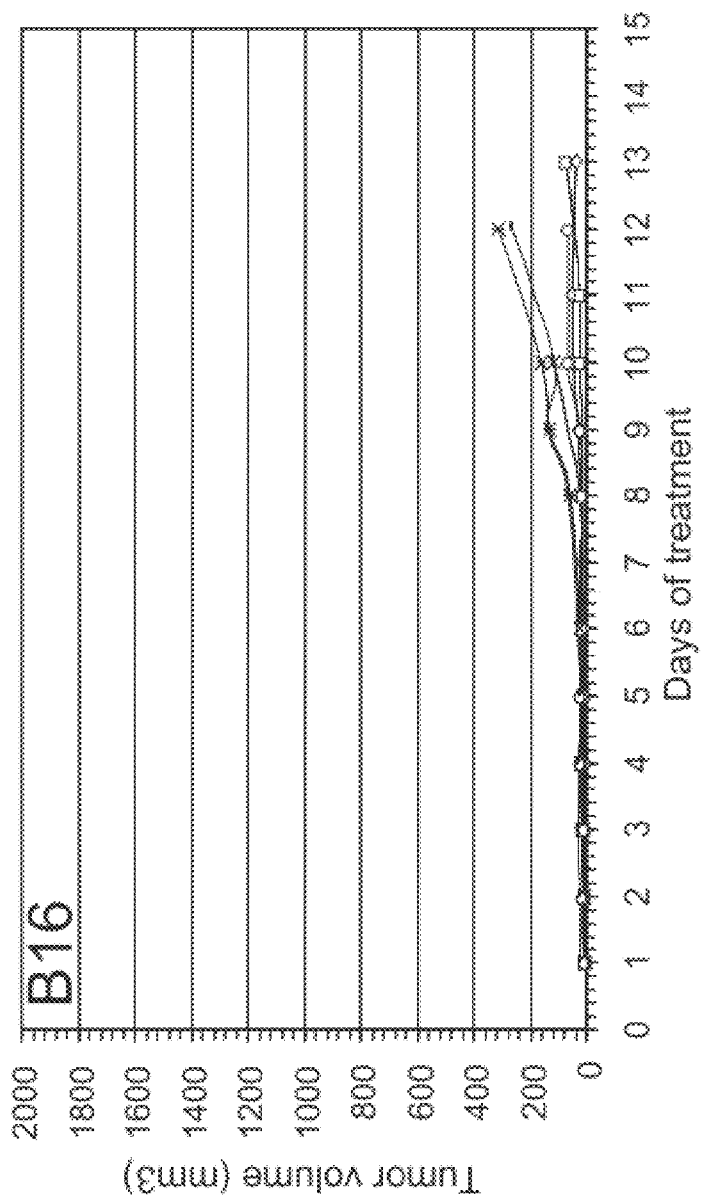

FIG. 3 is an average curve of tumor growth showing treatment of HCT116 colon carcinoma xenograft tumor with the compound of Example 7 and a control (MC). Tumors treated with the compound of Example 7 exhibit a substantially reduced tumor volume. The bars in the graph of tumor volume vs. days of treatment represent the standard deviation. FIGS. 8A-B contains plots showing the growth of individual tumors treated in mice with the control vehicle (FIG. 8A) and with the compound of Example 7 (FIG. 8B).

Figure 9A:
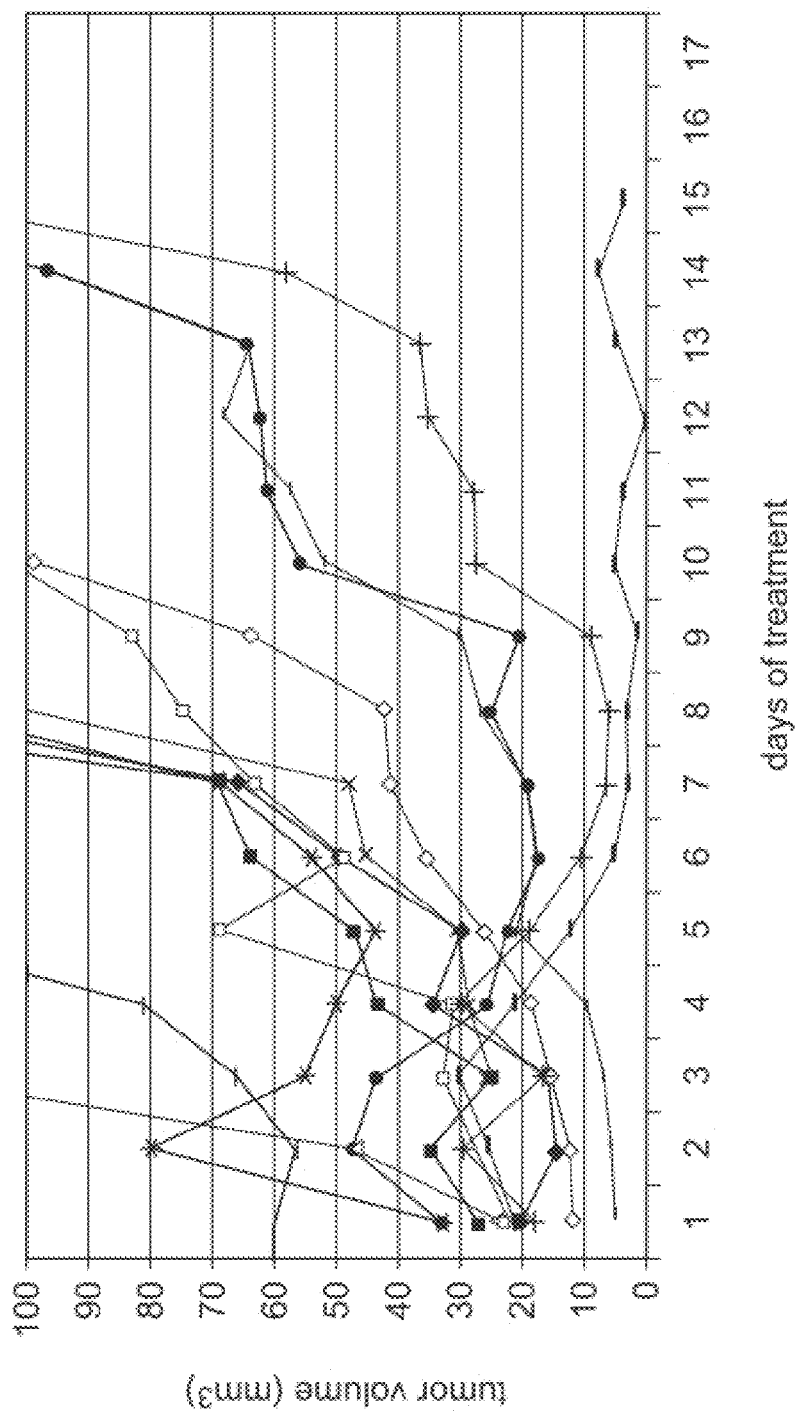
FIGS. 9A-C contain plots of tumor volume ($mm^3$) vs. days of treatment with a control vehicle (FIG. 9A) and with the compound of Example 7 (FIG. 9B and FIG. 9C)
Figure 9B:
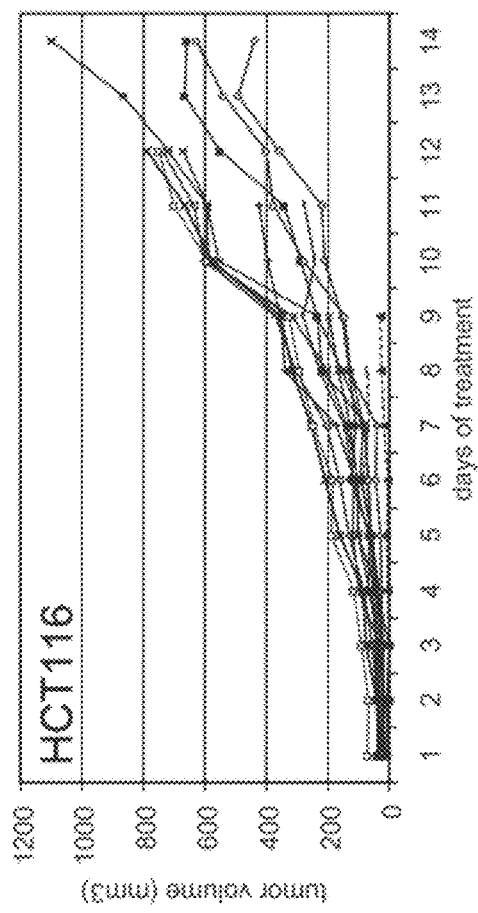
Figure 9C:
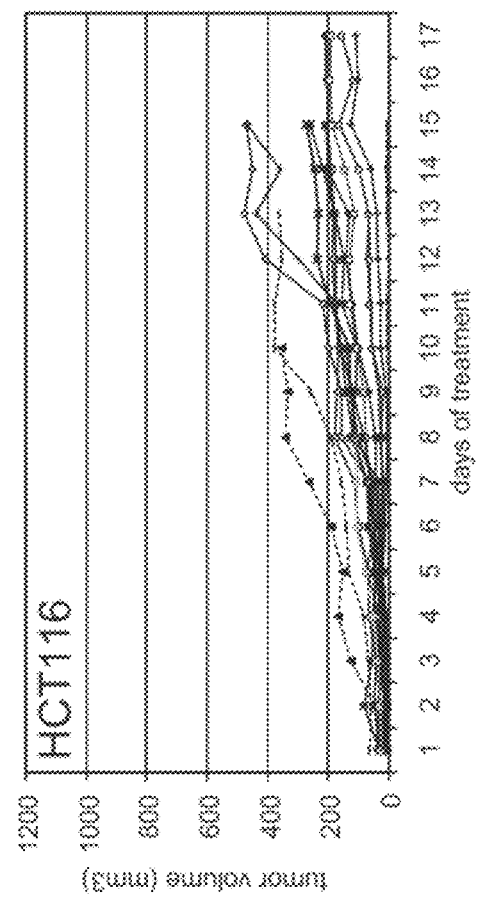
Figure 10B:
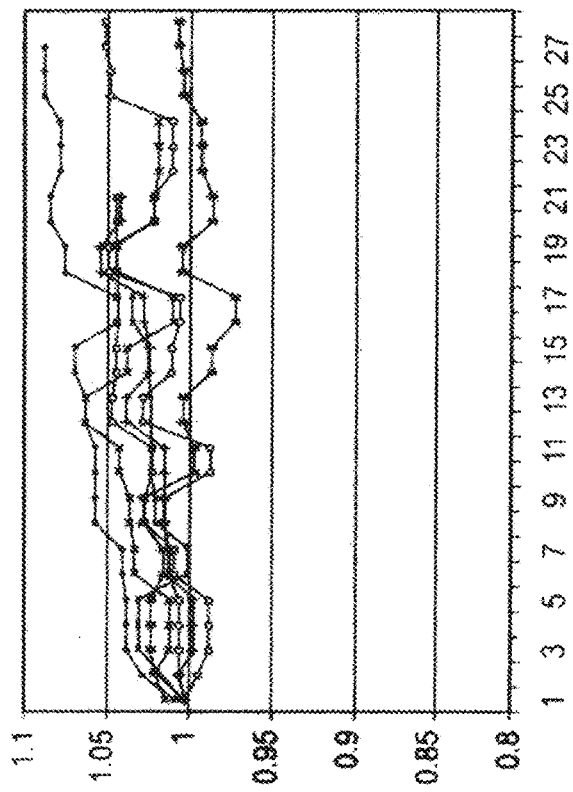
FIGS. 10A-B contain plots of the relative weight of individual mice vs. days after cell inoculation in mice treated with the control vehicle (FIG. 10A) and mice treated with the compound of Example 7 (FIG. 10B)
Figure 10A:
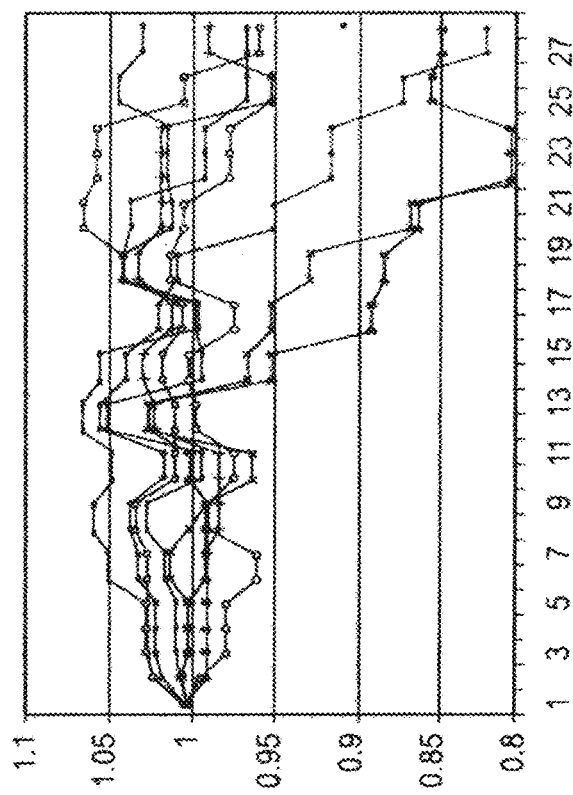

FIGS. 9A-C shows the growth of individual tumors, up to 100 $mm^3$, in mice treated with the compound of Example 7. FIGS. 10A-B show that tumor size decreased during the first days of treatment, and tumors that were cured.

TABLE 2

Experimental groups

| Group | Number of mice | Cell line | Treatment | Mode of administration | Dose schedule | Tumor measurement; monitoring |
|---|---|---|---|---|---|---|
| 1 (control) | 10 | HCT116 | 0.5% methylcellulose | po | Once a day D1-D5, D8-D12, D15-D19 once tumors reach 20-25 $mm^3$; volume of 250 ul per 25 g mouse weight | Every other day once tumors are visible; daily monitoring; mouse weights every other day |
| 2 | 10 | HCT116 | 7.5 mg/kg of Example 7 in 0.5% methylcellulose | po | Once a day D1-D5, D8-D12, D15-D19 once tumors reach 20-25 $mm^3$; volume of 250 ul per 25 g mouse weight | |

D—day

Figure 11:
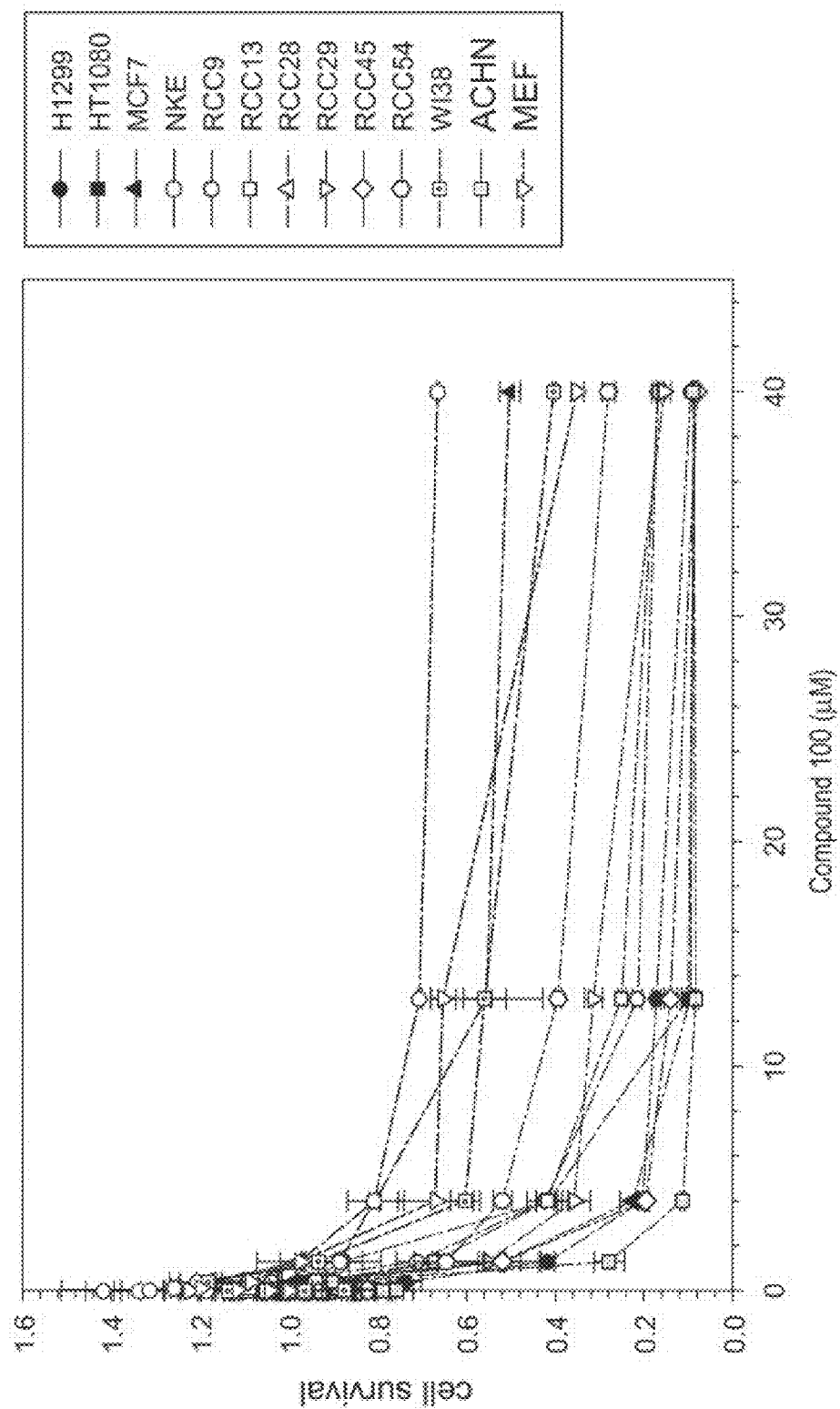
FIG. 11 contains plots of concentration of Compound 100 (μM) vs. relative cell survival for thirteen cancer cell lines showing that a present carbazole compound is an effective agent against numerous types of cancer.

In this test, 100% of the mice in Group 2 survived the experiment. No weight loss was observed in control vehicle treated group 1, whereas in group 2, three mice lost 15-20% weight by the end of experiment. The weight of the remain- FIG. 11 demonstrates a carbazole compound, i.e., Compound 100, that activates p53 in the above-described assay exhibits a significant anti-cancer activity against a wide variety of tested cancer cells. Each of the cell lines presented in FIG. 11 was seeded into 96 well plates. The next day, cells were treated with a range of concentrations of Compound 100. Treatment occurred for 24 hours, at which time compound-filled medium was replaced with compound-free medium and cells were allowed to grow until the control wells, which were treated with only vehicle control (DMSO), reached a monolayer (typically within 48 hours). Cells then were fixed and stained with 0.5% methylene blue in 50% methanol. The dye was eluted with 1% SDS and the absorbance measured at 650 nm. Data is presented as the absorbance at 650 nm versus the concentration of Compound 100.

The compounds of Examples 7, 15, and 13 showed a potent anticancer activity. In an efficacy test using these three compounds, athymic nude mice were inoculated subcutaneously with a suspension of Caki1 human renal cell carcinoma cells into both rear flanks. When at least one tumor in a mouse reached 20-50 mm$^3$, treatment was commenced. Mice were treated orally by gavage with either 30 mg/kg of Example 7, 5 mg/kg of Example 15, or 25 mg/kg of Example 13 formulated in 0.2% hydroxymethylcellulose. As a positive control, one group was treated with 40 mg/kg Sunitinib, an approved drug for the treatment of renal cell carcinoma. Treatment was given for 4 weeks on a 5 day on/2 day off schedule. After treatment was completed, mice were monitored for an additional 4 weeks to determine how quickly tumor growth returned to normal. All three compounds caused significant tumor growth inhibition compared to the vehicle control (Day 24 (end of treatment) Example 7 73% inhibition, Example 15 50% inhibition, Example 13 62% inhibition). This antitumor effect of Examples 7 and 13 and, to a lesser extent, Example 15 was substantially more than the Sunitinib control (42%). Interestingly, cessation of treatment with any of the present compounds did not lead to rapid regrowth of tumor. In contrast, the end of Sunitinib treatment resulted in immediate tumor growth such that by Day 40, there was no significant difference in tumor volume observed between the Sunitinib and vehicle control groups.

In summary, all three carbazoles caused tumor growth inhibition that persisted even after treatment was completed. The order of potency is Example 7 is greater than or equal to Example 13, which is greater than Example 15. Treatment with Example 7 caused no apparent side effects compared to Examples 13 and 15. The severest side effects were observed with Example 13, where two mice had to be taken off treatment short-term and one mouse was removed permanently due to weight loss that led to premature euthanasia. Thus, Example 7 appeared to be the "safest" carbazole in this test. Because Example 15 only caused 10-15% weight loss that was short-term, this compound was the second safest in this tumor model. Based on the results, Example 7 is a preferred compound with potent antitumor activity (70-80% inhibition) in the absence of side effects.

In another test, the antitumor activity and toxicity of Examples 7, 15, and 13, at the maximum tolerated dose (MTD) in nude mice bearing human HCT-8 ileocecal adenocarcinoma xenografts, and in nude mice bearing human HT-29 colon adenocarcinoma xenografts, were evaluated. A comparison of the antitumor efficacy and toxicity of Examples 7, 15, and 13 at the MTD side by side against human HCT-8 and HT-29 colon xenografts also was performed.

As shown above, Examples 7, 15, and 13 demonstrated antitumor efficacy against various human tumour xenografts sc in nude or SCID mice (such as HCT-16, DLD1, Caki1 and MDA-MB-231 tumors, with the tumor cells inoculated as a cell suspension in to the mice). The in vivo antitumor efficacy and toxicity of these three compounds were evaluated at their repetitive MTD against HCT-8 (relatively sensitive to chemotherapy, such as 5-FU and irinotecan) and HT-29 (relatively resistant to chemotherapy) xenografts established in nude mice by transplanting about 50 mg tumor pieces. In this study, the antitumor effect and toxicity of the three carbazoles against HCT-8 and HT29 colon cancer tumors were compared with treatment beginning when the tumor size reached 150-200 mg (about 7 days after tumor transplantation).

Materials and Methods

Animals. Eight to twelve-week-old female athymic nude mice (nu/nu, body weight 22-25 g) were obtained from Harlan Sprague Dawley Inc. (Indianapolis, Ind.) and maintained at five mice/cage with water and food ad libitum according to an institutionally approved animal protocol.

Drugs. All three compounds were formulated in 0.2% hydroxypropylmethylcellulose at concentrations of 0.5 mg/ml for Example 15, 3 mg/ml for Example 7, and 2.5 mg/ml for Example 13.

Tumors. Human ileocecal adenocarcinoma HCT-8 and colon adenocarcinoma HT-29 xenografts were used. The xenografts were initially established by injecting s.c 10$^6$ cultured cells and tumors were passed several generations by transplanting about 50 mg non-necrotic tumor (2-3 pieces) via a trocar from the passage tumors when the tumors reach to 1-1.5 g.

Drug doses and schedule. All the compounds were given by oral (p.o.) administration at the MTD with Example 15: 5 mg/kg/day; Example 7: 30 mg/kg/day; and Example 13: 25 mg/kg/day, 5 days a week for 4 weeks (5 days/week×5) or until the mouse had to be sacrificed due to a large tumor. Treatment was initiated 7 days after tumor transplantation when the tumors reached 150-200 mg. The mice in the control group received the vehicle (0.2% hydroxypropylmethylcellulose) at 200 µl per 20 g mouse body weight (same as the treatment groups). Five mice were used for each experimental group with 10 tumors (1 tumor each in the left and right side flanks).

Tumor Measurement. Two axes (mm) of tumor (L, longest axis; W, shortest axis) were measured with the aid of a Vernier caliper. Tumor weight (mg) was estimated using a formula: tumor weight=½ (L×W2). Tumor measurements were taken daily at the same time as drug treatment and 3-4 times a week of post therapy.

Maximum Tolerated Dose (MTD) and toxicity evaluation. The MTD was defined as the highest drug dose that did not cause drug-related lethality in mice with a weight loss less than 20% of original body weight and toxicities were reversible. The kinetics of drug-induced toxicities (body weight loss, diarrhea, and lethality) were determined daily for the first 10 days after treatment and every two days thereafter.

Antitumor Activity. Antitumor activity was assessed by maximum tumor growth inhibition (MTRI) which is the mean tumor weight of treated group (MTWTG) compared with untreated control group (MTWCG) at the same time point (MTRI=MTWTG−MTWCG)÷MTWCG×100%). The tumor doubling time (TDT) was defined as the mean time for the tumor to reach twice its initial weight. Tumor response was expressed as partial tumor response (PR) when tumor weight was reduced at least 50% of the initial tumor size and complete tumor response (CR) was defined as the inability to detect tumor upon palpation at the initial site of tumor appearance.

Results (a) The antitumor activity and toxicity of Example 15, 7, and 13 in nude mice bearing HCT-8 xenografts.

The data in the following table show the antitumor activity and toxicity of vehicle control, Example 15, Example 7, and Example 13 administered p.o. 5 days on and 2 days off per week to nude mice bearing HCT-8 xenografts. The data indicate that Example 13 and 15 had moderate antitumor activity against HCT-8 xenografts with inhibitory rates of 35-40% and delayed tumor growth by 17% (Example 13) and 57% (Example 15), respectively, compared to the vehicle control (double time: 4.8 days). The planned four courses of treatment for Examples 13 and 15 were not completed because of the large tumor volume that required the mice to be sacrificed. Example 7 was much more active than Examples 13 and 15 against HCT-8 xenografts with an inhibitory rate of 65.9% and a 142% delay of tumor growth. Example 7 did not produce any PR or CR. With respect to toxicity, the vehicle produced mild toxicity with the animal group of individual HCT-8 tumor 5 days on and 2 days off a week×2-4 weeks.

CONCLUSION

In conclusion, Examples 15 and 13 show moderate antitumor activity, while Example 7 had better antitumor efficacy against both HCT-8 and HT-29 xenografts;

Example 15 was more toxic than Examples 7 and 15 in the HT-29 study;

Unlike the response to most other chemotherapeutic agents, HT-29 xenografts were more sensitive to all three carbazoles compared to the response observed with HCT-8 xenografts;

The data shows that Example 7 is a preferred compound against both HCT-8 and HT-29 xenografts.

TABLE

Antitumor activity and toxicity of Examples 15, 7, and 13 in nude mice bearing human HCT-8 ileocecal adenocarcinoma xenografts

| Treatment | Antitumor | | Activity | | Toxicity (%) | |
|---|---|---|---|---|---|---|
| (mg/kg/d) | MTGI (%) | TDT (day) | PR (%) | CR (%) | MWL | lethality |
| Control-Vehicle | — | 4.8 ± 0.3 | 0 | 0 | 5.5 ± 1.9 | 0 |
| Example 15 (5) | 40.0 ± 18.6 | 7.5 ± 3.5 | 0 | 0 | 10.0 ± 3.8 | 0 |
| Example 7 (30) | 65.9 ± 11.0 | 11.6 ± 2.5 | 0 | 0 | 12.2 ± 6.8 | 0 |
| Example 13 (25) | 35.7 ± 20.0 | 5.6 ± 1.2 | 0 | 0 | 8.5 ± 2.9 | 0 |

MTRI: maximum tumor growth inhibition; TDT: tumor doubling time; PR: partial tumor response; CR: complete tumor response; MWL: maximum weight loss of pretreatment body weight. Control group was given 0.2% hydroxypropylmethylcellulose (vehicle) at 200 μl per 20 g mouse body weight. Five mice were used for each experimental group with 10 tumors (in left and right side flanks).
(b) The antitumor activity and toxicity of Examples 15, 7, and 13 in nude mice bearing HT-29 xenografts.

The data in the following table show the antitumor activity and toxicity of vehicle control, Example 15, Example 7, and Example 13 administered p.o. 5 days on and 2 days off per week to nude mice bearing HT-29 xenografts, which is more resistant to most chemotherapeutic agents compared to HCT-8. The data indicate that all three compounds were more active against this tumor than HCT-8. Similarly, Example 13 was the least active compound among the three, with inhibitory rates of 48% and delayed tumor growth by 50% (the tumor double time for the control was 7.8 days). While Example 15 produced similar tumor growth inhibition (58%), it had less of an effect on tumor growth delay (delaying 76% vs 122%) compared to Example 7. No PR or CR was produced by the three agents. With respect to toxicity, Example 7 and 13 produced less body weight loss. Example 7 was more toxic in the HT-29 experiment compared to the HCT-8 experiment with 18% weight loss and 40% lethality.

In another experiment, the anti-tumor activity of Example 7 in a murine model of neuroblastoma was demonstrated. The N-myc (TH-MYCN) transgenic mice carry the human N-myc oncogene under the control of a tyrosine hydroxylase promoter, which is expressed in neuroectodermal cells during early development, and the mice develop a murine equivalent of human neuroblastoma. These mice have proved to be an excellent model sharing several important features with the human disease, including site of the tumor and its metastases, the histology of the tumor, positive staining for neuroblastoma-associated marker proteins, the presence of synapses and neurosecretory granules, gains and losses of chromosomes in regions synthetic with those observed in human neuroblastoma, and the amplification of copy number of N-myc specifically in the tumors which develop.

Modern chemotherapy has dramatically improved the survival rates for many cancers. However, the development of multi-drug resistance in the clinical setting for neuroblastoma is one of the major causes of treatment failure, and

TABLE

Antitumor activity and toxicity of Examples 15, 7, and 13 in nude mice bearing human HT-29 colon adenocarcinoma xenografts.

| Treatment | Antitumor | | Activity | | Toxicity (%) | |
|---|---|---|---|---|---|---|
| (mg/kg/d) | MTGI (%) | TDT (day) | PR (%) | CR (%) | MWL | lethality |
| Control-Vehicle | — | 7.8 ± 0.8 | 0 | 0 | 5.6 ± 4.2 | 0 |
| Example 15 (5) | 58.4 ± 6.4 | 13.1 ± 2.3 | 0 | 0 | 17.9 ± 6.8 | 40 |
| Example 7 (30) | 58.5 ± 17.4 | 17.3 ± 4.8 | 0 | 0 | 7.6 ± 5.1 | 0 |
| Example 13 (25) | 47.6 ± 6.7 | 11.7 ± 1.2 | 0 | 0 | 4.4 ± 2.2 | 0 |

MTRI: maximum tumor growth inhibition; TDT: tumor doubling time; PR: partial tumor response; CR: complete tumor response; MWL: maximum weight loss of pretreatment body weight. Control group was given 0.2% hydroxypropylmethylcellulose (vehicle)) at 200 μl per 20 g mouse body weight. Five mice were used for each experimental group with 10 tumors (in left and right side flanks).

circumventing multi-drug resistance has enormous clinical potential. Drugs that target novel pathways not previously implicated in neuroblastoma could provide a new avenue for treatment protocols.

The test results showed that the compound of Example 7 has a remarkable anti-tumor activity in this model of neuroblastoma, although high doses proved toxic in some mice. Mice treated with 30 mg/kg of Example 7 lost weight rapidly and unexpectedly (2 g overnight in some case) and were found dead with small spleens and signs of dehydration. Mice that survived therapy were tumor free for a period extending from 15 to 47 days, however all mice were not treated according to the same schedule. Doses were altered according to weight loss. Based on the results, Example 7 exhibits good efficacy in the TH-MYCN model of neuroblastoma.

Modern chemotherapy has dramatically improved the survival rates for many cancers. However, the development of multi-drug resistance in the clinical setting for neuroblastoma is one of the major causes of treatment failure, and circumventing multi-drug resistance has enormous clinical potential. Drugs that target novel pathways not previously implicated in neuroblastoma could provide a new avenue for treatment protocols.

Daily administration of Example 7 also prevents tumor onset in an MMTV-neu transgenic mouse model of mammary cancerogenesis.

Breast cancer (BC) is a serious health care issue due to high incidence of this malignancy and limited success of available treatments. It is known that the family history of this disease along with several specific genetic factors with substantial degree of probability predispose individuals to BC. Therefore, women from high BC risk groups theoretically can benefit from a preventive anti-BC therapy. The present carbazole compounds can modulate several cancer-related cellular pathways in a direction that leads to tumor growth suppression. The compound of Example 7 causes no serious side effects in mice when administered at therapeutic doses (20-25 mg/kg). Example 7 showed no mutagenic activity in Ames assay. In this study, Example 7 was tested as a preventive agent for BC in mice.

Animal model: MMTV-neu female mice on the background of FVB strain express non-activated Her2 proto-oncogene under MMTV promoter responsive to estrogen stimulation. The mice develop spontaneous mammary tumors starting from 24 weeks of age with 70-80% of animals normally developing tumors by 10 months of age. The objectives of this test were to (a) compare tumor incidence in mice treated with Example 7 vs. vehicle control (water), and (b) compare weight gain and general appearance of mice treated with Example 7 vs. vehicle control.

Study design: 40 female mice were weaned from breeding parents at 21 days of age and placed in separate cages (4 mice/cage). At this moment, mice were labeled and assigned to treatment or control groups (20 mice in each). Body weight in both groups was measured once a week. Starting from 4 weeks of age, mice from the treatment group were provided with water containing Example 7. Liquid consumption in treatment and control groups was estimated every day. Based on these measurements, liquid consumption per gram of mouse weight was calculated, and Example 7 concentration in drinking water was adjusted to desirable therapeutic dose. Fresh solutions of Example 7 were prepared weekly. Mice were monitored once a week for tumor formation by the palpation of mammary glands. Mice were sacrificed at a moment when cumulative tumor size reached the volume of 1000 mm$^3$.

| Group | Number of mice | Targeted dose | Delivery mode |
| --- | --- | --- | --- |
| 1 | 20 | None (water) | Daily drinking |
| 2 | 20 | about 25 mg/kg Example 7 | Daily drinking |

Preliminary results: Mice from the treatment group were consuming Example 7 at average rate of 20 mg/kg daily. Variability is due to limited accuracy of drug delivery via drinking water. No differences between treatment and control group were observed in weight distribution or abnormalities in animal appearance.

In the course of the experiment several spontaneous deaths occurred in the treatment and control groups. The cause of death was not clear because the animals had no tumors and post-mortem gross pathology examination showed no obvious abnormalities. None of the mice died earlier than several weeks after the beginning of Example 7 administration. During the test, three control mice died at an age of about 15, 41 and 42 weeks, respectively. Seven mice died in the Example 7 group at different ages ranging from 12 to 45 weeks (from 7 to 41 weeks since the beginning of the experimental treatment).

Twenty-one and 19 mice reached tumor bearing age in the control and treatment groups, respectively. Among them, a tumor was developed in 14 (67%) of control mice and 7 (37%) of mice receiving Example 7.

This test showed:

(a) chronic administration of Example 7 with drinking water at about 20 mg/kg per day caused no changes in mouse body weight;

(b) a higher death rate in Example 7 treated group versus control group, but the difference was not statistically significant and there was no correlation between length and treatment period and death of mice; and (c) a lower rate of tumor burden among mice treated with Example 7 versus control animals.

Carbazole compounds of the present invention also exhibit antiparasite activity. In particular, the effect of carbazole compounds on the malaria parasite was tested by culturing *Plasmodium falciparum*: (strain D10) in vitro in the presence or absence of test compounds. Active and inactive carbazole compounds (with respect to activating p53) were selected for tested, as was quinacrine, a conventional anti-malaria agent. Table 3 summarizes the structures of the compounds, together with their $EC_{50}$ values in the p53 activation assay.

TABLE 3

Test compounds

| Compound | Structure | $EC_{50}$, μM |
| --- | --- | --- |
| Example 2 | 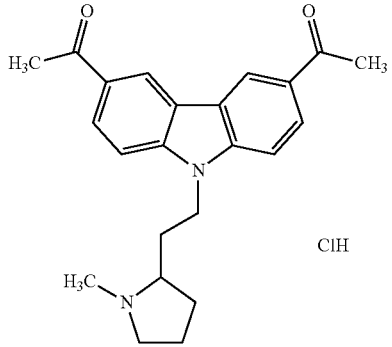 [SMILES: CC(=O)c1ccc2c(c1)c1cc(C(C)=O)ccc1n2CCC1CCCN1C ; Cl] | 0.64 |

TABLE 3-continued

Test compounds

| Compound | Structure | EC$_{50}$, μM |
|---|---|---|
| Compound 400 | 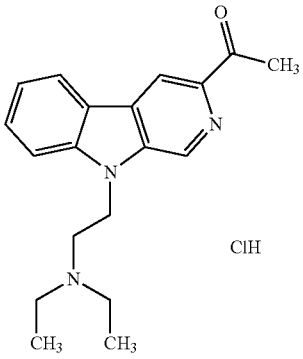 [SMILES: CCN(CC)CCn1c2ccccc2c2cc(C(C)=O)ncc21 ; Cl] ClH | Inactive |
| Example 7 | 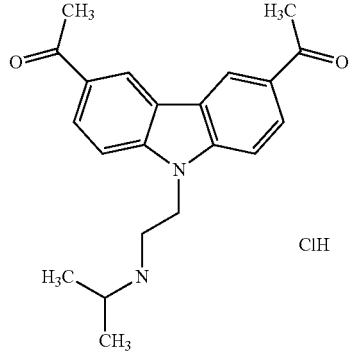 [SMILES: CC(=O)c1ccc2c(c1)c1cc(C(C)=O)ccc1n2CCNC(C)C ; Cl] ClH | 0.37 |
| Compound 500 | 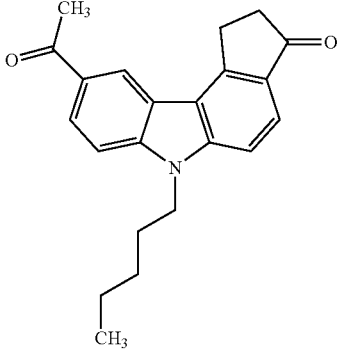 [SMILES: CCCCCn1c2ccc(C(C)=O)cc2c2c3c(ccc21)C(=O)CC3] | Inactive |
| Example 18 | 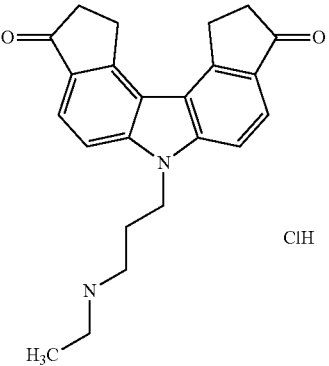 [SMILES: CCNCCCn1c2ccc3c(c2c2c4c(ccc21)C(=O)CC4)CCC3=O ; Cl] ClH | 0.09 |
| Quinacrine (QC) | 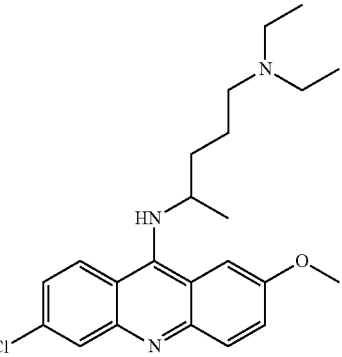 | about 5 |

Example 2, Compound 400, and Example 7 were tested at 29, 57, and 143 nM concentrations. Compound 500, Example 18, and quinacrine were tested at 143 nM only.

Figure 12:
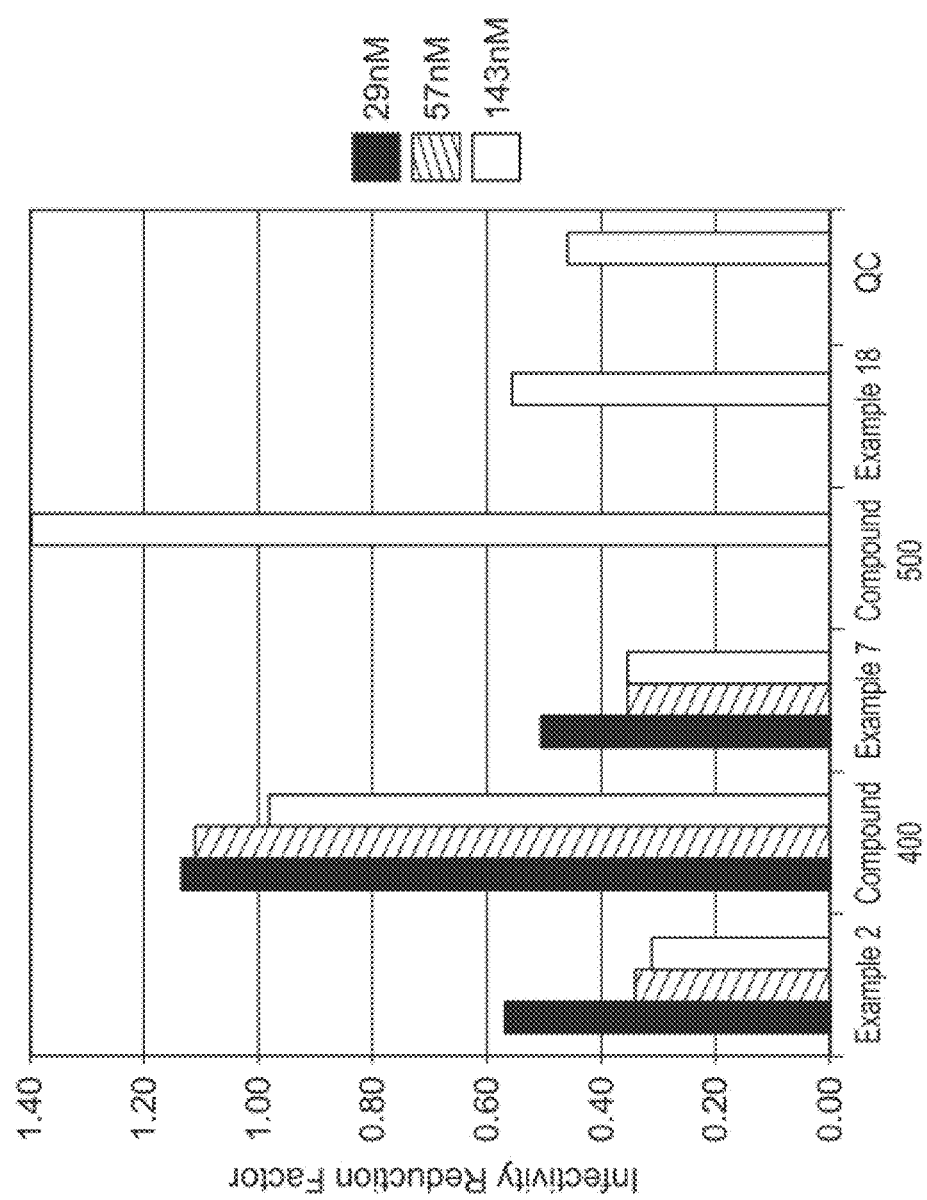
FIG. 12 contains bar graphs showing the antiparasitic activity of various carbazole compounds against *Plasmodium falciparum*(strain D10)

In each experiment, 1000 erythrocytes were assessed microscopically to determine the number of infected cells. In control experiments (no test compounds added or PBS added), the percentage of infected cells varied between 1.6% and 6.4%. Infectivity reduction indexes determined in the study are shown in FIG. 12. Potency of p53 activation assay clearly, but indirectly, correlated with the inhibition of *Plasmodium falciparum*: in vitro. Three compounds active in the p53 activation assay (Examples 2, 7, and 18) demonstrated anti-malarial activity comparable to quinacrine. Compounds inactive in the p53 activation assay (Compounds 400 and 500) showed no parasitemia reduction.

The compounds of Examples 7, 13, and 15 also showed anti-protozoan activity. Human African trypanosomiasis (HAT) or "sleeping sickness" is one of the most important, but equally most neglected, tropical infections. It is caused by a protozoan, *Trypanosoma brucei*, which is transmitted to humans through the bite of a tsetse fly (*Glossina* spp). Although nearly eliminated in the 1960s, HAT has reappeared on an epidemic scale in a number of sub-Saharan areas inhabited by the tsetse fly. According to the World Health Organization, about 500,000 people currently carry trypanosomes and will die if left untreated. The high mortality associated with HAT is due, at least in part, to a lack of efficacious drugs that can be easily administered.

The drugs currently used to treat HAT are old, toxic, and difficult to administer in the field. Suramin and pentamidine, which are used to treat early stage disease, must be injected in a clinic. However, access to health clinics is uncommon in the rural areas of Africa where the disease is endemic. Moreover, many early stage patients do not seek treatment because they are unaware that they are infected. This is due to poor screening of at risk populations, as well as the variable, intermittent, and relatively mild nature of early stage HAT symptoms. By the time obvious symptoms emerge, patients are often already in the late stage of the disease. Treatment of late-stage HAT is especially troublesome because it involves injection of melarsoprol, an arsenical that literally burns patients on injection. This treatment is so painful that many patients refuse treatment and have to be physically restrained and forced to receive the medication. Moreover, melarsoprol has significant adverse side effects that result in the death of 5-20% of treated patients. For these reasons, as well as the expected problem of drug resistance, there is an urgent need to create a pipeline of new, orally bioavailable drugs to take the place of the current antiquated medications.

Tests have shown that the compounds of Examples 7, 13, and 15 have remarkable anti-*T. brucei* activity (low nanomolar $IC_{50}$) in vitro. Preliminary *T. brucei* inactivation experiments were performed in vitro. The life cycle of *T. brucei* involves a "procyclic" developmental stage in a tsetse fly, and a "bloodstream" form in humans. All studies were performed with the bloodstream stage of the parasite, because it is the disease-causing developmental stage.

To evaluate the relative anti-trypanosome activities of Examples 7, 13, and 15, and to determine the concentration of each compound that killed 50% of the parasites ($IC_{50}$), *T. brucei* was exposed to a range of compound concentrations. Suramin, a conventional anti-HAT drug, was used as a positive control.

Bloodstream *T. brucei* was seeded ($3\times10^3$ cells/mL) in 24-well (500 uL of the media per well) plate. The concentrations of the compounds (0-200 nM for Example 7, 0-20 nM for Example 13, and 0-3 nM for Example 15) were added to the cells (duplicate cultures). Control cultures received equal volumes of DMSO. All three test compounds completely eliminated *T. brucei* because no parasites were detected after 48 hrs of culture in the presence of the drugs. Control cultures treated with DMSO (vehicle) contained parasites at a density of $3\times10^6$/mL.

Trypanocidal activity increased in the order Example 7 less than Example 13, which is less than Example 15, with $IC_{50}$ values of about 43 nM, about 6-11 nM, and about 0.5 nM, respectively. The $IC_{50}$ of Suramin is greater than 300 nM.

Therefore, compounds of the present invention are excellent for development as trypanocidal drugs.

The compound of Example 15 was tested for activity against different fungi strains. Example 15 in vitro susceptibility testing was done by the CLSI M27A3 and M38A2 methods for 31 clinical and laboratory fungal strains. In general, the strains selected demonstrate different susceptibility patterns for current antifungal drugs. For the evaluation of Example 15, 8 *Aspergillus* spp., 21 *Candida* spp., 1 *Cryptococcus neoformans*, and 1 *Debaryomyces hansenii* strains were tested.

*Aspergillus* Spp. Strains:

Eight *Aspergillus* spp. strains were used throughout the study. Six *A. fumigatus*, one *A. flavus* and one *A. terreus* also were used. The *A. fumigatus* group included two itraconazole-resistant strains (RIT13 and RIT5 strains) (1), one triazole cross-resistant strain (MUT10) (2, 3), one echinocandin cross-resistant strain (EMFRS678P) (4), and 2 wild type susceptible isolates (R21 and ATCC13073). The "non-*fumigatus*" strains were susceptible to all available antifungal with the exception of the *A. terreus* isolate (naturally less susceptible to amphotericin B) (5).

*Candida* spp. strains: 20 *Candida* spp. clinical isolates and one laboratory control strain (*C. albicans* SC5314) was used in the study. In the collection were included:

5 *C. albicans* isolates, two wild type strain (SC5314 and ATCC 36082), one echinocandin resistant isolate (M205) (6), and two fluconazole resistant clinical isolates (3795 and 3184) (7).

3 *C. krusei* strains, 1 ATCC control strain (ATCC 6258 CLSI control), and 2 isogenic clinical strains (98 and 100). 100 is echinocandin cross resistant (8, 9)

2 *C. glabrata* strains, one wild type clinical strain (3168), and one echinocandin cross-resistant isolate (3830) (10).

2 *C. tropicalis* strains, one ATCC control strain (ATCC 750), and one echinocandin cross-resistant (T3) (11).

2 *C. dubliniensis* strains one wild type strain (3949) and the other with echinocandin paradoxical effect (M204).

4 naturally reduced echinocandin susceptibility *Candida* spp. (12): 1 *C. orthopsilosis* (981224), 1 *C. metapsilosis* (2006-113), *C. parapsilosis* (ATCC 22019 CLSI control), and *C. guilliermondii* (ATCC6260) (13).

Other *Candida* spp. and genera: 1 *C. rugosa* (M83), 1 *C. lipolytica* (M159), *C. lusitaniae* (200450), 1 *Cryptococcus neoformans* (499), and 1 *Debaryomyces hansenii*.

Susceptibility Testing:

Example 15 in vitro susceptibility testing was done using the CLSI standardized methods for yeast (M27A3) (14) and for molds (M38A2) (15). The MIC (minimum inhibitory concentration) readings were performed at 24 and 48 hours.

TABLE 1

In vitro susceptibilities of fungal strains against Example 15

| | | | | Example 15 | |
|---|---|---|---|---|---|
| Strain | Organism | Genotype | Phenotype | MIC* (24 hs) | MIC* (48 hs) |
| ATCC13073 | *A. fumigatus* | WT | Susceptible | 2.56 | 5.13 |
| R21 | *A. fumigatus* | WT | Susceptible | 1.28 | 2.56 |
| MUT10 | *A. fumigatus* | Cyp51ApG138C | Triazole cross resistant | 0.66 | 1.28 |
| RIT5 [a] | *A. fumigatus* | AfuMDR3 and AfuMDR4 constitutively overexpressed | Itraconazole resistant | 0.66 | 1.28 |
| RIT13 [a] | *A. fumigatus* | AfuMDR3 and AfuMDR4 overexpression induced by azoles plus Cyp51Ap G54E | Itraconazole resistant | 1.61 | 1.28 |
| EMFRS678P | *A. fumigatus* | Fks1pS678P | Echinocandin cross-resistant | 1.28 | 2.56 |
| AFCLF9128 | *A. flavus* | WT | Susceptible | 0.33 | 0.33 |
| At123 | *A. terreus* | WT | Intrinsically AMB resistant | 0.08 | 1.28 |
| SC5314 | *C. albicans* | WT | Susceptible | 0.04 | 0.08 |
| ATCC36082 | *C. albicans* | WT | Susceptible | 0.04 | 0.04 |
| M205 | *C. albicans* | Fks1pS645P | Echinocandin cross-resistant | 0.16 | 0.33 |
| 3795 | *C. albicans* | Erg11pF136L/K134R | Fluconazole-resistant | 0.16 | 0.16 |
| 3184 | *C. albicans* | CDR1 overexpression | Fluconazole-resistant | 0.33 | 0.66 |
| 3168 | *C. glabrata* | WT | Susceptible | 0.16 | 0.16 |
| 3830 | *C. glabrata* | Fks2pS663P | Echinocandin cross- | 0.16 | 0.16 |

TABLE 1-continued

In vitro susceptibilities of fungal strains against Example 15

| | | | | Example 15 | |
|---|---|---|---|---|---|
| Strain | Organism | Genotype | Phenotype | MIC* (24 hs) | MIC* (48 hs) |
| ATCC 6258 | C. krusei | WT | resistant Susceptible (naturally fluconazole resistant) | 0.33 | 0.66 |
| 98[b] | C. krusei | WT | Susceptible (naturally fluconazole resistant) | 0.33 | 0.33 |
| 100[b] | C. krusei | Fks1pF655F/C | Echinocandin cross-resistant | 0.33 | 0.33 |
| ATCC750 | C. tropicalis | WT | Susceptible | 0.08 | 0.16 |
| T3 | C. tropicalis | Fks1pS645S/P [a] | Echinocandin cross-resistant | 0.04 | 0.08 |
| 3949 | C. dubliniensis | WT | Susceptible | 0.16 | 0.16 |
| 204 | C. dubliniensis | WT | Echinocandin paradoxical effect | 0.16 | 0.16 |
| M159 | C. lipolytica | WT | Susceptible | 0.02 | 0.08 |
| M83 | C. rugosa | WT | Susceptible | 0.16 | 0.66 |
| 200450 | C. lusitaniae | WT | Susceptible | 0.04 | 0.16 |
| ATCC6260 | C. guilliermondii | WT | Echinocandin cross-reduced susceptibility | 0.08 | 0.16 |
| ATCC 22019 | C. parapsilosis | WT | Echinocandin cross-reduced susceptibility | 0.08 | 0.08 |
| 981224 | C. orthopsilosis | WT | Echinocandin cross-reduced susceptibility | 0.16 | 0.16 |
| 2006-113 | C. metapsilosis | WT | Echinocandin cross-reduced susceptibility | 0.16 | 0.16 |
| 20124 | Debaryomyces hansenii | WT | Susceptible | 0.16 | 0.16 |
| 499 | Cryptococcus neoformans | WT | Susceptible | 0.02 | 0.08 |

*Geometric mean of two repetitions in µM.
[a] Amino acid number corresponding to the C. albicans equivalent.

*Aspergillus* spp. Example 15 susceptibilities: The *A. flavus* and *A. terreus* strains are more sensitive to Example 15 than *A. fumigatus* strains (24 hs MIC Geom. Means 0.40 and 1.59 µM, respectively). Moreover, there were no MIC differences between susceptible and azole or echinocandin resistant strains (Table 1).

Yeast Example 15 susceptibilities: There were no Example 15 MIC differences between azole- or echinocandin-resistant or -susceptible isolates. On average, yeast MICs were 8-fold lower than *Aspergillus* spp. MIC (Table 1). MICs obtained for Example 15 are compatible or better than MICs for conventional antifungal drugs. Azole and echinocandin resistant strains are sensitive for Example 15.

Effect of Example 15 on *Aspergillus fumigatus* viability: The antifungal activity of Example 15 on the Af293 strain of *A. fumigatus* using the XTT viability assay were evaluated. This strain was selected because it is one of the best characterized strains and was the strain used for sequencing the *A. fumigatus* genome. XTT viability assay is based on the reduction of the tetrazolium salt (XTT) in the presence of menadione as an electron-coupling agent. There is a relationship between the number of viable fungi and the amount of XTT reduction (16).

Methods

The same methods previously described in performing the XTT assay (17) were used. Af293 conidia were plated on Sabouraud BHI slants with chloramphenicol and gentamicin (Becton Dickinson, Md.), incubated for 7 to 10 days at room temperature, and harvested by washing the slant with 10 ml of 0.05% Tween 20 in normal saline (NS). The conidial suspension then was passed through a 100-µm filter, counted on a hemacytometer, and diluted to $2.0 \times 10^6$ CFU/ml. Conidia then were diluted 1:50 in MOPS (morpholinepropanesulfonic acid)-buffered RPMI (pH 7.0). A stock solution of Example 15 dissolved in DMSO was used. Example 15 was diluted in MOPS-buffered RPMI (pH 7.0) (final concentration of DMSO: 2% prior to addition to fungal suspensions). Following the addition of drug-containing medium to each well, the conidial suspension (100 µl) was added (t=0 h). Control wells contained conidia, medium, and vehicle without drug. Blank wells consisted of medium only without conidia. An initial experiment using a wide range of concentrations of Example 15 without added fungus showed that the Example 15 reagent did not affect optical density in the XTT assay. Plates were incubated at 37° C., and the XTT assay was performed at 24 h essentially as previously described (16), but with a minor adaptation. A stock solution of XTT (Sigma Chemical, St. Louis, Mo.) was dissolved in NS (1 mg/ml). A 10-mM solution of the electron-coupling agent menadione (Sigma Chemical) was prepared in acetone and then diluted 1:10 in NS. A working solution consisting of 4.0 ml XTT and 0.5 ml menadione was prepared immediately before use. Fifty microliters of the combination solution was added to each well, and plates were incubated for 2 h at 37° C. One hundred microliters of the supernatant was transferred to a new plate, and the optical density at 450 nm ($OD_{450}$) was determined by using a Labsystems Multiskan Plus plate reader. Final concentrations of XTT and menadione in each well were 200 µg/ml and 25 µM, respectively.

Example 15 had antifungal activity against Af293. The IC50 was approximately 2.5 µM. Complete suppression of fungal growth occurred at Example 15 concentrations greater than 12.5 µM, based on visual inspection of the wells.

1. A. M. Nascimento, et al., 2003, 47:1719-26.
2. G. Garcia-Effron, et al., 2008, *J Clin Microbiol*, 46:1200-6.

3. S. J. Howard, et al., 2006, *Int J Antimicrob Agents*, 28:450-3.
4. E. M. Rocha, et al., 2007, *Antimicrob Agents Chemother*, 51:4174-6.
5. W. J. Steinbach, et al., 2004, *Clin Infect Dis.*, 39: 192-8.
6. G. S. Garcia-Effron, et al. *Antimicrob Agents Chemother.*
7. S. Perea, et al., 2001, *Antimicrob Agents Chemother*, 45:2676-84.
8. M. Hakki, et al., 2006, *Antimicrob Agents Chemother*, 50:2522-4.
9. J. N. Kahn, et al., 2007, *Antimicrob Agents Chemother*, 51:1876-8.
10. J. D. Cleary, et al. 2008, *Antimicrob Agents Chemother*, 52:2263-5.
11. G. Garcia-Effron, et al. 2008, *Antimicrob Agents Chemother*, 52:4181-3.
12. G. Garcia-Effron, et al. 2008, *Antimicrob Agents Chemother*, 52:2305-12.
13. D. S. Perlin, 2007, *Drug Resist Update*, 10:121-30.
14. Clinical Laboratory Standard Institute, C.L.S.I., 2008, 3rd ed., 28 (14).
15. Clinical Laboratory Standard Institute, C.L.S.I., 2008, 2nd ed., 28(16).
16. J. Meletiadis, et al., 2001, *J Clin Microbiol*, 39:3402-8.
17. Y. F. Brun et al., 2007, *Antimicrob Agents Chemother*, 51(5):1804-12.

Figure 13A:
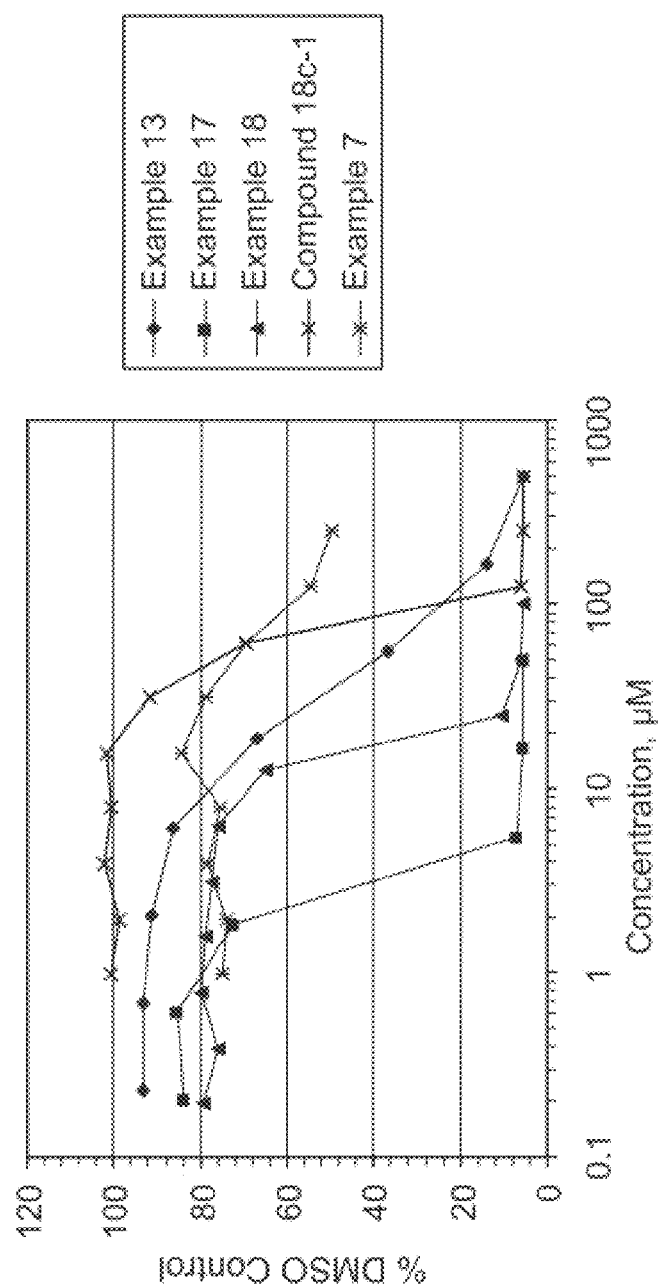
FIGS. 13A-B contain plots showing the antibacterial activity of various carbazole compounds against Gram negative (FIG. 13A) and Gram positive bacteria (FIG. 13B).
Figure 13B:
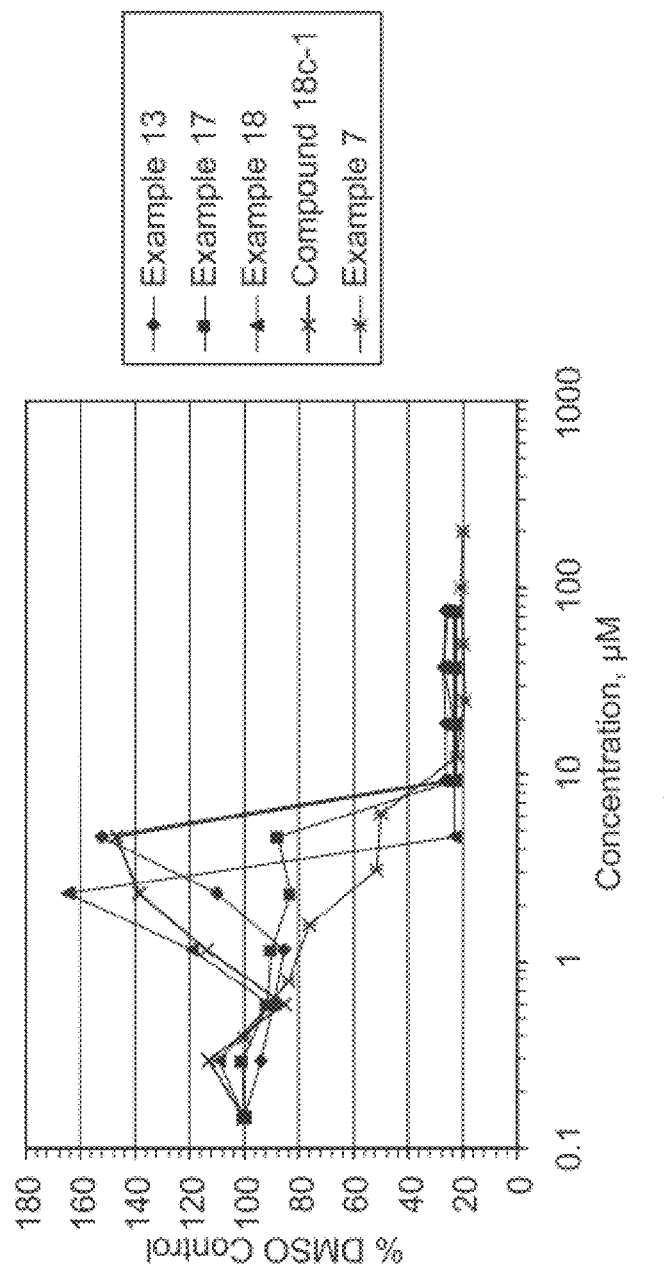

Carbazole compound of the present invention also exhibit antibacterial activity. In particular, the effect of carbazole compounds of the present invention on gram positive (*Bacillus subtilis*) and gram negative (DH5-α) bacteria was determined by the following procedure, and is summarized in FIGS. 13A and 13B.

In vitro test to evaluate the effect of carbazole compounds on gram(-) and gram(+) bacteria.

Equipment
  96 well plate reader (e.g Multiscan, LabSystems, Inc)
  Multichannel pipette 50-300 uL range
  Filter tips
  96 well plates (Corning Costar Cat. No.: 3598)
  100 mm petri dishes
  Sterile 1 µl inoculation loops (Fisher 22-170-209)
  14 ml snap-cap round bottom tubes (Falcon 352059)

Materials
  DH5-α (*E. coli*-gram(-) bacteria)
  *Bacillus subtilis* (gram(+) bacteria)
  Difco LB Agar (BD 244510—for DH5-α)
  Difco LB Broth (BD 244610—for DH5-α)
  Difco Nutrient Broth (BD 233000—for *B. subtilis*)
  Difco Nutrient Agar (BD 212000—for *B. subtilis*)

Method

Preparation of Reagents

To prepare plates for growing DH5-α, combine 40 g Difco LB agar per 1 liter MilliQ water. Autoclave on liquid setting. When the vessel containing the solution is cool, pour into 100 mm Petri dishes and leave lids slightly off to prevent build up of moisture as agar gels. Pop bubbles that form prior to the agar setting. Store at 4° C.

To prepare medium for growing DH5-α, combine 25 g Difco LB broth per 1 liter MilliQ water. Autoclave on liquid setting to sterilize.

To prepare plates for growing *B. subtilis*, combine 23 g Difco nutrient agar per 1 liter MilliQ water. Autoclave on liquid setting. When vessel containing the solution is cool, pour into 100 mm Petri dishes and leave lids slightly off to prevent build up of moisture as agar gels. Pop bubbles that form prior to the agar setting. Store at 4° C.

To prepare medium for growing *B. subtilis*, combine 8 g Difco nutrient broth per 1 liter MilliQ water. Autoclave on liquid setting to sterilize.

Preparation of Bacteria

Two days prior to the start of the cytotoxicity assay, inoculate DH5-α and *B. subtilis* into 1 ml of corresponding media from glycerol stocks. Allow to grow during the course of the day at 37° C. with shaking.

Streak each bacteria on the appropriate agar plates using a sterile inoculation loop and allow to grow overnight at 37° C. in the bacteria incubator.

Using a sterile inoculation loop, pick a single colony of bacteria and inoculate 5 ml of the corresponding media in a 14 ml snap cap tube. Grow overnight (~16 h) at 37° C. with shaking.

The next day, measure the OD600 nm for the culture to ensure that bacteria is in exponential growth (OD600 nm=0.4-0.8)

Cytotoxicity Assay (1)

Dilute 5 ml cultures of DH5-α and *B. subtilis* to an OD600 nm of 0.002, which corresponds to about $2 \times 10^6$ cells/ml in a volume sufficient for the experiment (dependent on the number of plates). Plate out 50 µl into each well of X 96-well plates (X=# plates needed for a given experiment).

Compounds will be added to plates in 3 fold dilutions from 0.005-50 µM according to Table 2.

Chemicals for testing are prepared by dilution of stock solutions in LB Broth or Nutrient Broth for DH5-α and *B. subtilis* studies, respectively. Cells are treated with the final chemical concentrations presented in the scheme below (Table 2). Stock solutions are made up in DMSO. Typically, chemicals are made up as 20 mM stock solutions. However, this concentration is dependent on the solubility of a given chemical and actual stock concentrations must be noted at time of experiment.

TABLE 4

Scheme of an experimental plate with final concentrations of chemicals

|  | Pos Control | Neg. Control | Carbazole compound (Cpd W, X, Y, Z) (µM) | | | | | | | | |
| --- | --- | --- | --- | --- | --- | --- | --- | --- | --- | --- | --- |
| Cpd W | 100 µg/ml ampicillin | DMSO | 0.00762 | 0.0229 | 0.0686 | 0.206 | 0.617 | 1.25 | 1.85 | 5.56 | 16.67 | 50 |
| Cpd W | 100 µg/ml ampicillin | DMSO | 0.00762 | 0.0229 | 0.0686 | 0.206 | 0.617 | 1.25 | 1.85 | 5.56 | 16.67 | 50 |
| Cpd X | 100 µg/ml ampicillin | DMSO | 0.00762 | 0.0229 | 0.0686 | 0.206 | 0.617 | 1.25 | 1.85 | 5.56 | 16.67 | 50 |

TABLE 4-continued

Scheme of an experimental plate with final concentrations of chemicals

| | Pos Control | Neg. Control | Carbazole compound (Cpd W, X, Y, Z) (µM) | | | | | | | | | |
|---|---|---|---|---|---|---|---|---|---|---|---|---|
| Cpd X | 100 µg/ml ampicillin | DMSO | 0.00762 | 0.0229 | 0.0686 | 0.206 | 0.617 | 1.25 | 1.85 | 5.56 | 16.67 | 50 |
| Cpd Y | 100 µg/ml ampicillin | DMSO | 0.00762 | 0.0229 | 0.0686 | 0.206 | 0.617 | 1.25 | 1.85 | 5.56 | 16.67 | 50 |
| Cpd Y | 100 µg/ml ampicillin | DMSO | 0.00762 | 0.0229 | 0.0686 | 0.206 | 0.617 | 1.25 | 1.85 | 5.56 | 16.67 | 50 |
| Cpd Z | 100 µg/ml ampicillin | DMSO | 0.00762 | 0.0229 | 0.0686 | 0.206 | 0.617 | 1.25 | 1.85 | 5.56 | 16.67 | 50 |
| Cpd Z | 100 µg/ml ampicillin | DMSO | 0.00762 | 0.0229 | 0.0686 | 0.206 | 0.617 | 1.25 | 1.85 | 5.56 | 16.67 | 50 |

Each library chemical to be tested requires 2 rows of a 96-well plate, thus 4 chemicals (e.g. W, X, Y, Z) can be tested in one plate simultaneously. In addition to test chemicals, each plate should include positive and negative controls. As positive control, ampicillin is used at 100 µg/ml. As a negative control, DMSO is used in an amount equal to the highest volume of test compound used (~0.25% DMSO for 50 µM).

Dilutions of chemicals to be added to the plate are made up as 2× concentrations in appropriate bacteria media and added to corresponding wells in a volume of 50 µl.

Chemicals are diluted in appropriate bacteria media by three-fold serial dilutions starting from 50 µM (e.g. 2× of highest concentration (e.g. 50 µM)=100 µM). 300 µl of highest 2× concentration is needed in order to use 1/3 to make 1st dilution and 200 µl media for all subsequent dilutions. 100 µl of the highest 2× concentration is mixed with 200 µl media and then 100 µl of the first dilution is mixed with 200 µl of media to produce the next dilution. This process is repeated until all 10 2× doses are prepared.

Besides a positive control added in one concentration on each plate, the positive control of ampicillin is added to each assay run in a full concentration range (3 fold dilutions) to ensure proper and robust assay performance (estimated by comparison of dose response curves among runs).

Following the addition of carbazole compounds to 96-well plates containing bacteria, plates are transferred to the 37° C. bacteria incubator for 48 hours. After the incubation, the OD600 mm for each well of the 96-well plates will be measured.

Data Analysis

The average OD600 nm of the test compound solutions are compared to that of the DMSO control by dividing the average OD600 nm of the test solution by that of the DMSO control and multiplying by 100 to produce the % DMSO control (i.e. % cytotoxicity). The % DMSO control is plotted vs compound concentration to generate sigmoid shaped curves. After three runs are complete, the raw data for all three runs is used for $IC_{50}$ calculations.

The test results showed that the carbazole compounds of Examples 15, 7, 4, 12, 13, 17, and 18 and Compound 18c-1 and demonstrated an antibacterial effect against B. subtilis and HB 101 E. coli over a range of potencies. Gram (+) bacteria appeared more sensitive to the present carbazole compounds. In addition, several of the carbazole compounds, e.g., Examples 15 and 17, were more effective against bacteria than the ampicillin control. The present carbazole compounds therefore demonstrate a definite antibacterial activity.

The invention claimed is:

1. A method for treating melanoma, comprising intraarterially administering to a patient in need thereof an effective amount of a compound of a structural formula:

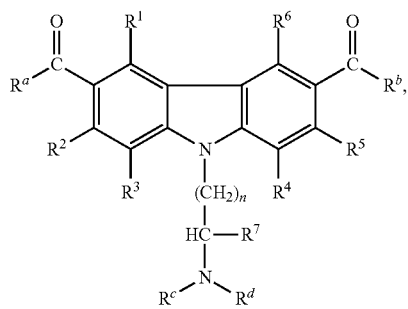

wherein $R^a$ is selected from the group consisting of $C_{1-6}$ alkyl, $C_{1-6}$ haloalkyl, cycloalkyl, heterocycloalkyl, aryl, heteroaryl, $OR^e$, $N(R^e)_2$, and $SR^e$; alternatively, either $R^a$ and $R^1$ or $NR^e$ and $R^1$ together with the carbon atoms to which they are attached form a five or six-membered aliphatic carbocyclic or heterocyclic ring;

$R^b$ is selected from the group consisting of $C_{1-6}$ alkyl, $C_{1-6}$ haloalkyl, cycloalkyl, heterocycloalkyl, aryl, heteroaryl, $OR^e$, $N(R_e)_2$, and $SR^e$, alternatively, either $R^b$ and $R^6$ or $NR^e$ and $R^6$ together with the carbon atoms to which they are attached form a five or six-membered aliphatic carbocyclic ring or a five or six-membered aliphatic carbocyclic or heterocyclic ring;

$R^c$ is selected from the group consisting of hydrogen, $C_{1-6}$ alkyl, $C_{1-6}$ hydroxyalkyl, cycloalkyl, heterocycloalkyl, aryl, heteroaryl, and $C(=O)R^e$, or $R^c$ and $R^d$ are taken together to form a five, six, or seven-membered aliphatic ring, optionally containing an oxygen atom;

$R^d$ is selected from the group consisting of hydrogen, $C_{1-6}$alkyl, cycloalkyl, heterocycloalkyl, aryl, heteroaryl, and $C(=O)R^e$, or $R^d$ and $R^7$ together with the atoms to which they are attached form a five or six-membered aliphatic ring;

$R^e$, independently, is selected from the group consisting of hydrogen, $C_{1-6}$alkyl, cycloalkyl, heterocycloalkyl, aryl, and heteroaryl, or two $R^e$ groups taken together with a nitrogen to which they are attached to form a five or six-membered aliphatic ring;

$R^1$, $R^2$, $R^3$, $R^4$, $R^5$, and $R^6$, independently, are selected from the group consisting of hydrogen, $C_{1-6}$alkyl, cycloalkyl, heterocycloalkyl, aryl, heteroaryl, halo, $OR^e$, $C(=O)R^e$, $C(=O)OR^e$, $OC(=O)R^e$, $C(=O)N(R^e)_2$, $C(=O)NR^eSO_2R^e$, $N(R^e)_2$, $NR^eC(=O)R^e$, $NR^eC(=O)N(R^e)_2$, CN, $NO_2$, $CF_3$, $OCF_3$, $SR^e$, $SOR^e$, $SO_2N(R^e)_2$, and $OSO_2CF_3$;

$R^7$ is selected from the group consisting of hydrogen, $C_{1-6}$alkyl, cycloalkyl, heterocycloalkyl, aryl, and heteroaryl; and n is 1, 2, 3, 4, or 5, or a pharmaceutically acceptable salt or hydrate thereof and wherein the intraarterial administration is intraarterial infusion.

2. The method of claim 1, wherein the compound is:

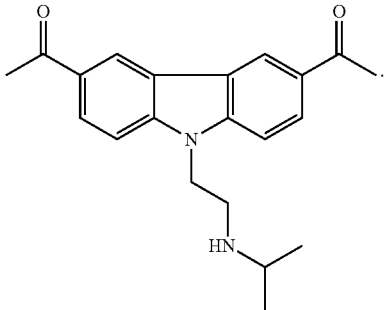 [SMILES: CC(=O)c1ccc2c(c1)c1cc(C(C)=O)ccc1n2CCNC(C)C]

3. The method of claim 1, wherein the melanoma is malignant melanoma.

4. The method of claim 3, wherein the malignant melanoma is metastatic.

5. The method of claim 1, wherein the intraarterial administering occurs at a frequency of one to four times per day.

6. The method of claim 5, wherein the intraarterial administering occurs at a frequency of one time per day.

7. The method of claim 1, wherein the intraarterial administering occurs at a frequency of one time per week.

8. A method for treating metastatic colon cancer, comprising intraarterially administering to a patient in need thereof an effective amount of a compound of a structural formula:

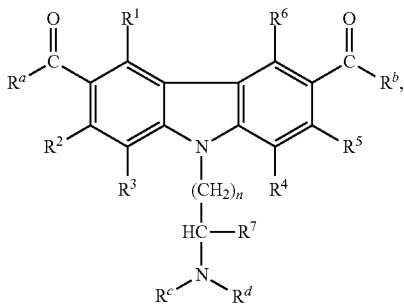

wherein $R^a$ is selected from the group consisting of $C_{1-6}$ alkyl, $C_{1-6}$ haloalkyl, cycloalkyl, heterocycloalkyl, aryl, heteroaryl, $OR^e$, $N(R^e)_2$, and $SR^e$; alternatively, either $R^a$ and $R^1$ or $NR^e$ and $R^1$ together with the carbon atoms to which they are attached form a five or six-membered aliphatic carbocyclic or heterocyclic ring;

$R^b$ is selected from the group consisting of $C_{1-6}$ alkyl, $C_{1-6}$ haloalkyl, cycloalkyl, heterocycloalkyl, aryl, heteroaryl, $OR^e$, $N(R_e)_2$, and $SR^e$, alternatively, either $R^b$ and $R^6$ or $NR^e$ and $R^6$ together with the carbon atoms to which they are attached form a five or six-membered aliphatic carbocyclic ring or a five or six-membered aliphatic carbocyclic or heterocyclic ring;

$R^c$ is selected from the group consisting of hydrogen, $C_{1-6}$ alkyl, $C_{1-6}$ hydroxyalkyl, cycloalkyl, heterocycloalkyl, aryl, heteroaryl, and $C(=O)R^e$, or $R^c$ and $R^d$ are taken together to form a five, six, or seven-membered aliphatic ring, optionally containing an oxygen atom;

$R^d$ is selected from the group consisting of hydrogen, $C_{1-6}$alkyl, cycloalkyl, heterocycloalkyl, aryl, heteroaryl, and $C(=O)R^e$, or $R^d$ and $R^7$ together with the atoms to which they are attached form a five or six-membered aliphatic ring;

$R^e$, independently, is selected from the group consisting of hydrogen, $C_{1-6}$alkyl, cycloalkyl, heterocycloalkyl, aryl, and heteroaryl, or two $R^e$ groups taken together with a nitrogen to which they are attached to form a five or six-membered aliphatic ring;

$R^1$, $R^2$, $R^3$, $R^4$, $R^5$, and $R^6$, independently, are selected from the group consisting of hydrogen, $C_{1-6}$alkyl, cycloalkyl, heterocycloalkyl, aryl, heteroaryl, halo, $OR^e$, $C(=O)R^e$, $C(=O)OR^e$, $OC(=O)R^e$, $C(=O)N(R^e)_2$, $C(=O)NR^eSO_2R^e$, $N(R^e)_2$, $NR^eC(=O)R^e$, $NR^eC(=O)N(R^e)_2$, CN, $NO_2$, $CF_3$, $OCF_3$, $SR^e$, $SOR^e$, $SO_2N(R^e)_2$, and $OSO_2CF_3$;

$R^7$ is selected from the group consisting of hydrogen, $C_{1-6}$alkyl, cycloalkyl, heterocycloalkyl, aryl, and heteroaryl; and n is 1, 2, 3, 4, or 5, or a pharmaceutically acceptable salt or hydrate thereof and wherein the intraarterial administration is intraarterial infusion.

9. The method of claim 8, wherein the compound is:

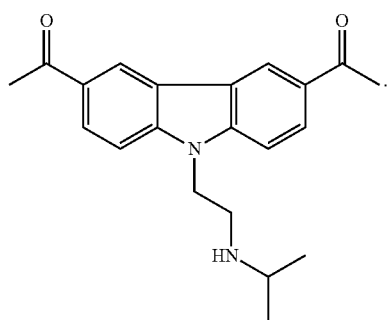 [SMILES: CC(=O)c1ccc2c(c1)c1cc(C(C)=O)ccc1n2CCNC(C)C]

10. The method of claim 8, wherein the colon cancer has metastasized to the liver.

11. The method of claim 8, wherein the intraarterial administering occurs at a frequency of one to four times per day.

12. The method of claim 11, wherein the intraarterial administering occurs at a frequency of one time per day.

13. The method of claim 8, wherein the intraarterial administering occurs at a frequency of one time per week.

14. A method for treating metastatic breast cancer, comprising intraarterially administering to a patient in need thereof an effective amount of a compound of a structural formula:

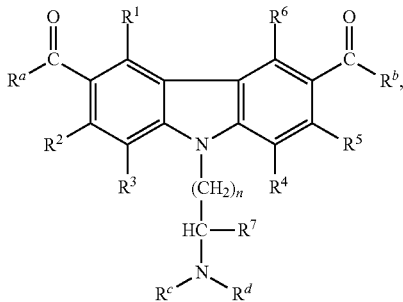

wherein R$^a$ is selected from the group consisting of C$_{1-6}$ alkyl, C$_{1-6}$ haloalkyl, cycloalkyl, heterocycloalkyl, aryl, heteroaryl, OR$^e$, N(R$^e$)$_2$, and SR$^e$; alternatively, either R$^a$ and R$^1$ or NR$^e$ and R$^1$ together with the carbon atoms to which they are attached form a five or six-membered aliphatic carbocyclic or heterocyclic ring;

R$^b$ is selected from the group consisting of C$_{1-6}$ alkyl, C$_{1-6}$ haloalkyl, cycloalkyl, heterocycloalkyl, aryl, heteroaryl, OR$^e$, N(R$_e$)$_2$, and SR$^e$, alternatively, either R$^b$ and R$^6$ or NR$^e$ and R$^6$ together with the carbon atoms to which they are attached form a five or six-membered aliphatic carbocyclic ring or a five or six-membered aliphatic carbocyclic or heterocyclic ring;

R$^c$ is selected from the group consisting of hydrogen, C$_{1-6}$ alkyl, C$_{1-6}$ hydroxyalkyl, cycloalkyl, heterocycloalkyl, aryl, heteroaryl, and C(=O)R$^e$, or R$^c$ and R$^d$ are taken together to form a five, six, or seven-membered aliphatic ring, optionally containing an oxygen atom;

R$^d$ is selected from the group consisting of hydrogen, C$_{1-6}$ alkyl, cycloalkyl, heterocycloalkyl, aryl, heteroaryl, and C(=O)R$^e$, or R$^d$ and R$^7$ together with the atoms to which they are attached form a five or six-membered aliphatic ring;

R$^e$, independently, is selected from the group consisting of hydrogen, C$_{1-6}$ alkyl, cycloalkyl, heterocycloalkyl, aryl, and heteroaryl, or two R$^e$ groups taken together with a nitrogen to which they are attached to form a five or six-membered aliphatic ring;

R$^1$, R$^2$, R$^3$, R$^4$, R$^5$, and R$^6$, independently, are selected from the group consisting of hydrogen, C$_{1-6}$alkyl, cycloalkyl, heterocycloalkyl, aryl, heteroaryl, halo, OR$^e$, C(=O)R$^e$, C(=O)OR$^e$, OC(=O)R$^e$, C(=O)N(R$^e$)$_2$, C(=O)NR$^e$SO$_2$R$^e$, N(R$^e$)$_2$, NR$^e$C(=O)R$^e$, NR$^e$C(=O)N(R$^e$)$_2$, CN, NO$_2$, CF$_3$, OCF$_3$, SR$^e$, SOR$^e$, SO$_2$N(R$^e$)$_2$, and OSO$_2$CF$_3$;

R$^7$ is selected from the group consisting of hydrogen, C$_{1-6}$alkyl, cycloalkyl, heterocycloalkyl, aryl, and heteroaryl; and n is 1, 2, 3, 4, or 5, or a pharmaceutically acceptable salt or hydrate thereof and wherein the intraarterial administration is intraarterial infusion.

15. The method of claim 14, wherein the compound is:

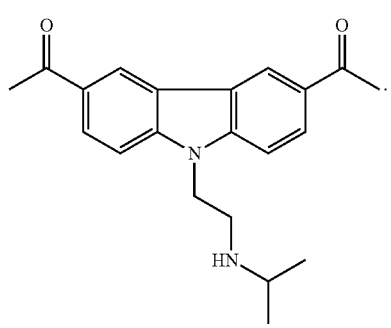 [SMILES: CC(=O)c1ccc2c(c1)c1cc(C(C)=O)ccc1n2CCNC(C)C]

16. The method of claim 14, wherein the breast cancer has metastasized to the liver.

17. The method of claim 14, wherein the intraarterial administering occurs at a frequency of one to four times per day.

18. The method of claim 17, wherein the intraarterial administering occurs at a frequency of one time per day.

19. The method of claim 14, wherein the intraarterial administering occurs at a frequency of one time per week.

* * * * *